(12) United States Patent
Olson et al.

(10) Patent No.: US 7,794,387 B2
(45) Date of Patent: Sep. 14, 2010

(54) METHODS AND DEVICES FOR STABILIZING TISSUE

(75) Inventors: Andrew L. Olson, Champlin, MN (US); Michael J. Hobday, Lino Lakes, MN (US); Steven C. Christian, New Brighton, MN (US); Tom P. Daigle, Corcoran, MN (US); Robert H. Reetz, Rockford, MN (US); Douglas H. Gubbin, Brooklyn Park, MN (US); Roderick E. Briscoe, Rogers, MN (US); William A. Steinberg, Coon Rapids, MN (US); Adam A. Podbelski, St. Paul, MN (US); Christopher J. Plott, St. Paul, MN (US); Patrick J. Cloutier, Andover, MN (US); Gerard C. Forest, Whispering Pines, NC (US); Christopher P. Olig, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 456 days.

(21) Appl. No.: 11/789,546

(22) Filed: Apr. 25, 2007

(65) Prior Publication Data

US 2008/0139879 A1 Jun. 12, 2008

Related U.S. Application Data

(60) Provisional application No. 60/795,240, filed on Apr. 26, 2006, provisional application No. 60/795,241, filed on Apr. 26, 2006, provisional application No. 60/795,243, filed on Apr. 26, 2006, provisional application No. 60/795,244, filed on Apr. 26, 2006, provisional application No. 60/795,245, filed on Apr. 26, 2006, provisional application No. 60/795,246, filed on Apr. 26, 2006, provisional application No. 60/795,651, filed on Apr. 27, 2006, provisional application No. 60/795,653, filed on Apr. 27, 2006, provisional application No. 60/795,655, filed on Apr. 27, 2006.

(51) Int. Cl.
*A61B 1/32* (2006.01)

(52) U.S. Cl. ...................................................... 600/37

(58) Field of Classification Search ............. 600/16–17, 600/37, 201, 210, 213–215, 217, 229, 231–232; 128/897–898; 604/65–67; 606/1, 198, 205–210; 607/119
See application file for complete search history.

(56) References Cited

U.S. PATENT DOCUMENTS 452,131 A 5/1891 Haughawout (Continued)

FOREIGN PATENT DOCUMENTS

DE 9004513 4/1990

(Continued)

OTHER PUBLICATIONS

Mammary Artery-Coronary Artery Anastomosis as Method of Treatment for Angina Pectoris, V.I Kolessov, MD/Thoracic and Cardiovascular Surgery, vol. 54, No. 4, Oct. 1967 pp. 535-544.

(Continued)

*Primary Examiner*—Samuel G Gilbert
(74) *Attorney, Agent, or Firm*—Mike Jaro; Jeffrey J. Hohenshell

(57) ABSTRACT

Tissue stabilizers including a clamp assembly, a turret assembly, an articulating arm having a tension element extending therethrough, a collet assembly and a head-link assembly are disclosed. Methods of stabilizing tissue are also disclosed.

48 Claims, 96 Drawing Sheets

U.S. PATENT DOCUMENTS

| | | | | |
|---|---|---|---|---|
| 2,590,527 A | 3/1952 | Fluck ........................... 123/67 |
| 3,497,668 A | 2/1970 | Hirsch |
| 3,577,982 A | 5/1971 | La Par ........................ 128/2 R |
| 3,720,433 A | 3/1973 | Rosfelder .................. 294/64 R |
| 3,783,873 A | 1/1974 | Jacobs ..................... 128/303 R |
| 3,786,815 A | 1/1974 | Ericson ....................... 128/321 |
| 3,858,926 A | 1/1975 | Ottenhues .................. 294/64 R |
| 3,916,909 A | 11/1975 | Kletschka et al .............. 128/54 |
| 3,951,138 A | 4/1976 | Akopov ........................ 128/17 |
| 3,983,863 A | 10/1976 | Janke et al. ................. 128/1 R |
| 3,999,795 A | 12/1976 | Barker ...................... 294/64 R |
| 4,047,532 A | 9/1977 | Phillips et al. .......... 128/303 R |
| 4,049,000 A | 9/1977 | Williams ..................... 128/276 |
| 4,049,002 A | 9/1977 | Kletschka et al. ........... 128/318 |
| 4,096,864 A | 6/1978 | Kletschka et al. ........... 128/354 |
| 4,306,561 A | 12/1981 | De Medinaceli ....... 128/303.13 |
| 4,314,568 A | 2/1982 | Loving ....................... 128/327 |
| 4,350,160 A | 9/1982 | Kolesov et al. ............. 128/334 |
| 4,366,819 A | 1/1983 | Kaster ..................... 128/334 C |
| 4,368,736 A | 1/1983 | Kaster ..................... 128/334 C |
| 4,428,368 A | 1/1984 | Torii ............................ 128/38 |
| 4,447,227 A | 5/1984 | Kotsanis ...................... 604/95 |
| 4,463,980 A | 8/1984 | Orii .......................... 294/64 R |
| 4,627,421 A | 12/1986 | Symbas et al. ................. 128/20 |
| 4,637,377 A | 1/1987 | Loop .......................... 128/1 R |
| 4,646,747 A | 3/1987 | Lundbáck ................... 128/643 |
| 4,655,673 A | 4/1987 | Hawkes |
| 4,688,570 A | 8/1987 | Kramer et al. .............. 128/305 |
| 4,711,247 A | 12/1987 | Fishman ..................... 128/743 |
| 4,718,418 A | 1/1988 | L'Esperance, Jr. ........ 128/303.1 |
| 4,726,356 A | 2/1988 | Santilli et al. ................. 128/20 |
| 4,736,749 A | 4/1988 | Lundback ................... 128/643 |
| 4,767,142 A | 8/1988 | Takahashi et al. .......... 294/64.1 |
| 4,808,163 A | 2/1989 | Laub .......................... 604/105 |
| 4,819,978 A | 4/1989 | Scheinman et al. |
| 4,852,552 A | 8/1989 | Chaux ......................... 128/20 |
| 4,854,318 A | 8/1989 | Solem et al. ................ 128/346 |
| 4,865,019 A | 9/1989 | Phillips ...................... 128/20 |
| 4,892,343 A | 1/1990 | Hall .......................... 294/64.1 |
| 4,904,012 A | 2/1990 | Nishiguchi et al. ........... 294/64 |
| 4,925,443 A | 5/1990 | Heilman et al. ............... 600/16 |
| 4,955,896 A | 9/1990 | Freeman ..................... 606/210 |
| 4,962,758 A | 10/1990 | Lasner et al. ................ 128/41 |
| 4,973,300 A | 11/1990 | Wright ........................ 600/37 |
| 4,989,587 A | 2/1991 | Farley ......................... 128/20 |
| 4,991,578 A | 2/1991 | Cohen .................... 128/419 D |
| 5,009,660 A | 4/1991 | Clapham ..................... 606/166 |
| 5,011,469 A | 4/1991 | Buckberg et al. .............. 604/4 |
| 5,053,041 A | 10/1991 | Ansari et al. ................ 606/148 |
| 5,078,140 A | 1/1992 | Kwoh |
| 5,098,369 A | 3/1992 | Heilman et al. ............... 600/16 |
| 5,108,412 A | 4/1992 | Krumeich et al. ........... 606/166 |
| 5,119,804 A | 6/1992 | Anstadt ....................... 128/64 |
| 5,131,905 A | 7/1992 | Grooters ..................... 600/16 |
| 5,133,737 A | 7/1992 | Grismer ..................... 606/205 |
| 5,167,223 A | 12/1992 | Koros et al. ................. 128/20 |
| 5,171,254 A | 12/1992 | Sher ......................... 606/166 |
| 5,193,963 A | 3/1993 | McAffee et al. |
| 5,207,467 A | 5/1993 | Smith ....................... 294/64.1 |
| 5,217,003 A | 6/1993 | Wilk |
| 5,222,499 A | 6/1993 | Allen et al. |
| 5,287,861 A | 2/1994 | Wilk ........................ 128/898 |
| 5,290,082 A | 3/1994 | Palmer et al. ............. 294/64.1 |
| 5,300,087 A | 4/1994 | Knoepfler .................. 606/207 |
| 5,305,203 A | 4/1994 | Raab |
| 5,324,087 A | 6/1994 | Shimose et al. ............ 294/64.1 |
| 5,336,252 A | 8/1994 | Cohen ....................... 607/119 |
| 5,365,921 A | 11/1994 | Bookwalter et al. ........... 128/20 |
| 5,372,124 A | 12/1994 | Takayama et al. .............. 128/4 |
| 5,374,277 A | 12/1994 | Hassler ..................... 606/207 |
| 5,383,840 A | 1/1995 | Heilman et al. ............... 600/17 |
| 5,397,323 A | 3/1995 | Taylor et al. |
| 5,402,801 A | 4/1995 | Taylor |
| 5,410,944 A | 5/1995 | Cushman |
| 5,417,210 A | 5/1995 | Funda et al. |
| 5,417,709 A | 5/1995 | Slater ........................ 606/205 |
| 5,423,648 A | 6/1995 | Akeel et al. |
| 5,425,705 A | 6/1995 | Evard et al. .................. 604/28 |
| 5,437,651 A | 8/1995 | Todd et al. .................. 604/313 |
| 5,452,733 A | 9/1995 | Sterman et al. ............. 128/898 |
| 5,458,574 A | 10/1995 | Machold et al. |
| 5,472,438 A | 12/1995 | Schmit et al. .................. 606/1 |
| 5,503,617 A | 4/1996 | Jako .......................... 600/201 |
| 5,509,890 A | 4/1996 | Kazama ...................... 600/37 |
| 5,545,123 A | 8/1996 | Oritz et al. .................. 600/235 |
| 5,556,147 A | 9/1996 | Somekh et al. ............ 294/64.1 |
| 5,572,999 A | 11/1996 | Funda et al. |
| 5,607,421 A | 3/1997 | Jeevanandam et al. ........ 606/15 |
| 5,613,937 A | 3/1997 | Garrison et al. ............. 600/201 |
| 5,631,973 A | 5/1997 | Green |
| 5,649,956 A | 7/1997 | Jensen et al. |
| 5,667,624 A | 9/1997 | Akimoto et al. ............. 156/389 |
| 5,676,673 A | 10/1997 | Ferre et al. |
| 5,695,500 A | 12/1997 | Taylor et al. |
| 5,697,939 A | 12/1997 | Kubota et al. |
| 5,702,420 A | 12/1997 | Sterling et al. .............. 606/205 |
| 5,727,569 A | 3/1998 | Benetti et al. ............... 128/898 |
| 5,730,757 A | 3/1998 | Benetti et al. ............... 606/198 |
| 5,738,649 A | 4/1998 | Macoviak |
| 5,744,363 A | 5/1998 | Hasson |
| 5,749,892 A | 5/1998 | Vierra et al. ................ 600/204 |
| 5,762,458 A | 6/1998 | Wang et al. |
| 5,772,583 A | 6/1998 | Wright et al. ............... 600/232 |
| 5,782,746 A | 7/1998 | Wright ........................ 600/37 |
| 5,784,542 A | 7/1998 | Ohm et al. |
| 5,791,908 A | 8/1998 | Gillio |
| 5,792,135 A | 8/1998 | Madhani et al. |
| 5,797,900 A | 8/1998 | Madhani et al. |
| 5,799,661 A | 9/1998 | Boyd et al. ................. 128/898 |
| 5,807,243 A | 9/1998 | Vierra et al. ................ 600/204 |
| 5,808,665 A | 9/1998 | Green |
| 5,827,216 A | 10/1998 | Igo et al. ...................... 604/21 |
| 5,836,311 A | 11/1998 | Borst et al. .................. 128/897 |
| 5,855,583 A | 1/1999 | Wang et al. |
| 5,865,730 A | 2/1999 | Fox et al. |
| 5,875,782 A | 3/1999 | Ferrari et al. ............... 128/898 |
| 5,876,325 A | 3/1999 | Mizuno et al. |
| 5,888,247 A | 3/1999 | Benetti ....................... 623/66 |
| 5,891,017 A | 4/1999 | Swindle et al. |
| 5,894,843 A | 4/1999 | Benetti et al. ............... 128/898 |
| 5,906,607 A | 5/1999 | Taylor et al. .................. 606/1 |
| 5,921,979 A | 7/1999 | Kovac et al. ................... 606/1 |
| 5,923,770 A | 7/1999 | O'Donnell et al. |
| 5,927,284 A | 7/1999 | Borst et al. .................. 128/898 |
| 5,931,832 A | 8/1999 | Jensen |
| 5,947,896 A | 9/1999 | Sherts et al. ................ 600/229 |
| 5,957,835 A | 9/1999 | Anderson et al. |
| 5,971,976 A | 10/1999 | Wang et al. |
| 5,976,080 A | 11/1999 | Farascioni .................. 600/213 |
| 5,976,171 A | 11/1999 | Taylor ....................... 606/198 |
| 6,007,523 A | 12/1999 | Mangosong |
| 6,015,378 A | 1/2000 | Borst et al. ................... 600/37 |
| 6,017,304 A | 1/2000 | Vierra et al. ................ 600/204 |
| 6,019,722 A | 2/2000 | Spence et al. ............... 600/210 |
| 6,032,672 A | 3/2000 | Taylor ....................... 128/898 |
| 6,036,641 A | 3/2000 | Taylor et al. ................ 600/231 |
| 6,050,266 A | 4/2000 | Benetti et al. ............... 128/898 |
| 6,063,021 A | 5/2000 | Hossain et al. ................ 600/37 |
| 6,071,235 A | 6/2000 | Furnish et al. .............. 600/235 |
| 6,074,375 A | 6/2000 | Stiles ........................ 604/268 |
| 6,102,854 A | 8/2000 | Cartier et al. |
| 6,110,187 A | 8/2000 | Donlon ...................... 606/151 |
| 6,120,436 A | 9/2000 | Anderson et al. |
| 6,132,370 A | 10/2000 | Furnish et al. .............. 600/235 |

| | | | | | | |
|---|---|---|---|---|---|---|
| 6,139,492 | A | 10/2000 | Vierra et al. ............... 600/204 | JP | 06012045 | 1/1994 |
| 6,149,583 | A | 11/2000 | Vierra et al. ............... 600/204 | JP | 02607600 | 5/1997 |
| 6,152,874 | A | 11/2000 | Looney et al. ............. 600/214 | WO | WO 87/04081 | 7/1987 |
| 6,161,543 | A | 12/2000 | Cox et al. | WO | WO 88/00481 | 1/1988 |
| 6,183,486 | B1 | 2/2001 | Snow et al. ................. 606/151 | WO | WO 94/03142 | 2/1994 |
| 6,193,652 | B1 | 2/2001 | Berky et al. | WO | WO 94/14383 | 7/1994 |
| 6,206,827 | B1 | 3/2001 | Chin et al. ................. 600/217 | WO | WO 94/14715 | 7/1994 |
| 6,210,323 | B1 | 4/2001 | Gilhuly et al. | WO | WO 94/18881 | 9/1994 |
| 6,213,941 | B1 | 4/2001 | Benetti et al. .............. 600/235 | WO | WO 95/01757 | 1/1995 |
| 6,231,506 | B1 | 5/2001 | Hu et al. | WO | WO 95/15715 | 6/1995 |
| 6,254,535 | B1 | 7/2001 | Furnish et al. ............. 600/213 | WO | WO 95/17127 | 6/1995 |
| 6,290,644 | B1 | 9/2001 | Green, II et al. ........... 600/235 | WO | WO 96/00033 | 1/1996 |
| 6,306,085 | B1 | 10/2001 | Farascioni ................. 600/213 | WO | WO 97/10753 | 3/1997 |
| 6,315,717 | B1 | 11/2001 | Benetti et al. .............. 600/210 | WO | WO 98/10705 | 3/1998 |
| 6,334,843 | B1 | 1/2002 | Borst et al. .................. 600/37 | WO | WO 98/17182 | 4/1998 |
| 6,338,738 | B1 | 1/2002 | Bellotti et al. | WO | WO 98/27869 | 7/1998 |
| 6,346,077 | B1 | 2/2002 | Taylor et al. ............... 600/204 | WO | WO 98/49947 | 11/1998 |
| 6,348,036 | B1 | 2/2002 | Looney et al. | WO | WO 99/09892 | 3/1999 |
| 6,350,229 | B1 | 2/2002 | Borst et al. .................. 600/37 | WO | WO 99/16367 | 4/1999 |
| 6,364,826 | B1 | 4/2002 | Borst et al. .................. 600/37 | WO | WO 99/50721 | 10/1999 |
| 6,371,906 | B1 | 4/2002 | Borst et al. .................. 600/37 | WO | 00/15119 | 3/2000 |
| 6,375,611 | B1 | 4/2002 | Voss et al. | WO | 2004/082487 | 9/2004 |
| 6,379,297 | B1 | 4/2002 | Furnish et al. ............. 600/213 | | | |
| 6,394,948 | B1 | 5/2002 | Borst et al. .................. 600/37 | | | |
| 6,394,951 | B1 | 5/2002 | Taylor et al. ............... 600/210 | | | |
| 6,398,726 | B1 | 6/2002 | Ramans et al. | | | |
| 6,464,629 | B1 | 10/2002 | Boone et al. | | | |
| 6,464,630 | B1 | 10/2002 | Borst et al. | | | |
| 6,464,691 | B1 | 10/2002 | Castaneda et al. | | | |
| 6,328,688 | B1 | 12/2002 | Borst et al. .................. 600/37 | | | |
| 6,659,939 | B2 | 12/2003 | Moll et al. | | | |
| 6,730,020 | B2 | 5/2004 | Peng et al. | | | |
| 6,740,028 | B2 | 5/2004 | Boone et al. | | | |
| 6,755,780 | B2 | 6/2004 | Borst et al. | | | |
| 6,758,808 | B2* | 7/2004 | Paul et al. ................... 600/229 | | | |
| 6,758,809 | B2* | 7/2004 | Briscoe et al. .............. 600/229 | | | |
| 6,849,075 | B2 | 2/2005 | Bertolero et al. | | | |
| 6,866,628 | B2 | 3/2005 | Goodman et al. | | | |
| 6,905,498 | B2 | 6/2005 | Hooven | | | |
| 6,932,811 | B2 | 8/2005 | Hooven | | | |
| 2002/0120177 | A1 | 8/2002 | Borst et al. .................. 600/37 | | | |
| 2002/0124856 | A1 | 9/2002 | Borst et al. .................. 128/898 | | | |
| 2003/0078470 | A1 | 4/2003 | Borst et al. .................. 600/37 | | | |
| 2003/0083555 | A1* | 5/2003 | Hunt et al. .................. 600/229 | | | |
| 2003/0120268 | A1 | 6/2003 | Bertolero et al. | | | |
| 2003/0158463 | A1 | 8/2003 | Julian et al. | | | |
| 2003/0158542 | A1 | 8/2003 | Nguyen et al. | | | |
| 2003/0195393 | A1* | 10/2003 | Goodman et al. ........... 600/228 | | | |
| 2004/0030223 | A1* | 2/2004 | Calafiore et al. ............ 600/229 | | | |
| 2004/0106918 | A1 | 6/2004 | Cox et al. | | | |
| 2004/0138522 | A1 | 7/2004 | Haarstad et al. | | | |
| 2004/0167549 | A1* | 8/2004 | Boone et al. ................ 606/151 | | | |
| 2004/0267097 | A1* | 12/2004 | Xiao et al. ................... 600/229 | | | |

FOREIGN PATENT DOCUMENTS

| | | |
|---|---|---|
| DE | 29708050 | 5/1997 |
| EP | 0 167 345 A1 | 1/1986 |
| EP | 0 293 760 A3 | 5/1988 |
| EP | 0 432 560 A2 | 11/1990 |
| EP | 0 630 629 A1 | 12/1994 |
| EP | 0 668 058 A1 | 8/1995 |
| EP | 0 808 606 A1 | 11/1997 |
| EP | 0 920 835 A1 | 6/1999 |
| EP | 0993 806 A2 | 9/1999 |
| EP | 0993806 A3 | 9/1999 |
| GB | 2 140 695 A | 12/1984 |
| GB | 2 214 428 A | 9/1989 |
| GB | 2233561 | 1/1991 |
| GB | 2 214 428 B | 6/1991 |
| GB | 2267827 | 12/1993 |
| JP | 59143408 | 8/1984 |
| JP | 01232945 | 9/1989 |

OTHER PUBLICATIONS

Direct Myocardial Revascularization by Saphenous Vein Graft, R.G. Favaloro, MD; DG Effler, MD; LK Groves, MD; WG Sheldon, MD; and FM Sones, Jr., MD / The Annals of Thoracic Surgery, vol. 10, No. 2, Aug. 1970.

A Simple Technique and Device To Provide a Bloodless Operative Field in Coronary Artery Surgery Without Cross-Clamping the Aorta, M. Riahi, RJ Schlosser and LA Tomastis/The Journal of Thoracic and Cardiovascular Surgery, vol. 66, No. 6, Dec. 1973, pp. 974-978.

To Use or Not To Use the Pump Oxygenator in Coronary Bypass Operations, Drs. WG Trapp and R. Bisarya/The Annals of Thoracic Surgery, vol. 19, No. 1, Jan 1975, pp. 108-109.

A Prospective Evaluation of the Pulsatile Assist Device, GL Zumbro, Jr., MD; G Shearer, CCP; ME Fishback, MD; and RF Galloway, MD / The Annals of Thoracic Surgery, vol. 28, No. 2 Aug. 1979, pp. 269-273.

Preservation of Interventricular Septal Function in Patients Having Coronary Artery Bypass Grafts Without Cardiopulmonary Bypass, CW Akins, MD; CA Boucher, MD; and GM Pohost, MD / American Heart Journal, vol. 107, No. 2, Feb. 1984, pp. 304-309.

Coronary Artery Revascularization Without Cardiopulmonary Bypass, R. Archer, DO; DA Ott, MD; R. Parravicini, MD; DA Cooley, MD; GJ Reul, MD; OH Frazier, MD; JM Duncan, MD; JJ Livesay, MD and WE Walker, MD, Texas Heart Institute Journal, vol. 11, No. 1, Mar. 1984, pp. 52-57.

Direct Myocardial Revascularization Without Cardiopulmonary Bypass, E. Buffolo; JCS Andrade, J Succi; LEV Leao; and C Gallucci. Thoac. Cardiovasc. Surgeon, 33 (1985) pp. 26-29.

Direct Coronary Surgery with Saphenous Vein Bypass Without Eigher Cardiopulmonary Bypass or Cardiac Arrest, FJ Benetti, The Journal of Cardiovascular Surgery, vol. 26, No. 3, May-Jun. 1985, pp. 217-222.

Heart-Mechanical Assist Device Interaction, JY Kresh; PLM Kerkhof; SM Goldman; and SK Brockman, Trans. Am. Soc. Artif. Intern. Organs, vol. XXXII, 1986, pp. 437-443.

Delayed Recovery of Severaly 'Stunned' Myocardium with the Support of a Left Ventricular Assist Device after Coronary Artery Bypass Graft Surgery, CM Ballantyne MD; MS verani, MD, FACC; HD Short, MD; C Hyatt, BSN, RN; GP Noon, MD, FACC, Journal of the American College of Cardiology, vol. 10, No. 3, Sep. 1987, pp. 710-712.

Long-Term Follow-up of Survivors of Postcardiotomy Circulatory Support, SA Ruzevich; KR Kanter; DG Pennington; MT Swartz; LR McBride; and DT Termuhlen, Trans. Am. Soc. Artif. Intern. Organs, vol. XXXIV, 1988, pp. 116-124.

Extended Clinical Support with an Implantable Left Ventricular Assist Device, MG McGee; SM Parnis; T Nakatani; T Myers; K Dasse; WD Hare; JM Duncan; VL Poirier; and OH Frazier, Trans Am. Soc. Artif. Intern. Organs, vol. XXXV, 1989, pp. 614-616.

Current Status of Cardiac Surgery: A 40-Year Review, WE Richenbacher, MD; JL Myers, MD, FACC; JA Walhausen, MD, FACC, Journal of American College of Cardiology, vol. 14, No. 3, Sep. 1989, pp. 535-544.

Transfemoral Placement of the Left Ventricular Assist Device "Hemopump" During Mechanical Resuscitation, KH Scholz; U Tebbe; M Chemnitius; H Kreuzer; T Schroder; JP Hering; P Uhlig; G Hellige; HJ Grone; R Autschbach; B Schorn; W Ruschewski; and H Dalichau, Thoracic and Cardiovascular Surgeon, vol. 38 (1990) pp. 69-72.

Direct Mechanical Ventricular Actuation for Cardiac Arrest in Humans, MP Anstadt, MD; RL Bartlett, MD; JP Malone, MD, FCCP; and GL Anstadt, VMD; Chest, vol. 100, No. 1, Jul. 1991.

Direct Myocardial Revascularization Without Extracorpoeal Circulation, FJ Benetti, MD; G Naselli, MD; M Wood, MD; and L Geffner, MD, Chest, vol. 100. No. 2, Aug. 1991, pp. 312-316.

Coronary Artery Bypass Without Cardiopulmonary Bypass, Pfister et al, The Annals of Thoracic Surgery, vol. 54 #6 Dec. 1992 pp. 1085-1092.

Coronary Artery Operation Supported by the Hemopump: An Experimental Study on Pig, U Lonn, MD; B Peterzen, MD; H Granfeldt, MD; and H Casimir-Ahn, MD, Ph.D. The Annals of Thoracic Surgery, vol. 58, No. 1, Jul. 1994, pp. 516-523.

Regional Cardiac Wall Immobilization for Open Chest and Closed Chest Coronary Artery Bypass Grafting on the Beating Heart: The 'Octopus' Method, Circulation, vol. 92. No. 8 Supplement 1, I-177 (Oct. 15, 1995).

A Minimally Invasive Surgical Method for Coronary Revascularization—Preliminary Experience in Five Patients, MC Robinson, DR Gross, and W Zeman, Circulation, (Oct. 15, 1995) vol. 92, No. 8, I-176.

Coronary Artery Bypass Grafting Without Cardiopulmonary Bypass and Without Interruption of Native Coronary Flow Using a Novel Astamosis Site Restraining Device ("Octopus"), C. Borst et al., Journal of the American College of Cardiology, vol. 27, No. 6, 1356-1364 (May 1996).

Cardiogenic Shock Complicating Acute Myocardial Infarction: the Use of Coronary Angioplasty and the Integration of the New Support Device into Patient Management, GM Gacioch, MD; Stephen G. Ellism, MD, FACC; L Lee, MD; ER Bates, MD, FACC; M Kirsh, MD, FACC; JA Walton, MD, FACC; EH Topol, MD, FACC, Journal of the American College of Cardiology, vol. 19, No. 3, Mar. 1, 1992.

Reoperative Coronary Artery Bypass Grafting Without Cardiopulmonary Bypass, WJ Fanning, MD; GS Kakos, MD; and TE Williams, Jr., MD, Ph.D., The Annals of Thoracic Surgery, vol. 55, No. 2, Feb. 1993, pp. 486-489.

Enhanced Preservation of Acutely Ischemic Myocardium with Transeptal Left Ventricular Assist, JD Fonger, MD; Y Zhou, MD; H Matsuura, MD; GS Aldea, MD; and RJ Shemin, MD, The Annals of Thoracic Surgery, vol. 57, No. 3, Mar. 1994, pp. 570-575.

Transcatheter Radiofrequency Ablation of Atrial Tissue Using a Suction Catheter, Th Lavergne et al. (PACE, vol. 12, Jan. 1989, Part II, pp. 177-186.

Abstract: "Closed Chest Coronary Artery Bypass With Cardioplegic Arrest in the Dog", Stevens et al. $67^{th}$ Scientific Sessions.

Placement of Coronary Artery Bypass Graft without Pump Oxygenator, Trapp et al., Journal of the Society of Thoracic Surgeons and the Southern Thoracic Surgical Assn. vol. 19. No. 7 Jan. 1975.

Experimental Videothoracoscopic Cannulation of the Left Atrial Appendix: A Feasible Rapid Approach for Initiating Left Heart Bypass? PF Gründeman; DW Meijer; JJG Bannenberg; R tukkie; and PJ Klopper, Surgical Endoscopy (1993) 7: 511-513.

A New Retractor to Aid In Coronary Artery Surgery, A.J. Delrossi, M.D., And G.M. Lemore, M.D., The Annals of Thoracic and Cardiovascular Surgery, vol. 36 Jul. 1983 pp. 101-102.

Less Invasive Coronary Surgery: Consensus From the Oxford Meeting, Stephen Westaby, FRCS, And Federico J. Benetti, MD, Annals of Thoracic Surgery 1996; 62: 924-31.

The Surgery of Coronary Arteries of the Heart, Kolessov V.I., Leningrad, Meditsina, 1977, pp. 360. (Russian Article).

The Surgery of Coronary Arteries of the Heart, Kosesssov V.I., Leningrad, Meditsina., 1977, pp. 360. (English Translation).

U.S. Appl. No. 90/005,995 dated May 3, 2001.
U.S. Appl. No. 90/005,994 dated May 3, 2001.

* cited by examiner

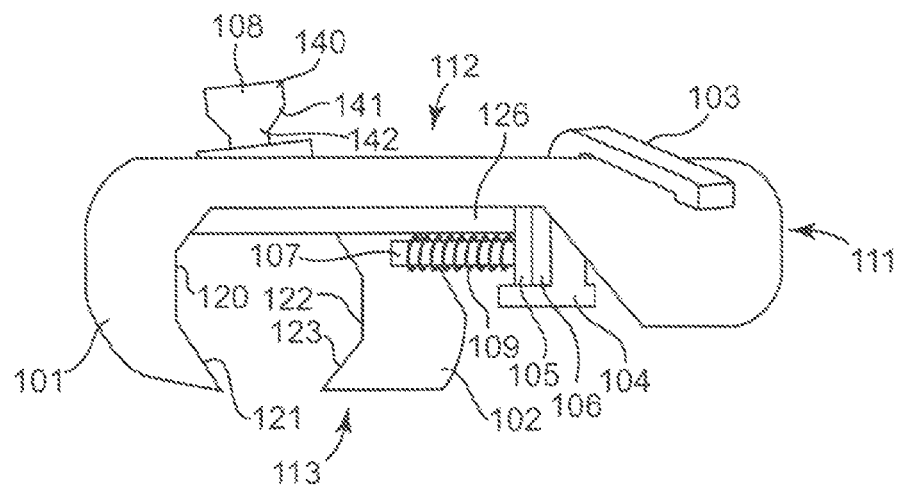
Fig. 2D
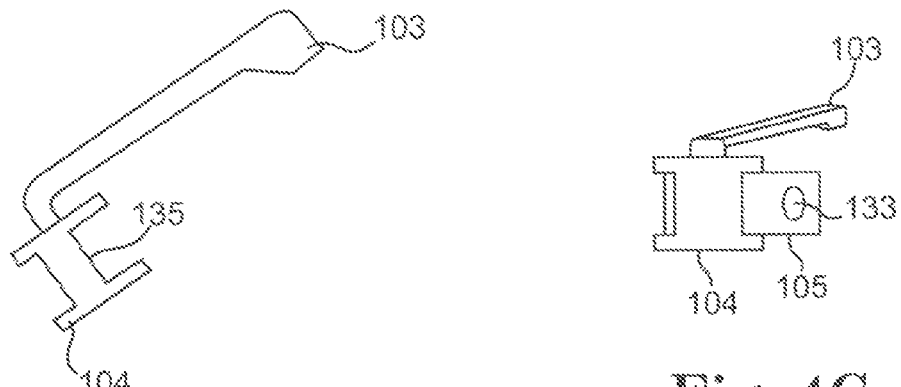
Fig. 4A
Fig. 4C
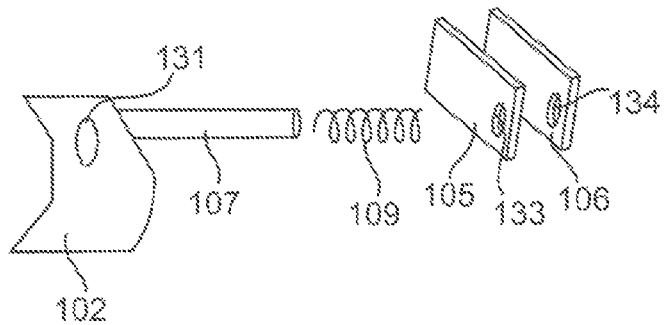
Fig. 4B

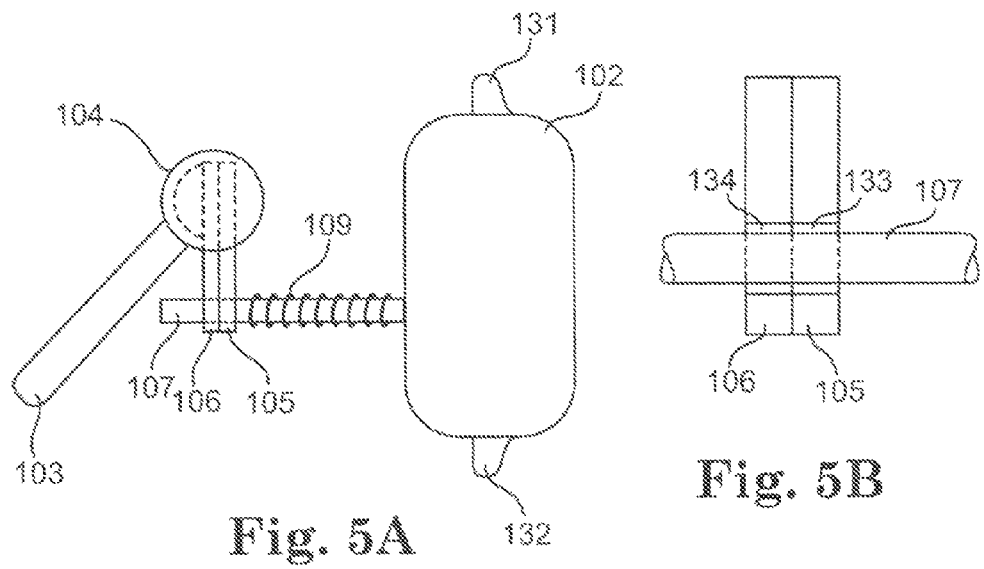
Fig. 5A
Fig. 5B
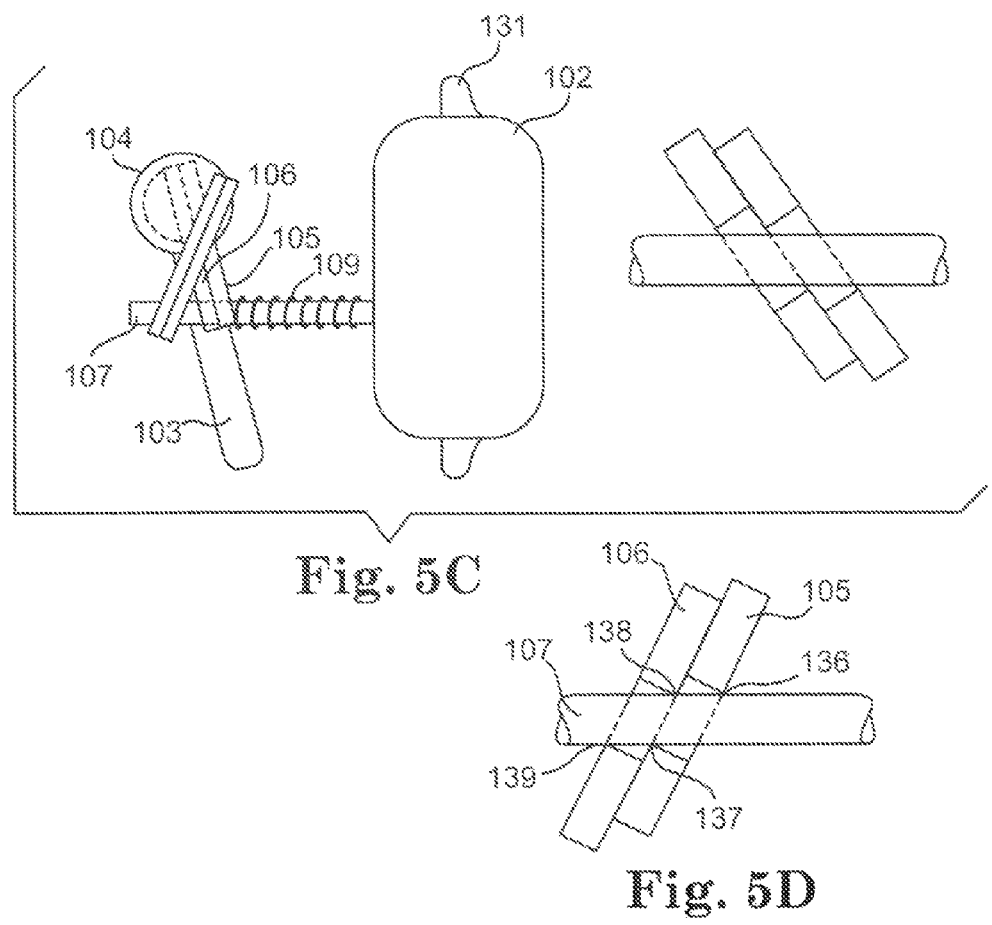
Fig. 5C
Fig. 5D

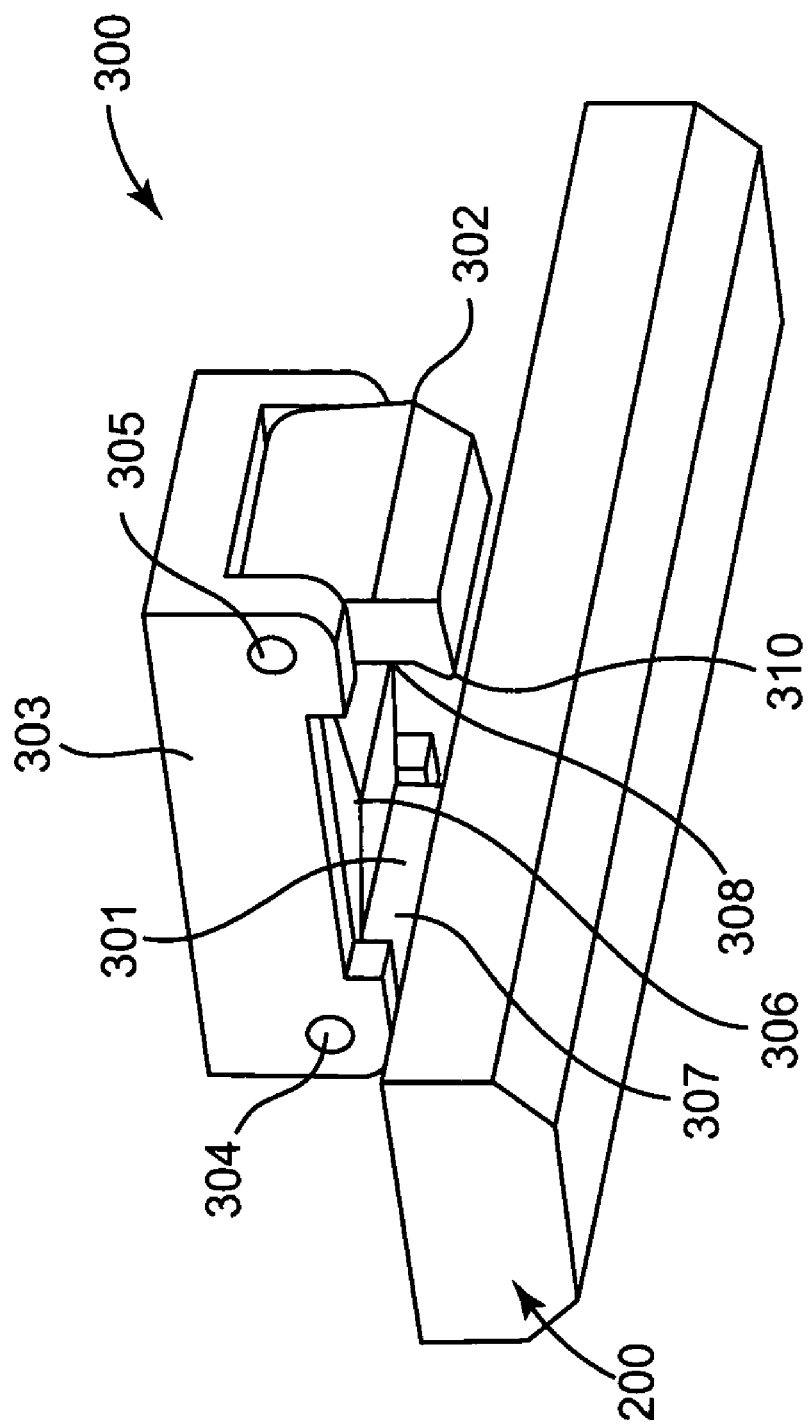

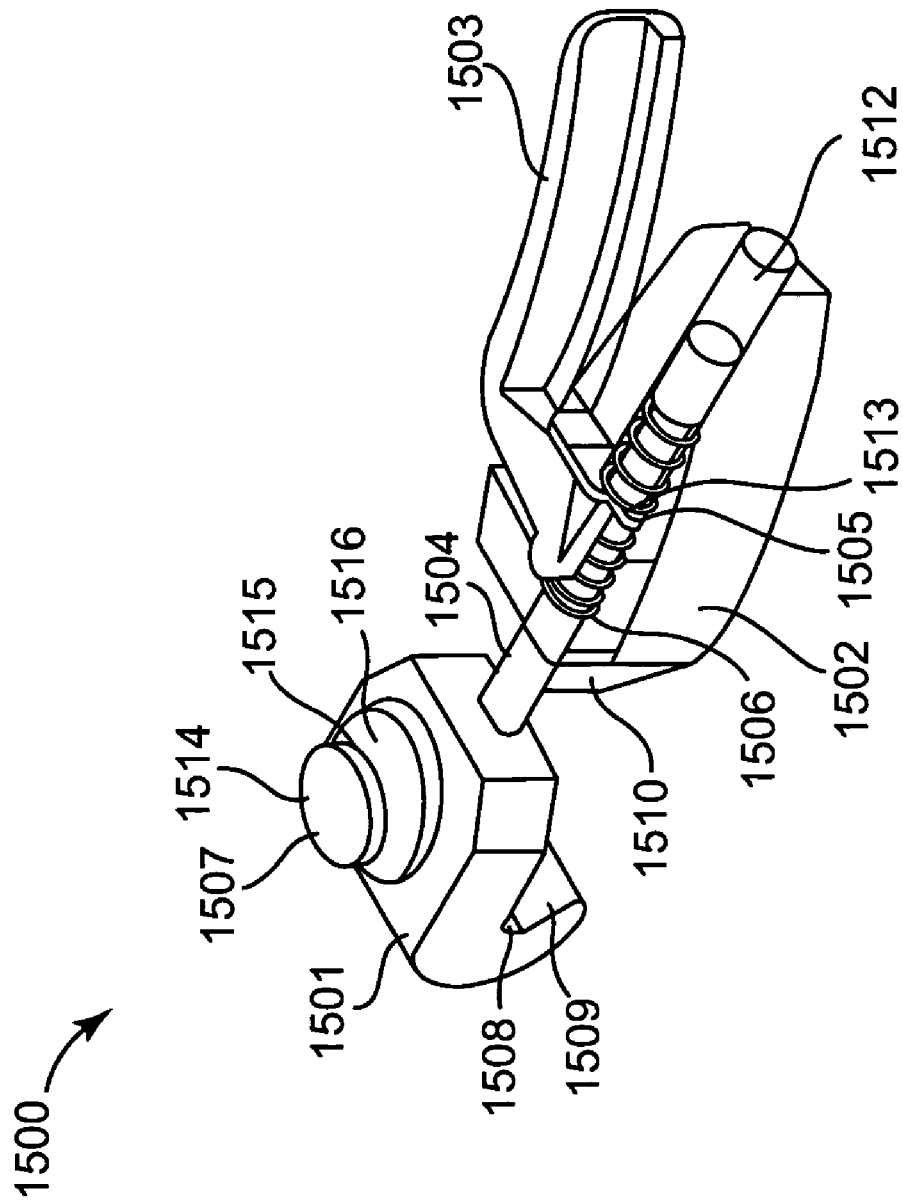

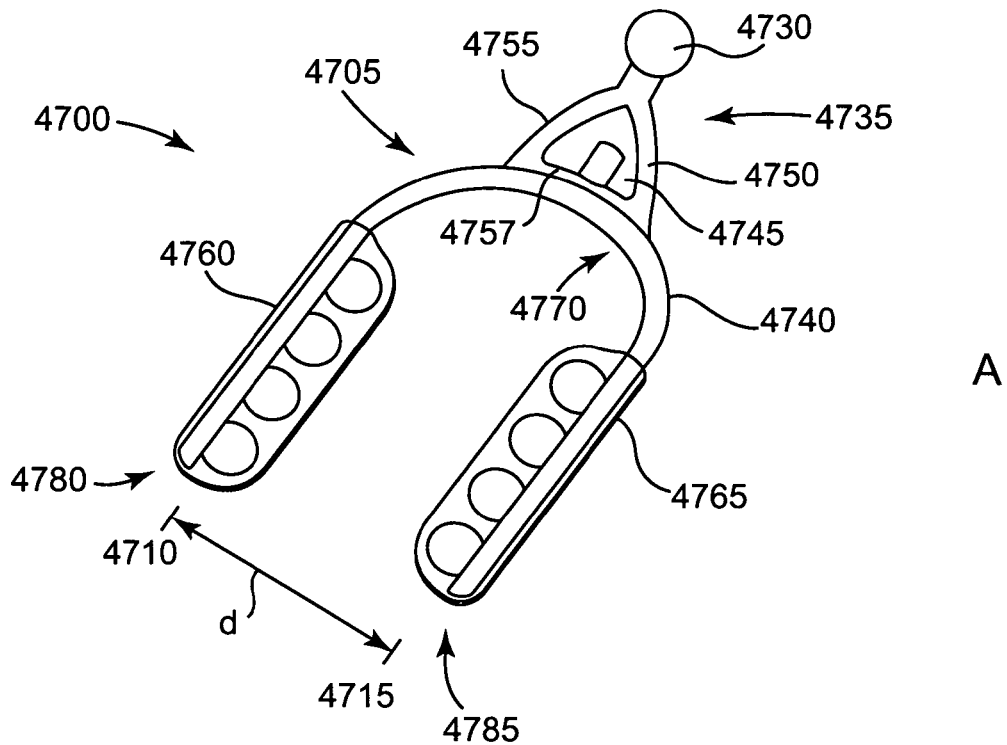
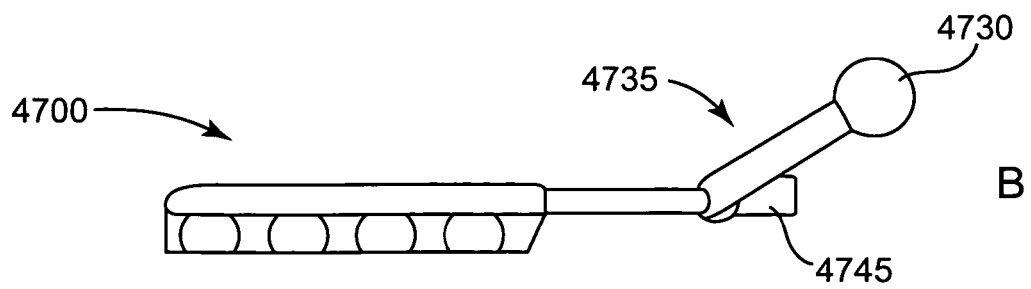
Fig. 66

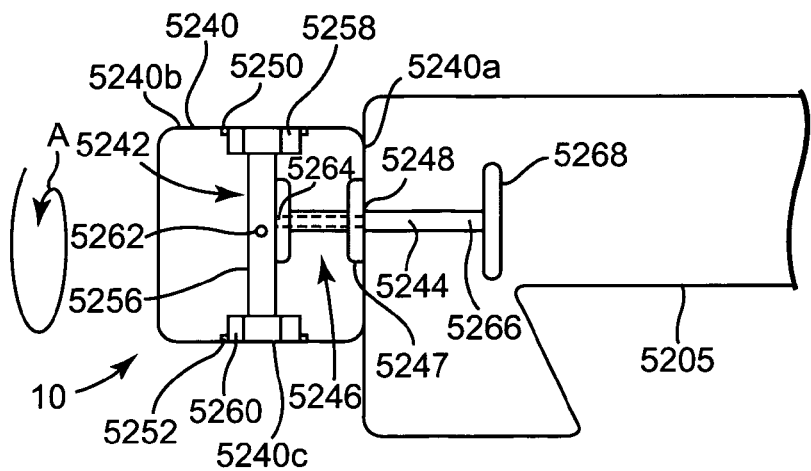
Fig. 76
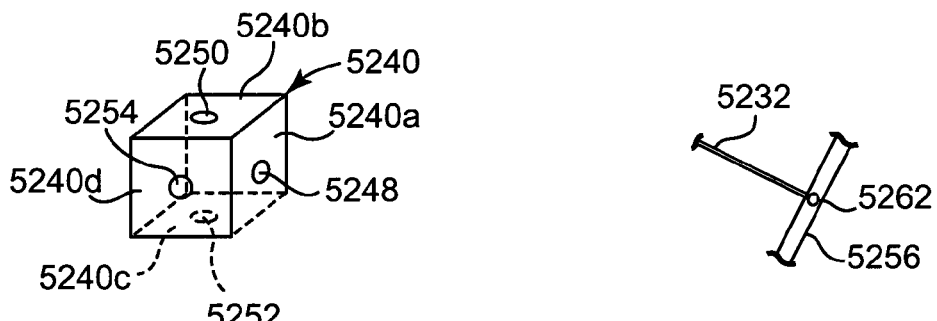
Fig. 77     Fig. 78
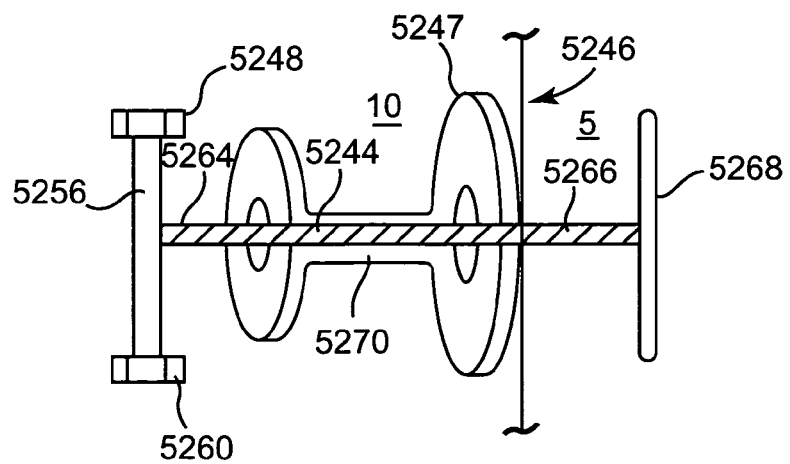
Fig. 79

METHODS AND DEVICES FOR STABILIZING TISSUE

CROSS-REFERENCE TO RELATED APPLICATIONS

This application claims the benefit of U.S. Provisional Patent Application Ser. No. 60/795,240, filed Apr. 26, 2006, U.S. Provisional Patent Application Ser. No. 60/795,241, filed Apr. 26, 2006, U.S. Provisional Patent Application Ser. No. 60/795,243, filed Apr. 26, 2006, U.S. Provisional Patent Application Ser. No. 60/795,244, filed Apr. 26, 2006, U.S. Provisional Patent Application Ser. No. 60/795,245, filed Apr. 26, 2006, U.S. Provisional Patent Application Ser. No. 60/795,246, filed Apr. 26, 2006, U.S. Provisional Patent Application Ser. No. 60/795,651, filed Apr. 27, 2006, U.S. Provisional Patent Application Ser. No. 60/795,653, filed Apr. 27, 2006, and U.S. Provisional Patent Application Ser. No. 60/795,655, filed Apr. 27, 2006, the entire contents of which are incorporated herein by reference.

BACKGROUND OF THE INVENTION

Approximately 300,000 patients in the United States undergo coronary artery grafting operations every year. Conventional coronary artery grafting operations required that the beating of the heart be ceased during the procedure. A heart-lung machine was used to pump and oxygenate the patient's blood while the heart was stopped. Off-pump surgery, or beating-heart surgery, however, has become an attractive alternative to traditional surgery incorporating a heart-lung machine.

Tissue stabilizers are used in beating-heart surgery for holding, lifting, and rotating the beating heart to expose coronary arteries on any of the heart's surfaces, and to hold the tissue almost stationary where the surgeon is working. Tissue stabilizers typically include suction pods that hold a surface tissue of the heart stable while a surgeon attaches a transplanted vessel around blockages in one or more coronary arteries. The tissue stabilizer can help the surgeon to position the suction pods on a target area of the heart surface, stabilize a suture site, and work with an unimpeded view as a bypass is sutured in place.

SUMMARY OF THE INVENTION

The invention provides various embodiments of a tissue stabilizer for supporting an organ during surgery. In one embodiment, the tissue stabilizer includes a clamp assembly including a front clamp, a rear clamp slidably coupled to the front clamp, a shaft mounted to one of the front clamp or the rear clamp, a clutch plate mounted to the shaft on a side of the rear clamp opposite the front clamp, an actuator operably coupled to the clutch plate, and a turret mount mounted to the front clamp. The actuator may be operable to rotate the clutch plate into the shaft to prevent the rear clamp from sliding.

In one embodiment, the tissue stabilizer includes a collet assembly including a collet coupled to a tension element. The collet may include a base and a head. The collet may be configured to couple to a head-link assembly. The collet assembly may include a collet receiving element configured to receive the base and to compress the head when the collet is drawn into the collet receiving element. Tensioning the tension element can draw the collet into the collet receiving element and loosening the tension element can allow the head to move out of the collet receiving element. The head-link assembly may be placed at any angle above a plane perpendicular to the collet receiving element when the tension element is loosened.

In one embodiment, the present invention provides a method of positioning an arm mounted on a spherical base. A tension element coupled to a collet is loosened. The arm is positioned at an angle above a plane perpendicular to a collet receiving element. The tension element is tensioned. The collet is drawn into the collet receiving element. A head of the collet is compressed by the collet receiving element. The spherical base is locked in position by a force created by compressing the head.

In one embodiment, the tissue stabilizer includes a head-link assembly including a base configured to be received by a collet and a pair of arms supported by the base. The arms may be deflected from a first position in which the arms are separated from one another by a first distance to a second position in which the arms are separated from one another by a second distance and are biased to return to the first position in the absence of an external force.

In one embodiment, the invention provides a method of supporting an organ for surgery. A head-link may be positioned over the organ and may be secured in position. A pair of arms of the head-link may be manually deflected from a first position to a second position closer toward one another. A vacuum can be applied to the head-link to create suction at a plurality of cups on the pair of arms. The suction force may be removed in order to allow the pair of arms to return to the first position in order to stretch the organ between them.

In one embodiment, the tissue stabilizer includes a turret assembly including a clamp and an articulating arm having a tension element. The turret assembly can include a cylinder adapted to be rotatably coupled to the clamp, a body supported by the cylinder, the body adapted to be coupled to the articulating arm, and a locking mechanism adapted to be coupled to the tension element. The locking mechanism can be capable of exerting a tensioning force on the tension element and can be capable of clamping the body to the clamp.

In one embodiment, the tissue stabilizer includes a clamp, an articulating arm having a tension element extending therethrough, a collet assembly, a head-link assembly, and a turret assembly. The turret assembly may include a cylinder rotatably coupled to the clamp, a body supported by the cylinder and coupled to the articulating arm, and a locking mechanism coupled to the tension element. The locking mechanism may exert a tensioning force on the tension element and clamping the body to the clamp.

In one embodiment, the invention provides a method of stabilizing tissue in a surgical field. The method may include positioning an articulating arm in the surgical field, the articulating arm being rotatably mounted to a clamp with a turret assembly, so that the turret assembly is angled toward a front portion of the clamp. A tensioning force may be exerted on the articulating arm by pivoting a lever arm of the turret assembly into a closed position. The turret assembly may be prevented from rotating relative to the clamp by pivoting the lever arm into the closed position.

In one embodiment, the tissue stabilizer includes a turret assembly including a housing rotatably coupled to a clamp and a spool within the housing. The spool may be rotatable relative to the housing and may be coupled to a tension element. Rotation of the spool in a first direction may tension the tension element and rotation of the spool in a second direction may loosen the tension element. In some embodiments, a height clearance of the housing may be less than or equal to a height clearance of the clamp.

In one embodiment, the tissue stabilizer includes a clamp assembly adapted to be clamped on a retractor, an articulating arm having a tension element extending therethrough, a turret assembly rotatably coupling a proximal end of the articulating arm to the clamp assembly, the turret assembly including a locking mechanism coupled to the tension element, the locking mechanism being capable of applying a tensioning force on the tension element, a head-link assembly, a collet assembly coupled to the tension element, the collet assembly rotatably coupling the head-link assembly to a distal end of the articulating arm, wherein tensioning of the tension element locks the head-link assembly to the collet, locks the articulating arm in position, and locks the turret assembly to the clamp, and wherein loosening of the tension element allows the head-link assembly to rotate relative to the collet, the articulating arm to articulate, and the turret assembly to rotate relative to the clamp.

In one embodiment, the invention provides a method of stabilizing tissue in a surgical field. The method may include clamping a tissue stabilizer to a retractor, applying a deflecting force on a pair of arms of a head-link assembly of the tissue stabilizer to deflect the arms from a first position to a second position in which the pair of arms are closer to one another, positioning at least a portion of the deflected arms against the tissue, applying a vacuum to the head-link assembly to create a suction force at a plurality of cups on each one of the pair of arms, the vacuum securing the arms to the tissue, removing the deflecting force to allow the pair of arms to return to the first position in order to stretch a portion of the tissue, and applying a tensioning force to the tension element to simultaneously lock the head-link assembly to the collet, lock the articulating arm in position, and lock the turret assembly to the clamp assembly.

Other aspects of the invention will become apparent by consideration of the detailed description and accompanying drawings.

BRIEF DESCRIPTION OF THE DRAWINGS

FIG. 2D is a cut-away of the cardiac tissue stabilizer clamp of FIGS. 2A-2C.

FIG. 4A is a side view of a handle and a cam of the cardiac tissue stabilizer clamp of FIGS. 2A-2D.

FIG. 4B is an exploded view of a rear clamp, a shaft, a spring, and a plurality of clutch plates of the cardiac tissue stabilizer clamp of FIGS. 2A-2D.

FIG. 4C illustrates a coupling of the cam of FIG. 4A with a clutch plate.

FIGS. 5A and 5B illustrate the position of the handle, cam, and plurality of clutch plates of the cardiac tissue stabilizer clamp of FIGS. 2A-2D in an unlocked position.

FIGS. 5C and 5D illustrate the position of the handle, cam, and plurality of clutch plates of the cardiac tissue stabilizer clamp of FIGS. 2A-2D in a locked position.

FIGS. 7A and 7B are perspective views of an embodiment of a snap-lock clamp for a cardiac tissue stabilizer in open and closed positions.

FIGS. 31A and 31B are perspective views of an embodiment of a bar clamp lock clamp for a cardiac tissue stabilizer in open and closed positions with the rear clamp shown in transparency.

FIG. 66A is a perspective view of a head-link assembly according to another embodiment of the invention.

FIG. 66B is a side view of the head-link assembly of FIG. 66A.

FIG. 76 is a side cut-away view of the turret and clamp of FIG. 75.

FIG. 77 is a perspective view of a turret housing according to one embodiment of the invention.

FIG. 78 is a schematic view of a tension element and an attachment area of a shaft for use with the turret, turret housing, and clamp of FIGS. 75-77.

FIG. 79 is a side view of a spool, a pin, a locking mechanism, and an anchor for use with the turret, turret housing, and clamp of FIGS. 75-78.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Figure 1A:
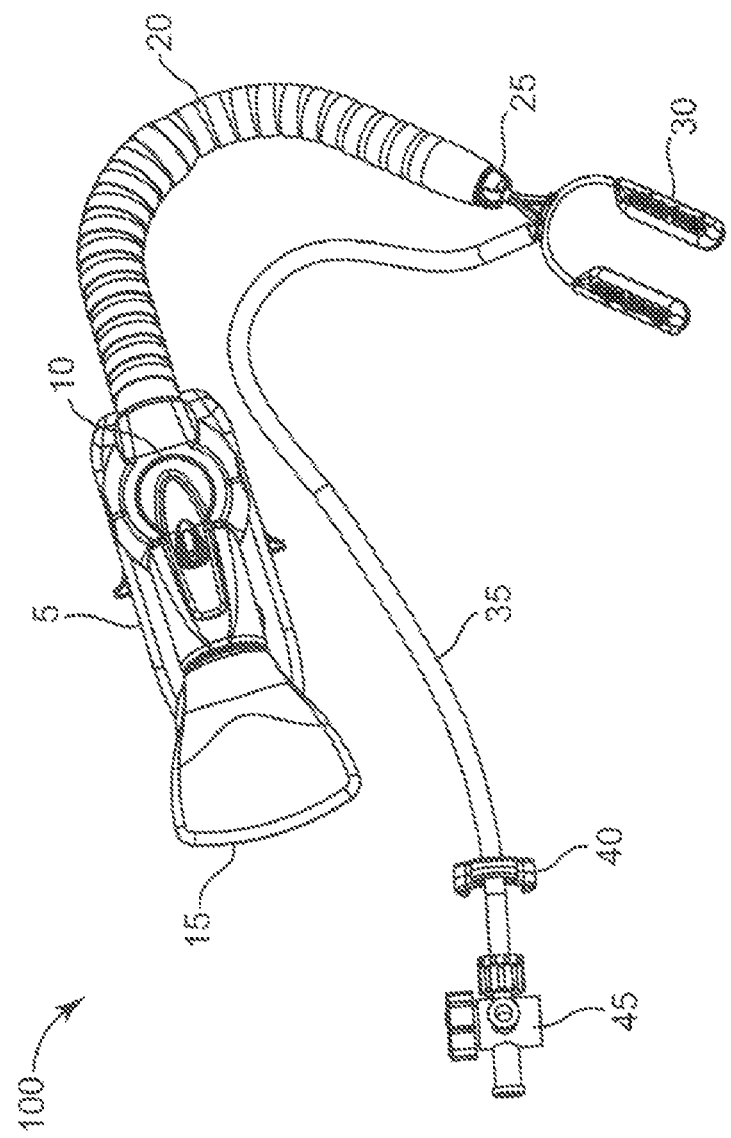
FIGS. 1A and 1B are perspective views of an embodiment of an entire tissue stabilizer assembly.
Figure 1B:
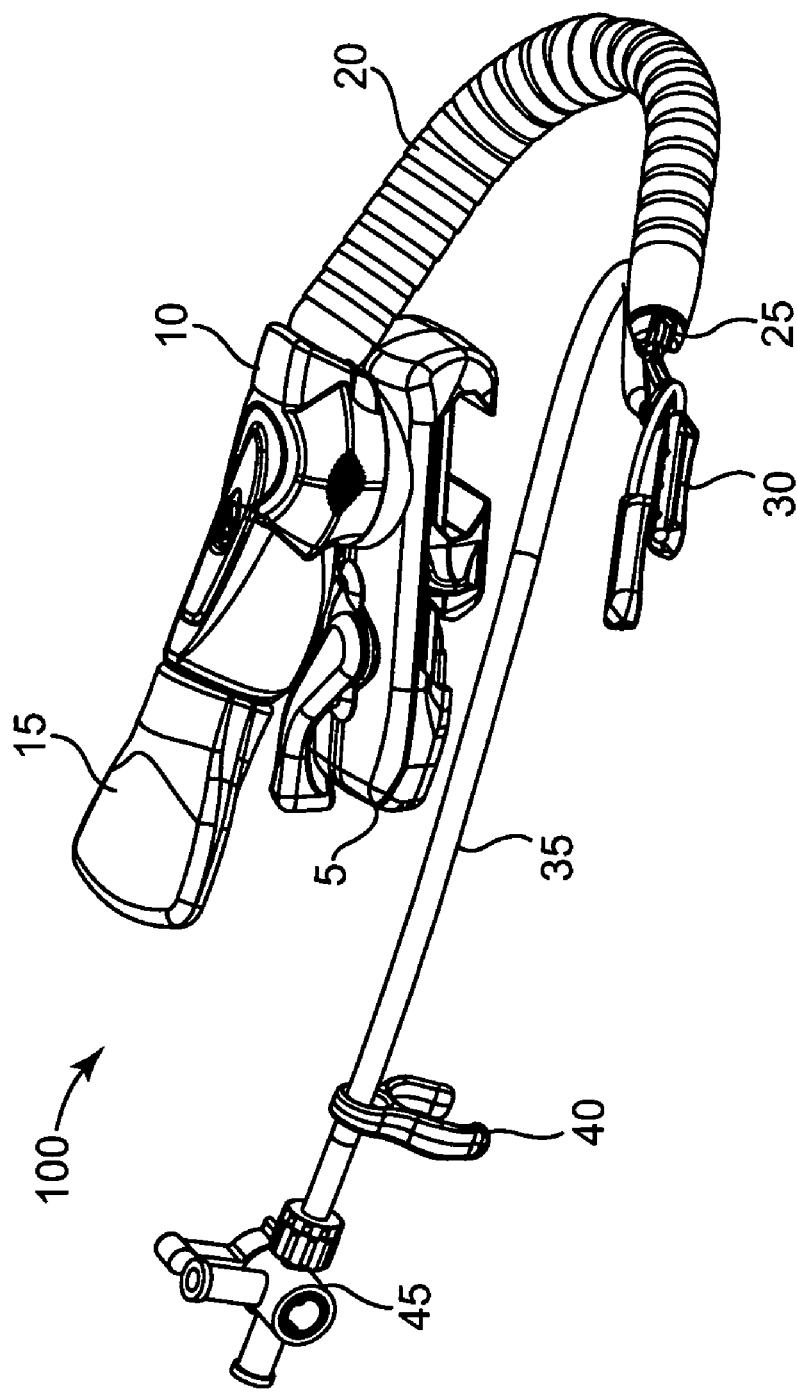

FIGS. 1A and 1B illustrate a tissue stabilizer 100 according to one embodiment of the invention for use in supporting an organ, such as the heart, during a surgical procedure. The tissue stabilizer 100 can include a clamp 5, a turret 10, a handle 15, an articulating arm 20, a collet assembly 25, a head-link assembly 30, a vacuum tube 35, a vacuum tube clamp 40, and a vacuum tube valve 45.

FIGS. 2A to 2D illustrate an embodiment of a cardiac tissue stabilizer clamp 5. The clamp 5 can include a front clamp 101, a rear clamp 102, an actuation lever 103, a cam 104, a first clutch plate 105, a second clutch plate 106, a shaft 107, a turret mount 108 and spring 109.

The front clamp 101 can be in a generally C-shape and can include a front flat surface 120 and a front angled surface 121. The front clamp 101 can be held stationary at a front 114 of a bottom 113 of the clamp 5 with the front flat surface 120 perpendicular to the bottom 113 of the clamp 5 and facing toward a rear 111 of the clamp 5. The rear clamp 102 can be in a generally C-shape and can include a rear flat surface 122 and a rear angled surface 123. The rear clamp 102 can be slidably mounted on the bottom 113 of the clamp 5 closer to the rear 111 than the front clamp 101 with the rear flat surface 122 parallel and facing the front flat surface 120. The surfaces 120, 121, 122, 123 are sized and shaped to contact and capture a sternal retractor rail. The angled surfaces 121, 123 urge the retractor rail 200 into tighter engagement as the rear clamp 102 is urged towards the front clamp 101. Other shapes for the clamp 5 are within the scope of a clamp in accordance with the invention. For example, front clamp 101 and rear clamp 102 may each include only the flat surface 120, 122 or only the angled surface 121, 123, or a combination thereof. In addition, the clamp surfaces may be curved or have some other shape so as to be complementary to a retractor rail or other stabilizing object. The shaft 107 can be coupled to the rear clamp 102 and can extend toward the rear 111 of the clamp 5. The spring 109 can surround the shaft 107 between the first clutch plate 105 and the rear clamp 102.

A first beam 125 and a second beam 126 can be integrated along opposite edges of the clamp 5 in parallel orientation on the bottom 113 of the clamp 5. The first and second beams 125 and 126 can extend from the front flat surface 120 of the front clamp 101 to a point near the rear 111 of the clamp 5. The rear clamp 102 can slidably couple to a first track 127 of the first beam 125 and a second track 128 of the second beam 126 on the bottom 113 of the clamp 5. The spring 109 can bias the rear clamp 102 to slide on the first and second tracks 127 and 128 toward the front clamp 101. A first stopper 129 and a second stopper 130 can be integrated into the bottom 113 of the clamp 5 adjacent to the front clamp 101. The first and second stoppers 129 and 130 can contact the rear clamp 102 to prevent the rear clamp 102 from sliding too far to the front 114 of the clamp 5 and allowing the shaft 107 to disengage from the first and second clutch plates 105 and 106.

Figure 2A:
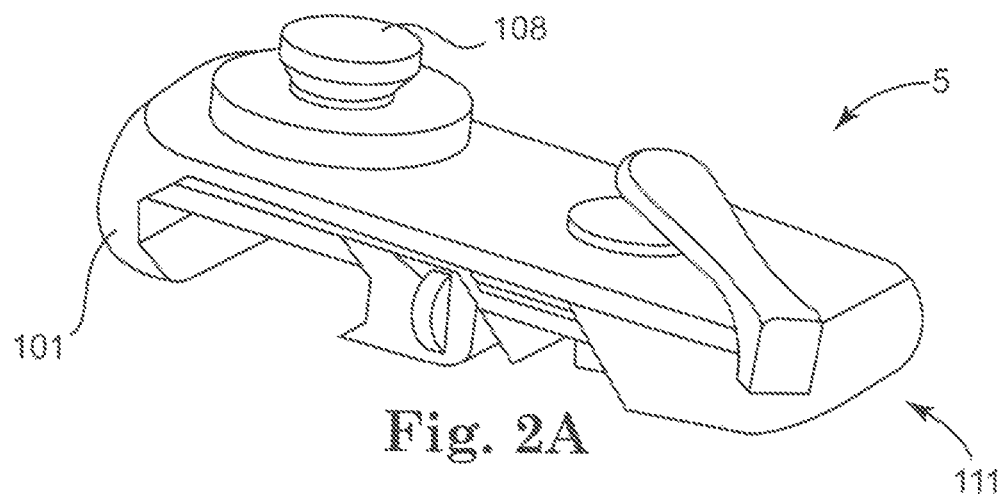
FIGS. 2A to 2C illustrate perspective, top and bottom views of an embodiment of a cardiac tissue stabilizer clamp.
Figure 2B:
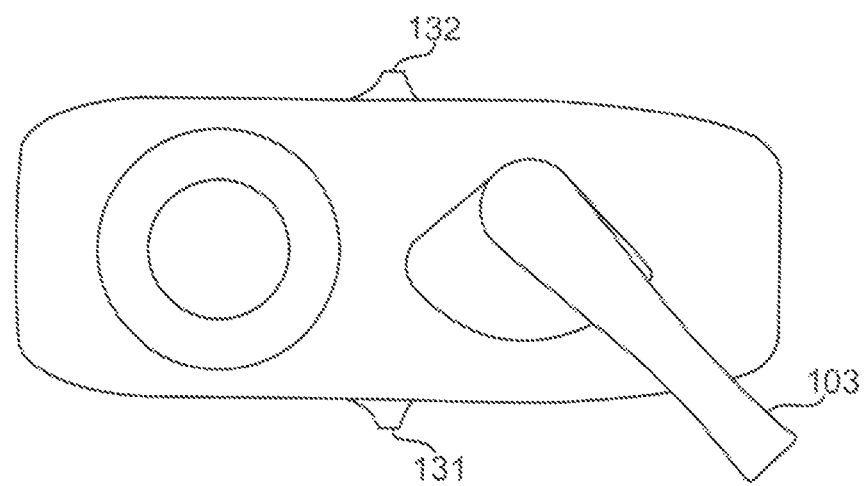
Figure 3A:
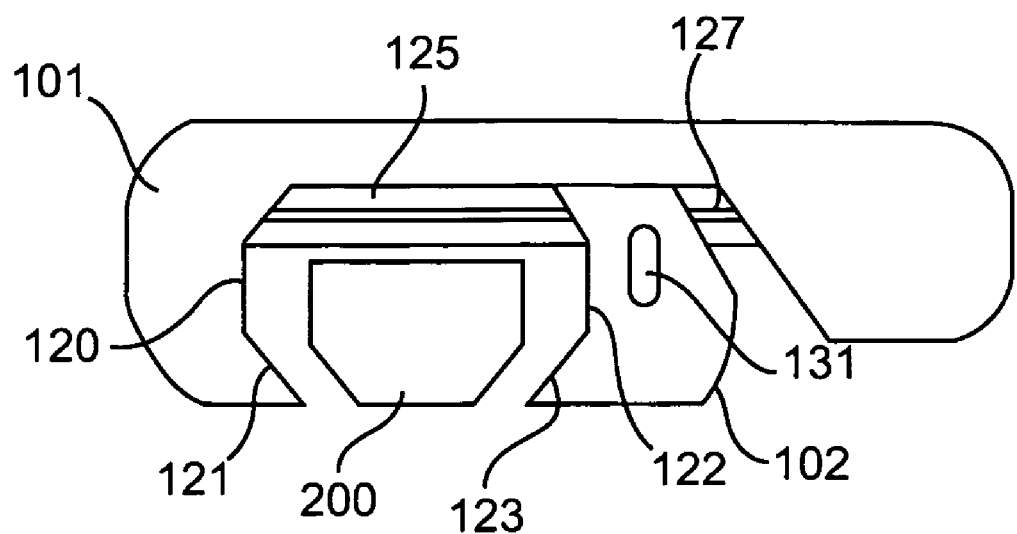
FIG. 3A is a side view of the cardiac tissue stabilizer clamp of FIGS. 2A-2D in an unlocked position.
Figure 3B:
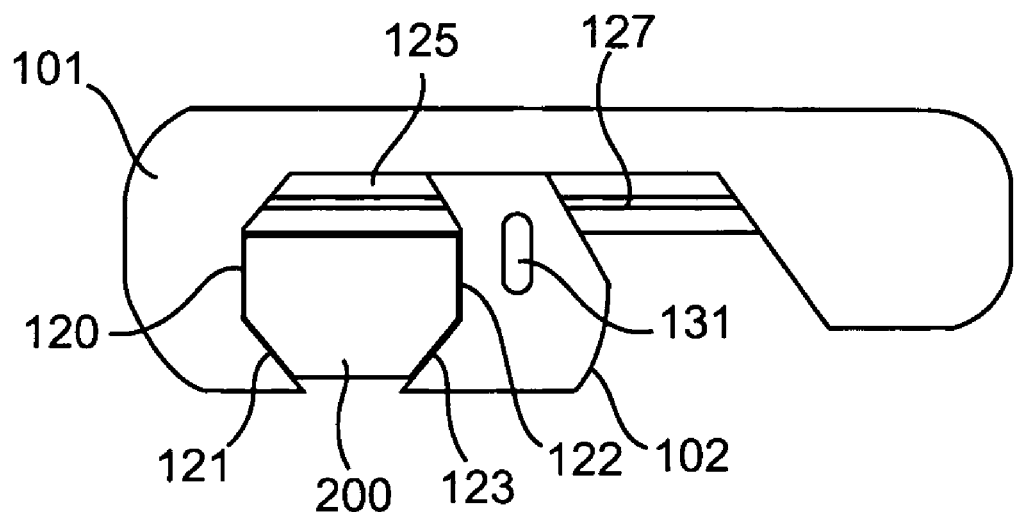
FIG. 3B is a side view of the cardiac tissue stabilizer clamp of FIGS. 2A-2D in a locked position.

FIG. 2B illustrates how a first handle 131 and a second handle 132 can be situated on opposite sides of the rear clamp 102. FIG. 3A illustrates a position of the rear clamp 102, relative to the front clamp 101, when a force opposing the spring 109 is applied to the first and second handles 131 and 132 and the rear clamp 102 is slid towards the rear 111 of the clamp 5. FIG. 3B illustrates how the rear clamp 102 can slide toward the front clamp 101 when the force is removed. FIG. 3B also shows how the clamp 5 can mount to a retractor rail 200. The front flat surface 120 and rear flat surface 122 can contact opposite sides of the retractor rail 200 preventing lateral motion of the clamp 5. The front angled surface 121 and the rear angled surface 123 can slide under the retractor rail 200 to prevent the clamp 5 from lifting away from the retractor rail 200.

FIG. 4A illustrates an embodiment of the actuation lever 103 coupled to the cam 104. In some embodiments, the actuation lever 103 can be mounted on a top 112 of the clamp 5, closer to the rear 111 of the clamp 5 than the rear clamp 102. The actuation lever 103 can extend through the clamp 5 to the bottom 113 and be coupled to the cam 104. The first and second clutch plates 105 and 106 can include a first aperture 133 and a second aperture 134 respectively. The first and second apertures 133 and 134 can have a diameter slightly larger than the diameter of the shaft 107. The shaft 107 can slide through the first and second apertures 133 and 134. The first and second clutch plates 105 and 106 can fit into a notch 135 in the cam 104 as illustrated in FIG. 4C.

FIG. 5A illustrates the actuation lever 103, the cam 104, and the first and second clutch plates 105 and 106 in an unlocked position. The first and second apertures 133 and 134 of the first and second clutch plates 105 and 106 can be perpendicular to the shaft 107 and the shaft 107 can slide freely through the first and second apertures 133 and 134. FIG. 5B illustrates the spacing of the first and second apertures 133 and 134 relative to the shaft 107 in the unlocked position. The actuation lever 103 can be rotated from the unlocked position (FIG. 5A) to a locked position (FIG. 5C). Rotating the actuation lever 103 can also rotate the cam 104. When rotating the actuation lever 103 to the locked position, the first and second clutch plates 105 and 106 can be cammed by the notch 135 of the cam 104. When the first and second clutch plates 105 and 106 rotate, the first and second apertures 133 and 134 can contact the shaft 107 as illustrated in FIG. 5D. The first clutch plate 105 can contact the shaft 107 at a first contact point 136 and a second contact point 137. The second clutch plate 106 can contact the shaft 107 at a third contact point 138 and a fourth contact point 139. A binding force at the first, second, third, and fourth contact points 136, 137, 138, and 139 can pressure the first and second clutch plates 105 and 106 into rigid contact with the shaft 107. Friction between the first, second, third, and fourth contact points 136, 137, 138, and 139 and the shaft 107 can hold the shaft 107 in position in the first and second apertures 133 and 134 of the first and second clutch plates 105 and 106. Binding the shaft 107 with the first and second clutch plates 105 and 106 can hold the rear clamp 102 in position.

Returning to FIGS. 2A and 2D, the turret mount 108 can be positioned on the top 112 of the clamp 5 between the actuation lever 103 and the front clamp 101. The turret mount 108 can include a cylindrical top 140, an angled groove 141, and a flat groove 142. A turret (see FIG. 1) of a cardiac tissue stabilizer can mount to the turret mount 108 and can be locked in place.

The front clamp 101, the turret mount 108, the first and second beams 125 and 126, and the first and second stoppers 129 and 130 can be formed integrally by injection molding. The rear clamp 102 and the shaft 107 coupled to the rear clamp 102 can slide onto the first and second beams 125 and 126 by the rear 111 of the clamp 5. The actuation lever 103 can mount on the top 112 of the clamp 5 and integrally form with the cam 104 on the bottom 113 of the clamp 5. A first pin 143 and a second pin 144 can press fit a base 145 to the bottom 113 and the rear 111 of the clamp 5. The base 145 can prevent the rear clamp 102 and shaft 107 from sliding off the rear 111 of the first and second beams 125 and 126. The base 145 can be formed to partially surround and support the cam 104.

Figure 6A:
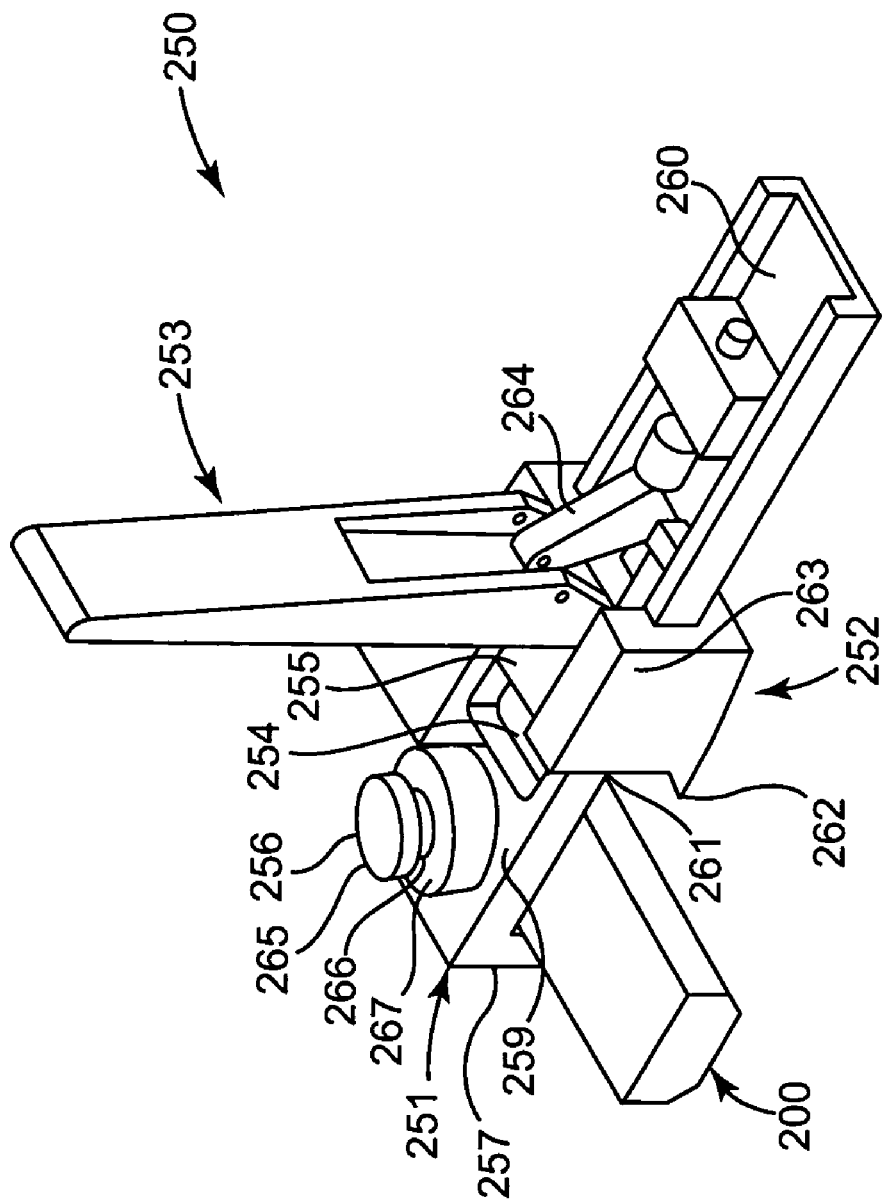
FIGS. 6A and 6B are perspective views of an embodiment of an auto-lock clamp for a cardiac tissue stabilizer in open and closed positions.
Figure 6B:
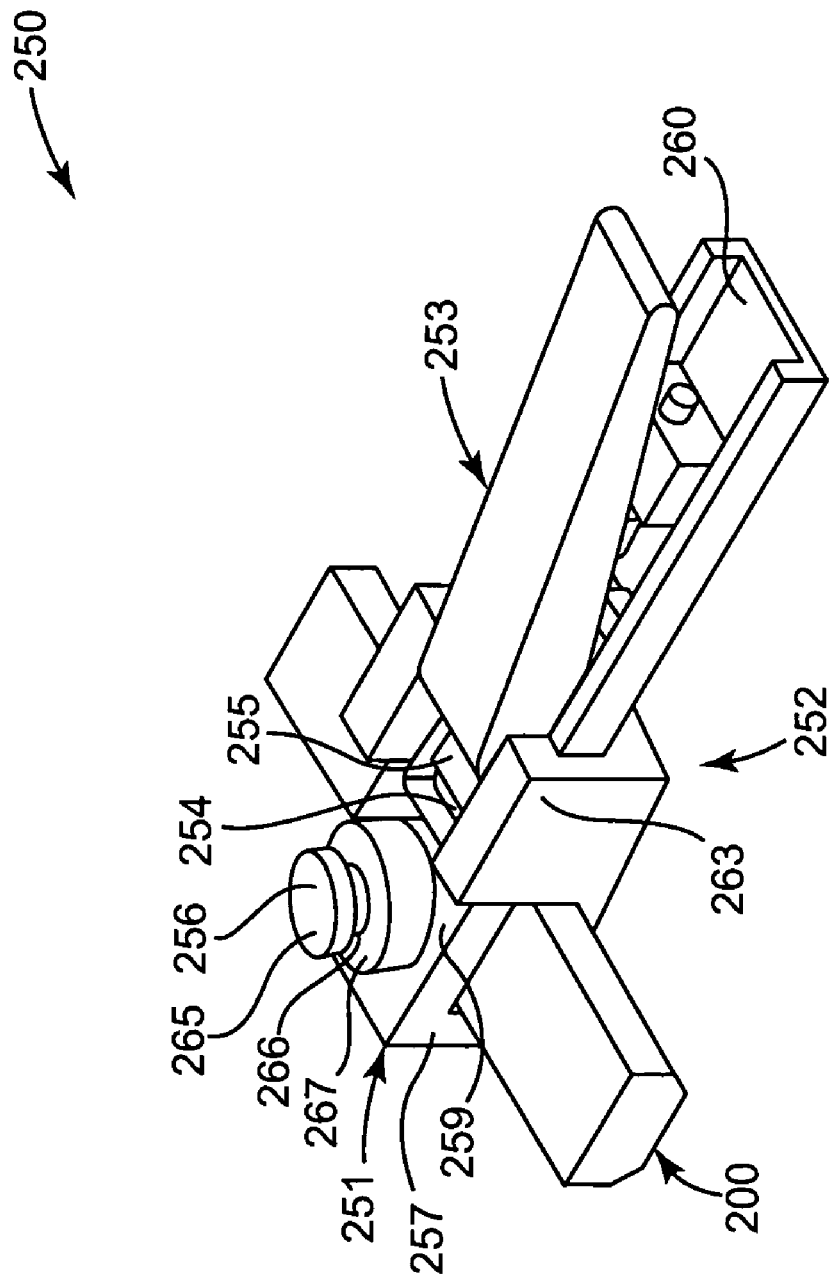

FIGS. 6A and 6B illustrate another embodiment of a cardiac tissue stabilizer clamp 250. The clamp 250 can include a front clamp 251, a rear clamp 252, an actuation lever 253, a first wedge 254, a second wedge 255, and a turret mount 256. The front clamp 251 can be in a generally C-shape and can include a front flat surface 257 and a front angled surface (not visible). The front clamp 251 can include a body 259 extending perpendicular from the front flat surface 257 opposite the front angled surface. The body 259 can include a groove 260 starting at a short distance from the front clamp 251 and extending along the body 259 away from the front clamp 251. The rear clamp 252 can be in a generally C-shape and can include a rear flat surface 261 and a rear angled surface 262. The rear clamp 252 can slidably mount to the body 259 of the front clamp 251 with the rear flat surface 261 parallel and facing the front flat surface 257. The front flat surface 257 and rear flat surface 261 can contact the retractor rail 200 in a locked position and can prevent the clamp 250 from moving laterally on the retractor rail 200. The front angled surface 258 and rear angled surface 262 can slide under the retractor rail 200 to prevent the clamp 250 from lifting away from the retractor rail 200.

The actuation lever 253 can couple to the rear clamp 252 by a pivot rod 263. Pivoting the actuation lever 253 about the pivot rod 263 can slide the rear clamp 252 toward the front clamp 251 until the rear flat surface 261 contacts the retractor rail 200 as illustrated in FIG. 6B. The first and second wedges 254 and 255 can couple to the actuation lever 253 and extend into the body 259 of the front clamp 251. After the rear flat surface 261 contacts the retractor rail 200, further pivoting of the actuation lever 253 around the pivot rod 263 can move the first and second wedges 254 and 255 in an opposing longitudinal motion. The opposing longitudinal motion can create a distance between the first and second wedges 254 and 255 inside the body 259 of the front clamp 251. The distance generated by the first and second wedges 254 and 255 can lock the rear clamp 252 to the body 259 of the front clamp 251.

Further pivoting of the actuation lever 253 around the pivot rod 263 can pressure the rear clamp 252 closer to the front clamp 251 and tighten the clamp 250 around the retractor rail 200. A locking hinge 264 can be coupled to the actuation lever 253 and can be positioned in the groove 260. When the actuation lever 253 pivots around the pivot rod 263 enough to contact the groove 260 of the body 259, the locking hinge 264 can lock the actuation lever 253 in place and can prevent the actuation lever 253 from inadvertently moving back to an unlocked position illustrated in FIG. 6A. An upward force can be applied to the actuation lever 253 to release the actuation lever 253 from its locked position.

The turret mount 256 can be positioned on the body 259 between the front flat surface 257 and the groove 260 in the body 259 of the front clamp 251. The turret mount 256 can include a cylindrical top 265, an angled groove 266, and a flat groove 267. A turret (not shown) of a cardiac tissue stabilizer can mount to the turret mount 256.

Figure 7B:
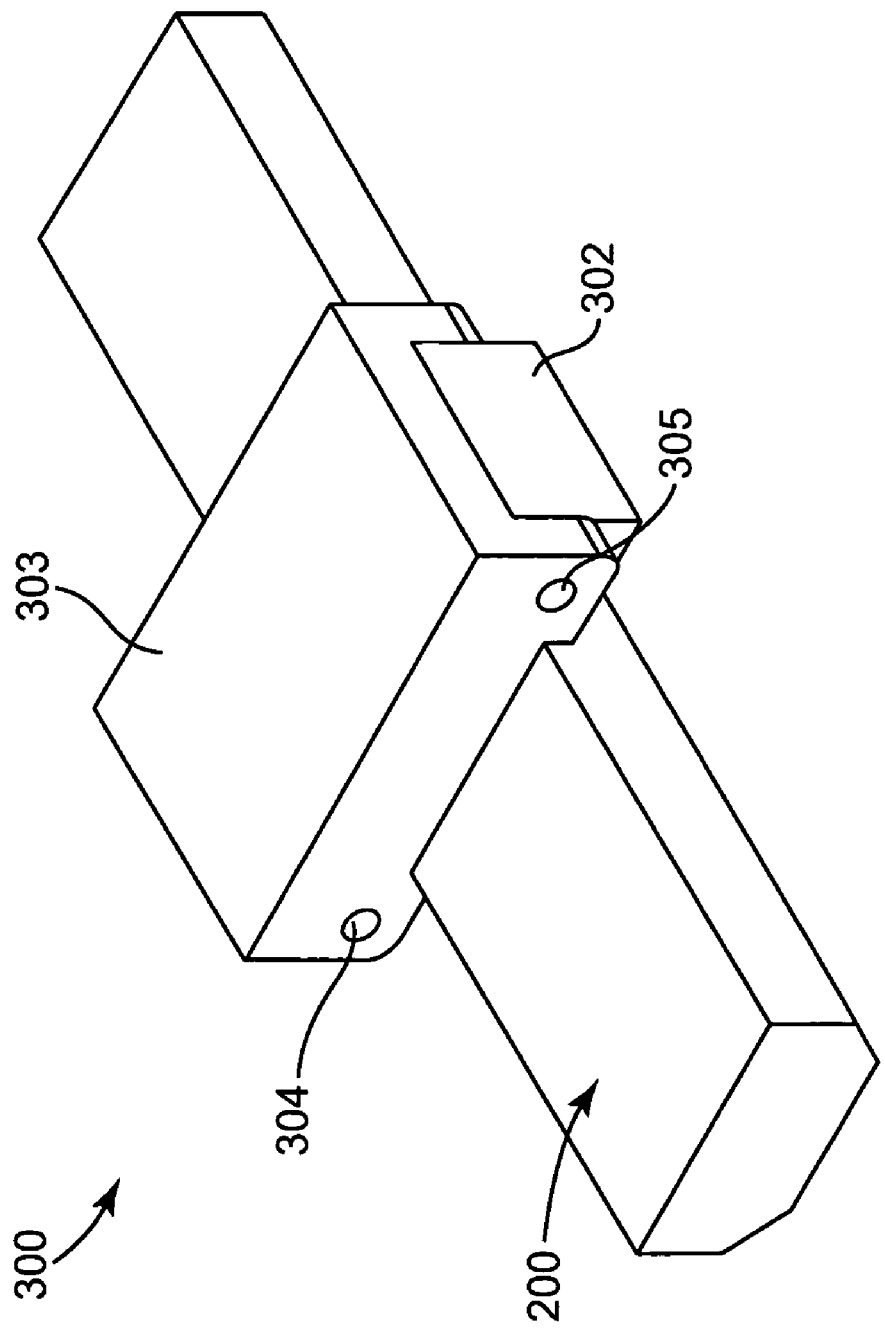

FIGS. 7A and 7B illustrate another embodiment of a cardiac tissue stabilizer clamp 300. The clamp 300 can include a front clamp 301, a rear clamp 302, a housing 303, a first hinge 304, a second hinge 305 and a turret mount (not shown). The front clamp 301 can mount to the housing 303 by the first hinge 304 and the rear clamp 302 can mount to the housing 303 by the second hinge 305. A series of interlocking teeth (not shown) can couple the front clamp 301 and the rear clamp 302. The series of interlocking teeth can rotate the front clamp 301 and the rear clamp 302 about the first and second hinge 304 and 305 respectively in a synchronized motion. The housing 303 can contain a contact point 306 centrally located where the series of interlocking teeth of the front clamp 301 and the rear clamp 302 contact.

Pressing the clamp 300 onto the retractor rail 200 can cause the contact point 306 to move into the housing 303. Movement of the contact point 306 into the housing 303 can actuate the series of interlocking teeth. The series of interlocking teeth can rotate the front clamp 301 about the first hinge 304 and the rear clamp 302 about the second hinge 305 simultaneously. A front flat surface 307 of the front clamp 301 and a rear flat surface 308 of the rear clamp 302 can contact opposite sides of the retractor rail 200 and can prevent lateral motion. A front angled surface 309 of the front clamp 301 (not shown) and a rear angled surface 310 of the rear clamp 302 can slide under the retractor rail 200 and prevent the clamp 300 from lifting away from the retractor rail 200.

Applying an upward force to the clamp 300 can slide the front angled surface 309 of the front clamp 301 and the rear angled surface 310 of the rear clamp 302 from under the retractor rail 200. Sliding the front angled surface and rear angled surface 310 away from the retractor rail 200 can rotate the front clamp 301 about the first hinge 304 and the rear clamp 302 about the second hinge 305. The rotation can increase the distance between the front flat surface 307 of the front clamp 301 and the rear flat surface 308 of the rear clamp 302 allowing the clamp 300 to be lifted off of the retractor rail 200.

Figure 8A:
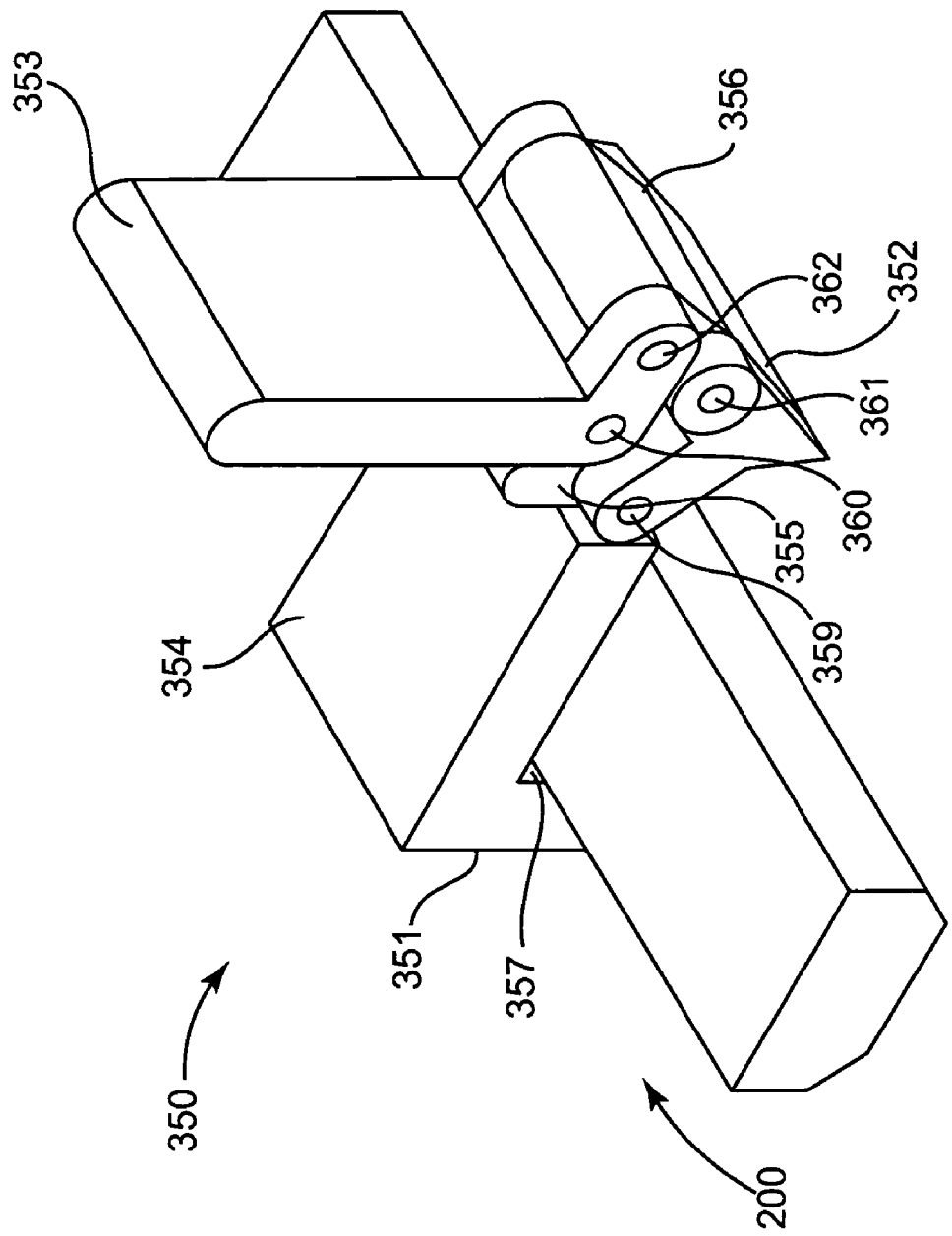
FIGS. 8A and 8B are perspective views of an embodiment of a quick-lock clamp for a cardiac tissue stabilizer in open and closed positions.
Figure 8B:
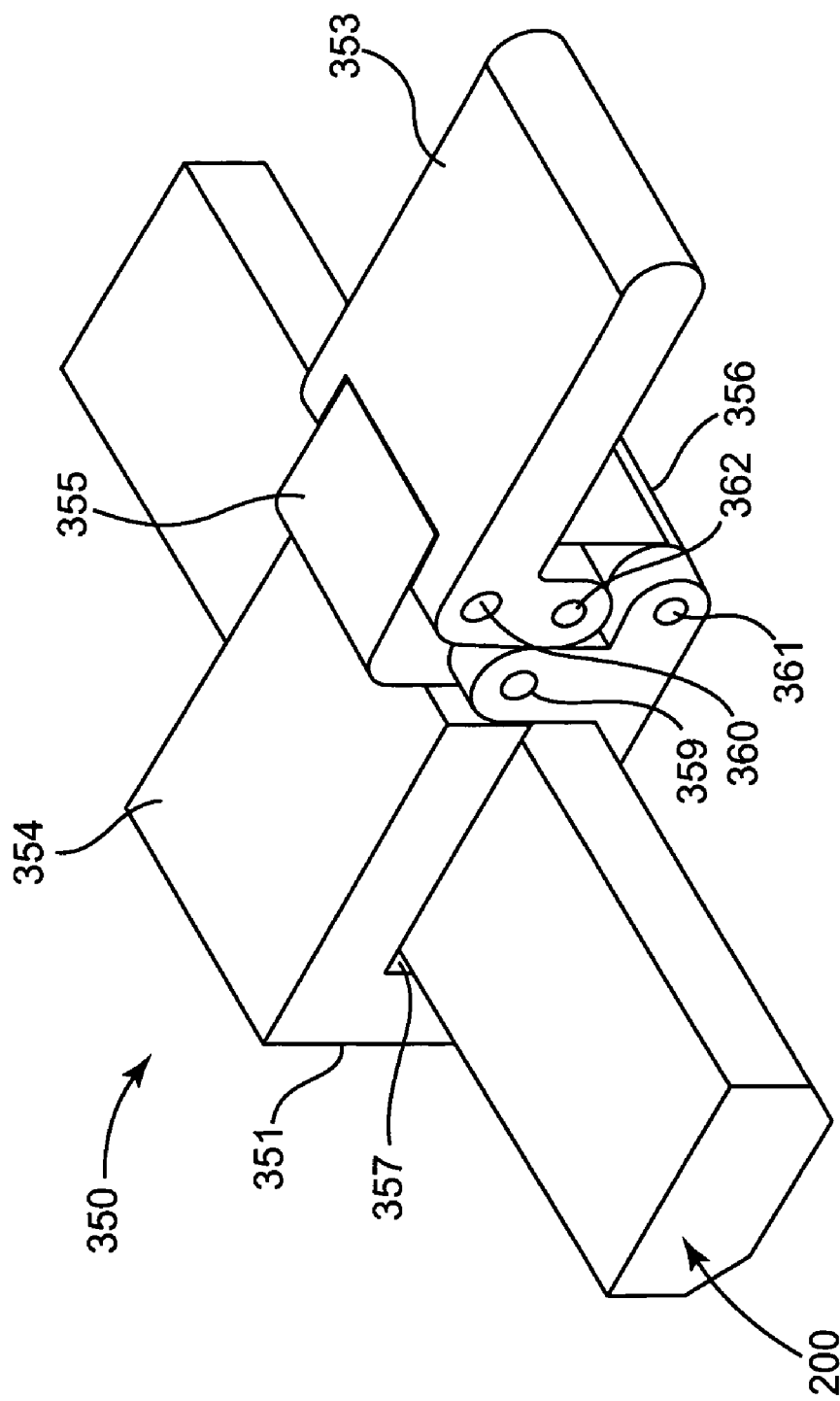

FIGS. 8A and 8B illustrate another embodiment of a cardiac tissue stabilizer clamp 350. The clamp 350 can include a front clamp 351, a rear clamp 352, an actuation lever 353, a base 354, a hinge 355, a link 356 and a turret mount (not shown). The front clamp 351 can include a front flat surface 357 and a front angled surface (not shown). The front flat surface 357 can contact a side of the retractor rail 200 and the front angled surface can slide under the retractor rail 200. The base 354 can extend perpendicular from the front clamp 351 opposite the front angled surface. The hinge 355 can be mounted on the base 354 opposite the front clamp 351 and can be coupled to the rear clamp 352 via a first pin 359 and the actuation lever 353 via a second pin 360. The link 356 can be coupled to the rear clamp 352 via a third pin 361 and the actuation lever 353 via a fourth pin 362.

Actuation of the actuation lever 353 can rotate the actuation lever 353 around the hinge 355. Rotating the actuation lever 353 can cause relative movement of the link 356 coupled by the fourth pin 362. Movement of the link 356 can push the rear clamp 352 coupled by the third pin 361 and can rotate the rear clamp 352 about the hinge 355 coupled by the first pin 359. The rear clamp 352 can rotate to cause a rear flat surface 363 of the rear clamp 352 to contact a side of the retractor rail 200 and a rear angled surface 364 to slide under the retractor rail 200. An L-shape of the actuation lever 353 can slide into a receiving L-shape of the rear clamp 352. The link 356 can continue to rotate to a vertical orientation between the actuation lever 353 coupled by the fourth pin 362 and the rear clamp 352 coupled by the third pin 361. The vertical orientation of the link 356 can lock the clamp 350 to the retractor rail 200. Applying an upward force on the actuation lever 353 can pull the link 356 from the vertical orientation under the hinge 355. The link 356 can pull the rear clamp 352 coupled by the third pin 361 and move the rear clamp 352 out of contact with the retractor rail 200.

Figure 9A:
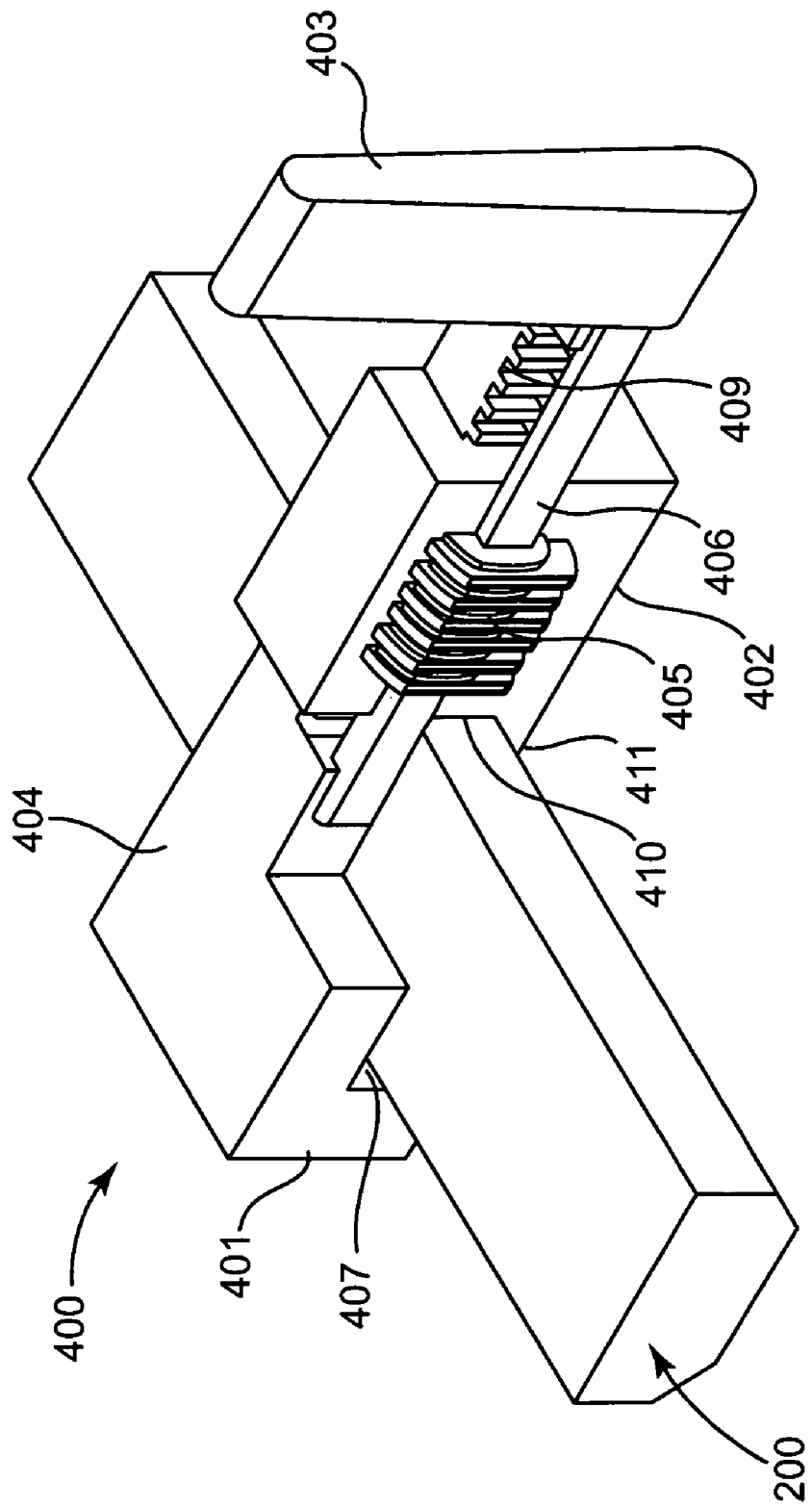
FIGS. 9A and 9B are perspective views of an embodiment of a screw-lock clamp for a cardiac tissue stabilizer in open and closed positions, with the body partially cut-away.
Figure 9B:
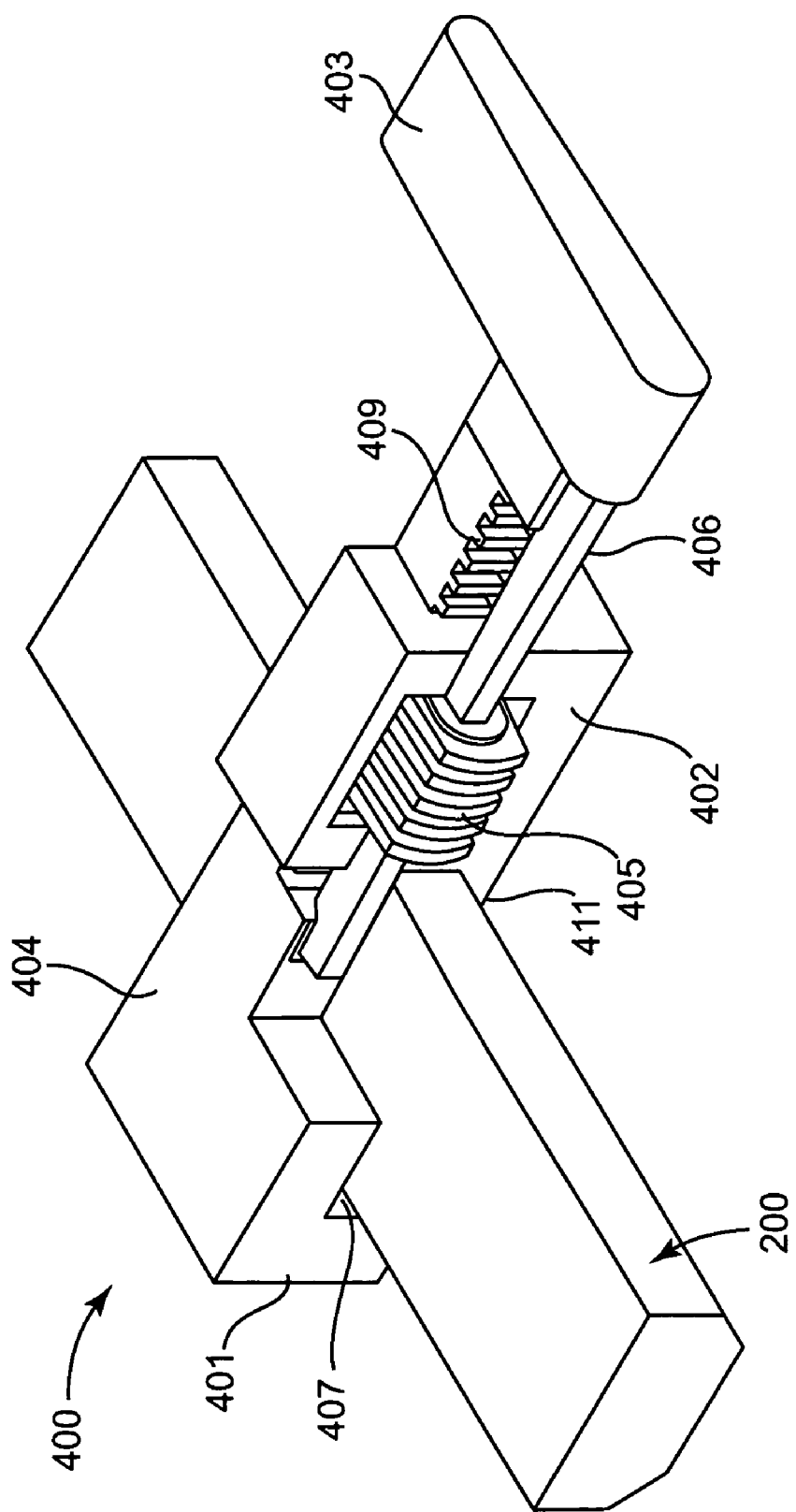

FIGS. 9A and 9B illustrate another embodiment of a cardiac tissue stabilizer clamp 400. The clamp 400 can include a front clamp 401, a rear clamp 402, an actuation lever 403, a base 404, a screw 405, a shaft 406, and a turret mount (not shown). The front clamp 401 can include a front flat surface 407 and can contact a side of the retractor rail 200. The front clamp 401 can also include a front angled surface (not shown) which can slide under the retractor rail 200. The rear clamp 402 can include a rear flat surface 410 and can contact a side of the retractor rail 200 opposite the side contacted by the front flat surface 407. The rear clamp 402 can also include a rear angled surface 411 which can slide under the retractor rail 200.

The base 404 can extend perpendicular to the front clamp 401 from an end of the front flat surface 407 opposite the front angled surface 408. The base 404 is partially cut-away in FIGS. 9A and 9B to help illustrate positioning of the rear clamp 402, screw 405, and shaft 406. A series of teeth 409 can be integrally formed on an inner edge of the base 404. The series of teeth 409 can extend from a short distance from the front clamp 401 to another end of the base 404. The rear clamp 402 can slidably mount to the base 404 adjacent to the series of teeth 409. The screw 405 can be embedded in the rear clamp 402 behind the rear flat surface 410. The shaft 406 can mount on the base 404 close to the front clamp 401 and extend through the screw 405 to the other end of the base 404. The actuation lever 403 can be coupled to the shaft 406 and can be mounted to the rear clamp 402.

FIG. 9A shows the actuation lever 403 in a perpendicular orientation to the retractor rail 200. When the actuation lever 403 is in this position, the screw 405 can be disengaged from the series of teeth 409 and the rear clamp 402 can slide freely. Sliding the rear clamp 402 forward on the base 404, the rear flat surface 410 can contact the retractor rail 200. FIG. 9B illustrates clamp 400 in a locked position Rotating the lever 403 clock-wise from the unlocked position can cause the screw 405 to engage the series of teeth 409. As the screw 405 engages the series of teeth 409, further turning of the actuation lever 403 can force the rear clamp 402 forward and can cause the front and rear clamps 401 and 402 to bind to the retractor rail 200. Rotating the lever 403 approximately 90° can provide enough binding force to securely bind the clamp 400 to the retractor rail 200. Actuation of the actuation lever 403 back to its orientation in FIG. 9A can allow the rear clamp 402 to slide away from the retractor rail 200 and unlock the clamp 400.

Figure 10A:
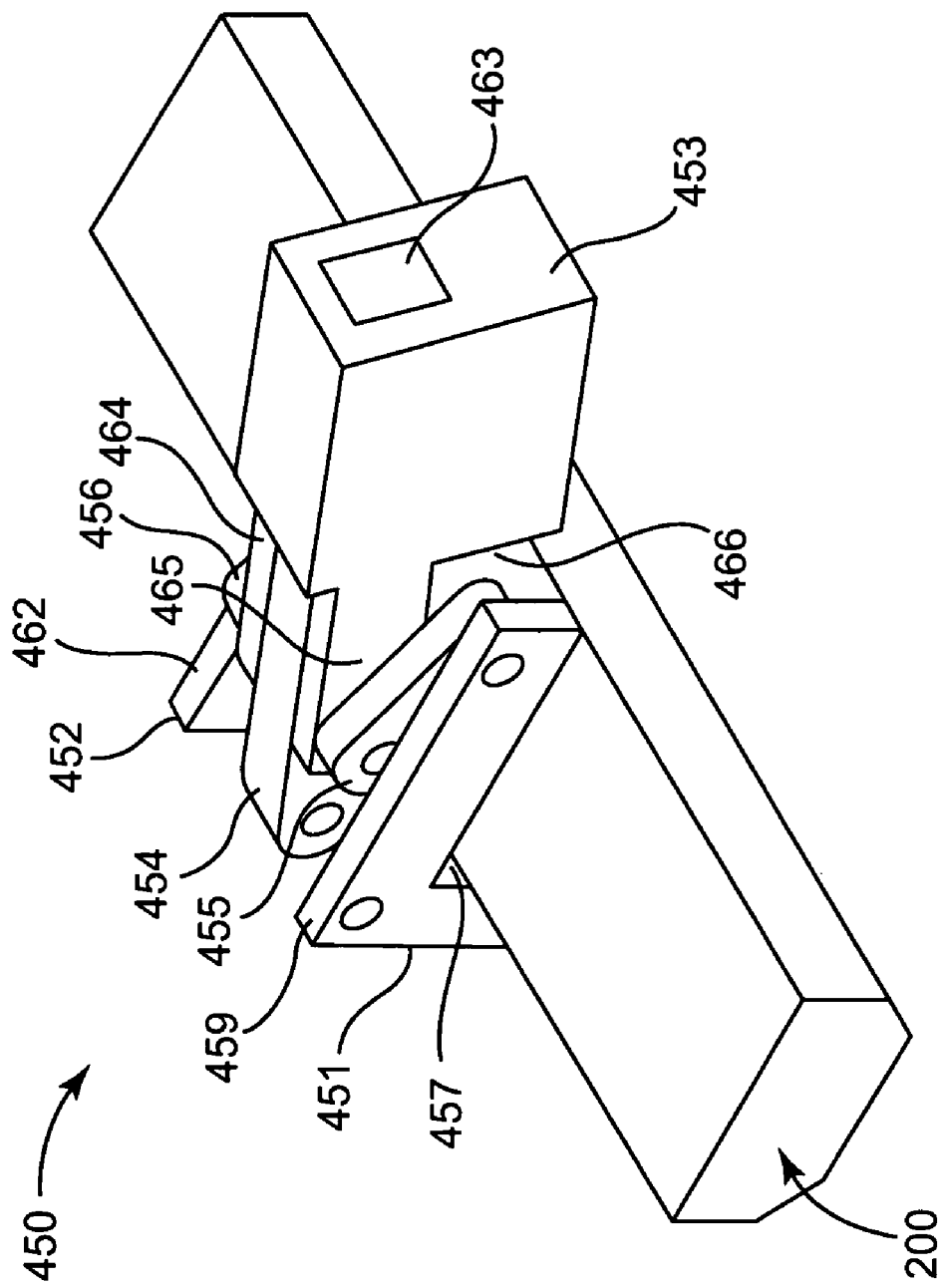
FIGS. 10A and 10B are perspective views of an embodiment of a device-lock clamp for a cardiac tissue stabilizer in open and closed positions, with the body partially cut-away.
Figure 10B:
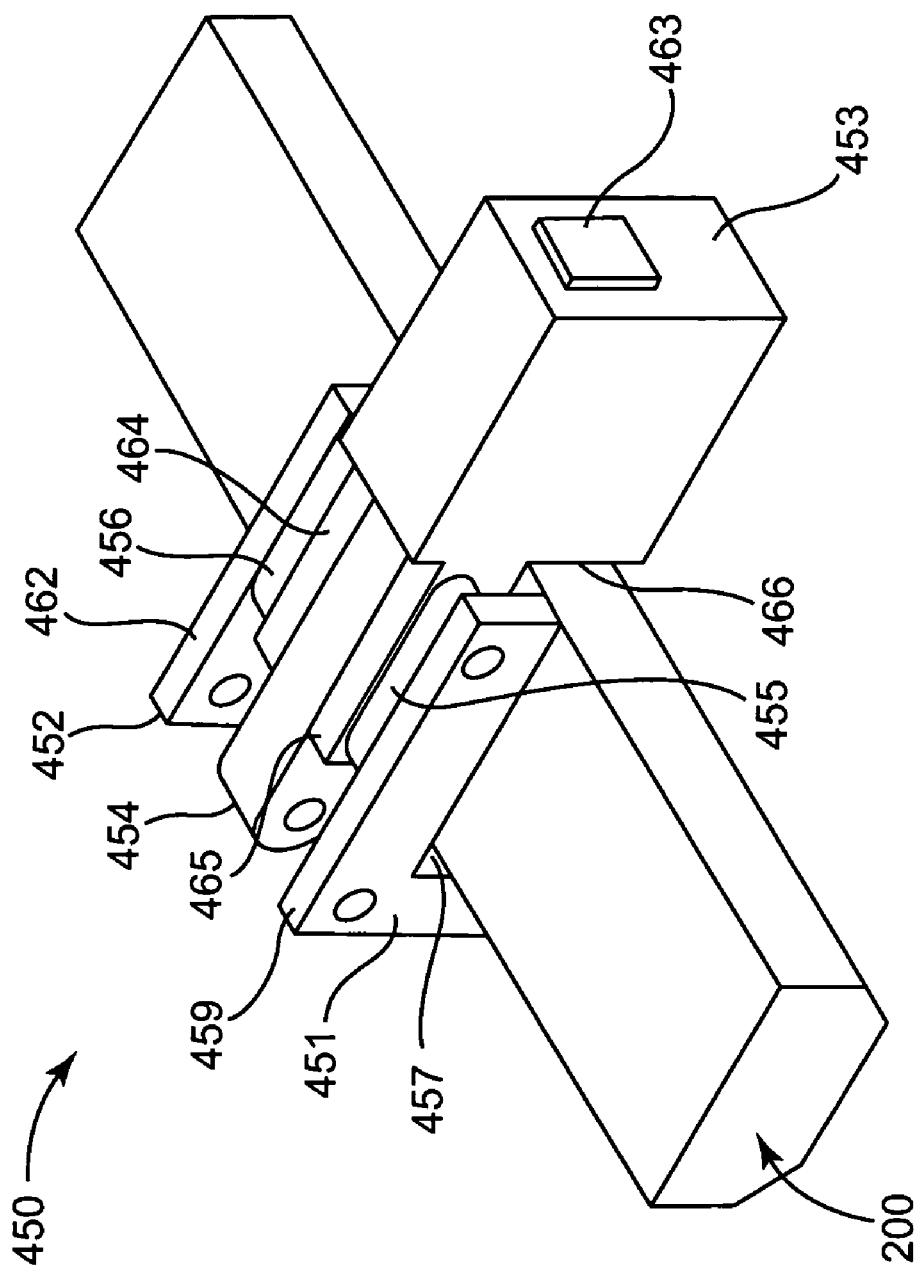

FIGS. 10A and 10B illustrate another embodiment of a cardiac tissue stabilizer clamp 450. The clamp 450 can include a first front clamp 451, a second front clamp 452, a rear clamp 453, a base 454, a first link 455, and a second link 456 and a turret mount (not shown). The first front clamp 451 can include a first front flat surface 457 that can contact a side of the retractor rail 200 and a first angled surface 458 which can slide under the retractor rail 200 (not shown). The first front clamp 451 can also include a first bar 459 perpendicular to the first front flat surface 457. The second front clamp 452 can include a second front flat surface 460 that can contact a side of the retractor rail 200 and a second angled surface which can slide under the retractor rail 200 (not shown). The second front clamp 452 can also include a second bar 462 perpendicular to the second front flat surface. The first and second front clamps 451 and 452 can be situated in parallel and spaced apart.

The base 454 can mount to the rear clamp 453 by extending through an aperture 463 in the rear clamp 453 and between a first prong 464 and a second prong 465 of the rear clamp 453. The base 454, the first prong 464, and the second prong 465 can be positioned between the first front clamp 451 and the second front clamp 452. The first link 455 can couple the first prong 464 to the first front clamp 451. The second link 456 can couple the second prong 465 to the second front clamp 452.

The rear clamp 453 and the base 454 can rotate with respect to the first and second front clamps 451 and 452. Moving the rear clamp 453 to the position in FIG. 9B can cause a rear flat surface 466 of the rear clamp 453 to contact a side of the retractor rail 200. When the rear flat surface 466 is parallel to the front flat surface 457, the clamp 450 can lock in place. In this locked position, the first and second prongs 464 and 465 of the rear clamp 453 can contact a top of the retractor rail 200 and can situate in parallel to the first and second bars 459 and 462. The first and second links 455 and 456 can likewise contact the top of the retractor rail 200 and situate in parallel to the first and second bars 459 and 462. Applying an upward force to the rear clamp 453 can rotate the rear flat surface 466 out of contact with the retractor rail 200 and unlock the clamp 450 from the retractor rail 200.

Figure 11A:
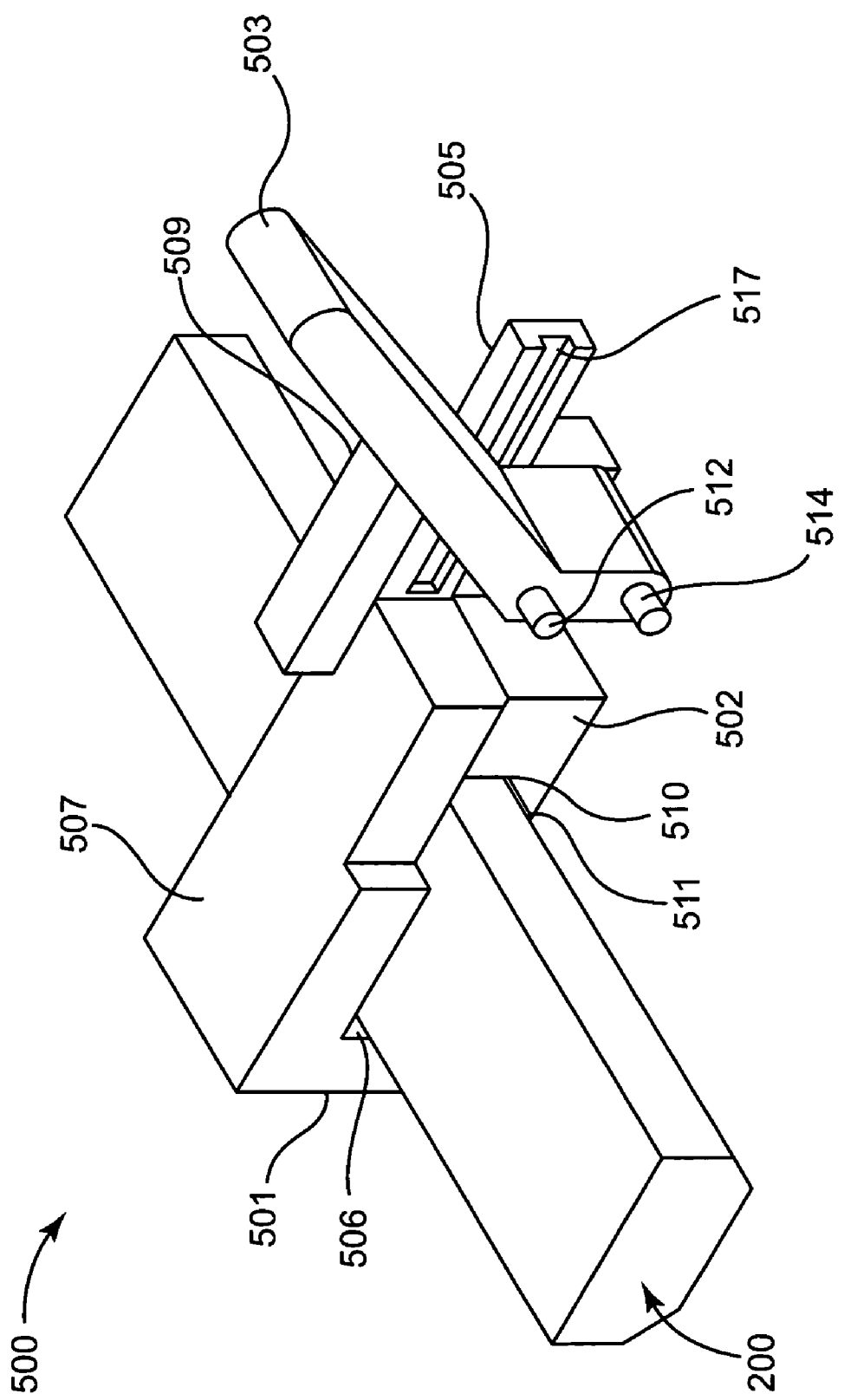
FIGS. 11A and 11B are perspective views of an embodiment of a cam-lock clamp for a cardiac tissue stabilizer in open and closed positions, with the body partially cut-away in FIG. 11A.
Figure 11B:
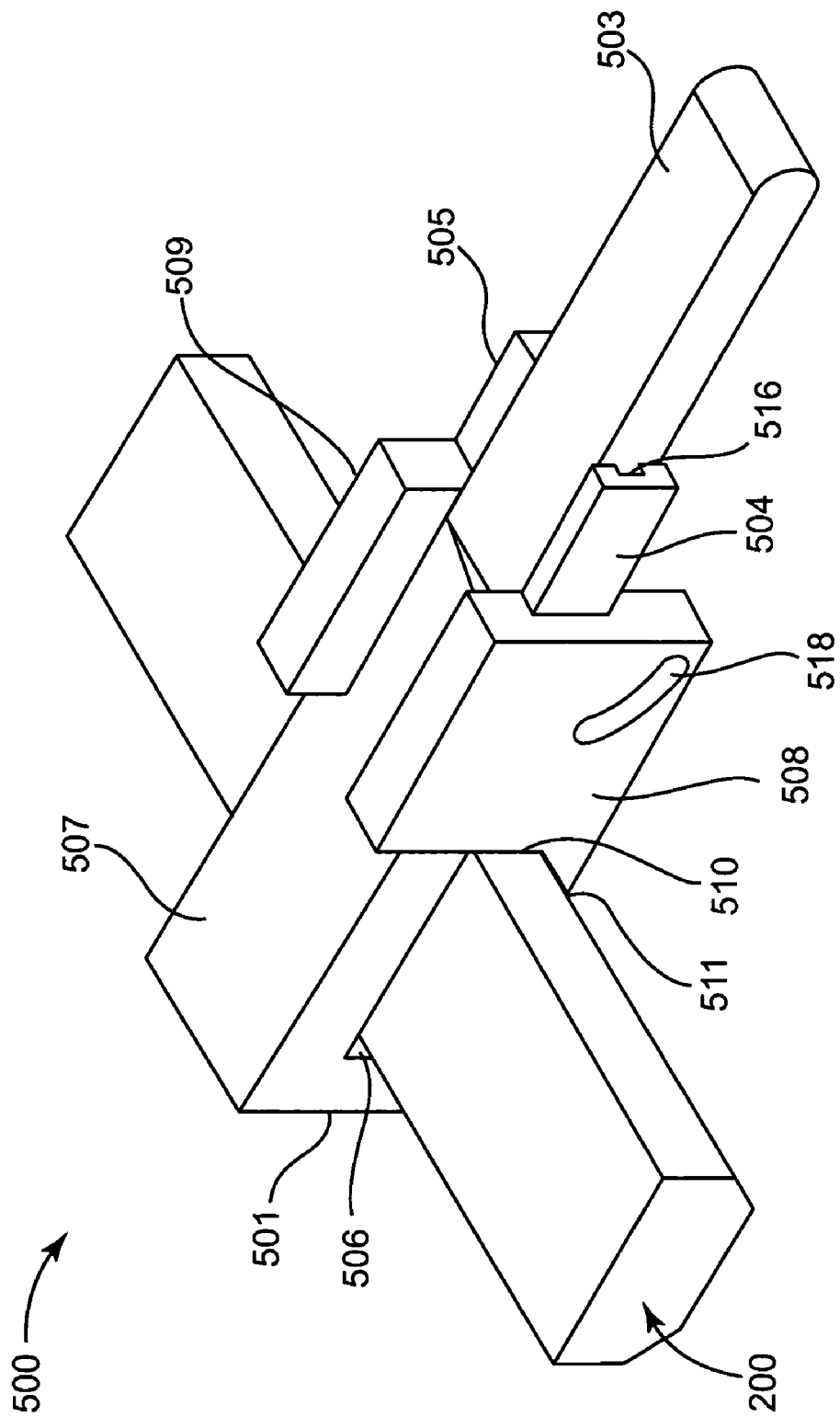

FIGS. 11A and 11B illustrate another embodiment of a cardiac tissue stabilizer clamp 500. The clamp 500 can include a front clamp 501, a rear clamp 502, an actuation lever 503, a first beam 504, a second beam 505, and a turret mount (not shown). The front clamp 501 can include a front flat surface 506 that can contact a side of the retractor rail 200 and a front angled surface (not shown) which can slide under the retractor rail 200. A body 507 can extend from the front clamp 501 across the top of the retractor rail 200. The first and second beams 504 and 505 can mount spaced apart and in parallel to the body 507 opposite the front clamp 501. The rear clamp 502 can include a first side 508 and a second side 509. The rear clamp 502 can slidably mount underneath the first and second beams 504 and 505 by the first and second sides 508 and 509. The rear clamp 502 can include a rear flat surface 510 that can contact a side of the retractor rail 200 and a rear angled surface 511 which can slide under the retractor rail 200.

The actuation lever 503 can include a first tooth 512 and a second tooth (not shown) on opposite sides of the lever 503 and a first post 514 and a second post (not shown) on opposite sides of the lever 503. The first tooth 512 can couple to a first groove 516 in the first beam 504 and the second tooth can couple to a second groove 517 in the second beam 505. The first post 514 can couple to a first slot 518 in the first side 508 of the rear clamp 502 and the second post can couple to a second slot in the second side 509 of the rear clamp 502 (not shown). Actuation of the actuation lever 503 can pivot the first and second teeth 512 and 513 in the first and second grooves 516 and 517 and can slide the first and second posts 514 and 515 in the first and second slots 518 and 519. The actuation lever 503 can press against the rear clamp 502 and can provide a force to lock the clamp 500 in place. A first cam dwell (not shown) in the first slot 518 and a second cam dwell in the second slot (not shown) can lock the actuation lever 503 in place. Applying an upward force to the actuation lever 503 can slide the first and post 514 back in the first slot 518 and the second post back in the second slot (not shown), allowing the rear clamp 502 to slide freely away from the retractor rail 200.

Figure 12:
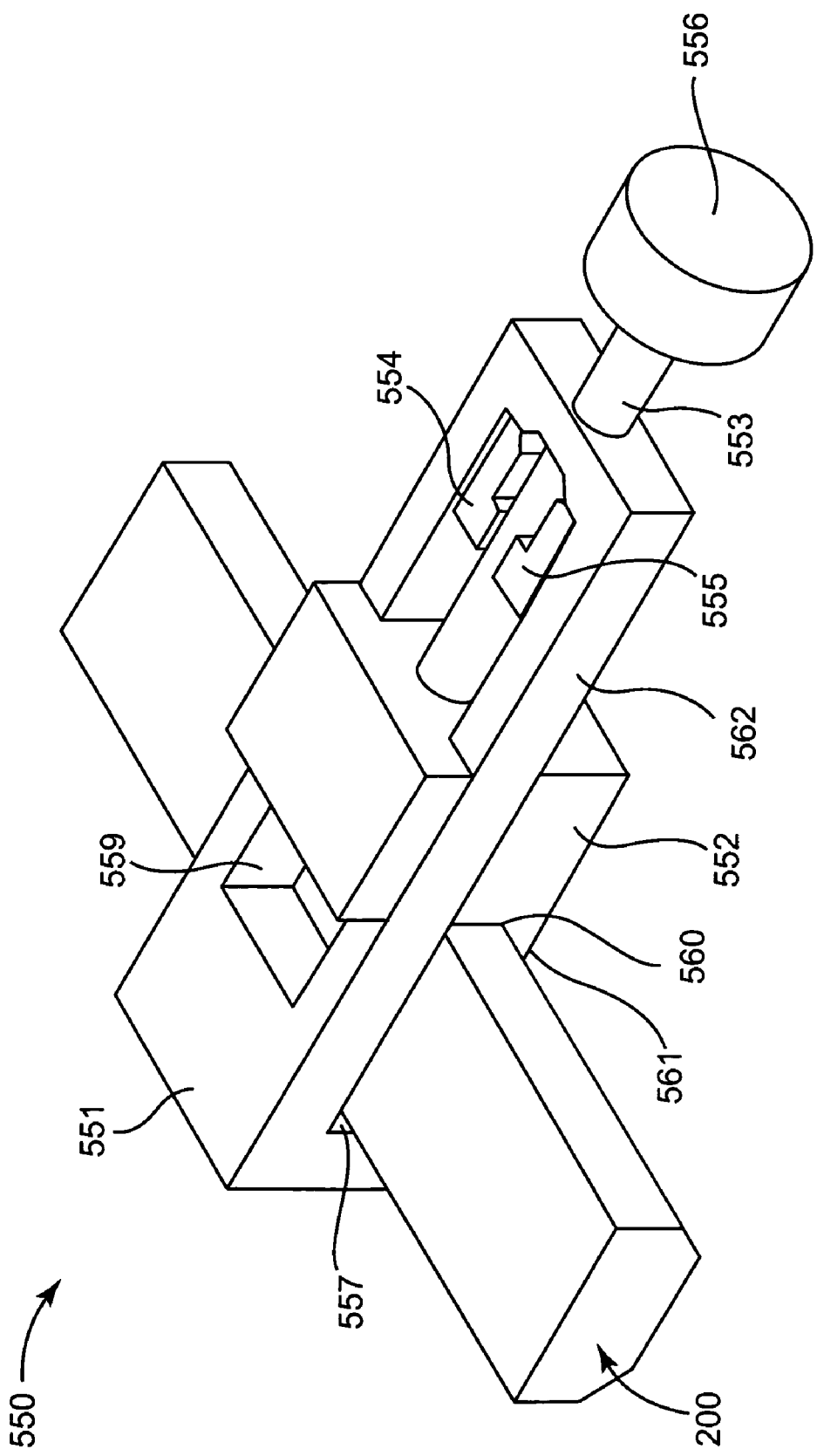
FIG. 12 is a perspective view of an embodiment of a ratchet-screw clamp for a cardiac tissue stabilizer.

FIG. 12 illustrates another embodiment of a cardiac tissue stabilizer clamp 550. The clamp 550 can include a front clamp 551, a rear clamp 552, a threaded shaft 553, a first threaded pawl 554, a second threaded pawl 555, an adjustment knob 556 and a turret mount (not shown). The front clamp 551 can include a front flat surface 557 that can contact a side of the retractor rail 200 and a front angled surface (not shown) to slide under the retractor rail 200. The front clamp 551 can have a body 562 that extends across the top of the retractor rail 200 and includes a relatively large slot 559. The rear clamp 552 can slidably mount to the body 562 by extending through the slot 559. The rear clamp 552 can include a rear flat surface 560 that can contact a side of the retractor rail 200 and a rear angled surface 561 which can slide under the retractor rail 200. The threaded shaft 553 can rotatably couple at a first end to the rear clamp 552 and can extend through the slot 559, through an aperture 563 in the body 562 and past the body 562. The adjustment knob 556 can couple to the threaded shaft 553 at an end opposite of the rear clamp 552. The first and second threaded pawls 554 and 555 can be positioned inside the slot 559 on either side of the threaded shaft 553.

Applying a force to the adjustment knob 556 toward the retractor rail 200 can slide the rear clamp 552 toward the retractor rail 200. The threaded shaft 553 can slide between the first and second pawls 554 and 555. A ratchet-type interface between the threaded shaft 553 and first and second pawls 554 and 555 can allow the rear clamp 552 to slide freely toward the front clamp 551, but can prevent the rear clamp 552 from sliding away from the front clamp 551. When the rear flat surface 560 contacts a side of the retractor rail 200, the adjustment knob 556 can be rotated clockwise such that the threads of the shaft 553 travel along the threads of the pawls 554, 555 so as to tighten the rear clamp 552 against the retractor rail 200 and lock the clamp 550 to the retractor rail 200. Rotating the adjustment knob 556 counter-clockwise can move the rear clamp 552 away from the retractor rail 200 and unlock the clamp 550 from the retractor rail 200.

In some embodiments, the clamp 550 described above can be modified to include a plurality of rollers (not shown) instead of the first and second threaded pawls 554 and 555. The rollers can embed in the adjustment knob 556. Rotating the adjustment knob 556 clockwise can tighten the rollers around the threaded shaft 553 and lock the rear clamp 552 in place. Rotating the adjustment knob 556 counter-clockwise can release the rollers from the threaded shaft 553 and can allow the rear clamp 552 to slide freely.

Figure 13A:
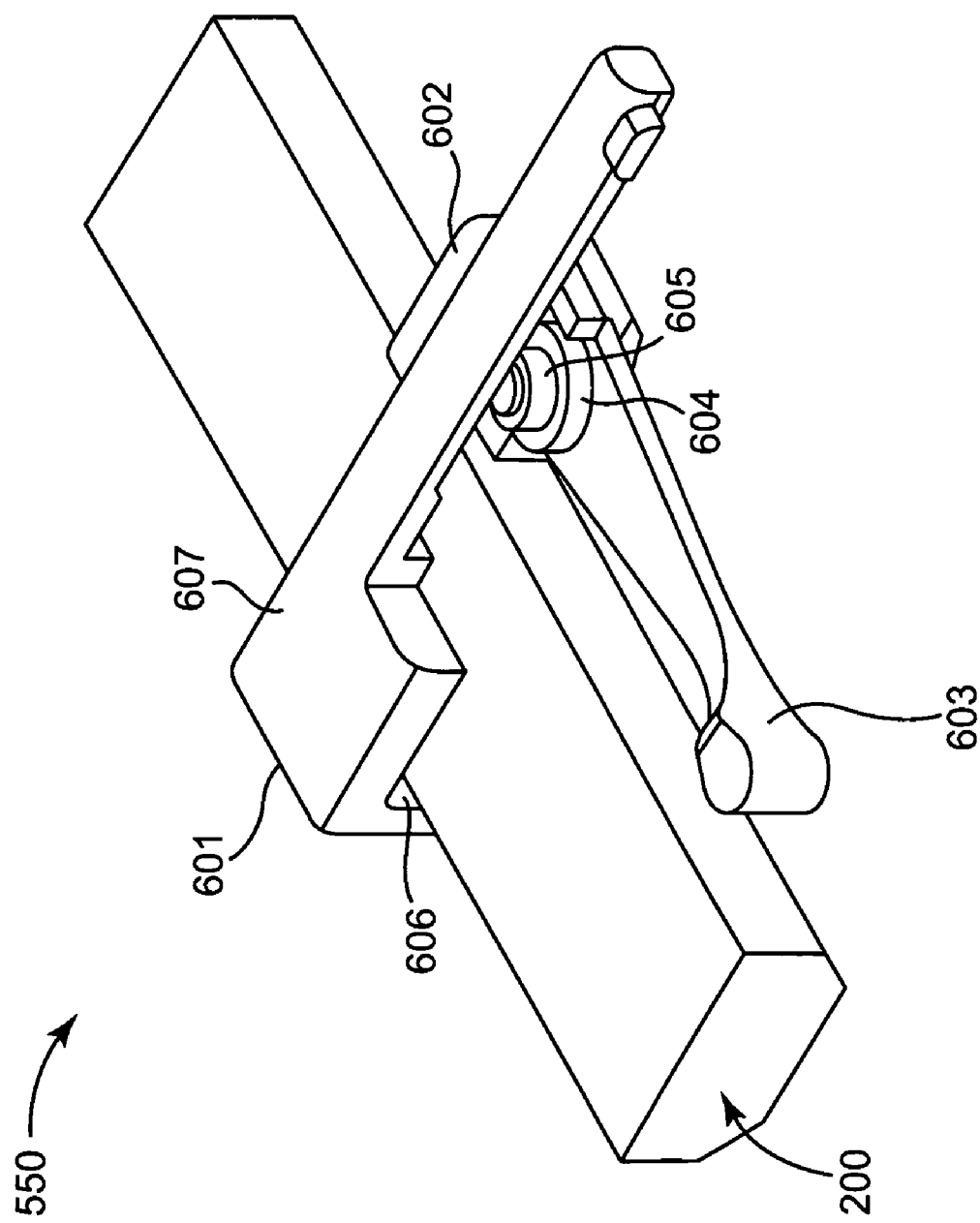
FIGS. 13A and 13B are perspective views of an embodiment of a dual-cam lock clamp for a cardiac tissue stabilizer in open and closed positions with the body partially cut away.
Figure 13B:
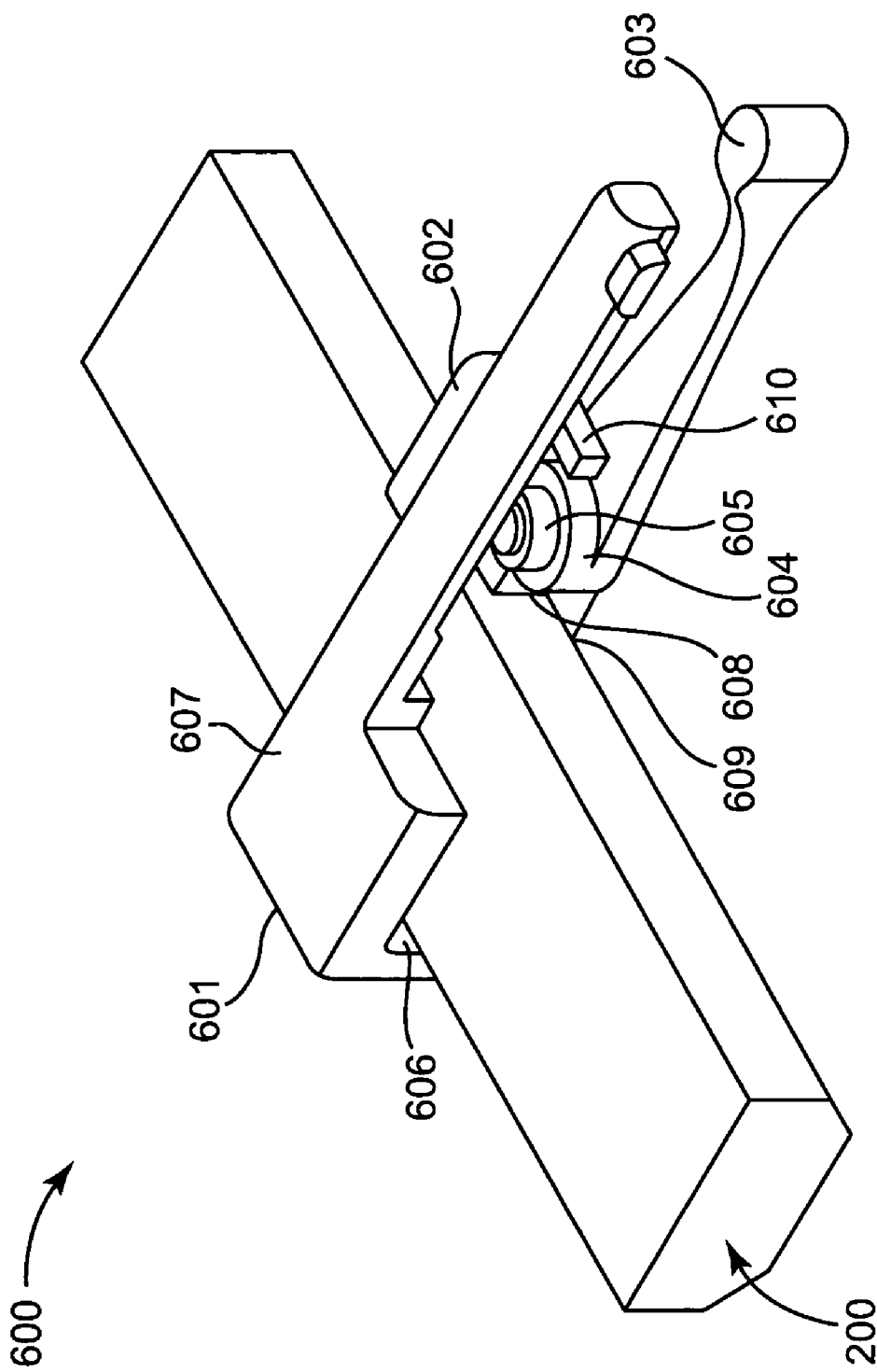

FIGS. 13A and 13B illustrate another embodiment of a cardiac tissue stabilizer clamp 600. The clamp 600 can include a front clamp 601, a rear clamp 602, an actuation lever 603 and a turret mount (not shown). The front clamp 601 can include a front flat surface 606 that can contact a side of the retractor rail 200 and a front angled surface (not shown) which can slide under the retractor rail 200. A body 607 can extend from the front clamp 601 across and substantially past the top of the retractor rail 200. The rear clamp 602 can slidably mount to the body 607. The rear clamp 602 can include a rear flat surface 608 that can contact a side of the retractor rail 200 and a rear angled surface 609 which can slide under the retractor rail 200.

FIG. 13B illustrates a locked position for the clamp 600. The actuation lever 603 can include a lower cam 604 and smaller upper cam 605. The lower cam 604 can be positioned in a slot 610 in the rear clamp 602. The actuation lever 603 can be rotated 90° away from the retractor rail 200 rotating the lower cam 604 and the upper cam 605. The lower cam 604 can rotate and push the rear clamp 602 closer to the front clamp 601. The upper cam 605 can rotate to engage with body 607 and lock the rear clamp 602 in place. A cam dwell (not shown) can prevent the actuation lever 603 from freely rotating to an unlocked position. Applying a force to the actuation lever 603 toward the retractor rail 200 can rotate the lower cam 604 and the upper cam 605. FIG. 13A shows the clamp 600 in an unlocked position. The lower cam 604 can rotate and push the rear clamp 602 away from the front clamp 601 by a small distance. The upper cam 605 can rotate and disengage from the body 607 and can enable the rear clamp 602 to slide freely.

Figure 14:
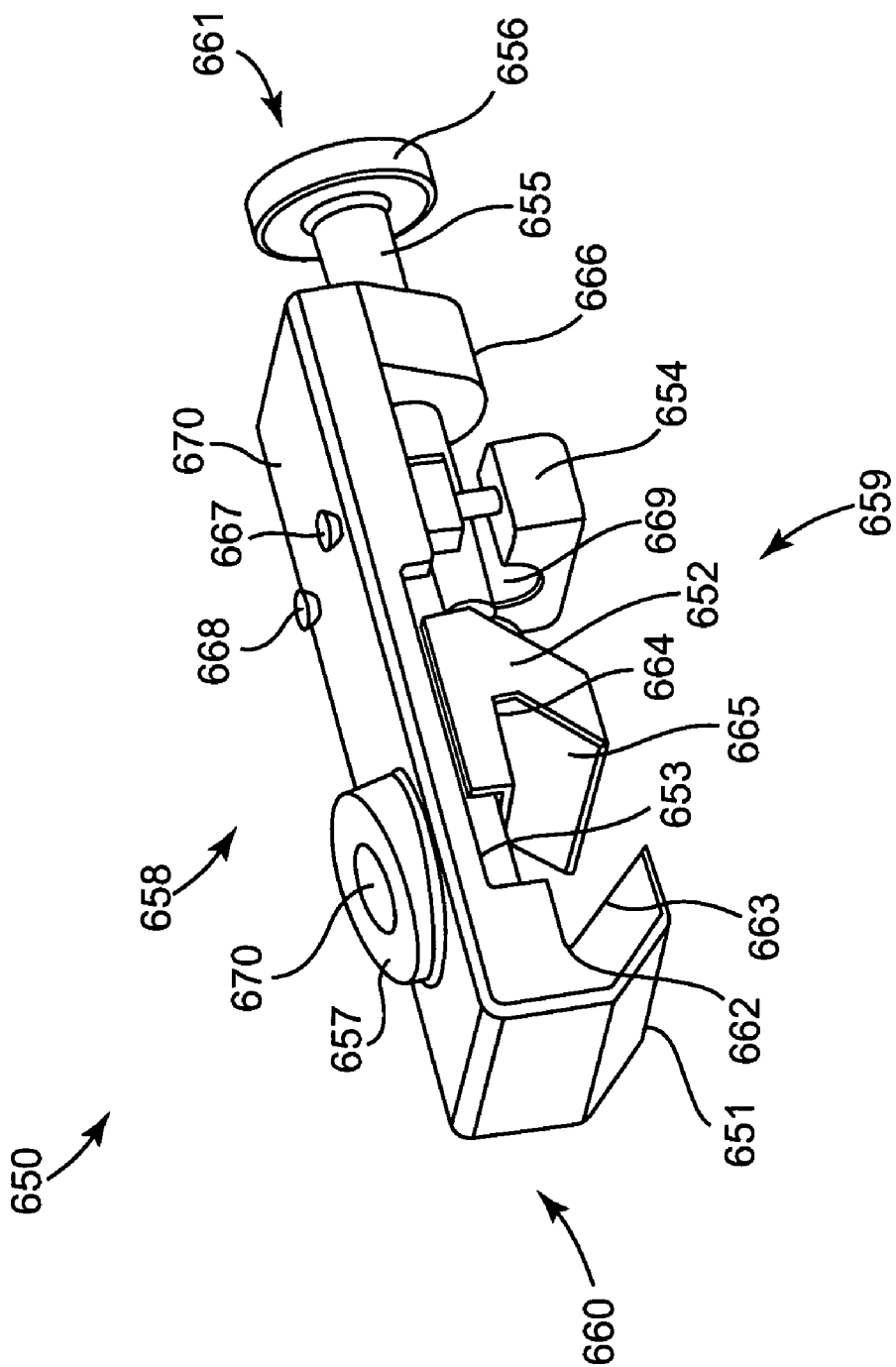
FIG. 14 is a perspective view of an embodiment of a quick-detach screw-lock clamp for a cardiac tissue stabilizer.

FIG. 14 illustrates another embodiment of a cardiac tissue stabilizer clamp 650. The clamp 650 can include a front clamp 651, a rear clamp 652, a beam 653, a releasable threaded guide 654, a threaded shaft 655, an adjustment knob 656, and a turret mount 657. The front clamp 651 can include a front flat surface 662 that can contact a side of the retractor rail and a front angled surface 663 which can slide under the retractor rail (not shown). A clamp body 670 can extend from the front clamp 651 over the retractor rail. The beam 653 can be positioned on the bottom 659 of the clamp body 670 and extend rearwardly from the front clamp 651. The rear clamp 652 can include a rear flat surface 664 that can contact a side of the retractor rail and a rear angled surface 665 which can slide under the retractor rail. The rear clamp 652 can slidably mount to the beam 653 so the rear flat surface 664 is parallel to and facing the front flat surface 662.

The threaded shaft 655 can couple to a side of the rear clamp 652 opposite the rear flat surface 664 and can extend past a rear 661 of the clamp body 670. A support 666 can be positioned on the bottom 659 of the rear 661 of the clamp body 670 and can hold the threaded shaft 655 parallel to the clamp body 670. The adjustment knob 656 can be coupled to an end of the threaded shaft 655 opposite the rear clamp 652. The releasable threaded guide 654 can mount to the bottom 659 of the clamp body 670 between the rear clamp 652 and the support 666 by way of a first pin 667 and a second pin 668.

The first and second pins 667 and 668 can extend from the releasable threaded-guide 654 and through to a top 658 of the clamp body 670. The releasable threaded guide 654 can include a threaded niche 669 to fit the threaded shaft 655. The first and second pins 667 and 668 can include on or more springs (not shown) to bias the guide 654 toward the clamp body 670.

When the threaded shaft 655 is received in the niche 669, the clamp 650 is in the closed position. In the closed position the adjustment knob 656 can rotate clockwise to move the rear clamp 652 closer to the front clamp 651 and tighten the clamp 650 to the retractor rail 200. Rotating the adjustment knob 656 counter-clockwise can move the rear clamp 652 away from the front clamp 651. The clamp 650 can be put in an open position by applying a force to the threaded guide 654 in a direction away from the top 658 of the clamp body 670. In the open position, the threaded shaft 655 and rear clamp 652 can slide freely toward and away from the front clamp 651. Removal of the force to pull the threaded guide 654 away from the clamp 650 can allow the bias of the one or more springs to position the threaded guide 654 back to the closed position.

The turret mount 657 can be positioned on the top 658 of the clamp 650 between the front clamp 651 and the rear clamp 652. The turret mount 657 can be cylindrical in shape and can include an aperture 670. A turret (not shown) can mount to the turret mount 657 and can be locked in place.

Figure 15:
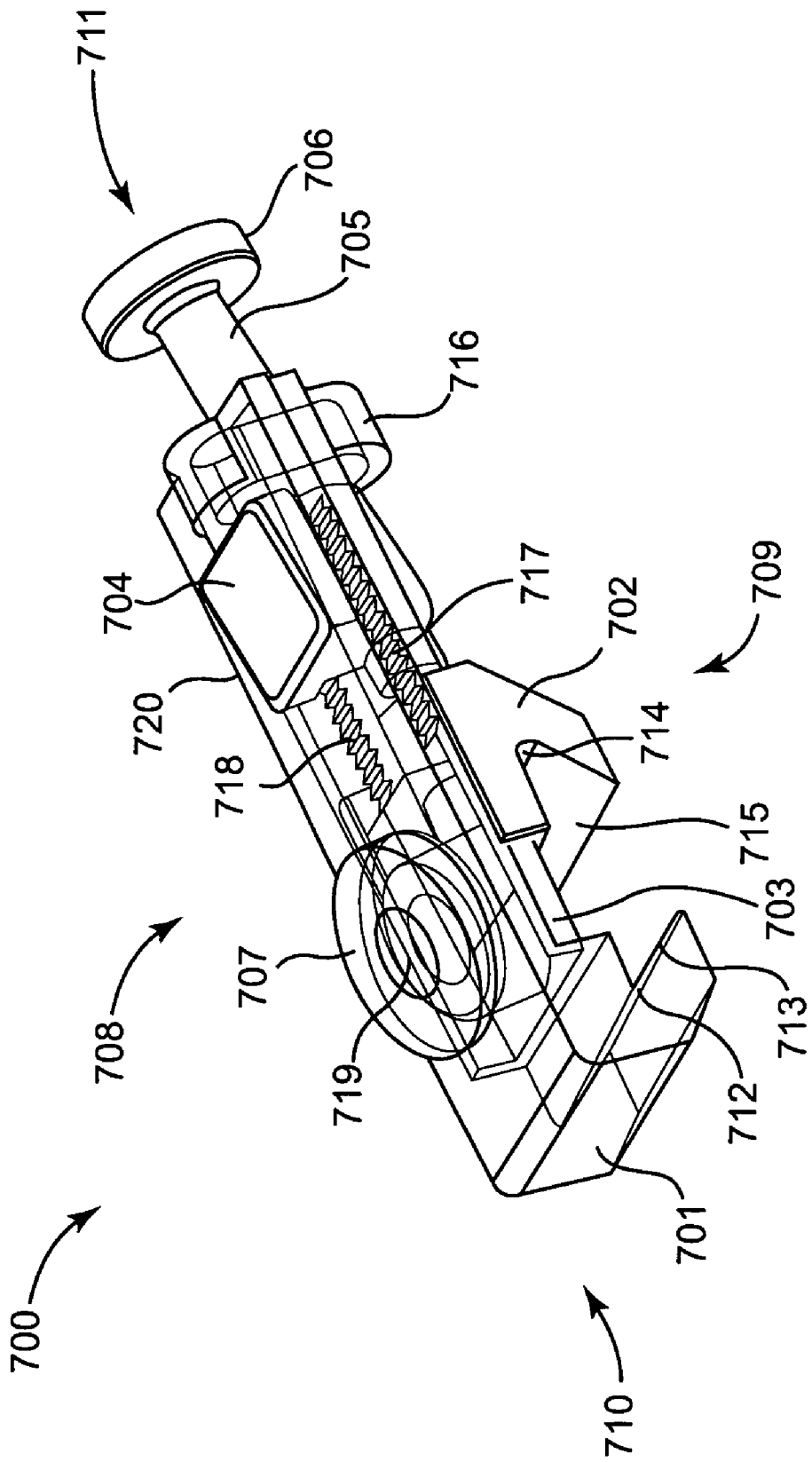
FIG. 15 is a perspective view of another embodiment of a quick-detach screw-lock clamp for a cardiac tissue stabilizer with the body depicted in transparency.

FIG. 15 illustrates another embodiment of a cardiac tissue stabilizer clamp 700. The clamp 700 can include a front clamp 701, a rear clamp 702, a beam 703, a releasable ratchet guide 704, a threaded shaft 705, an adjustment knob 706, and a turret mount 707. The front clamp 701 can include a front flat surface 712 that can contact a side of the retractor rail and a front angled surface 713 which can slide under the retractor rail (not shown). A clamp body 720 can extend from the front clamp 701 over the retractor rail. The rear clamp 702 can include a rear flat surface 714 that contacts a side of the retractor rail and a rear angled surface 715 which can slide under the retractor rail. The beam 703 can be positioned on a bottom 709 of the clamp body 720 and extend rearwardly from the front clamp 701. The rear clamp 702 can slidably mount to the beam 703 so the rear flat surface 714 is parallel to and facing the front flat surface 712.

The threaded shaft 705 can couple to a side of the rear clamp 702 opposite the rear flat surface 714 and can extend past a rear 711 of the clamp body 720. A support 716 can be positioned on the bottom 709 of the rear 711 of the clamp body 720 and can guide the threaded shaft 705. The adjustment knob 706 can couple to an end of the threaded shaft 705 opposite the rear clamp 702. The releasable ratchet guide 704 can be positioned on a top 708 of the clamp body 720 between the rear clamp 702 and the support 716. The releasable ratchet guide 704 can extend through the bottom 709 of the clamp body 720 and surround the threaded shaft 705. A first series of teeth 717 and a second series of teeth 718 can integrally form inside the beam 703. The first and second series of teeth 717 and 718 can be positioned in parallel to each other and can extend from the support 716 to a point near a front 710 of the clamp body 720.

The releasable ratchet guide 704 can couple to the first and second series of teeth 717 and 718. In a closed position, the releasable ratchet guide 704 can contact the first and second series of teeth 717 and 718 and prevent the rear clamp 702 from freely sliding away from the front clamp 701. The rear clamp 702 can still move toward the front clamp 701. The adjustment knob 706 can rotate clockwise to move the shaft 705 through the releasable ratchet guide 704 toward the front clamp 701 and push the rear clamp 702. The adjustment knob 706 can rotate counter-clockwise to move the shaft 705 away from the front clamp 701 and pull the rear clamp 702. Applying a force to lift the shaft 705 and adjustment knob 706 away from the bottom 709 of the clamp body 720 can move the releasable ratchet guide 704 out of contact with the first and second series of teeth 717 and 718. In this position, the rear clamp 702 can slide freely towards or away from the front clamp 701. Removal of the force can lower the releasable ratchet guide 701 back into contact with the first and second series of teeth 717 and 718.

The turret mount 707 can be positioned on a top 708 of the clamp body 720 between the front clamp 701 and the rear clamp 702. The turret mount 707 can be cylindrical in shape and can include an aperture 719. A turret (not shown) can mount to the turret mount 707 and can be locked in place.

Figure 16:
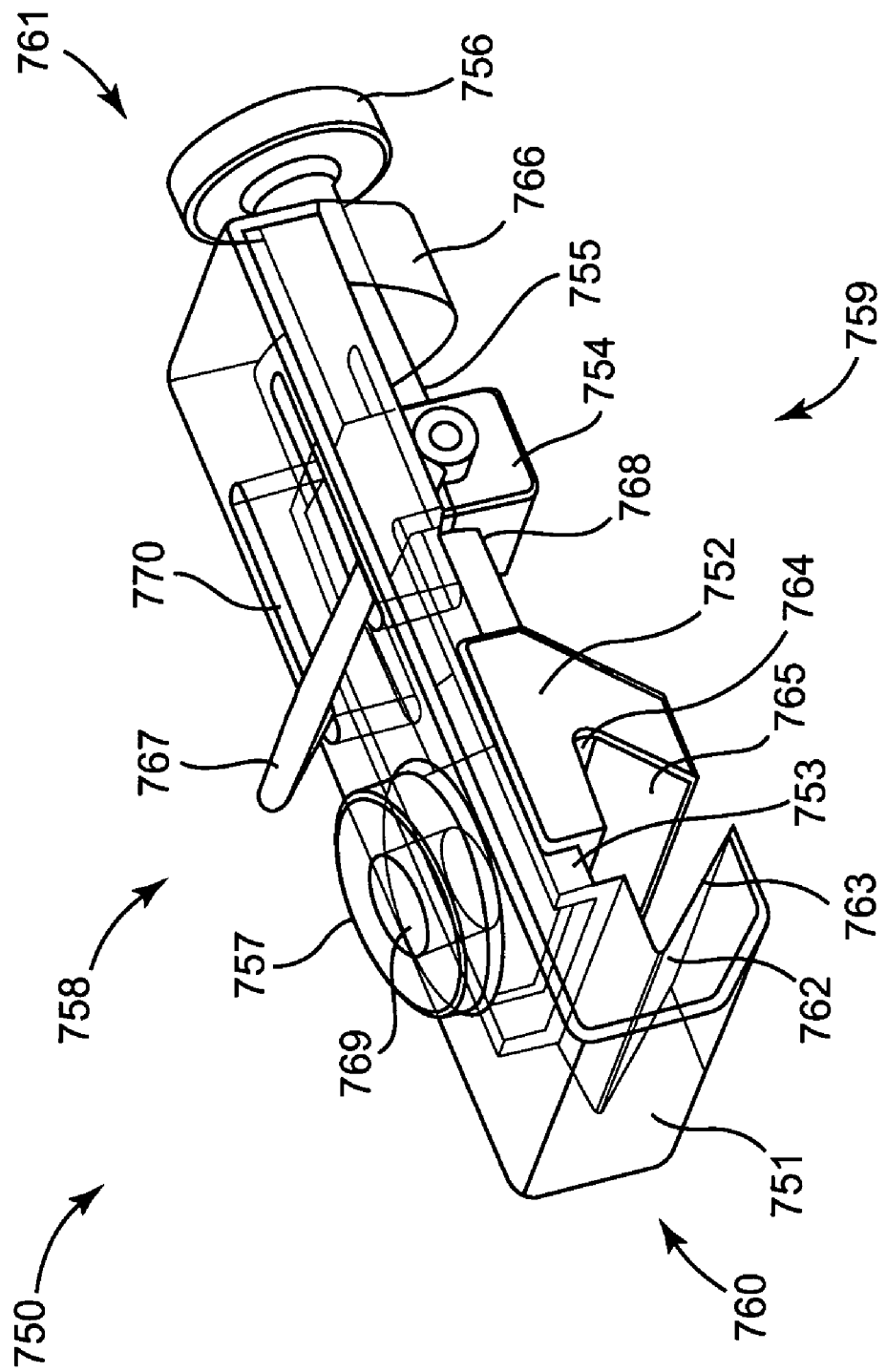
FIG. 16 is a perspective view of another embodiment of a quick-detach screw-lock clamp for a cardiac tissue stabilizer with the body depicted in transparency.

FIG. 16 illustrates another embodiment of a cardiac tissue stabilizer clamp 750. The clamp 750 can include a front clamp 751, a rear clamp 752, a beam 753, a releasable threaded guide 754, a threaded shaft 755, an adjustment knob 756, and a turret mount 757. The front clamp 751 can include a front flat surface 762 that can contact a side of the retractor rail and a front angled surface 763 which can slide under the retractor rail (not shown). A clamp body 770 can extend from the front clamp 751 over the retractor rail. The beam 753 can be positioned on a bottom 759 of the clamp body 770 and extend from the front clamp 751 to a point near a rear 761 of the clamp body 770. The rear clamp 752 can include a rear flat surface 764 that contact a side of the retractor rail and a rear angled surface 765 which can slide under the retractor rail. The rear clamp 752 can slidably mount to the beam 753 so the rear flat surface 764 is parallel to and facing the front flat surface 762.

The threaded shaft 755 can couple to a side of the rear clamp 752 opposite the rear flat surface 764 and can extend past the rear 761 of the clamp body 770. A support 766 can be positioned on the bottom 759 of the rear 761 of the clamp 770 and can hold the threaded shaft 755 parallel to the clamp body 770. The adjustment knob 756 can be coupled to an end of the threaded shaft 755 opposite the rear clamp 752. The releasable threaded guide 754 can mount to the bottom 759 of the clamp body 770 between the rear clamp 752 and the support 766. An actuation lever 767 can be coupled to the releasable threaded guide 754 and can extend through a top 758 of the clamp body 770. The releasable threaded guide 754 can include a threaded niche 768 to receive the threaded shaft 755.

Actuating the actuation lever 767 toward the rear 761 of the clamp body 770 can move the releasable threaded guide 754 and threaded niche 768 into contact with the threaded shaft 755, a closed position. In the closed position, the releasable threaded guide 754 can lock the shaft 755. When the shaft 755 is locked, the rear clamp 752 cannot be slid toward or away from the front clamp 751. The adjustment knob 756 can rotate clockwise to move the shaft 755 towards the front clamp 751 and push the rear clamp 752. The adjustment knob 756 can rotate counter-clockwise to move the shaft 755 away from the front clamp 751 and pull the rear clamp 752. Actuating the actuation lever 767 toward a front 760 of the clamp body 770 can move the releasable threaded guide 754 and threaded niche 768 out of contact with the threaded shaft 755, an open position. In the open position, the shaft 755 can slide freely and can push the rear clamp 752 toward or away from the front clamp 751.

The turret mount 757 can be positioned on the top 758 of the clamp body 770 between the front clamp 751 and the rear clamp 752. The turret mount 757 can be cylindrical in shape and can include an aperture 769. A turret (not shown) can mount on the turret mount 757 and can be locked in place.

Figure 17:
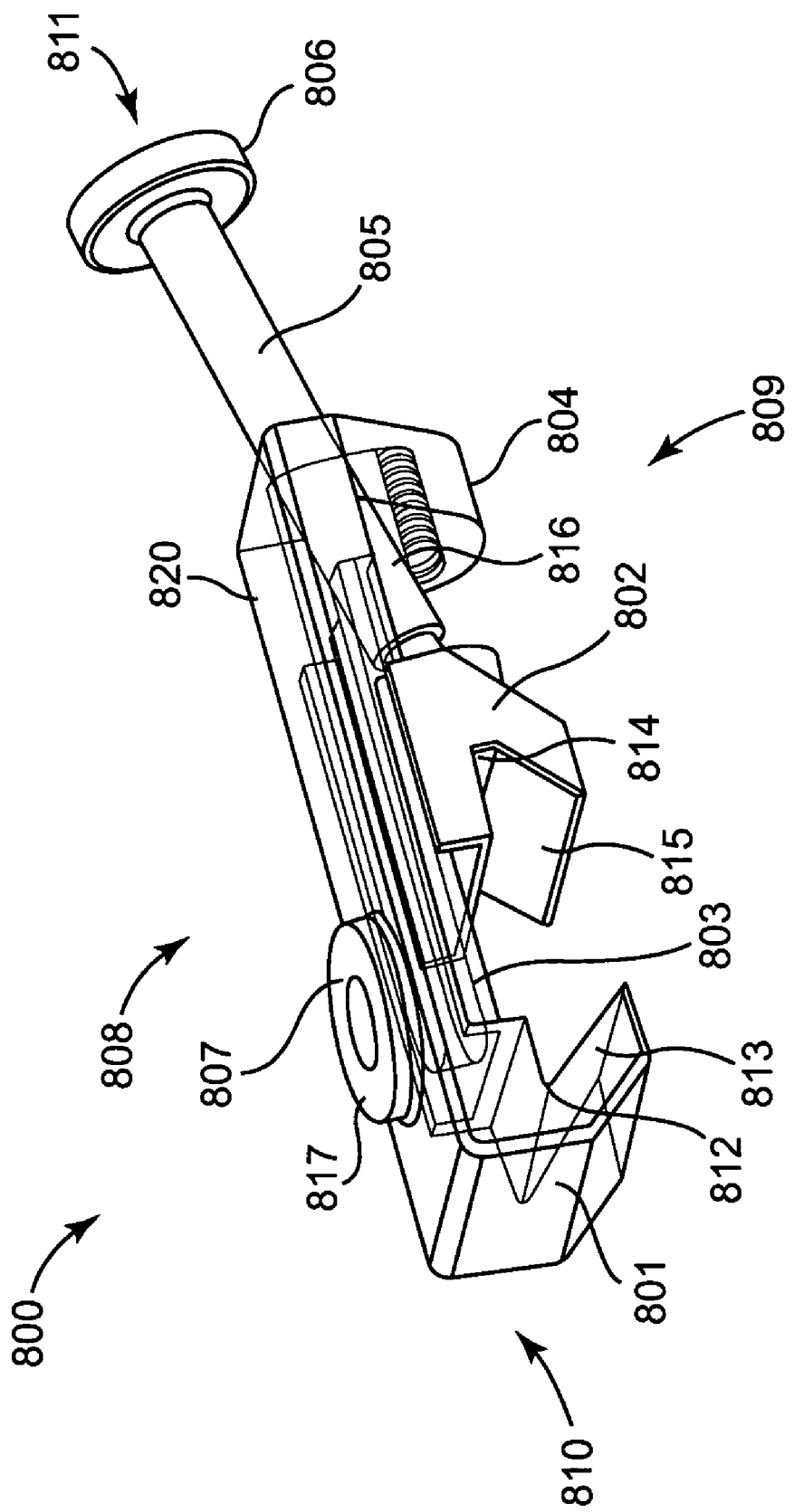
FIG. 17 is a perspective view of another embodiment of a quick-detach screw-lock clamp for a cardiac tissue stabilizer with the body depicted in transparency.

FIG. 17 illustrates another embodiment of a cardiac tissue stabilizer clamp 800. The clamp 800 can include a front clamp 801, a rear clamp 802, a beam 803, a threaded support 804, a threaded shaft 805, an adjustment knob 806, and a turret mount 807. The front clamp 801 can include a front flat surface 812 that can contact a side of the retractor rail and a front angled surface 813 which can slide under the retractor rail (not shown). A clamp body 820 can extend from the front clamp 801 over the retractor rail. The beam 803 can be positioned on a bottom 809 of the clamp body 820 and extend from the front clamp 801 to a point near a rear 811 of the clamp body 820. The rear clamp 802 can include a rear flat surface 814 that can contact a side of the retractor rail and a rear angled surface 815 which can slide under the retractor rail. The rear clamp 802 can slidably mount to the beam 803 so that the rear flat surface 814 is parallel to and facing the front flat surface 812.

The threaded shaft 805 can couple to a side of the rear clamp 802 opposite the rear flat surface 814 and can extend past the rear 811 of the clamp body 820. The threaded support 804 can be positioned on the bottom 809 of the rear 811 of the clamp body 820. The threaded support 804 can included threading 816 on a bottom interior half. The adjustment knob 806 can be coupled to an end of the threaded shaft 805 opposite of the rear clamp 802.

The threaded shaft 805 can be biased into a closed position in which the threaded shaft 805 can contact the threading 816 in the threaded support 804. In the closed position, the rear clamp 802 cannot be slid toward or away from the front clamp 801. The adjustment knob 806 can rotate clockwise to move the shaft 805 towards the front clamp 801 and push the rear clamp 802. The adjustment knob 806 can rotate counter-clockwise to move the shaft 805 away from the front clamp 801 and pull the rear clamp 802. Lifting the threaded shaft 805 and adjustment knob 806 toward a top 808 of the clamp body 820 can bring the threaded shaft 805 out of contact with the threading 816 in the threaded support 804, an open position. In the open position, the rear clamp 802 can slide freely toward or away from the front clamp 801.

The turret mount 807 can be positioned on the top 808 of the clamp body 820 between the front clamp 801 and the rear clamp 802. The turret mount 807 can be cylindrical in shape and can include an aperture 817. A turret (not shown) can mount to the turret mount 807 and can be locked in place.

Figure 18:
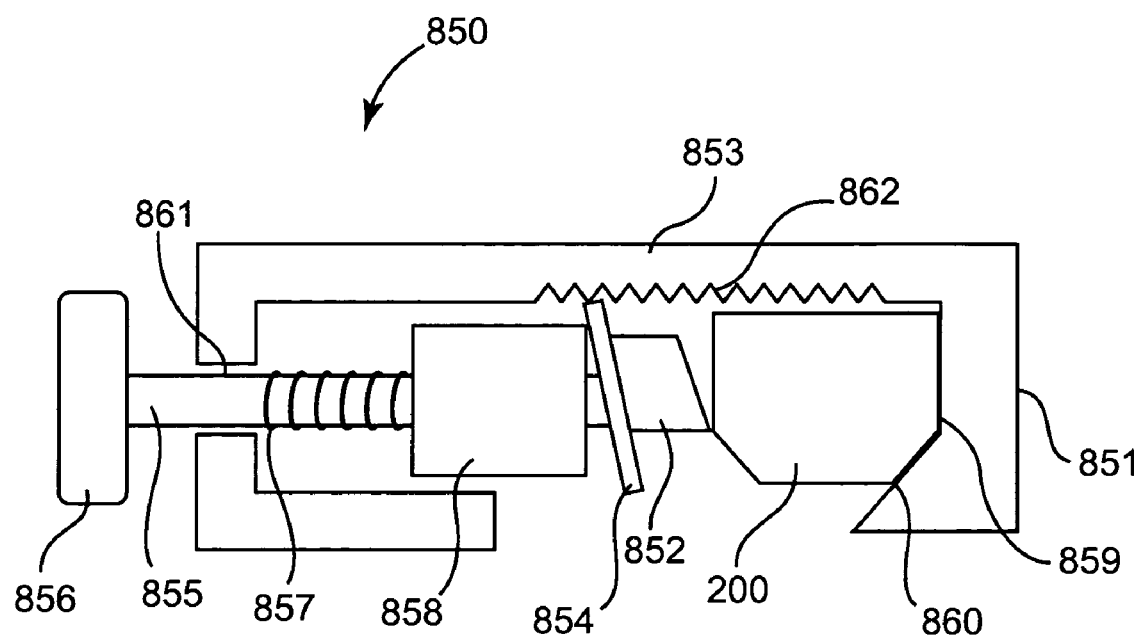
FIG. 18 is a side cut-away view of an embodiment of a ratchet lock clamp for a cardiac tissue stabilizer.

FIG. 18 illustrates another embodiment of a cardiac tissue stabilizer clamp 850. The clamp 850 can include a front clamp 851, a rear clamp 852, a body 853, a disc 854, a shaft 855, a handle 856, a spring 857, and a stopper 858. The front clamp 851 can include a front flat surface 859 that can contact a side of the retractor rail 200 and a front angled surface 860 which can slide under the retractor rail 200. The body 853 can extend from the front clamp 851 over the retractor rail 200. The shaft 855 can enter the body 853 through a gap 861 in the body 853 on an end opposite of the front clamp 851. The shaft 855 can extend to a point near the front clamp 851. The rear clamp 852 can couple to the shaft 854 on an end close to the front clamp 851. The disc 854 can be situated on the shaft 855 adjacent to the rear clamp 852. The stopper 858 can couple to the shaft 855 at a small distance from the disc 854. The spring 857 can surround the shaft 855 between the stopper 858 and the gap 861 in the body 853. The handle 856 can mount to the shaft 855 opposite of the rear clamp 855 outside of the gap 861 in the body 853.

When the rear clamp 852 contacts a side of the retractor rail 200, the rear clamp 852 can pivot on the shaft 855 and force the disc 854 to a vertical orientation. The disc 854 can engage a series of teeth 862 on the inside of the body 853. The bias of the spring 857 can rotate the disc 854 in the series of teeth 862. Rotation of the disc 854 in the series of teeth 862 can move the rear clamp 852 into flush contact with the retractor rail 200. The bias of the spring 857 and engagement between the disc 854 and series of teeth 862 can prevent the rear clamp 852 from moving away from the front clamp 851, locking the clamp 850 to the retractor rail 200.

Applying a force to the handle 856 against the bias of the spring 857 and rotating the handle 856 can move the rear clamp 852 away from the front clamp 851. The force and the rotation can move the disc 854 out of engagement with the series of teeth 862 and into a non-vertical orientation. Moving the rear clamp 852 away from the front clamp 851 can unlock the clamp 850 from the retractor rail 200.

Figure 19A:
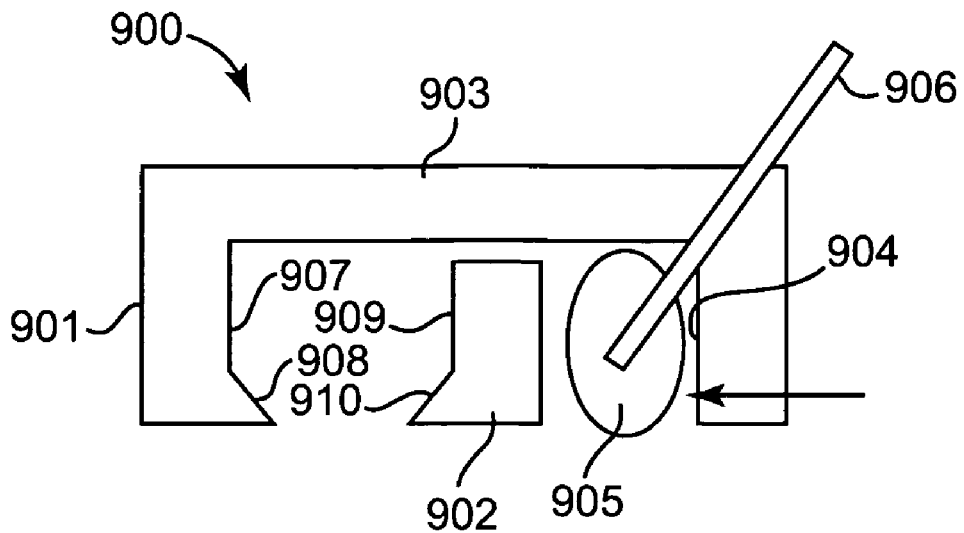
FIGS. 19A and 19B are side views of another embodiment of a cam-lock clamp for a cardiac tissue stabilizer in open and closed positions.
Figure 19B:
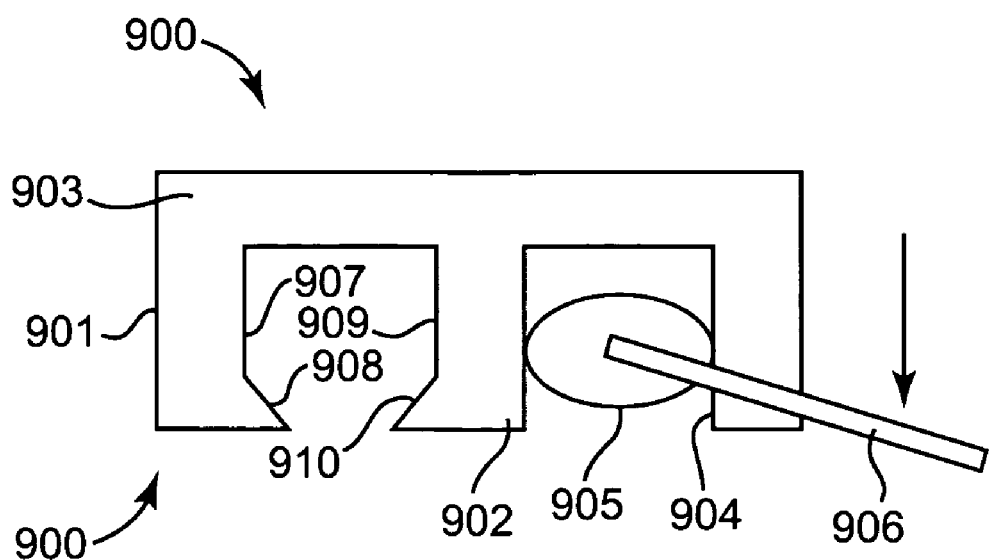

FIGS. 19A and 19B illustrate another embodiment of a cardiac tissue stabilizer clamp 900. The clamp 900 can include a front clamp 901, a rear clamp 902, a body 903, a support surface 904, a cam 905, and an actuation lever 906. The front clamp 901 can include a front flat surface 907 that can contact a side of the retractor rail and a front angled surface 908 which can slide under the retractor rail (not shown). A clamp body 903 can extend from the front clamp 901 over the retractor rail. The support surface 904 can be an inner surface of the body 903 opposite the front clamp 901 so the support surface 904 is parallel to the front flat surface 907 of the front clamp 901. The rear clamp 902 can include a rear flat surface 909 that can contact a side of the retractor rail and a rear angled surface 910 which can slide under the retractor rail. The rear clamp 902 can slidably mount to the clamp body 903 between the front clamp 901 and the support surface 904 with the rear flat surface 909 facing and parallel to the front flat surface 907.

The cam 905 can mount to the body 903 between the rear clamp 902 and the support surface 904. The actuation lever 906 can couple to the cam 905. FIG. 19A illustrates the clamp 900 in an unlocked position. In the unlocked position, the cam 905 can be in a vertical orientation so a distance between the front clamp 901 and the rear clamp 902 is the greatest. The rear clamp 902 has a limited sliding range to accommodate insertion of the clamp 900 over the retractor rail. Actuating the actuation lever 906 can convert the clamp 900 from the unlocked position to a locked position. FIG. 19B illustrates the locked position. In the locked position, the cam 905 can rotate and make the distance between the rear clamp 902 and the front clamp 901 smaller. A dwell (not shown) can hold the cam 905 in position between the rear clamp 902 and the anchor 904. Applying an upward force to the actuation lever 906 can rotate the cam 905 back to the vertical orientation and can allow the rear clamp 902 to slide away from the front clamp 901.

Figure 20A:
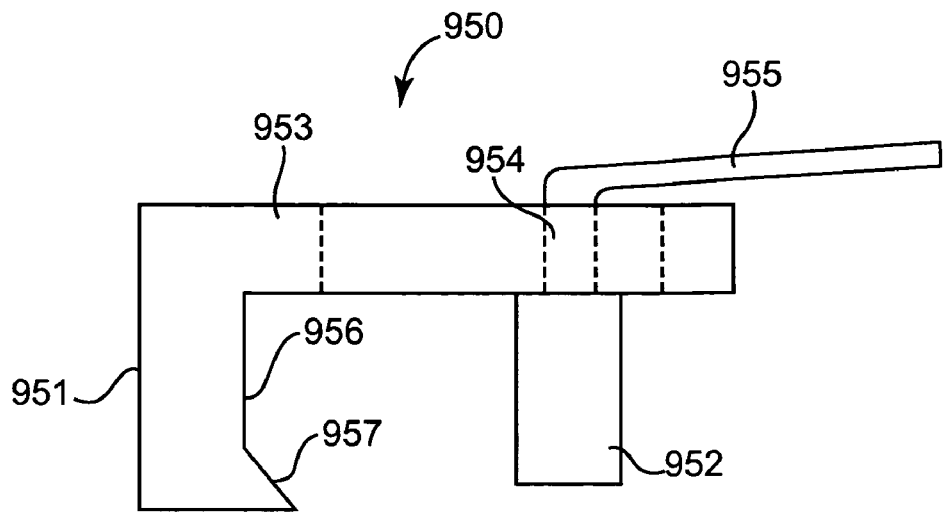
FIGS. 20A and 20B are side and top views of an embodiment of a rotating rear cam-lock clamp for a cardiac tissue stabilizer.
Figure 20B:
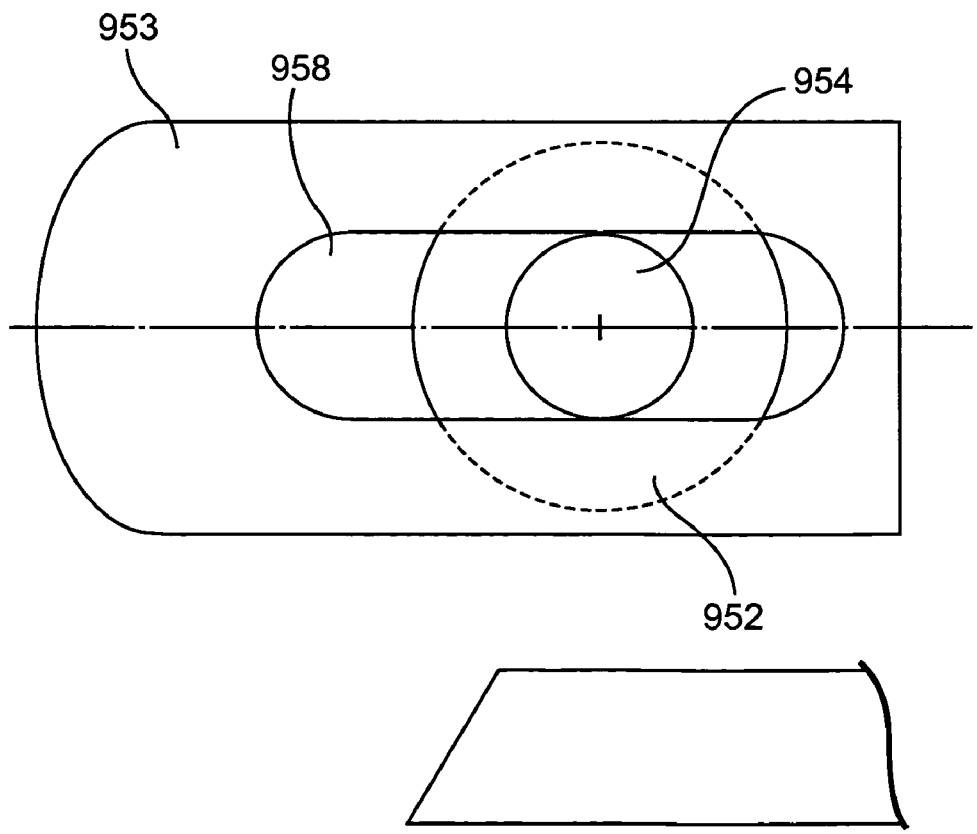

FIGS. 20A and 20B illustrate another embodiment of a cardiac tissue stabilizer clamp 950. The clamp 950 can include a front clamp 951, a rear clamp 952, a body 953, a cylinder 954, and an actuation lever 955. The front clamp 951 can include a front flat surface 956 that can contact a side of the retractor rail and a front angled surface 957 which can slide under the retractor rail (not shown). The body 953 can extend from the front clamp 951 over the retractor rail perpendicular to the front flat surface 956. The body 953 can include a slot 958. The cylinder 954 can slidably mount in the slot 958. The rear clamp 952 can be cam-shaped. The rear clamp 952 can be coupled to the cylinder 954 mounted in the slot 958 of the body 953. The actuation lever 955 can be coupled to the cylinder 954 on a side opposite of the rear clamp 952.

The rear clamp 952 and cylinder 954 can slide freely in the slot 958 to contact the retractor rail. Rotating the actuation lever 955 can rotate the rear clamp 952. The cam-shape of the rear clamp 952 can push against the retractor rail and can lock the retractor rail between the front clamp 951 and the rear clamp 952. A dwell (not shown) in the slot 958 can lock the cylinder 954 and actuation lever 955 in place. Applying a force to rotate the actuation lever 955 out of the dwell can unlock the clamp 950 from the retractor rail. The rear clamp 952 and cylinder 954 can then slide freely away from the retractor rail. The lower cam 604 can be positioned in a slot 610 in the rear clamp 602.

Figure 21:
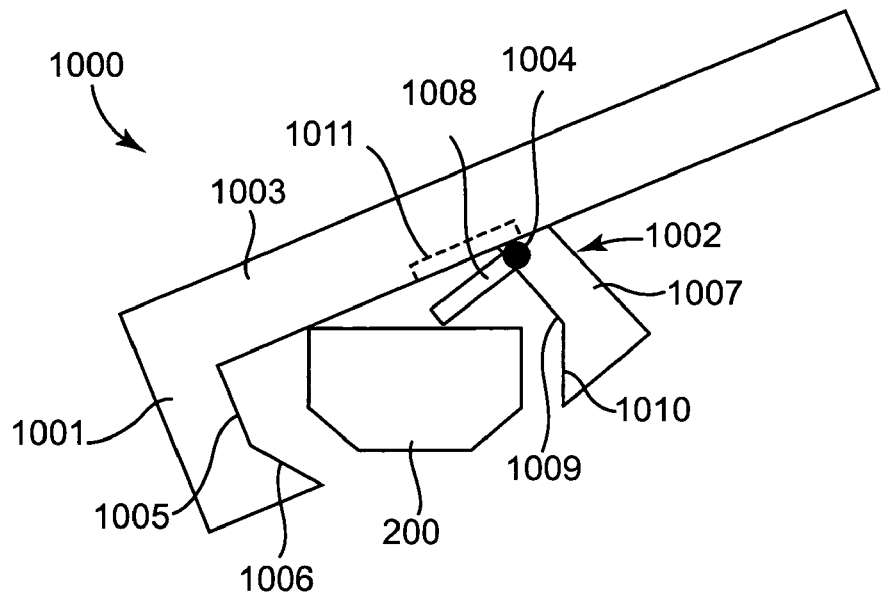
FIG. 21 is a side view of an embodiment of a device-lock clamp for a cardiac tissue stabilizer.

FIG. 21 illustrates another embodiment of a cardiac tissue stabilizer clamp 1000. The clamp 1000 can include a front clamp 1001, a rear clamp 1002, and a body 1003. The front clamp 1001 can include a front flat surface 1005 that can contact a side of the retractor rail 200 and a front angled surface 1006 which can slide under the retractor rail 200. The body 1003 can extend from the front clamp 1001 over the retractor rail 200 so the front flat surface 1005 is perpendicular to the body 1003. The rear clamp 1002 can include a contact arm 1007 and a lock arm 1008. The contact arm 1007 can include a rear flat surface 1009 that can contact a side of the retractor rail 200 and a rear angled surface 1010 which can slide under the retractor rail 200. The rear clamp 1002 can pivotally couple to the body 1003 at a hinge 1004. The hinge 1004 can mount on the body 1003 at a distance from the front clamp 1001 such that the lock arm 1008 can extend towards the front clamp 1001 and the contact arm 1007 can extend perpendicular to the body 1003. The rear clamp 1002 can freely pivot about the hinge 1004.

The clamp 1000 can press onto the retractor rail 200 between the front clamp 1001 and the contact arm 1007 of the rear clamp 1002. Applying a force on the clamp 1000 towards the retractor rail 200 can pivot the rear flat surface 1009 of the contact arm 1007 parallel to the front flat surface 1005 of the front clamp 1001 and can push the lock arm 1006 into a mating slot 1011 in the body 1003. The lock arm 1008 can lock in the slot 1011 and can hold the clamp 1000 on the retractor rail 200. Applying an upward force on the body 1003 can release the lock arm 1008 from the slot 1011. The clamp 1000 can then move freely away from the retractor rail 200.

Figure 22:
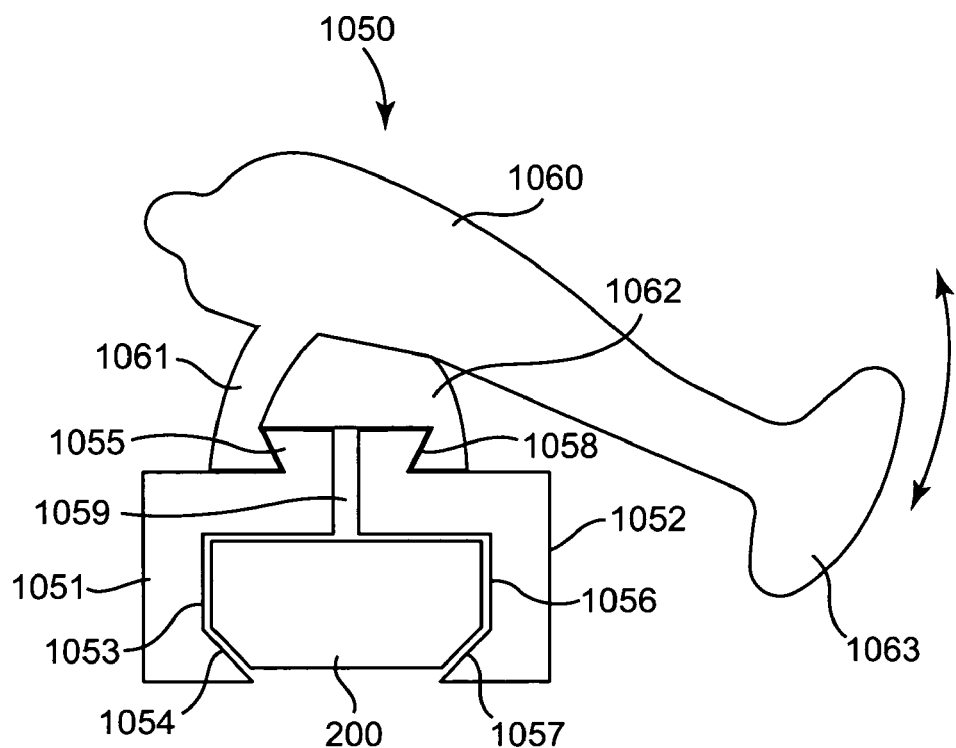
FIG. 22 is a side view of another embodiment of a device-lock clamp for a cardiac tissue stabilizer.

FIG. 22 illustrates another embodiment of a cardiac tissue stabilizer clamp 1050. The clamp 1050 can include a front clamp 1051 and a rear clamp 1052. The front clamp 1050 can include a front flat surface 1053 and can contact a side of the retractor rail 200 and a front angled surface 1054 which can slide under the retractor rail 200. The front clamp 1051 can also include a front notch 1055. The rear clamp 1052 can include a rear flat surface 1056 that can contact a side of the retractor rail 200 and a rear angled surface 1057 which can slide under the retractor rail 200. The rear clamp 1052 can also include a rear notch 1058. The front notch 1055 of the front clamp 1051 and the rear notch 1058 of the rear clamp 1052 can be situated on the retractor rail 200 adjacent to each other and can be separated by a small distance 1059.

A turret 1060 can include a front clasp 1061, a rear clasp 1062, and a handle 1063. The front clasp 1061 can mount on the front notch 1055 of the front clamp 1051 and the rear clasp 1062 can mount on the rear notch 1058 of the rear clamp 1052. The turret 1060 supports the front and rear clamp 1051, 1052 adjacent one another. Raising the handle 1063 away from the rear clamp 1052 can actuate the turret 1060 about the front notch 1055 of the front clamp 1051. The front clasp 1061 can push the front notch 1055 towards the rear notch 1058 and can make the distance 1059 smaller. When the distance 1059 is made smaller, the front clamp 1051 and the rear clamp 1052 can lock the clamp 1050 on the retractor rail 200. Applying a force to lower the knob 1063 towards the rear clamp 1052 can slide the front clasp 1061 away from the front notch 1055 of the front clamp 1051. The front clamp 1051 can move away from the rear clamp 1052 can increase the distance 1059. An increase in the distance 1059 can unlock the clamp 1050 from the retractor rail 200.

Figure 23A:
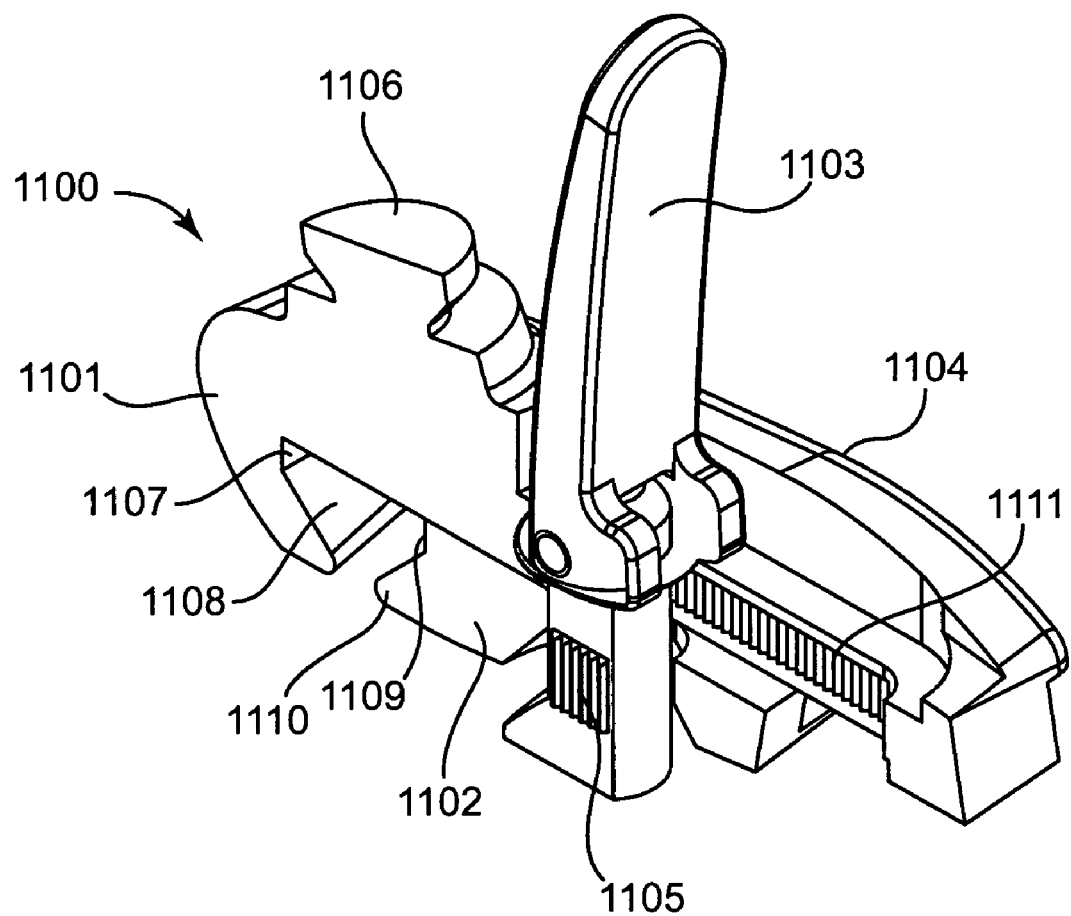
FIGS. 23A and 23B are perspective views of an embodiment of a wedge-lock clamp for a cardiac tissue stabilizer in open and closed positions with clamp partially cut-away in FIG. 23A.
Figure 23B:
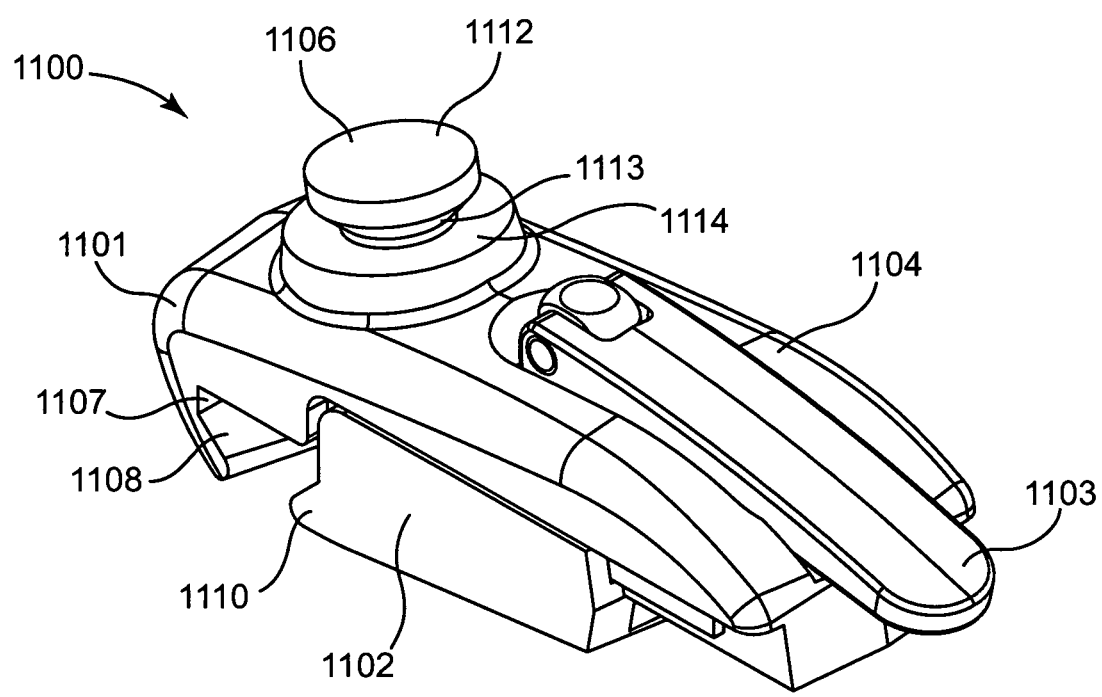

FIGS. 23A and 23B illustrate another embodiment of a cardiac tissue stabilizer clamp 1100. The clamp 1100 can include a front clamp 1101, a rear clamp 1102, an actuation lever 1103, a housing 1104, a wedge 1105, and a turret mount 1106. The front clamp 1101 can include a front flat surface 1107 and can contact a side of the retractor rail (not shown). The front clamp 1101 can also include a front angled surface 1108 which can slide under the retractor rail. The front clamp 1101 can be situated on the housing 1104 so the front flat surface 1107 is perpendicular to the housing 1104. The rear clamp 1102 can include a rear flat surface 1109 that can contact a side of the retractor rail opposite the side contacted by the front flat surface 1107. The rear clamp 1102 can also include a rear angled surface 1110 which can slide under the retractor rail. The rear clamp 1102 can slidably mount to the housing 1104 so the rear flat surface 1109 is parallel to and facing the front flat surface 1107.

The housing 1104 can include a slot 1111. The slot 1111 can start a small distance from the front clamp 1101 and can extend to a point near the opposite end of the housing 1104. The wedge 1105 can slidably mount in the slot 1111 behind the rear clamp 1102 and can couple to the rear clamp 1102. The actuation lever 1103 can couple to the wedge 1105. FIG. 23A illustrates an unlocked position. In the unlocked position, the wedge 1105 can be in a vertical orientation and the rear clamp 1102 can slide freely away from the front clamp 1101.

The actuation lever 1103, the wedge 1105, and the rear clamp 1102 can slide toward the front clamp 1101 until the rear clamp 1102 contacts the retractor rail. Actuating the actuation lever 1103 towards the housing 1104 can convert the clamp 1100 to a locked position illustrated in FIG. 23B. In the locked position, the wedge 1105 can rotate with the actuation of the actuation lever 1103 and can push the rear clamp 1102 against the retractor rail. Rotation of the wedge 1105 to a more horizontal position can prevent the rear clamp 1102 from sliding away from the front clamp 1101 and can lock the clamp 1100 on the retractor rail. Applying an upward force to the actuation lever 1103 can rotate the wedge 1105 back to the vertical orientation and can unlock the clamp 1100 from the retractor rail.

The turret mount 1106 can be situated on the housing 1104 between the slot 1111 and the front clamp 1101. The turret mount 1106 can include a cylindrical top 1112, an angled groove 1113, and a flat groove 1114. A turret (not shown) can mount to the turret mount 1106 and can be locked in place.

Figure 24:
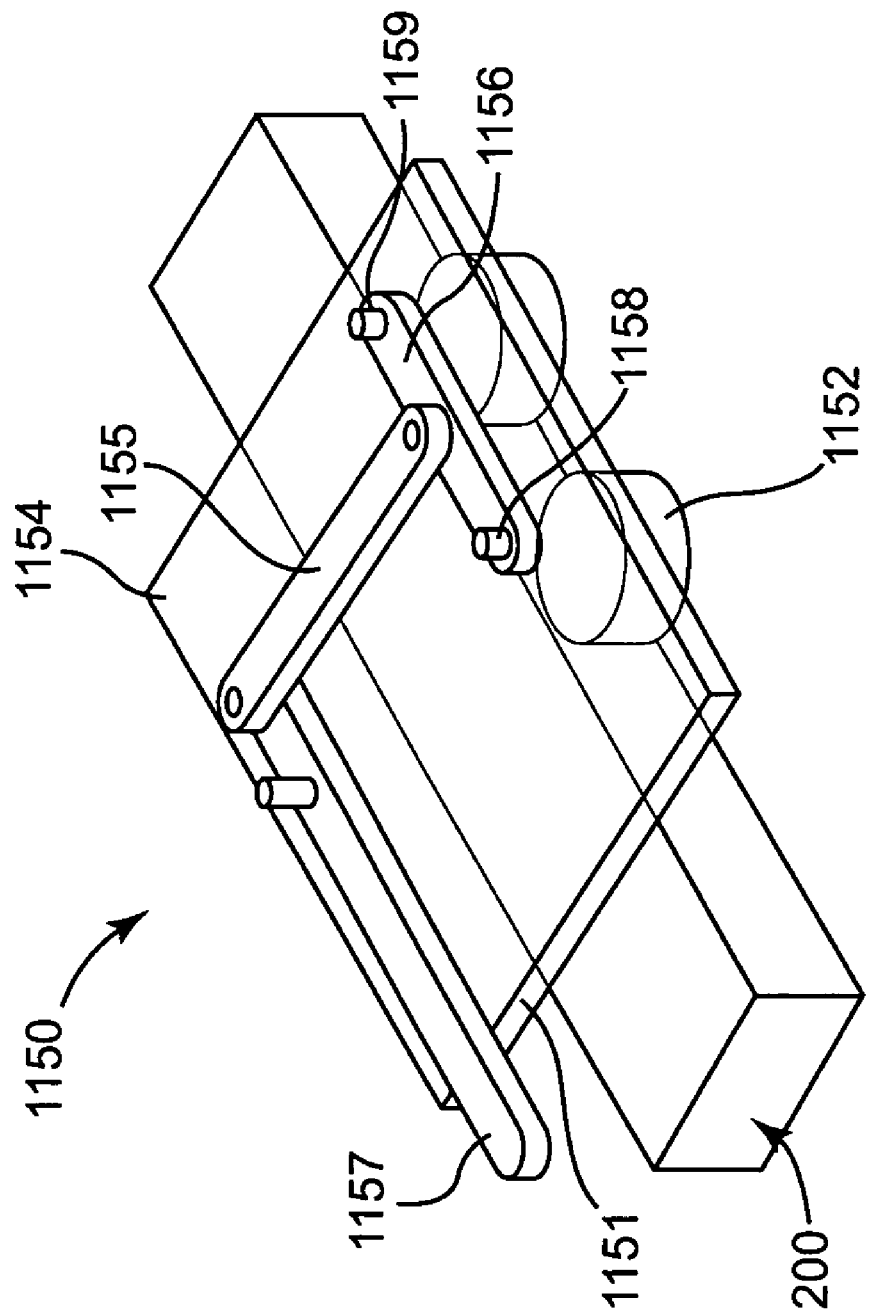
FIG. 24 is a perspective view of an embodiment of a parallel-lock clamp for a cardiac tissue stabilizer with the body shown in transparency.

FIG. 24 illustrates another embodiment of a cardiac tissue stabilizer clamp 1150. The clamp can include a front clamp 1151, a first cam 1152, a second cam 1153, a body 1154, a cross support 1155, an actuation lever 1157, and a cam support 1156. The front clamp 1151 can mount underneath the body 1154. The cross support 1155 can couple to the actuation lever 1157 and can be extended across the body 1154. The cam support 1156 can couple to the cross support 1155 on an end opposite of the front clamp 1151. The first cam 1152 can couple to an end of the cam support 1156 by a first pin 1158. The second cam 1153 can couple to an end of the cam support 1156 opposite the end coupled to the first cam 1152 by a second pin 1159. The first cam 1152 can rotate freely about the first pin 1158 and the second cam 1153 can rotate freely about the second pin 1159.

Sliding the clamp 1150 on top of the retractor rail 200 in a parallel fashion can rotate the first and second cams 1152 and 1153. Rotation of the first and second cams 1152 and 1153 can cam the retractor rail 200 between the first and second cams 1152 and 1153 and the front clamp 1151. Actuating the actuation lever 1157 locks and unlocks the clamp 1150 to the retractor rail 200. Friction between the first cam 1152 and the retractor rail 200 and between the second cam 1153 and the retractor rail 200 can hold the first and second cams 1152 and 1153 in contact with the retractor rail 200. Applying a force opposite the original direction of sliding can rotate the first and second cams 1152 and 1153 out of contact with the retractor rail 200. Loss of contact between the first and second cams 1152 and 1153 and the retractor rail 200 can unlock the clamp 1150 from the retractor rail 200.

Figure 25:
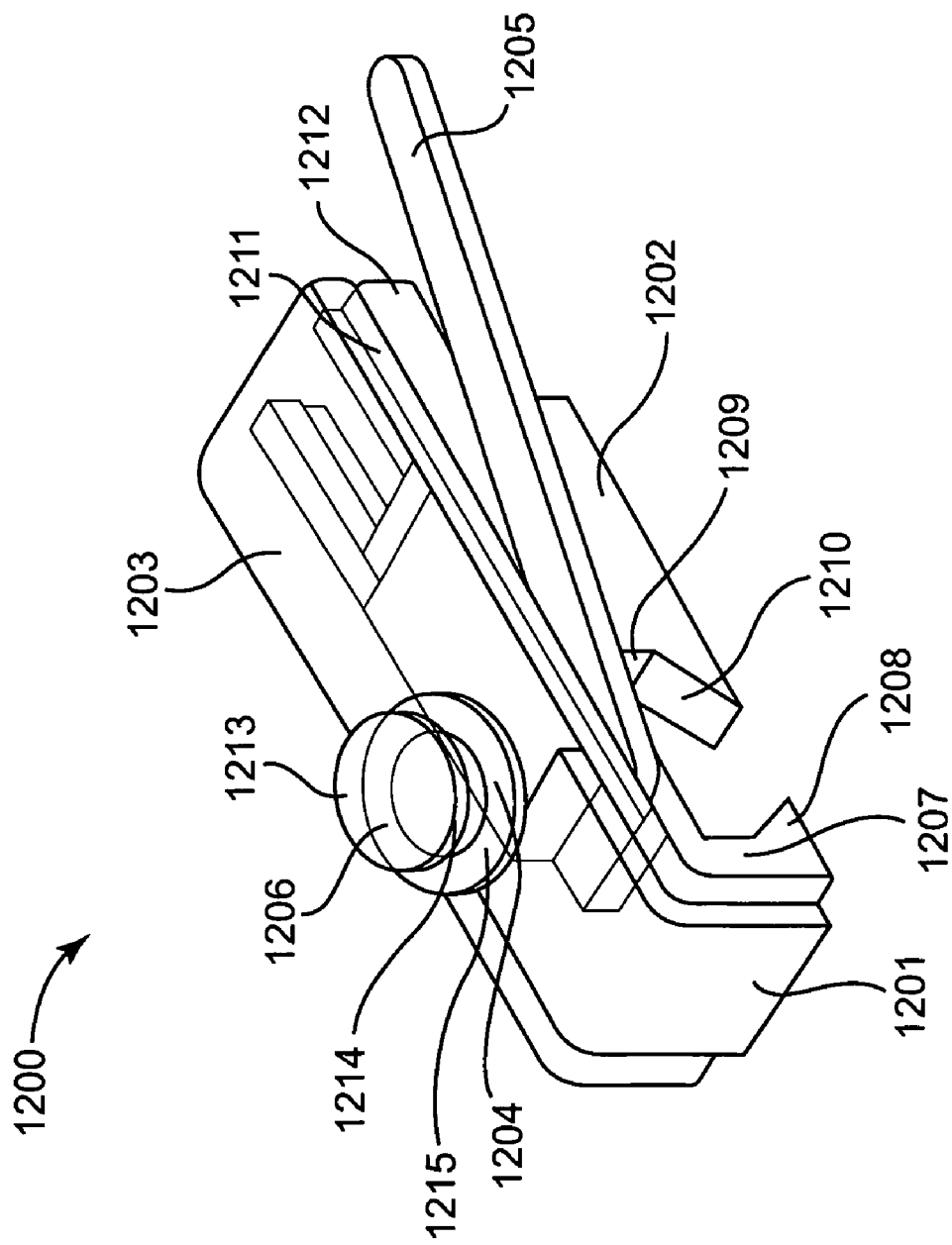
FIG. 25 is a perspective view of an embodiment of a side-lock clamp for a cardiac tissue stabilizer with the body shown in transparency.

FIG. 25 illustrates another embodiment of a cardiac tissue stabilizer clamp 1200. The clamp 1200 can include a front clamp 1201, a rear clamp 1202, a body 1203, a cam post 1204, an actuation lever 1205, and a turret mount 1206. The front clamp 1201 can include a front flat surface 1207 that can contact a side of the retractor rail and a front angled surface 1208 which can slide under the retractor rail (not shown). The body 1203 can extend from the housing 1203 over the retractor rail so the front flat surface 1207 is perpendicular to the body 1203. The rear clamp 1202 can include a rear flat surface 1209 that can contact a side of the retractor rail and a rear angled surface 1210 which can slide under the retractor rail. The rear clamp 1202 can slidably mount to the body 1203 so the rear flat surface 1210 is parallel to and facing the front flat surface 1207. The cam post 1204 can couple to the rear clamp 1202. The body 1203 can include a slot 1211 on a side 1212 of the body 1203. The slot 1211 can start at the front clamp 1201 and extend to the other end of the body 1203. The actuation lever 1205 can extend through the slot 1211 and couple to the cam post 1204.

The rear clamp 1202 can slide toward the front clamp 1202 until the rear flat surface 1209 contacts the side of the retractor rail. Actuating the actuation lever 1205 into the slot 1211 can rotate the cam post 1204 and can bind the rear clamp 1202, locking the clamp 1200 to the retractor rail. In a locked position, the rear clamp 1202 cannot slide away from the front clamp 1201. Applying a force to actuate the actuation lever 1205 away from the body 1203 can rotate the cam post 1204 to an unbound orientation with the rear clamp 1202, unlocking the clamp 1200 from the retractor rail. The rear clamp 1202 can then slide freely away from the front clamp 1201.

The turret mount 1206 can be situated on the body 1203 above the cam post 1204. The turret mount 1206 can include a cylindrical top 1213, an angled groove 1214, and a flat groove 1215. A turret (not shown) can mount to the turret mount 1206 and can be locked in place.

Figure 26:
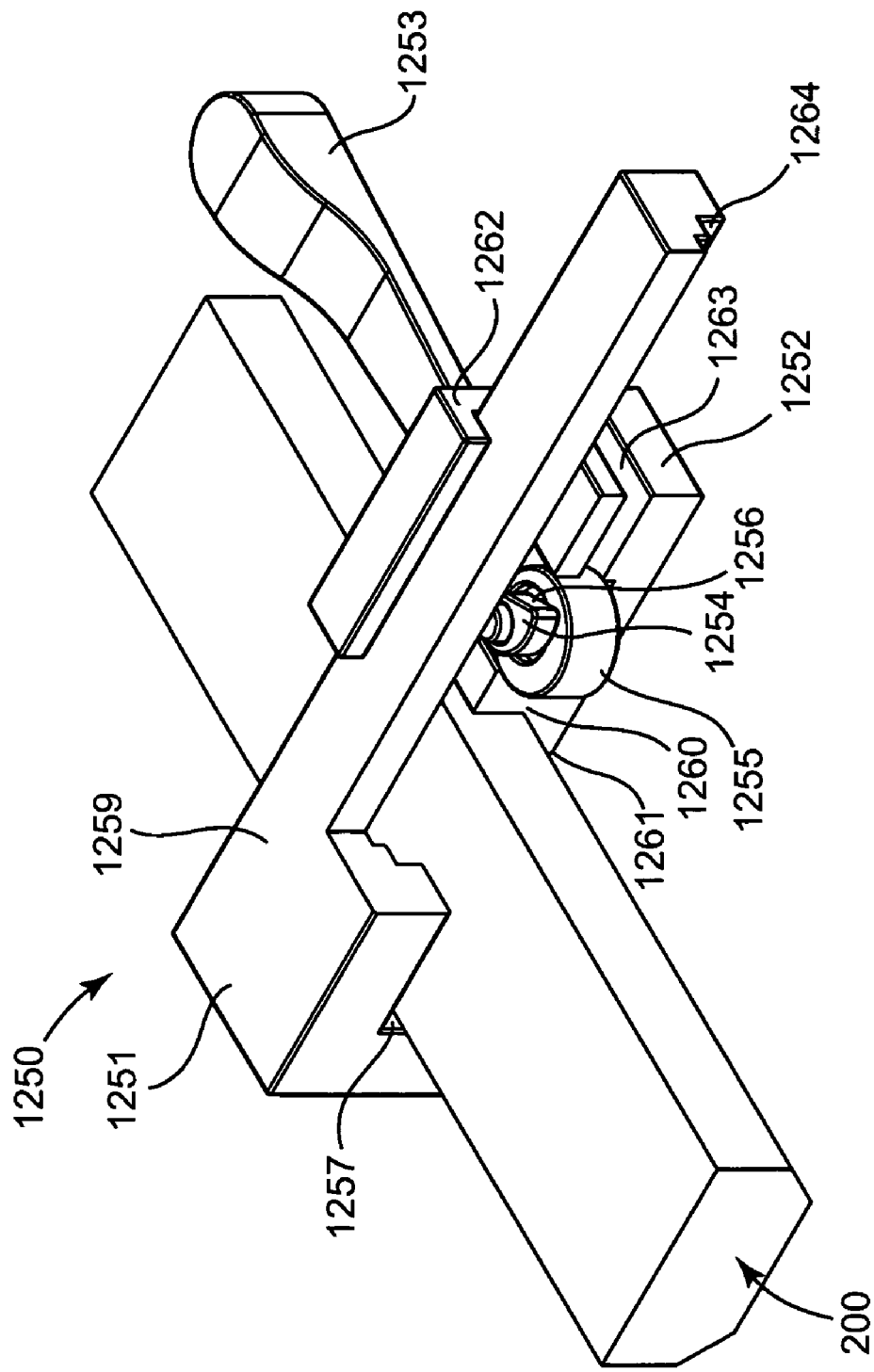
FIG. 26 is a perspective view of an embodiment of a dual-cam with a torsional spring clamp for a cardiac tissue stabilizer with the body partially cut-away.

FIG. 26 illustrates another embodiment of a cardiac tissue stabilizer clamp 1250. The clamp 1250 can include a front clamp 1251, a rear clamp 1252, an actuation lever 1253, an upper cam 1254, a lower cam 1255, and a torsional spring 1256. The front clamp 1251 can include a front flat surface 1257 that can contact a side of the retractor rail 200 and a front angled surface (not shown) which can slide under the retractor rail 200. The front clamp 1251 can also include a body 1259 which can be extended across the retractor rail 200. The body 1259 of the front clamp 1251 is partially cut-away to reveal the positioning of the rear clamp 1252, the upper cam 1254, and the lower cam 1255. The rear clamp 1252 can include a rear flat surface 1260 that can contact a side of the retractor rail 200 and a rear angled surface 1261 which can slide under the retractor rail 200. The rear clamp 1252 can also include a jaw 1262. The jaw 1262 can slidably mount the rear clamp 1252 to the body 1259 of the front clamp 1251 so the rear flat surface 1260 is parallel to and facing the front flat surface 1257.

The lower cam 1255 can be situated in a notch 1263 in the rear clamp 1252. The upper cam 1254 can couple on top of the lower cam 1255 in a groove 1264 in the body 1259 of the front clamp 1251. The torsional spring 1256 can mount between the upper cam 1254 and the lower cam 1255. The actuation lever 1253 can integrally form with the lower cam 1255 and can extend away from the rear clamp 1252.

The rear clamp 1252 can slide toward the front clamp 1251 until the rear flat surface 1260 contacts the side of the retractor rail 200. Actuating the actuation lever 1253 can rotate the upper cam 1254 and the lower cam 1255. The upper cam 1254 can engage the groove 1264 in the body 1259 of the front clamp 1251 and can lock the rear clamp 1252 in place. Rotation of the torsional spring 1256 can bias the upper cam 1254 away from the lower cam 1255. Continued actuation of the actuation lever 1253 can rotate only the lower cam 1255. The lower cam 1255 can cam the rear clamp 1252 into the retractor rail 200, locking the clamp 1250 to the retractor rail 200. An upper cam dwell (not shown) can hold the upper cam 1254 in place. A lower cam dwell (not shown) can hold the lower cam 1255 in place.

Applying a force to the actuation lever 1253 can rotate the actuation lever 1253 back to an unlocked position. Rotation of the actuation lever 1253 can unlock the lower cam 1255 from the lower cam dwell and the upper cam 1255 from the upper cam dwell. Rotation of the actuation lever 1253 can apply a force against the bias of the torsional spring 1256 and can couple the upper cam 1254 with the lower cam 1255. In the unlocked position, the rear clamp 1252 can slide freely away from the front clamp 1251.

Figure 27:
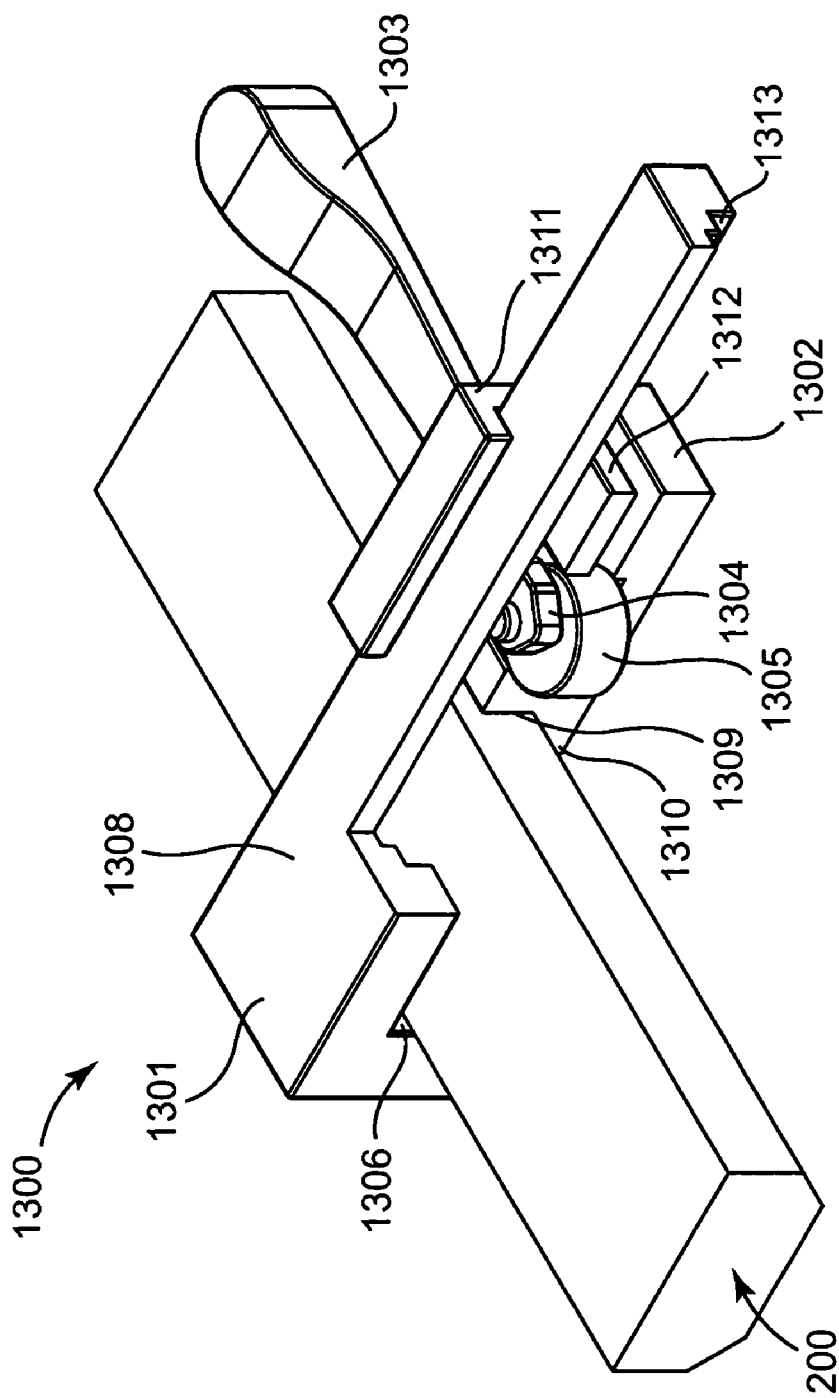
FIG. 27 is a perspective view of an embodiment of a dual-cam with dimples clamp for a cardiac tissue stabilizer with the body partially cut-away.

FIG. 27 illustrates another embodiment of a cardiac tissue stabilizer clamp 1300. The clamp 1300 can include a front clamp 1301, a rear clamp 1302, an actuation lever 1303, an upper cam 1304, and a lower cam 1305. The front clamp 1301 can include a front flat surface 1306 that can contact a side of the retractor rail 200 and a front angled surface (not shown) which can slide under the retractor rail 200. The front clamp 1301 can also include a body 1308 which can be extended across the retractor rail 200. The body 1308 of the front clamp 1301 is partially cut-away to reveal the positioning of the rear clamp 1302, the upper cam 1304, and the lower cam 1305. The rear clamp 1302 can include a rear flat surface 1309 that can contact a side of the retractor rail 200 and a rear angled surface 1310 which can slide under the retractor rail 200. The rear clamp 1302 can also include a jaw 1311. The jaw 1311 can slidably mount the rear clamp 1302 to the body 1308 of the front clamp 1301 so the rear flat surface 1309 is parallel to and facing the front flat surface.

The lower cam 1305 can be situated in a notch 1312 in the rear clamp 1302. The upper cam 1304 can couple on top of the lower cam 1305 in a groove 1313 in the body 1308 of the front clamp 1301. The upper cam 1304 can include a plurality of dimples (not shown). The lower cam 1305 can include a plurality of recesses (not shown) which can engage the plurality of dimples from the upper cam 1304. In an unlocked position, the plurality of dimples of the upper cam 1304 can be engaged with the plurality of recesses of the lower cam 1305 so the upper cam 304 and lower cam 1305 can rotate together. The actuation lever 1303 can integrally form with the lower cam 1305 and can extend away from the rear clamp 1302.

The rear clamp 1302 can slide toward the front clamp 1301 until the rear flat surface 1309 contacts the side of the retractor rail 200. Actuating the actuation lever 1303 can rotate the upper cam 1304 and the lower cam 1305. The upper cam 1304 can engage the groove 1313 in the body 1308 of the front clamp 1301 and can lock the rear clamp 1302 in place. Continued actuation of the actuation lever 1303 can rotate only the lower cam 1305 and can move the plurality of dimples of the upper cam 1304 out of engagement with the plurality of recesses of the lower cam 1305. Moving the plurality of dimples of the upper cam 1304 out of the plurality of recesses of the lower cam 1305 can separate the upper cam 1304 and the lower cam 1305. The lower cam 1305 can rotate and can cam the rear clamp 1302 into the retractor rail 200, locking the clamp 1300 to the retractor rail 200. An upper cam dwell (not shown) can hold the upper cam 1304 in place. A lower cam dwell (not shown) can hold the lower cam 1305 in place.

Applying a force to the actuation lever 1303 can rotate the actuation lever 1303 back to an unlocked position. Rotation of the actuation lever 1303 can unlock the lower cam 1305 from the lower cam dwell. The plurality of recesses of the lower cam 1305 can engage the plurality of dimples of the upper cam 1304. Continued rotation of the actuation lever 1303 can unlock the upper cam 1304 from the upper cam dwell. The upper cam 1304 can rotate with the lower cam 1305 and can move out of engagement with the groove 1313. In the unlocked position, the rear clamp 1302 can slide freely away from the front clamp 1301.

Figure 28A:
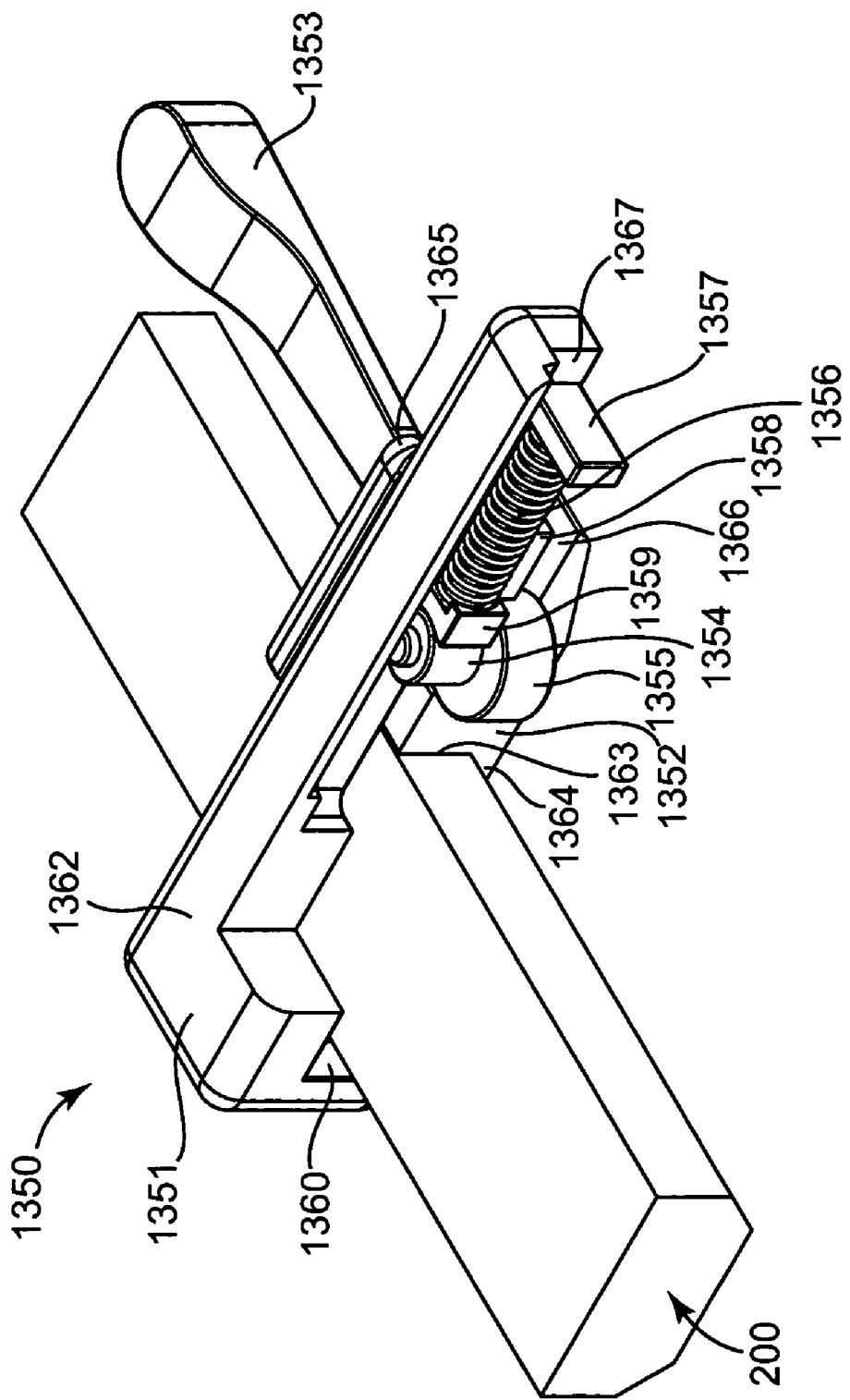
FIGS. 28A and 28B are perspective views of an embodiment of a dual-cam with a wedge and spring clamp for a cardiac tissue stabilizer in open and closed positions with the body partially cut-away.
Figure 28B:
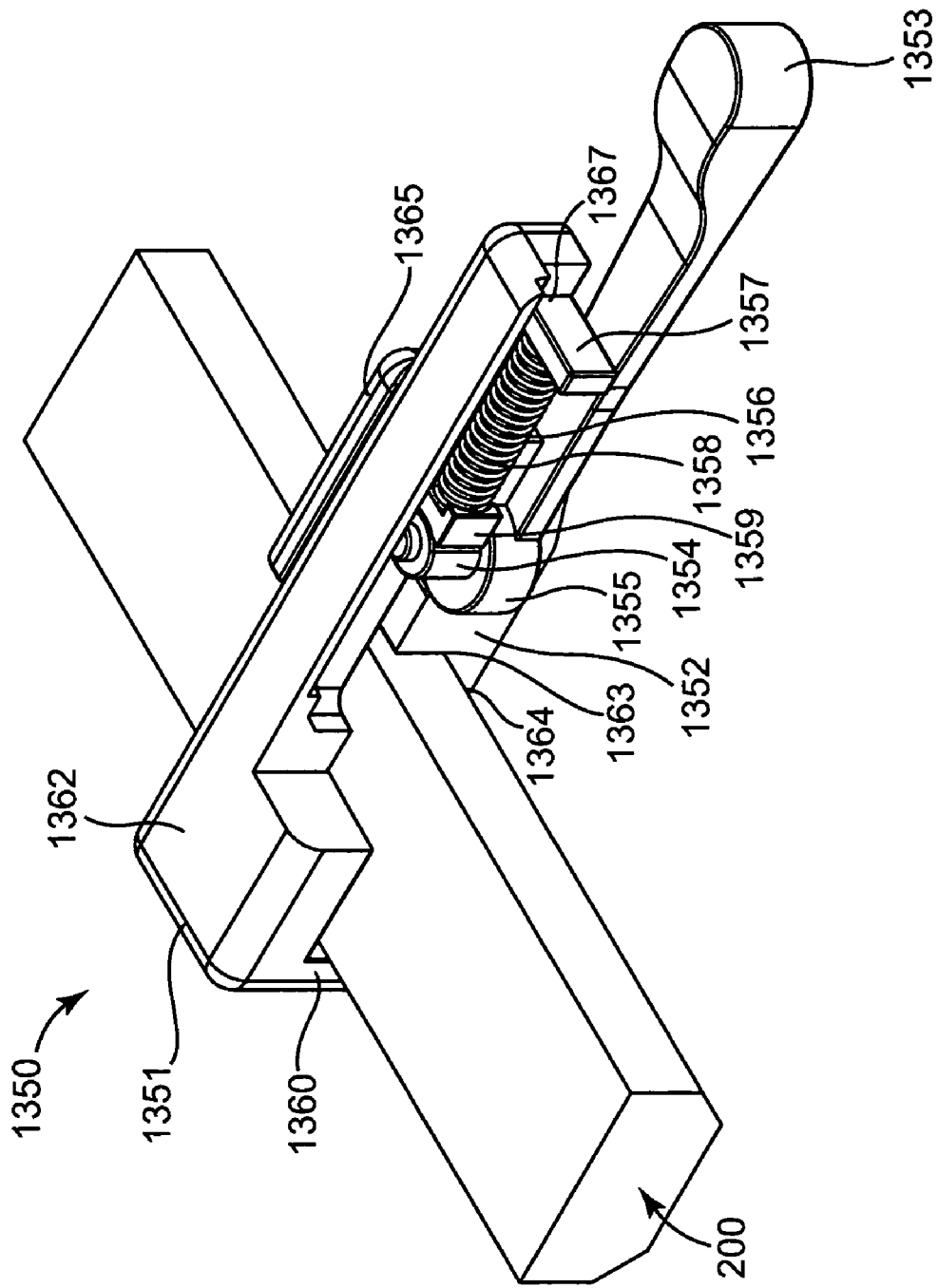

FIGS. 28A and 28B illustrate another embodiment of a cardiac tissue stabilizer clamp 1350. The clamp 1350 can include a front clamp 1351, a rear clamp 1352, an actuation lever 1353, an upper cam 1354, a lower cam 1355, a shaft 1356, a brace 1357, a spring 1358, and a wedge 1359. The front clamp 1351 can include a front flat surface 1360 that can contact a side of the retractor rail 200 and a front angled surface (not shown) which can slide under the retractor rail 200. The front clamp 1351 can also include a body 1362 which can be extended across the retractor rail 200. The body 1362 of the front clamp 1351 is partially cut-away to reveal the positioning of the rear clamp 1352, the upper cam 1354, the lower cam 1355, the shaft 1356, the brace 1357, the spring 1358, and the wedge 1359. The rear clamp 1352 can include a rear flat surface 1363 that can contact a side of the retractor rail 200 and a rear angled surface 1364 which can slide under the retractor rail 200. The rear clamp 1352 can also include a jaw 1365. The jaw 1365 can slidably mount the rear clamp 1352 to the body 1362 of the front clamp 1361 so the rear flat surface 1363 is parallel to and facing the front flat surface 1360.

The lower cam 1355 can be situated in a notch 1366 in the rear clamp 1362. The upper cam 1354 can couple on top of the lower cam 1355 in a groove 1367 in the body 1362 of the front clamp 1361. The brace 1357 can be situated in the groove 1367 of the body 1362 of the front clamp 1361. The shaft 1356 can couple to the brace 1357 and can extend to a point near the upper cam 1354. The wedge 1359 can couple to the shaft 1356 opposite the brace 1357 and can contact the upper cam 1354. The spring 1358 can surround the shaft 1356 and can bias the wedge 1359 into contact with the upper cam 1354. The actuation lever 1353 can integrally form with the lower cam 1355 and can extend away from the rear clamp 1352.

The rear clamp 1352 can slide toward the front clamp 1351 until the rear flat surface 1363 contacts the side of the retractor rail 200. Actuating the actuation lever 1353 can rotate the upper cam 1354 and the lower cam 1355. The upper cam 1355 can engage the groove 1367 in the body 1362 of the front clamp 1351 and can lock the rear clamp 1352 in place. When the upper cam 1354 engages the groove 1367, the wedge 1359 can prevent further rotation of the upper cam 1354. Continued actuation of the actuation lever 1353 can rotate only the lower cam 1355. The lower cam 1355 can cam the rear clamp 1352 into the retractor rail 200, locking the clamp 1350 to the retractor rail 200 as shown in FIG. 28B. An upper cam dwell (not shown) can hold the upper cam 1354 in place. A lower cam dwell (not shown) can hold the lower cam 1355 in place.

Applying a force to the actuation lever 1353 can rotate the actuation lever 1353 back to an unlocked position. Rotation of the actuation lever 1353 can unlock the lower cam 1355 from the lower cam dwell and the upper cam 1354 from the upper cam dwell. Rotation of the actuation lever 1353 can apply a force against the wedge 1359 and the bias of the spring 1358 and can couple the upper cam 1354 with the lower cam 1355. In the unlocked position shown in FIG. 28A, the rear clamp 1352 can slide freely away from the front clamp 1351.

Figure 29A:
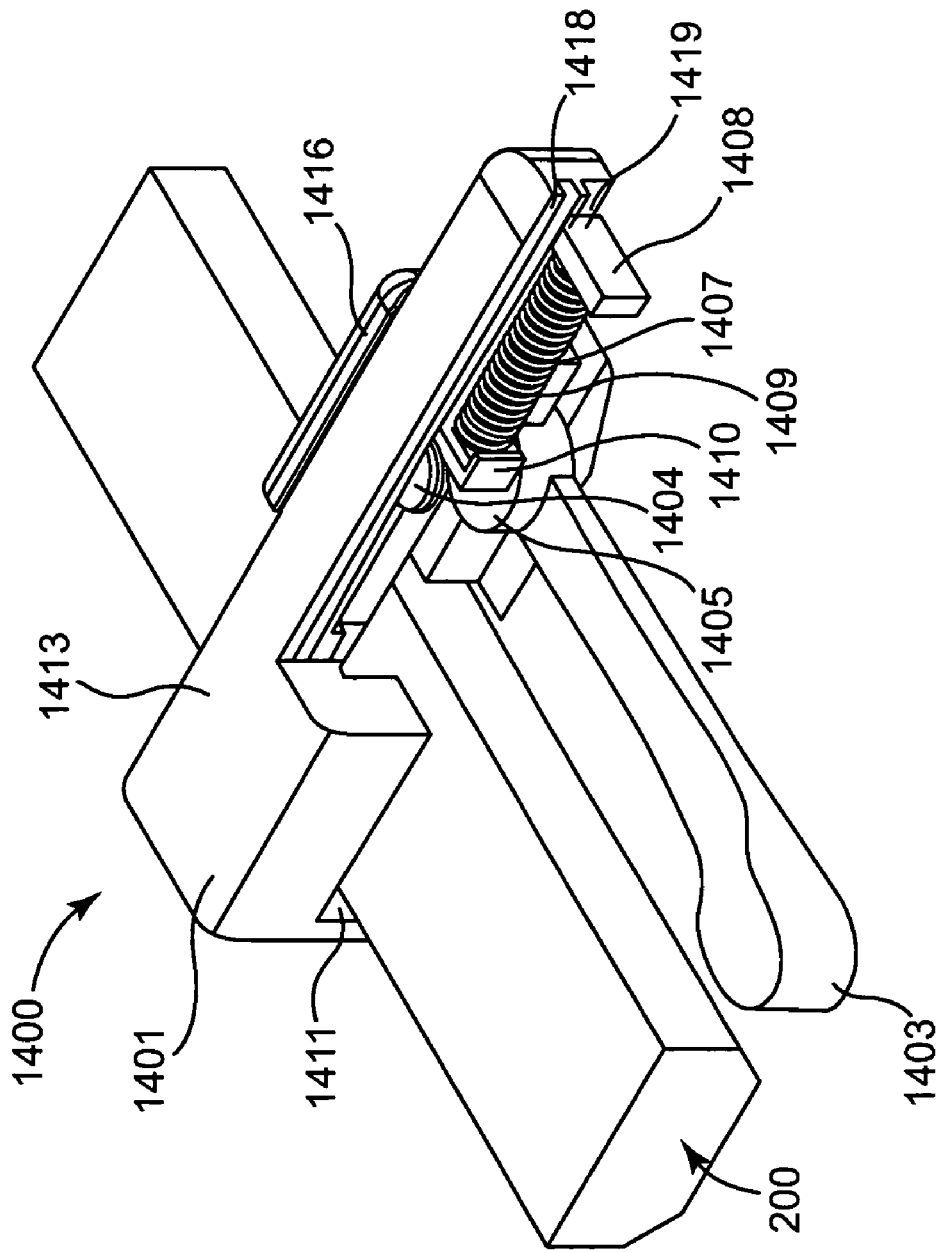
FIGS. 29A and 29B are perspective views of an embodiment of a split dual-cam with a wedge and spring clamp for a cardiac tissue stabilizer in open and closed positions with the body partially cut-away.
Figure 29B:
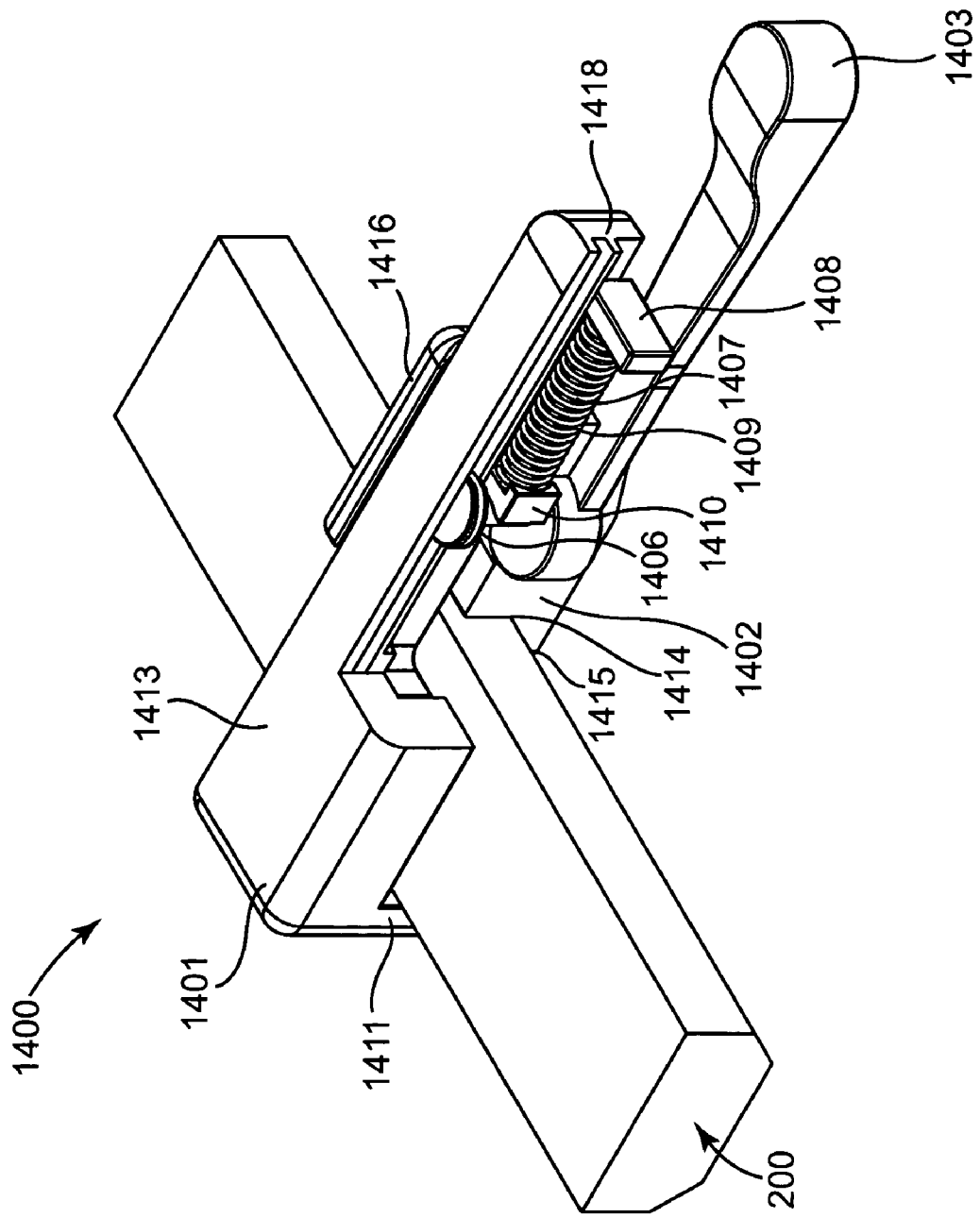

FIGS. 29A and 29B illustrate another embodiment of a cardiac tissue stabilizer clamp 1400. The clamp 1400 can include a front clamp 1401, a rear clamp 1402, an actuation lever 1403, an upper cam 1404, a lower cam 1405, a post 1406, a shaft 1407, a brace 1408, a spring 1409, and a wedge 1410. The front clamp 1401 can include a front flat surface 1411 that can contact a side of the retractor rail 200 and a front angled surface (not shown) which can slide under the retractor rail 200. The front clamp 1401 can also include a body 1413 which can be extended across the retractor rail 200. The body 1413 of the front clamp 1401 is partially cut-away to reveal the positioning of the rear clamp 1402, the upper cam 1404, the lower cam 1405, the post 1406, the shaft 1407, the brace 1408, the spring 1409, and the wedge 1410. The rear clamp 1402 can include a rear flat surface 1414 that can contact a side of the retractor rail 200 and a rear angled surface 1415 which can slide under the retractor rail 200. The rear clamp 1402 can also include a jaw 1416. The jaw 1416 can slidably mount the rear clamp 1402 to the body 1413 of the front clamp 1401 so the rear flat surface 1414 is parallel to and facing the front flat surface 1411.

The lower cam 1405 can be situated in a notch 1417 in the rear clamp 1402. The post 1406 can be extended vertically upwards from the lower cam 1405. The upper cam 1404 can couple to the post 1406 and can be situated in a groove 1418 in the body 1413 of the front clamp 1401. The brace 1408 can be situated in a groove 1419 of the body 1413 of the front clamp 1401. The shaft 1407 can couple to the brace 1408 and can extend to a point near the post 1406. The wedge 1410 can couple to an end of the shaft 1407 opposite the brace 1408 and can engage the upper cam 1404. The spring 1409 can surround the shaft 1407 and can bias the wedge 1410 into contact with the upper cam 1404. The bias from the wedge 1410 can translate through the post 1406 and can bias the rear clamp 1402 toward the front clamp 1401. The actuation lever 1403 can integrally form with the lower cam 1405 and can extend away from the rear clamp 1402.

The rear clamp 1402 can slide toward the front clamp 1401 until the rear flat surface 1414 contacts the side of the retractor rail 200. Actuating the actuation lever 1403 can rotate the upper cam 1404 and the lower cam 1405. The upper cam 1404 can engage the groove 1418 in the body 1413 of the front clamp 1401 and can lock the upper cam 1404 to the long arm 1413 of the front clamp 1401. The lower cam 1405 can cam the rear clamp 1402 into the retractor rail 200. FIG. 29B shows the clamp 1400 locked to the retractor rail 200. An upper cam dwell (not shown) can hold the upper cam 1404 in place. A lower cam dwell (not shown) can hold the lower cam 1405 in place.

FIG. 29A illustrates an unlocked position. Applying a force to the actuation lever 1403 can rotate the actuation lever 1403. Rotation of the actuation lever 1403 can unlock the lower cam 1405 from the lower cam dwell and the upper cam 1404 from the upper cam dwell. Rotation of the actuation lever 1403 can unlock the upper cam 1404 from the body 1413 of the front clamp 1401 and can un-cam the lower cam 1405 from the rear clamp 1402. Applying a force opposing the bias of the spring 1409 can slide the rear clamp 1402 away from the front clamp 1401.

Figure 30A:
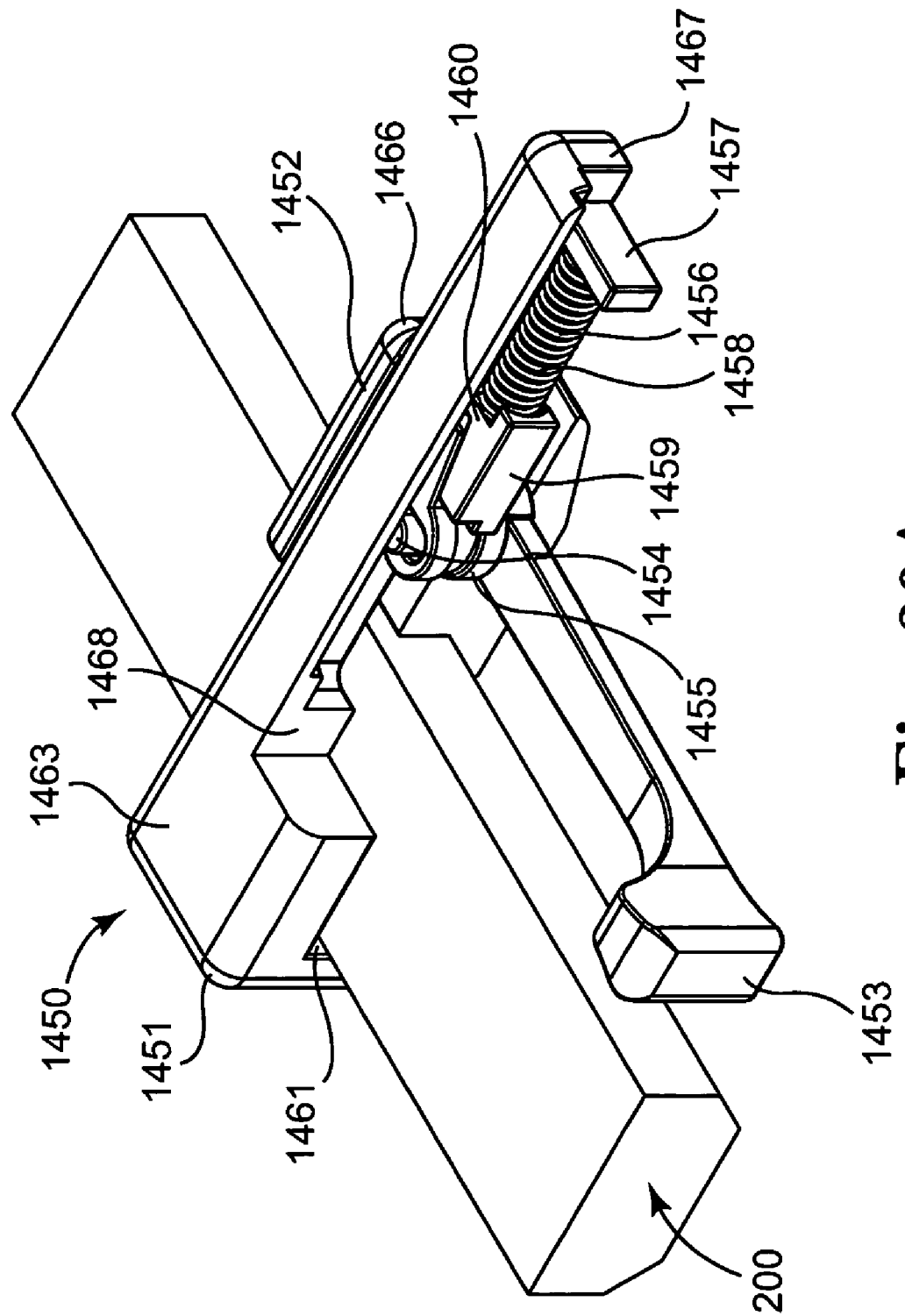
FIGS. 30A and 30B are perspective views of an embodiment of a dual-cam with wedge-lock clamp for a cardiac tissue stabilizer in open and closed positions with the body shown in transparency.
Figure 30B:
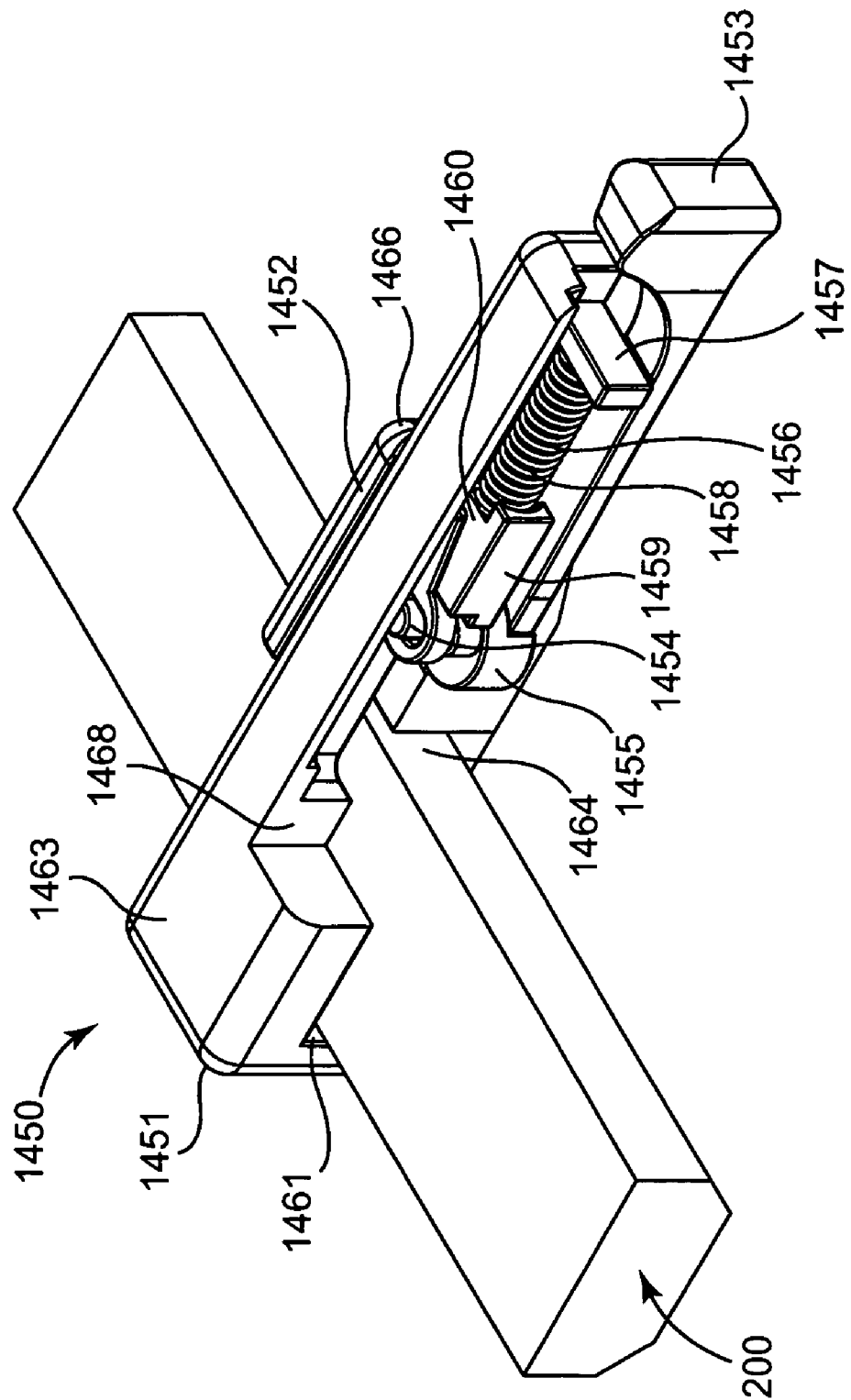

FIGS. 30A and 30B illustrate another embodiment of a cardiac tissue stabilizer clamp 1450. The clamp 1450 can include a front clamp 1451, a rear clamp 1452, an actuation lever 1453, an upper cam 1454, a lower cam 1455, a shaft 1456, a brace 1457, a spring 1458, a first wedge 1459, and a second wedge 1460. The front clamp 1451 can include a front flat surface 1461 that can contact a side of the retractor rail 200 and a front angled surface (not shown) which can slide under the retractor rail 200. The front clamp 1451 can also include a body 1463 which can be extended across the retractor rail 200. The rear clamp 1452 can include a rear flat surface 1464 that can contact a side of the retractor rail 200 and a rear angled surface (not shown) which can slide under the retractor rail 200. The rear clamp 1452 can also include a jaw 1466. The jaw 1466 can slidably mount the rear clamp 1452 to the body 1463 of the front clamp 1451 so the rear flat surface 1464 is parallel to and facing the front flat surface 1461.

The lower cam 1455 can be situated in a notch 1467 in the rear clamp 1452. The upper cam 1454 can couple on top of the lower cam 1455 in a groove 1468 in the body 1463 of the front clamp 1451. The brace 1457 can be situated in the groove 1468 in the body 1463 of the front clamp 1451. The shaft 1456 can couple to the brace 1457 and extend to a point near the upper cam 1454. The first and second wedges 1459 and 1460 can couple to an end of the shaft 1456 opposite the brace 1457 and can engage the upper cam 1454. The spring 1458 can surround the shaft 1456 and can bias the first and second wedges 1459 and 1460 into contact with the upper cam 1454. The upper cam 1454 can position over the second wedge 1460 and can bias the second wedge 1460 in an offset position from the first wedge 1459. The actuation lever 1453 can integrate with the lower cam 1455 and can extend away from the rear clamp 1452.

The rear clamp 1452 can slide toward the front clamp 1452 until the rear flat surface 1464 contacts the side of the retractor rail 200. Actuating the actuation lever 1453 can rotate the upper cam 1454 and the lower cam 1455. The upper cam 1454 can slide off of the second wedge 1460. The second wedge 1460 can translate adjacent to the first wedge 1459. The first and second wedges 1459 and 1460 can lock in the groove 1468 in the body 1463 of the front clamp 1451. Continued actuation of the actuation lever 1453 can rotate only the lower cam 1455. The lower cam 1455 can cam the rear clamp 1452 into the retractor rail 200. FIG. 30B shows the clamp 1450 in a locked position. An upper cam dwell (not shown) can hold the upper cam 1454 in place. A lower cam dwell (not shown) can hold the lower cam 1455 in place.

FIG. 30A illustrates an unlocked position. Applying a force to the actuation lever 1453 can rotate the actuation lever 1453. Rotation of the actuation lever 1453 can unlock the lower cam 1455 from the lower cam dwell and the upper cam 1454 from the upper cam dwell. Rotation of the actuation lever 1453 can slide the upper cam 1454 over the second wedge 1460 and can unlock the first and second wedges 1459 and 1460 from the groove 1468. Applying a force opposing the bias of the spring 1458 can slide the rear clamp 1452 away from the front clamp 1451.

Figure 31B:
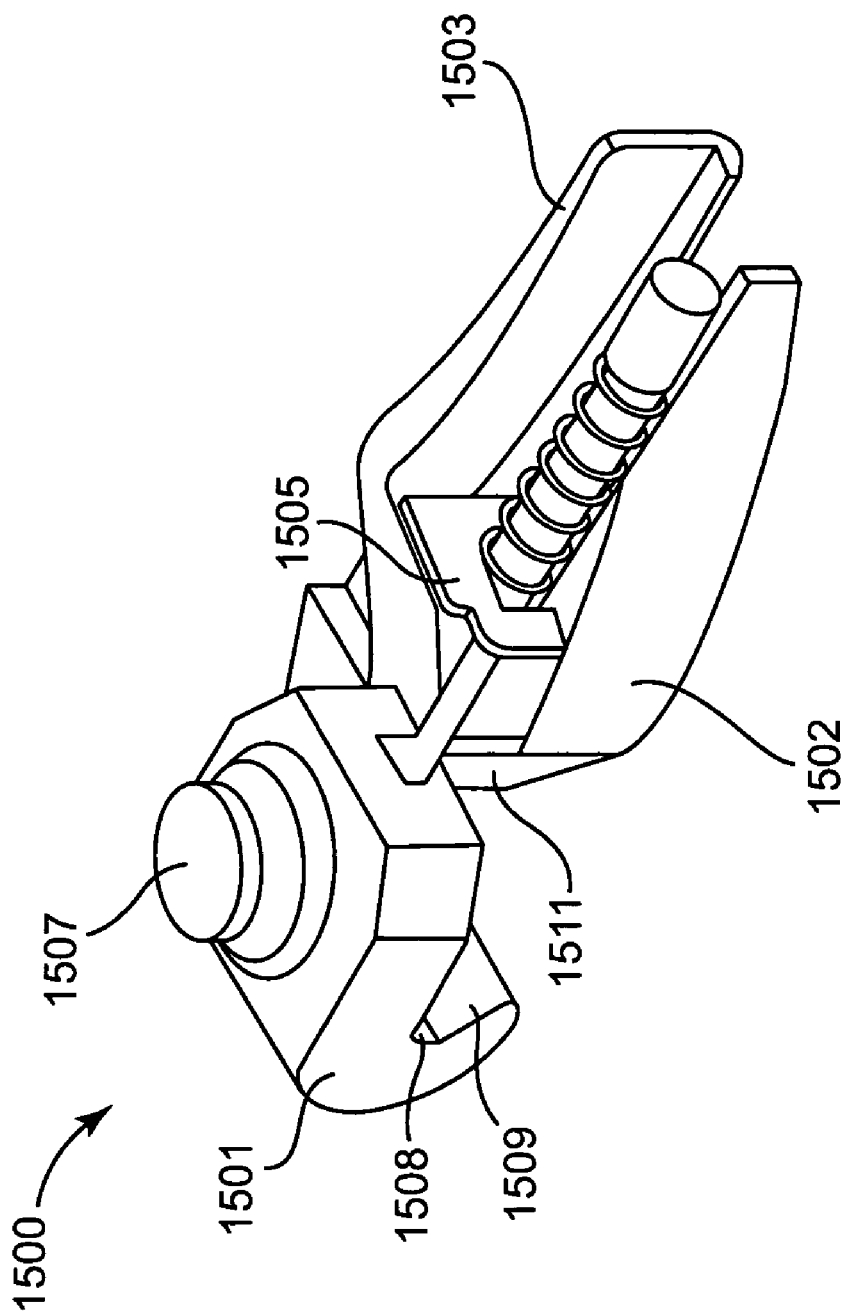

FIGS. 31A and 31B illustrate another embodiment of a cardiac tissue stabilizer clamp 1500. The clamp 1500 can include a front clamp 1501, a rear clamp 1502, an actuation lever 1503, a shaft 1504, a clutch plate 1505, a spring 1506, and a turret mount 1507. The front clamp 1501 can include a front flat surface 1508 that can contact a side of the retractor rail and a front angled surface 1509 which can slide under the retractor rail (not shown). The shaft 1504 can be situated on the front clamp 1501 and can extend perpendicular to the front flat surface 1508. The rear clamp 1502 can include a rear flat surface 1510 that can contact a side of the retractor rail and a rear angled surface 1511 which can slide under the retractor rail. The rear clamp 1502 can also include a cavity 1512. The rear clamp 1502 can mount to the shaft 1504 by sliding the shaft 1504 through the cavity 1512 of the rear clamp 1502. The rear clamp 1502 can be situated such that the rear flat surface 1510 is parallel to and facing the front flat surface 1508.

The actuation lever 1503 can mount to the shaft 1504 inside the rear clamp 1502. The clutch plate 1505 can couple to the actuation lever 1503. The shaft 1504 can extend through an aperture 1513 in the clutch plate 1505. The spring 1506 can surround the shaft 1504 and can bias the rear clamp 1502 towards the front clamp 1501. FIG. 31A illustrates the clamp 1500 in an unlocked position. In the unlocked position, the clutch plate 1505 can orient perpendicular to the shaft 1504 such that the shaft 1504 can slide freely through the aperture 1513 in the clutch plate 1505. FIG. 31B illustrates the clamp 1500 in a locked position. Actuation of the actuation lever 1503 can slightly rotate the clutch plate 1505 causing the clutch plate 1505 to bind the shaft 1504. Binding the shaft 1504 can hold the rear clamp 1502 in position. Further actuation of the actuation lever 1503 can push the rear clamp 1502 slightly toward the front clamp 1501. Actuating the actuation lever 1503 back to the unlocked position can rotate clutch plate 1505 back to the perpendicular orientation with the shaft 1504. Applying a force against the bias of the spring 1506 can slide the rear clamp 1502 away from the front clamp 1501 and can release the clamp 1500 from the retractor rail.

The turret mount 1507 can be situated on the front clamp 1501 opposite from the front angled surface 1509. The turret mount 1507 can include a cylindrical top 1514, an angled groove 1515, and a flat groove 1516. A turret (not shown) can mount to the turret mount 1507 and can be locked in place.

Figure 32A:
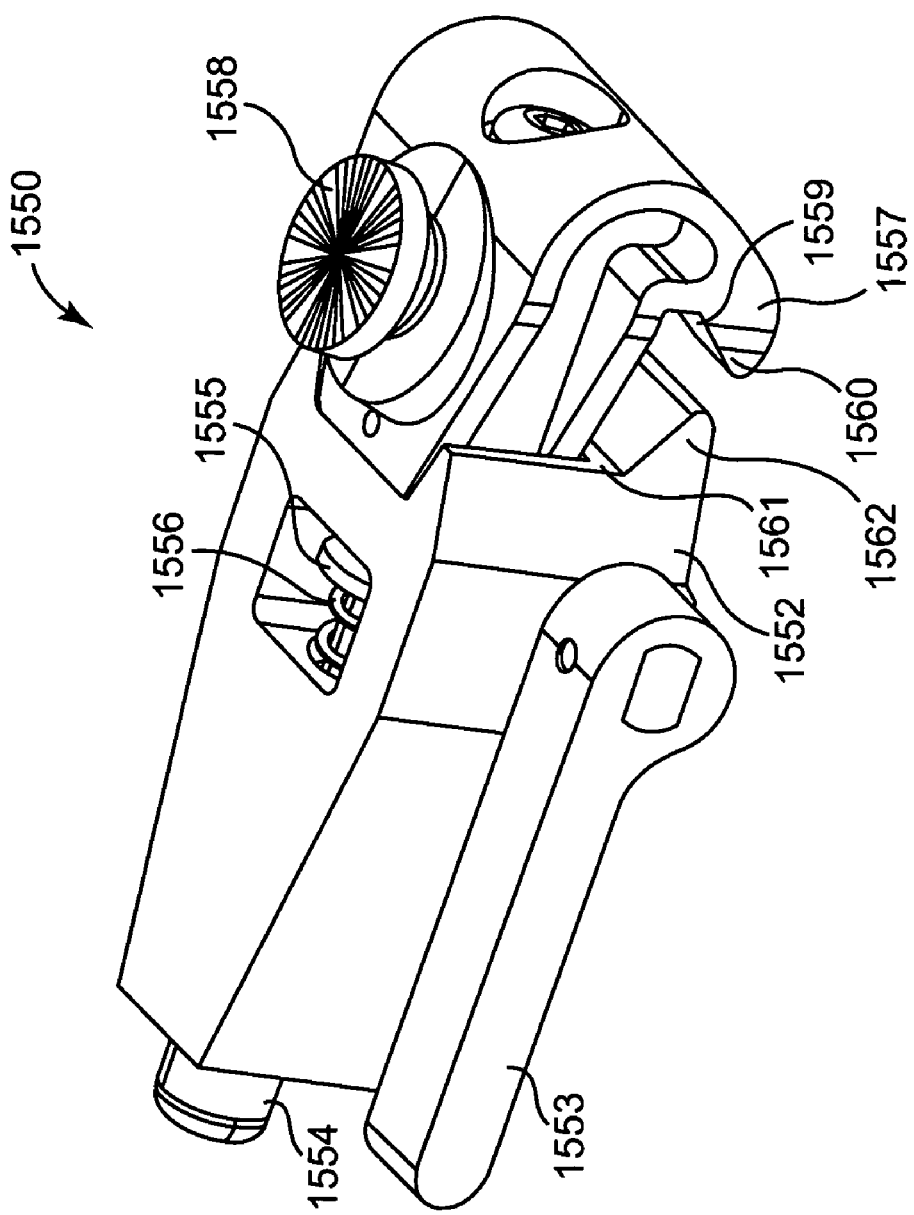
FIGS. 32A and 32B are perspective and side cut-away views of an embodiment of a cardiac tissue stabilizer clamp with the rear clamp shown in transparency in FIG. 32A.
Figure 32B:
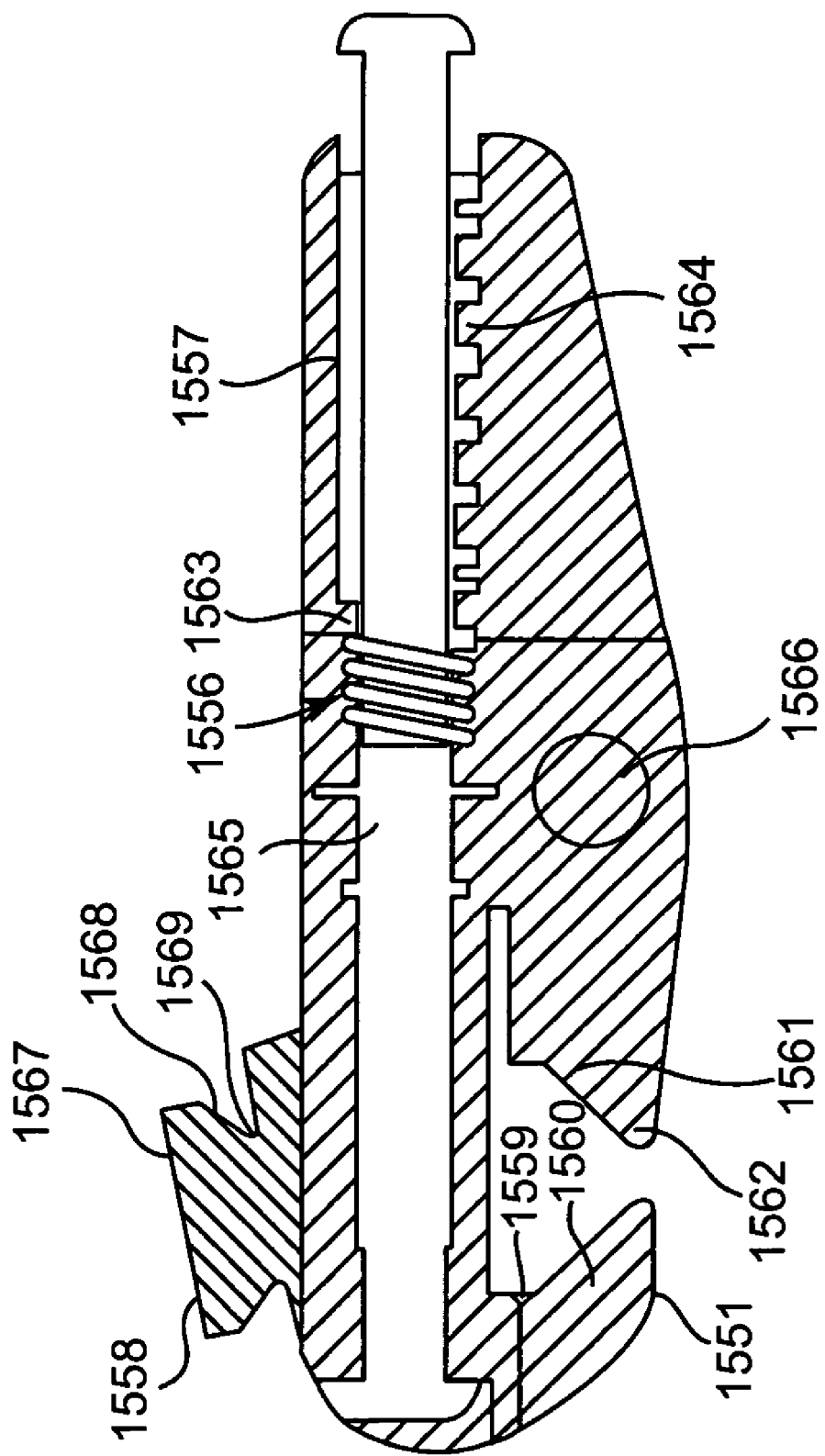

FIGS. 32A and 32B illustrate another embodiment of a cardiac tissue stabilizer clamp 1550. The clamp 1550 can include a front clamp 1551, a rear clamp 1552, an actuation lever 1553, a shaft 1554, a clutch plate 1555, a clutch spring 1556, a shaft spring 1557, and a turret mount 1558. The front clamp 1551 can include a front flat surface 1559 that can contact a side of the retractor rail and a front angled surface 1560 which can slide under the retractor rail. The shaft 1554 can be situated on the front clamp 1551 and can extend perpendicular to the front flat surface 1559. The rear clamp 1552 can include a rear flat surface 1561 that can contact another side of the retractor rail and a rear angled surface 1562 which can slide under the retractor rail. The rear clamp 1552 can also include a first bore 1563 and a second bore 1564. The rear clamp 1552 can mount to the shaft 1554 by sliding the shaft 1554 through the first and second bores 1563 and 1564 of the rear clamp 1552. The rear clamp 1552 can be situated such that the rear flat surface 1561 is parallel to and facing the front flat surface 1559.

The actuation lever 1553 can be coupled to the shaft 1554 inside the rear clamp 1552. The clutch plate 1555 can be coupled to the actuation lever 1553. The shaft 1554 can extend through an aperture 1565 in the clutch plate 1555. The clutch spring 1556 can surround the shaft 1554 in the first bore 1563 and can bias the clutch plate 1555 towards the front clamp 1551. The shaft spring 1557 can surround the shaft 1554 in the second bore 1564 and can bias the rear clamp 1552 towards the front clamp 1551. In an unlocked position, the clutch plate 1555 can couple to a notch 1566 in the actuation lever 1553. The aperture 1565 in the clutch plate 1555 can orient perpendicular to the shaft 1554 such that the shaft 1554 can slide freely through the aperture 1565 in the clutch plate 1555.

FIG. 32B illustrates a locked position. Actuating the actuation lever 1553 can rotate the notch 1566 out of contact with the clutch plate 1555. The clutch plate 1555 can slightly rotate and the aperture 1565 of the clutch plate 1555 can bind the shaft 1554. Binding the shaft 1554 can hold the rear clamp 1552 in place. Actuating the actuation lever 1553 back to an unlocked position can rotate the notch 1566 into contact with the clutch plate 1555. The clutch plate 1555 can rotate and can bring the aperture 1565 of the clutch plate 1555 back to the perpendicular orientation with the shaft 1554. Applying a force against the bias of the shaft spring 1557 can slide the rear clamp 1552 away from the front clamp 1551 and can release the clamp 1550 from the retractor rail.

The turret mount 1558 can be situated on the front clamp 1551 opposite from the front angled surface 1560. The turret mount 1558 can include a cylindrical top 1567, an angled groove 1568, and a flat groove 1569. A turret (not shown) can mount to the turret mount 1558 and can be locked in place.

Figure 33A:
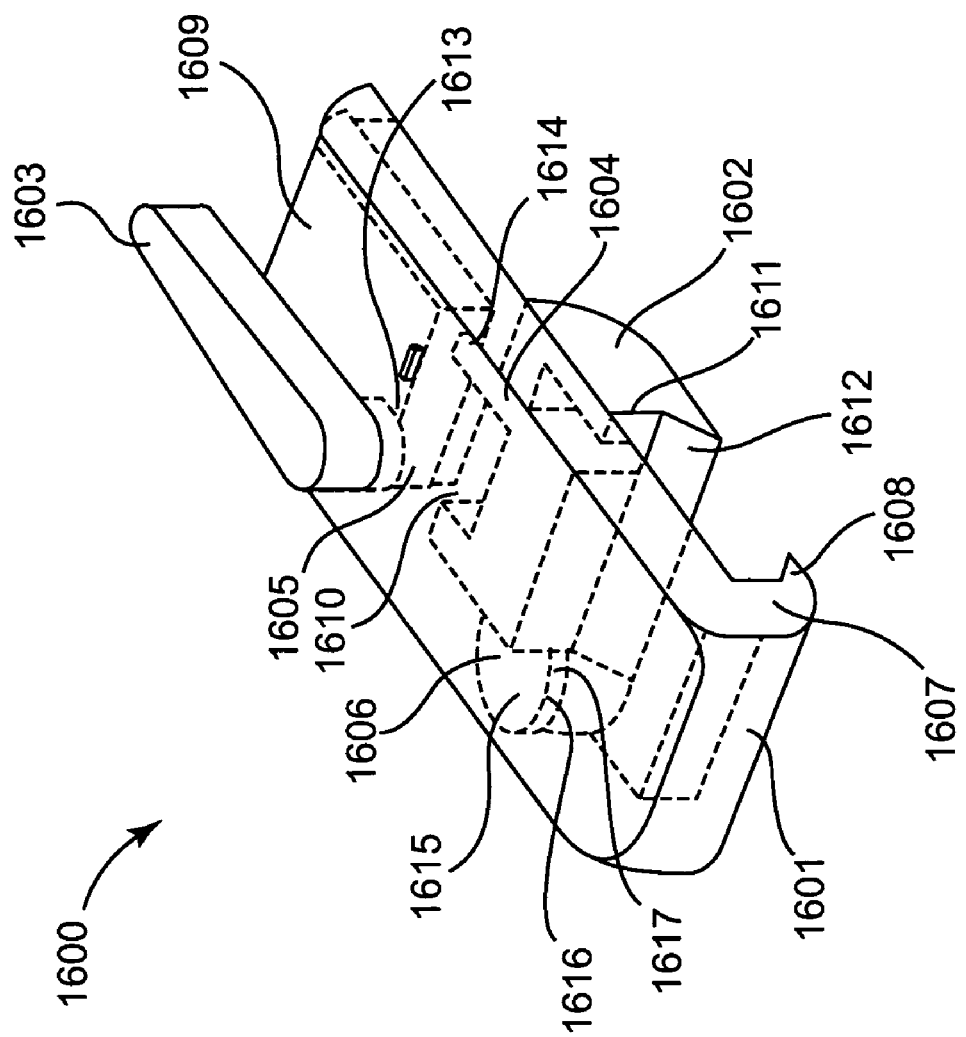
FIGS. 33A and 33B are perspective views of an embodiment of a bar clamp for a cardiac tissue stabilizer in open and closed positions with the body shown in transparency.
Figure 33B:
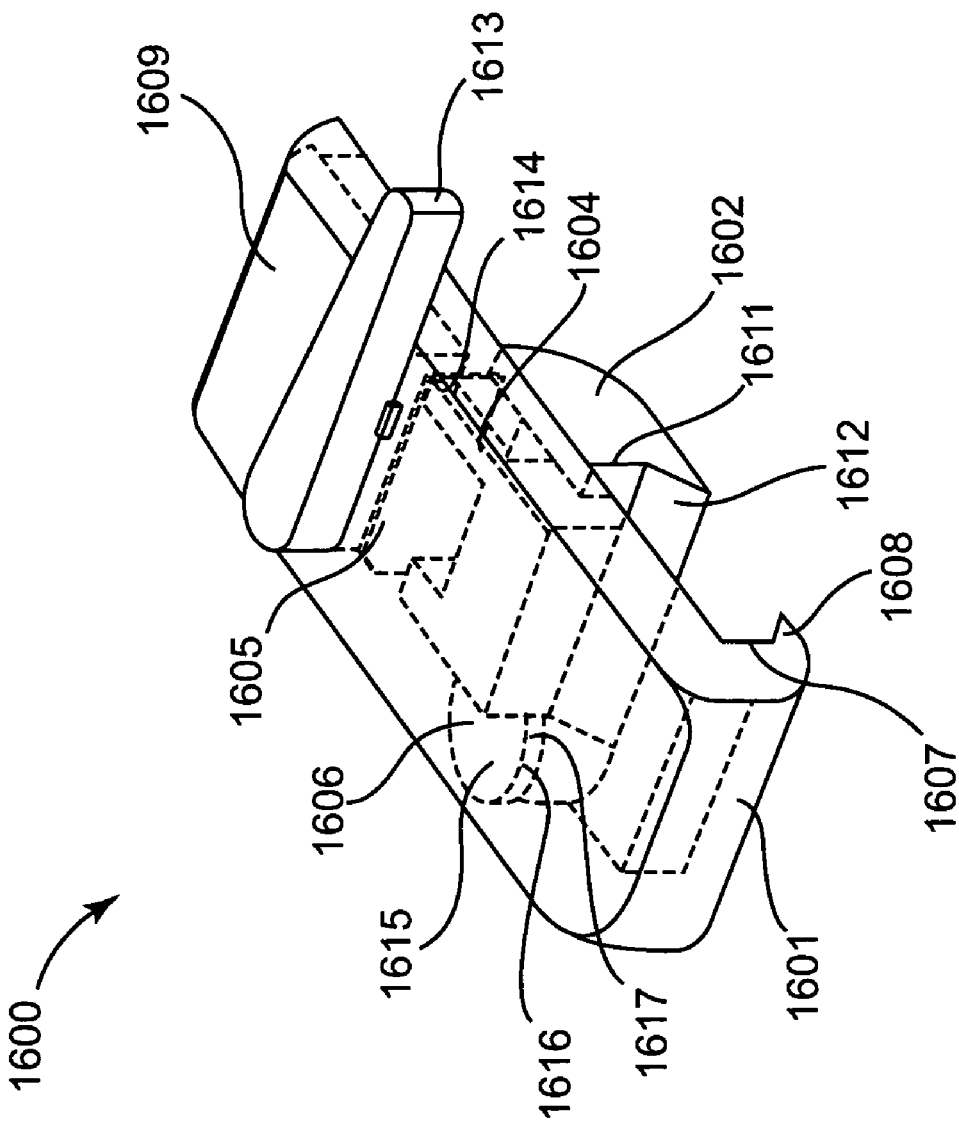

FIGS. 33A and 33B illustrate another embodiment of a cardiac tissue stabilizer clamp 1600. The clamp 1600 can include a front clamp 1601, a rear clamp 1602, an actuation lever 1603, a shaft 1604, a clutch plate 1605, and a turret mount 1606. The front clamp 1601 can include a front flat surface 1607 that can contact a side of the retractor rail and a front angled surface 1608 which can slide under the retractor rail. The front clamp 1601 can also include a body 1609 which can be extended across the retractor rail. The body 1609 of the front clamp 1601 can include a chamber 1610. The rear clamp 1602 can include a rear flat surface 1611 that can contact a side of the retractor rail and a rear angled surface 1612 which can slide under the retractor rail. The shaft 1604 can couple to the rear clamp 1602. The shaft 1604 can slidably mount inside the chamber 1610 of the body 1609. The rear clamp 1602 can be oriented such that the rear flat surface 1611 is parallel to and facing the front flat surface 1607 of the front clamp 1601. The actuation lever 1603 can be situated on the body 1609 of the front clamp 1601 and can extend into the chamber 1610. The clutch plate 1605 can couple to a notch 1613 in the actuation lever 1603. The shaft 1604 can couple through an aperture 1614 in the clutch plate 1605.

FIG. 33A illustrates the clamp 1600 in an unlocked position. In the unlocked position, the clutch plate 1605 can orient perpendicular to the shaft 1604 such that the shaft 1604 can slide freely through the aperture 1614 in the clutch plate 1605. FIG. 33B illustrates the clamp 1600 in a locked position. Actuating the actuation lever 1603 can rotate the notch 1613 in the actuation lever 1603 out of contact with the clutch plate 1605. The clutch plate 1605 can slightly rotate and the aperture 1614 in the clutch plate 1605 can bind the shaft 1604. Binding the shaft 1604 can hold the rear clamp 1602 in place. Further actuation of the actuation lever 1603 can push the rear clamp 1602 toward the front clamp 1601. Actuating the actuation lever 1603 back to the unlocked position can rotate the clutch plate 1605 back to the perpendicular orientation with the shaft 1604. The rear clamp 1602 can slide freely away from the front clamp 1601 and can release the clamp 1600 from the retractor rail.

The turret mount 1606 can be situated on the body 1609 of the front clamp 1601 between the front flat surface 1607 and the rear flat surface 1611. The turret mount 1606 can include a cylindrical top 1615, an angled groove 1616, and a flat groove 1617. A turret (not shown) can mount to the turret mount 160 and be locked in place.

The embodiments of the clamps described herein have been described in relation to a cardiac tissue stabilizer and sternal retractors. However, the clamps may also be used to secure a cardiac tissue stabilizer to an operating table, other surgical equipment, or another stable object near the patient. The clamps may also be used to secure other types of devices to other types of structures having suitable shapes. In addition, the shape of the clamp gripping surfaces, for example, front flat surface, front angle surface, rear flat surface and rear angled surface may have other configurations and/or shape profiles to better grip or make contact with sternal retractors and other devices having differently shaped rails. In one embodiment, the shape of the clamp gripping surfaces is approximately complementary to a shape of the rail which it is intended to be secured to.

Figure 2C:
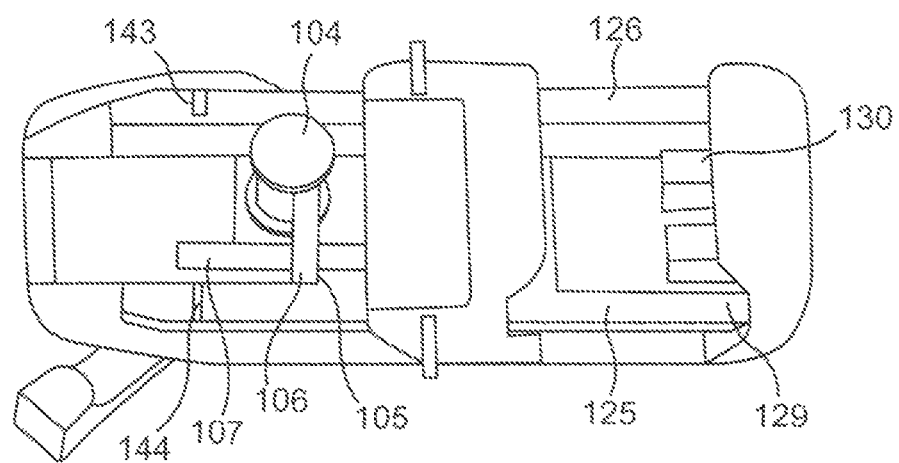

As shown in FIGS. 34A-34D, a tissue stabilizer 100 clamped or mounted to a sternal retractor 50 may be adjusted to move the head-link assembly 30 to a desired position (e.g., inside the chest cavity adjacent the heart 55). The turret 10 can rotate up to 360 degrees to position a proximal end 2185 of the articulating arm 20 so that the articulating arm 20 does not obstruct the operating arena. For example, FIG. 2C illustrates the turret 10 rotated about 0 degrees, FIGS. 2B and 2D illustrate the turret 10 rotated about 45 degrees, and FIG. 2A illustrates the turret 10 rotated about 90 degrees. The articulating arm 20 is movable to position the head-link assembly 30 over the surgical field, and the head-link assembly 30 is movable to contact the surface of the heart.

In one embodiment, the handle 15 is coupled to the turret 10, the articulating arm 20, the collet assembly 25, and the head-link assembly 30. The handle 15 is operable to permit or prevent relative movement therebetween. In one embodiment, the handle 15 may be rotated in a loosening direction (e.g., counter clockwise) to release a holding force, such as tension on the tissue stabilizer 100, and permit movement of the turret 10, articulating arm 20, collet assembly 25, and head-link assembly 30. When in such a loosened condition, the surgeon is able to manipulate the components of the tissue stabilizer 100 in order to position the head-link assembly 30 where desired within the surgical field. The handle 15 may be rotated in a tightening direction (e.g., clockwise) to exert a holding force, such as tension on the tissue stabilizer 100, and prevent movement of the turret 10, articulating arm 20, collet assembly 25, and head-link assembly 30. When in such a tightened condition, the tissue stabilizer 100 is substantially immobilized in order to stabilize the position and position of the head-link assembly 30.

Figure 35:
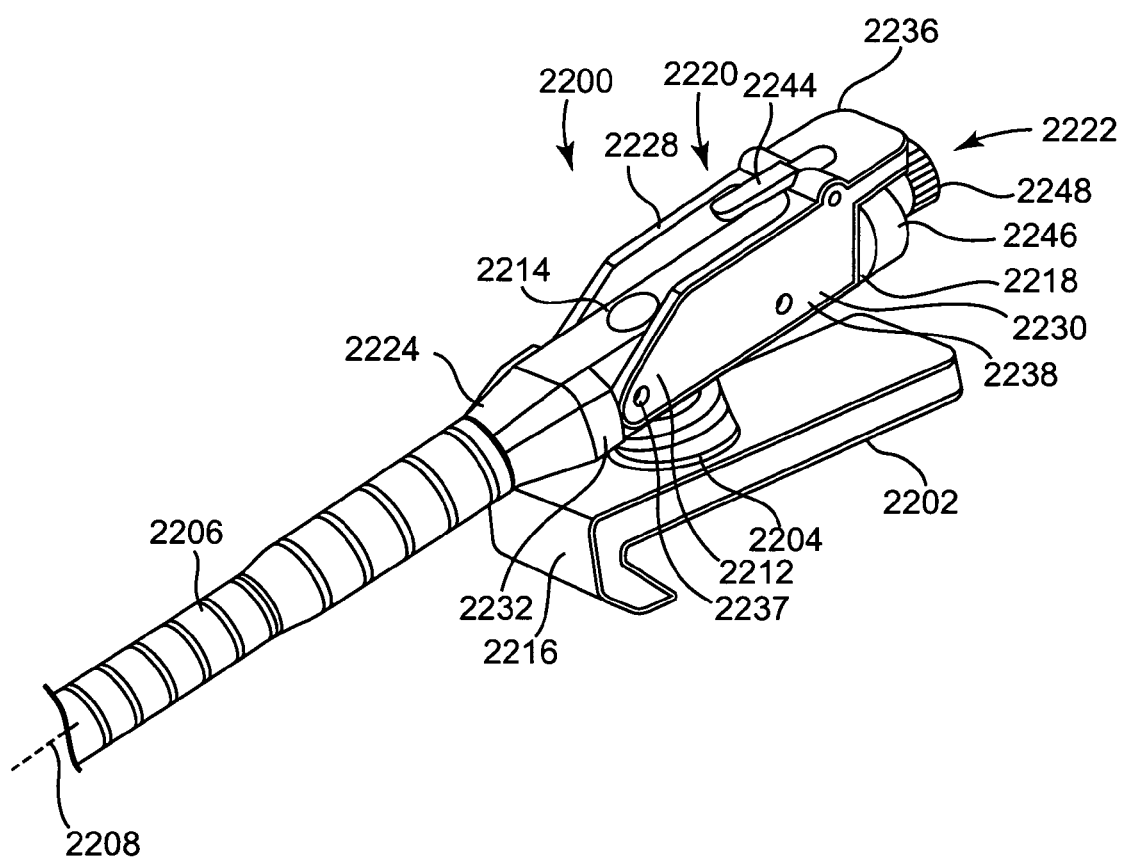
FIG. 35 is a perspective view of a turret assembly for a tissue stabilizer according to one embodiment of the invention.
Figure 36:
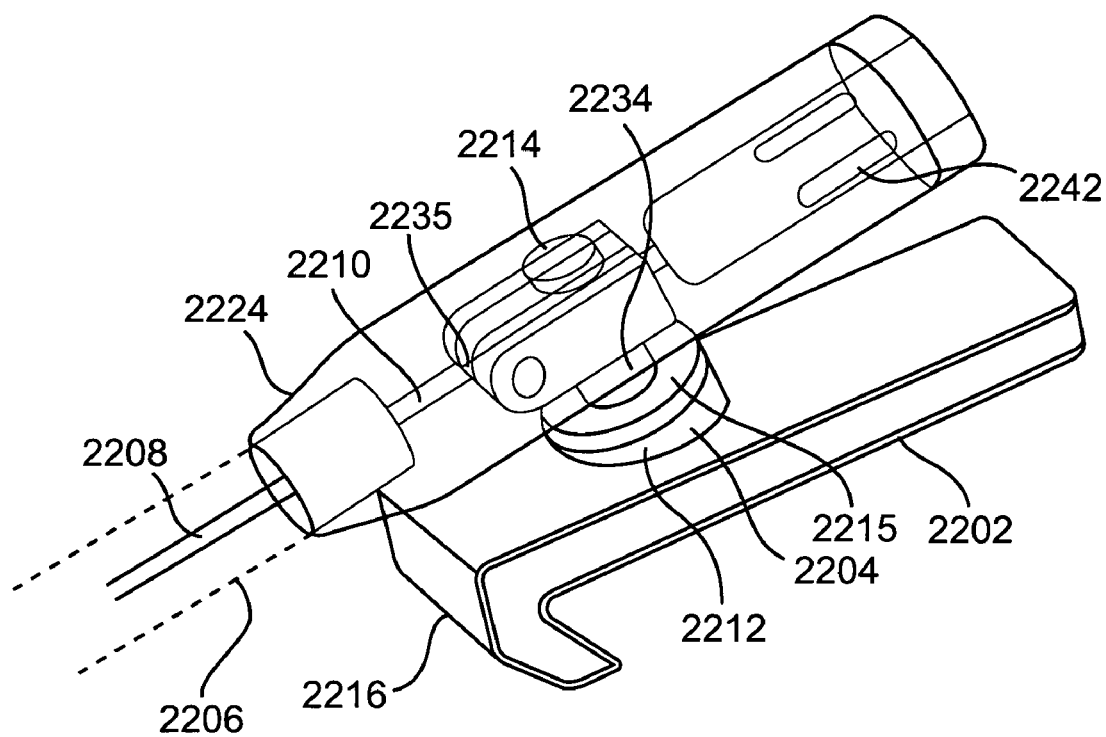
FIG. 36 is a perspective, partially transparent view of the turret assembly of FIG. 35 with the lever arm removed.

FIGS. 35-39 illustrate a turret assembly 2200 according to one embodiment of the invention. The turret assembly 2200 can be rotatably mounted to a clamp member 2202 with a turret mount assembly 2204. An articulating arm 2206 can be coupled to the turret assembly 2200 and can rotate with the turret assembly 2200 relative to the clamp member 2202. A tension element 2208 can extend through the articulating arm 2206 and can be coupled at a proximal end 2210 (as shown in FIG. 36) to the turret assembly 2200. The turret assembly 2200 can be operable to exert a tensioning force on the tension element 2208 in order to lock the articulating arm 2206 into a selected position. Upon release of the tensioning force, the tension element 2208 can be loosened so that the articulating arm 2206 can be manipulated.

The turret mount assembly 2204 can include a base 2212 and a cylinder 2214 rotatably mounted to the base 2212. The turret mount assembly 2204 can include a plate 2215 supporting the cylinder and being rotatably mounted to the base 2212 (as shown in FIG. 36). The base 2212 can be mounted to the clamp member 2202 or can be an integral part of the clamp member 2202. The base 2212 can be angled or beveled so that the plate 2215 and the cylinder 2214 can be angled relative to the clamp member 2202. For example, the cylinder 2214 can be angled toward a front portion 2216 of the clamp member 2202. The turret assembly 2200 can be mounted to the cylinder 2214 in order to rotate relative to the clamp member 2202. The turret assembly 2200 can also be mounted to the cylinder 2214 in order to extend at an angle relative to the clamp member 2202, according to the angle of the plate 2215 and the cylinder 2214 relative to the clamp member 2202. By angling the turret assembly 2200, and thus the articulating arm, downward relative to the front portion 2216 of the clamp member 2202 into the surgical field, the articulating arm can be oriented into the surgical field with a reduced clearance relative to the clamp member 2202. This can help reduce the portion of the surgical field needed to accommodate the articulating arm.

Figure 37:
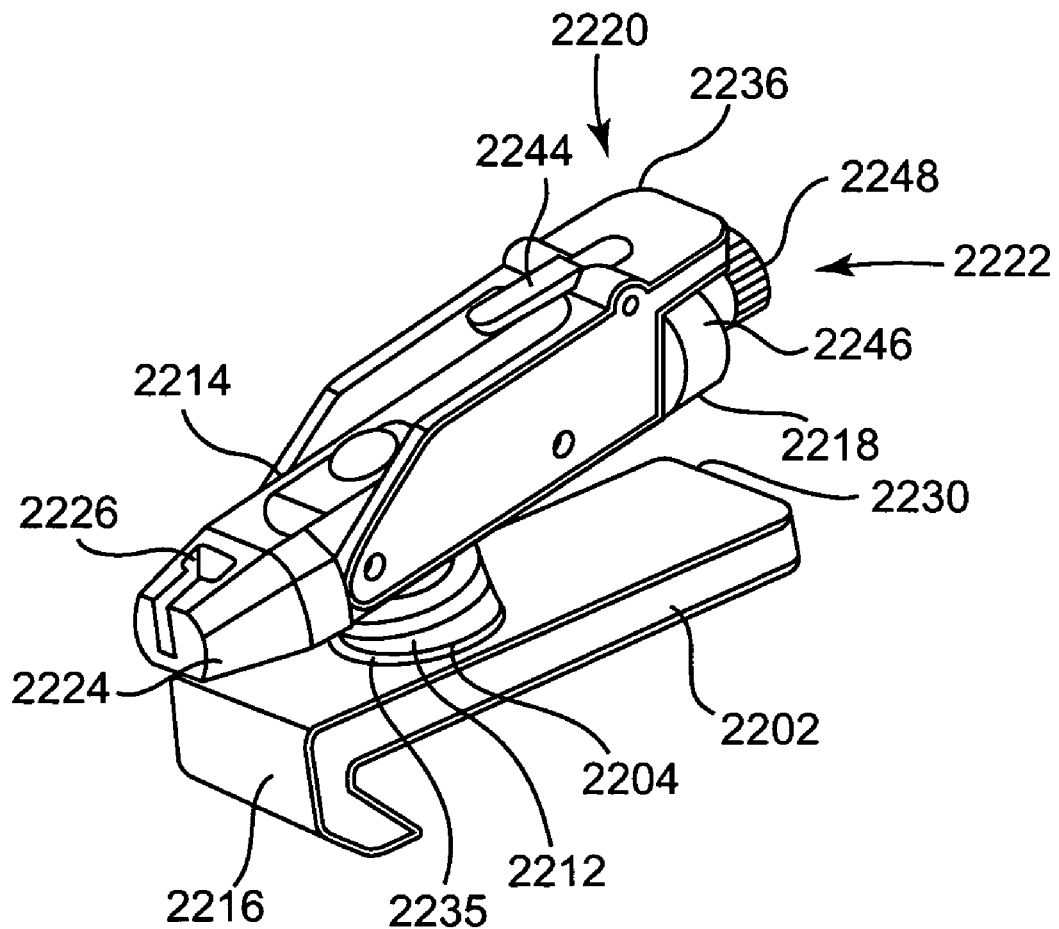
FIG. 37 is a perspective, partially transparent view of internal elements of the turret assembly of FIG. 35 with the lever arm in a closed position.

The turret assembly 2200 can include a body 2218, a locking mechanism 2220 and an adjustment mechanism 2222. The body 2218 can be supported on a clamping member 2234 (as shown in FIG. 36) that is can be coupled to the cylinder 2214. The body 2218 can have a nose 2224 adapted for coupling to the articulating arm 2206. The nose 2224 can include a keyed slot 2226 (as shown in FIG. 37) adapted for receiving a mating feature (not shown) on the articulating arm 2206.

The locking mechanism 2220 can include a lever arm 2228 and a pair of links 2230 for coupling the tension element 2208 to the lever arm 2228. The lever arm 2228 can have a pivoting end 2232 and a free end 2236. The clamping body 2234 can have a pair of pins 2235 (as shown in FIG. 36) received in cylindrical openings 2237 at the pivoting end 2232 of the lever arm 2228 to pivotably couple the lever arm 2228 to the clamping body 2234. The free end 2236 can be actuated to pivot or toggle the lever arm 2228 between an open or raised position and a closed or lowered position.

Figure 38:
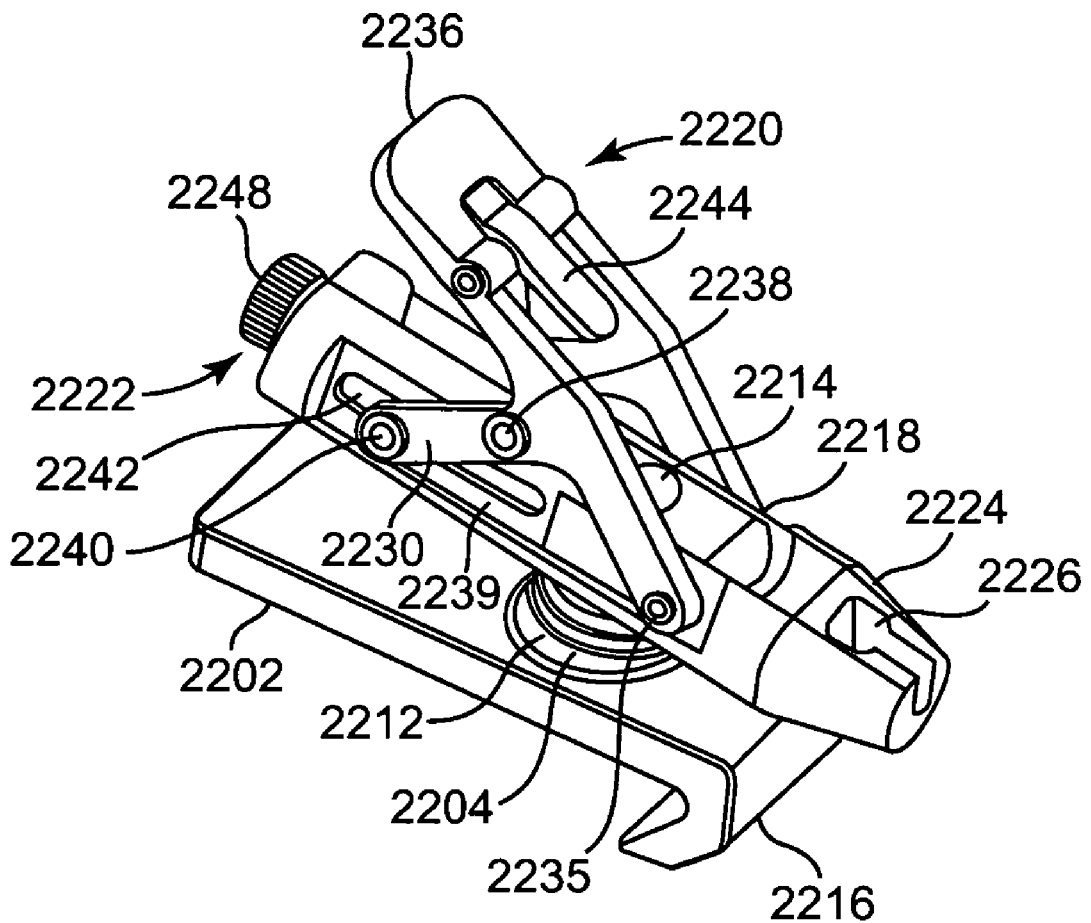
FIG. 38 is a perspective, partially transparent view of the turret assembly of FIG. 35 with the lever arm in an open position.
Figure 39:
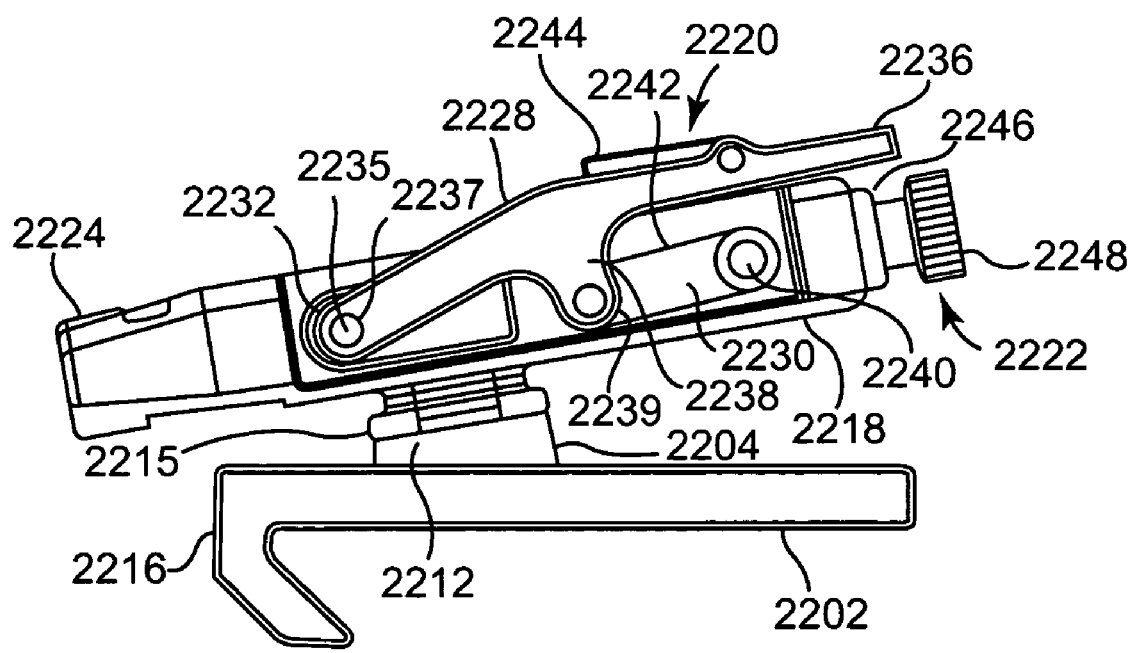
FIG. 39 is a side view of the turret assembly of FIG. 35 with the lever arm in the closed position.

As shown in FIG. 35, a first end 2238 of the links 2230 can be pivotably coupled to the lever arm 2228 between the pivoting end 2232 and the free end 2236. A second end 2240 (as shown in FIG. 38) of the links 2230 can be slidable along guides 2242 (as shown in FIG. 36) in the body 2218. The guides 2242 can be slots, as shown in FIG. 36, or alternately, recesses or grooves. Pivoting the lever arm 2228 about the pins 2235 can cause the second end 2240 of each link 2230 to slide within the respective guide 2242. Comparing FIGS. 38 and 39, when the lever arm 2228 is in an open position, the second end 2240 of the link 2230 can be positioned forward of the guide 2242 closer to the nose 2224 of the body 2218. When the lever arm 2228 is in a closed position, the second end 2240 of the link 2230 can slide rearward of the guide 2242 away from the nose 2224.

As shown in FIG. 36, the proximal end 2210 of the tension element 2208 can be coupled to the link 2230 so that a tensioning force can be exerted on the tension element 2208 when the lever arm 2228 is in the closed position. For example, when the lever arm 2228 is moved into the closed position shown in FIG. 37, the link 2230 can slide back in the guide 2242 and can pull on the tension element 2208, exerting a tensioning force on the tension element 2208. Likewise, when the lever arm 2228 is moved to the open position shown in FIG. 38, the link 2230 can move toward the nose 2224, releasing the tensioning force on the tension element 2208. The lever arm 2228 can be over-centered so that the tension exerted on it by the tensioned tension element 2208 when in the closed position prevents the lever arm 2228 from inadvertently toggling to the open position.

The tensioning force exerted on the tension element 2208 can prevent articulation and manipulation of the articulating arm 2206. The amount of slack in the tension element 2208 and the amount of travel by the second end 2240 of the link 2230 in the guide 2242 can be varied to control the tensioning force exerted by the locking mechanism 2220 on the tension element 2208. In one embodiment, the locking mechanism 2220 is adapted to exert a tensioning force on the tension element 2208 sufficient to immobilize the articulating arm 2206 when the lever arm 2228 is toggled to the closed position.

The locking mechanism 2220 can also clamp the turret assembly 2200 onto the turret mount assembly 2204 in order to prevent rotation of the turret assembly 2200 relative to the clamp member 2202. As the lever arm 2228 is pivoted into the closed position, the tensioning force exerted on the tension element 2208 can cause the clamping body 2234 to clamp the body 2218 against the turret mount 2212. This can create a friction force between the body 2218 and the turret mount 2212, preventing relative rotation. When the lever arm 2228 is moved into the open position, the tension on the tension element 2208 can be released so that the compression force between the body 2218 and the turret mount 2212 can be released, permitting the turret assembly 2200 to rotate relative to the clamp member 2202.

The lever arm 2228 can further include a tongue 2244 pivotably coupled to the free end 2236 of the lever arm 2228. The tongue 2244 can brace against the body 2218 when the lever arm 2228 is being moved from the closed or lowered position to the open or raised position. The tongue 2244 can help the user to overcome the tension exerted by the tensioned cable 2208 on the closed lever arm 2228, because of the lever arm 2228 over-center position, to more easily raise the lever arm 2228 to the open position.

The adjustment mechanism 2222 can include a threaded member 2246 supporting a knob 2248 and can be coupled to the tension element 2208. The knob 2248 can be operable to rotate the threaded member 2246 relative to the body 2218 in order to pull the tension element 2208 distally, thereby tensioning the tension element 2208. Thus, the adjustment mechanism 2222 can exert a tensioning force on the tension element 2208 without pivoting the lever arm 2228. In this manner, the tension element 2208 can be pre-loaded with a tensioning force. The adjustment mechanism 2222 can pre-load a tensioning force on the tensioning cable 2208 to increase the shape-retaining characteristics of the articulating arm 2206 while the user is positioning the articulating arm 2206 over the surgical field. The adjustment mechanism 2222 can also compensate for overly loose or tight tension elements, for example, stretched tension elements.

The user can lock or immobilize the articulating arm 2206 as well as the turret assembly 2200 by pivoting the lever arm 2228 downwardly. With the lever arm 2228 in the closed position, the turret assembly 2200 has a relatively flat profile. The turret assembly 2200 thus can provide a convenient location for the user to lean or brace against. The user can release the articulating arm 2206 for articulation and release the turret assembly 2200 for rotation by pivoting the lever arm

2228 upwardly. When positioning the articulating arm 2206 over a surgical field, for example, the user can use one hand to manipulate the head-link assembly 30 into a particular position and can use the other hand to adjust the tension in the articulating arm 2206 with the adjustment mechanism 2222 and to lock the articulating arm 206 and the turret assembly 2200 with the lock mechanism 2220.

Figure 40:
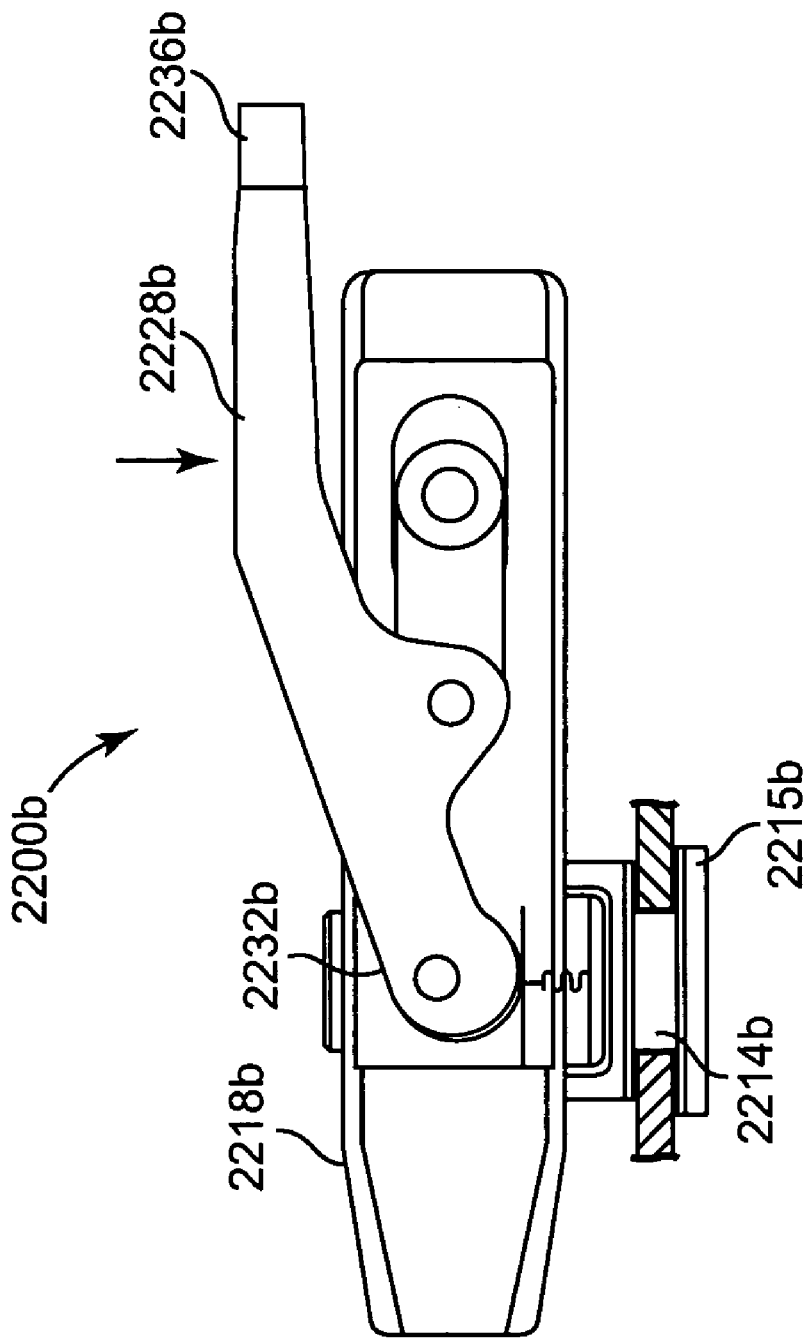
FIG. 40 is a side view of a turret assembly for a tissue stabilizer according to another embodiment of the invention.

FIG. 40 illustrates a turret assembly 2200b that is generally similar to the turret assembly 2200 of FIGS. 35-39, with like parts given like numbering. As shown in FIG. 40, the pivoting end 2232b of the lever arm 2228b can be cammed. When the lever arm 2228b is moved to the closed position, the pivoting end 2232b engages the body 2218b. This helps to lock the lever arm 2228b into the closed position and prevent the lever arm 2228b from inadvertently raising to the open position.

Figure 41:
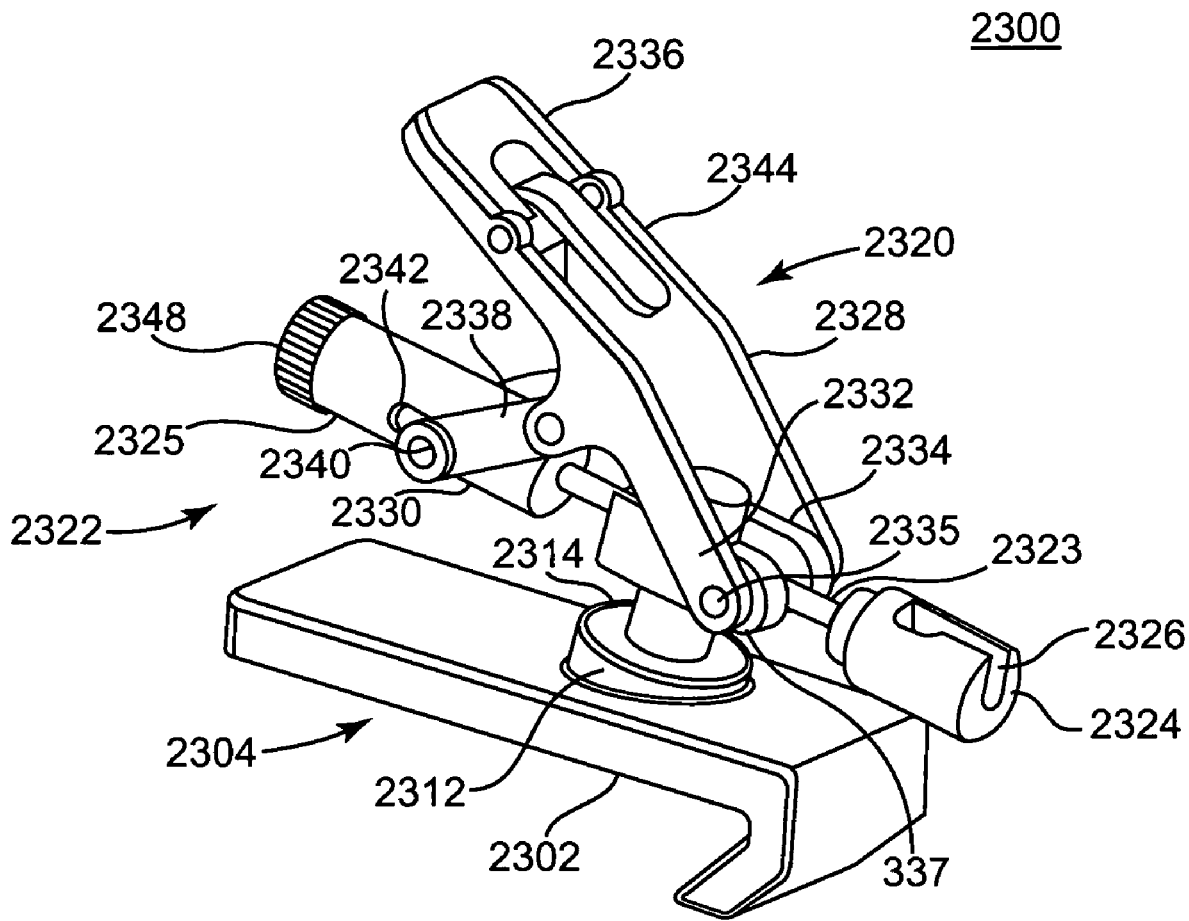
FIG. 41 is a perspective view of a turret assembly for a tissue stabilizer according to another embodiment of the invention.

FIG. 41 illustrates a turret assembly 2300 according to another embodiment of the invention. The turret assembly 2300 can be rotatably mounted to a clamp member 2302 with a turret mount assembly 2304. The turret mount assembly 2304 can include a base 2312 and a cylinder 2314 rotatably mounted to the base 2312. The turret assembly 2300 can be mounted to the cylinder 2314 in order to be rotatable relative to the clamp 2302. The turret assembly 2300 can include a clamping body 2334 supporting a locking mechanism 2320 and an adjustment mechanism 2322. The clamping body 2334 can be coupled to the cylinder 2314. A rod 2323 can extend through the cylinder 2314. The rod 2323 can have a first end with a nose 2324 with a keyed slot 2326 adapted for coupling to an articulating arm (not shown). The rod 2323 can have a second end supporting a housing 2325.

The locking mechanism 2320 can include a lever arm 2328 and a pair of links 2330. The lever arm 2328 can have a pivoting end 2332 and a free end 2336. The pivoting end 2332 can be pivotably coupled to the clamping body 2334 with a pair of pins 2335 received in cylindrical openings 2337 at the pivoting end 2332 of the lever arm 2328.

A first end 2338 of the links 2330 can be pivotably coupled to the lever arm 2328 between the pivoting end 2332 and the free end 2336. A second end 2340 of the links 2330 can be slidable along guides 2342 in the housing 2325. Pivoting the lever arm 2328 about the pins 2335 can cause the links 2330 to slide within the guides 2342. When the free end 2336 of the lever arm 2328 is in an open position, the second end 2340 of the links 2330 can be positioned forward of the guides 2342 closer to the nose 2324. When the free end 2336 of the lever arm 2328 is in a closed position, the second end 2340 of the links 2330 can be slid in the guides 2342 away from the nose 2324. A tension element (not shown) can be coupled to the links 2330 so that a tensioning force can be exerted on the tension element when the lever arm 2328 is in the closed position. Likewise, the tensioning force on the tension element can be released by moving the lever arm 2328 to the open position.

The locking mechanism 2320 can clamp the clamping body 2334 onto the turret mount assembly 2304 in order to prevent rotation of the turret assembly 2300 relative to the clamp 2302. As the lever arm 2328 is moved toward the housing 2335, the tensioning force exerted on the tension element can also cause the clamping body 2334 to clamp onto the cylinder 2314. This can create a friction force between the clamping body 2334 and the cylinder 2314, preventing relative rotation. When the lever arm 2328 is moved upwardly away from the housing 2335, the tension on the tension element can be released so that the compression force on the cylinder 2314 can be released, permitting the turret assembly 2300 to rotate relative to the cylinder 2314.

The lever arm 2328 can further include a tongue 2344 pivotably coupled to the free end 2336 of the lever arm 2328. The tongue 2344 can brace against the housing 2335 when the lever arm 2328 is being moved from the closed position to the open position. The tongue 2344 can help the user to raise the lever arm 2328 to the open position.

The adjustment mechanism 2322 can include a threaded member (not shown) supported in the housing 2335 and operably coupled to a knob 2348. The threaded member can be coupled to the tension element. The knob 2348 can be operable to rotate the threaded member relative to the housing 2335 so as to tension the tension element. In this manner, the tension element can be pre-loaded with a tensioning force.

The user can thus lock or immobilize the articulating arm as well as the turret assembly 2300 with a single action, i.e., by pivoting the lever arm 2328 downwardly. Likewise, the user can release the articulating arm for articulation and release the turret assembly 2300 for rotation by a single action, i.e., by pivoting the lever arm 2328 upwardly. When positioning the articulating arm over a surgical field, for example, the user can use one hand to manipulate the head-link assembly 30 (as shown in FIGS. 34A-34D) into a particular position and can use the other hand to adjust the tension in the articulating arm with the adjustment mechanism 2322 and/or to actuate the locking mechanism 2320 to substantially lock or immobilize the articulating arm and the turret assembly 2300.

FIGS. 42-45 illustrate a turret assembly 2400 according to another embodiment of the invention. The turret assembly 2400 can be rotatably mounted to a clamp 2402 with a turret mount assembly 2404. The turret mount assembly 2404 can include an angled base 2412 and a cylinder 2414 extending upwardly from the base 2412.

Figure 45:
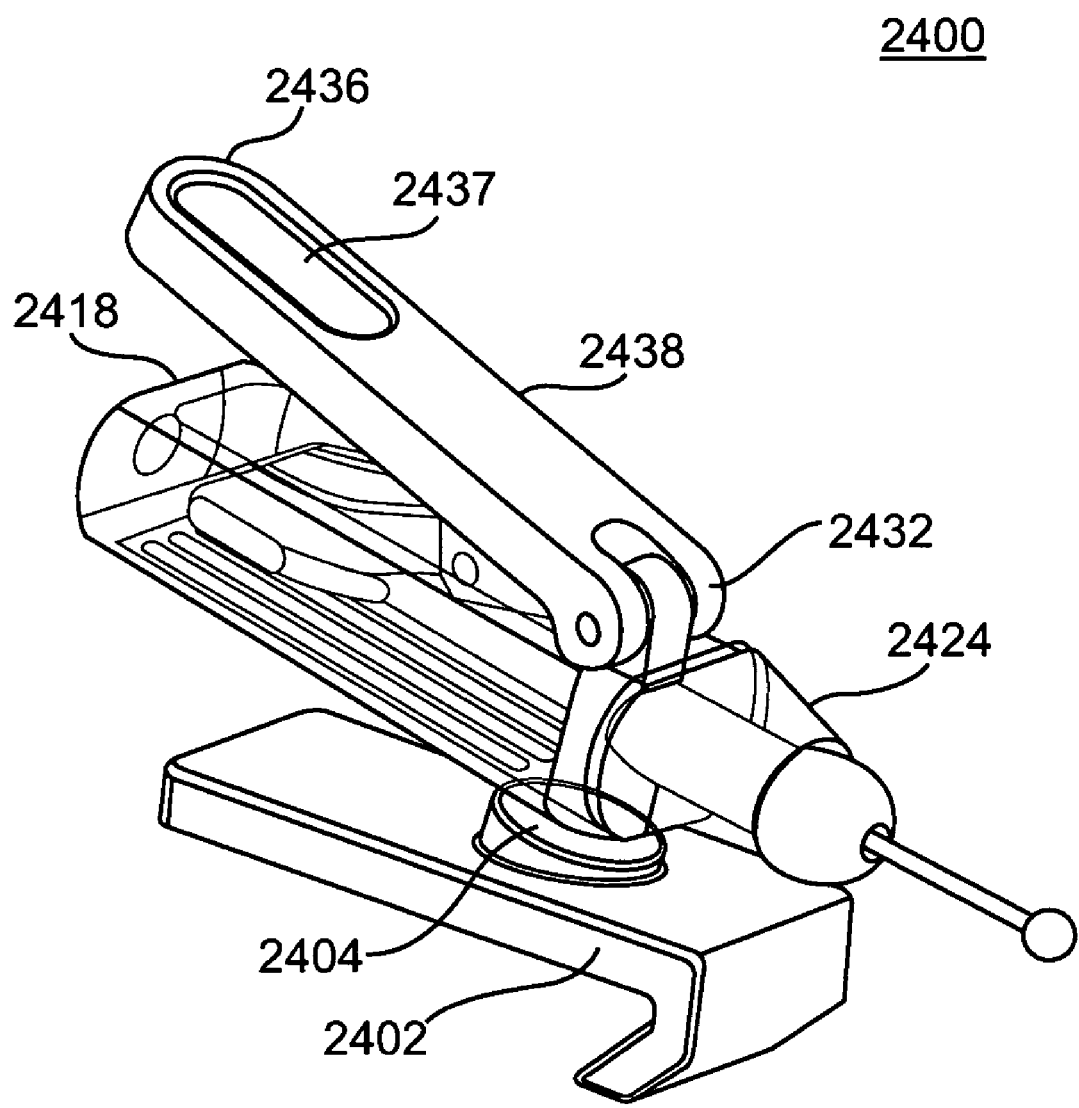
FIG. 45 is a perspective, partially transparent view of the turret assembly of FIG. 43.

The turret assembly 2400 can include a body 2418 and a locking mechanism 2420. The body 2418 can be coupled to the cylinder 2414 and can have a nose 2424 adapted to be coupled to an articulating arm (not shown). The locking mechanism 2420 can include a lever arm 2428 and a link 2430. The lever arm 2428 can have a pivoting end 2432 and a free end 2436. The pivoting end 2432 can be cammed and can be pivotably coupled to the cylinder 2414 over pins 2435. As shown in FIG. 45, the free end 2436 can include a recess 2437. The recess 2437 can be a visual and tactical locater for helping the user to locate and manipulate the locking mechanism 2420.

Figure 42:
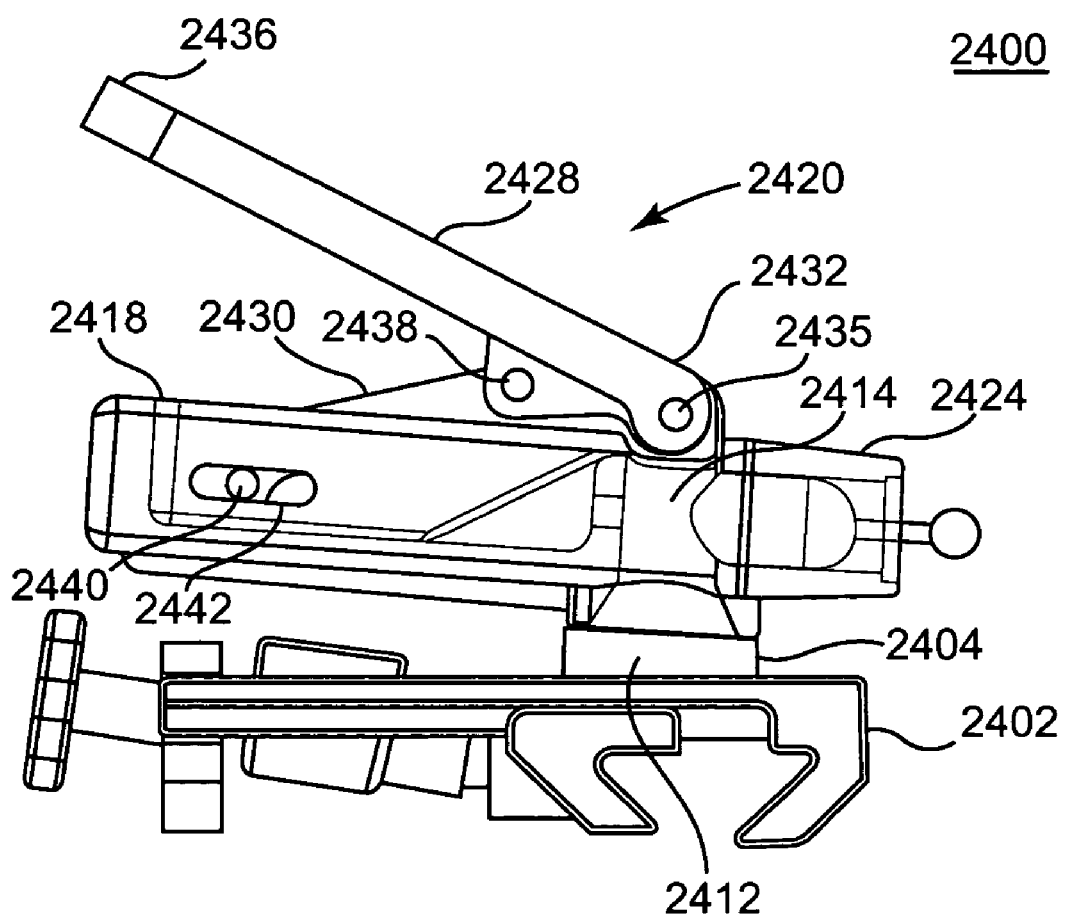
FIG. 42 is a side, partially transparent view of a turret assembly for a tissue stabilizer according to another embodiment of the invention.
Figure 43:
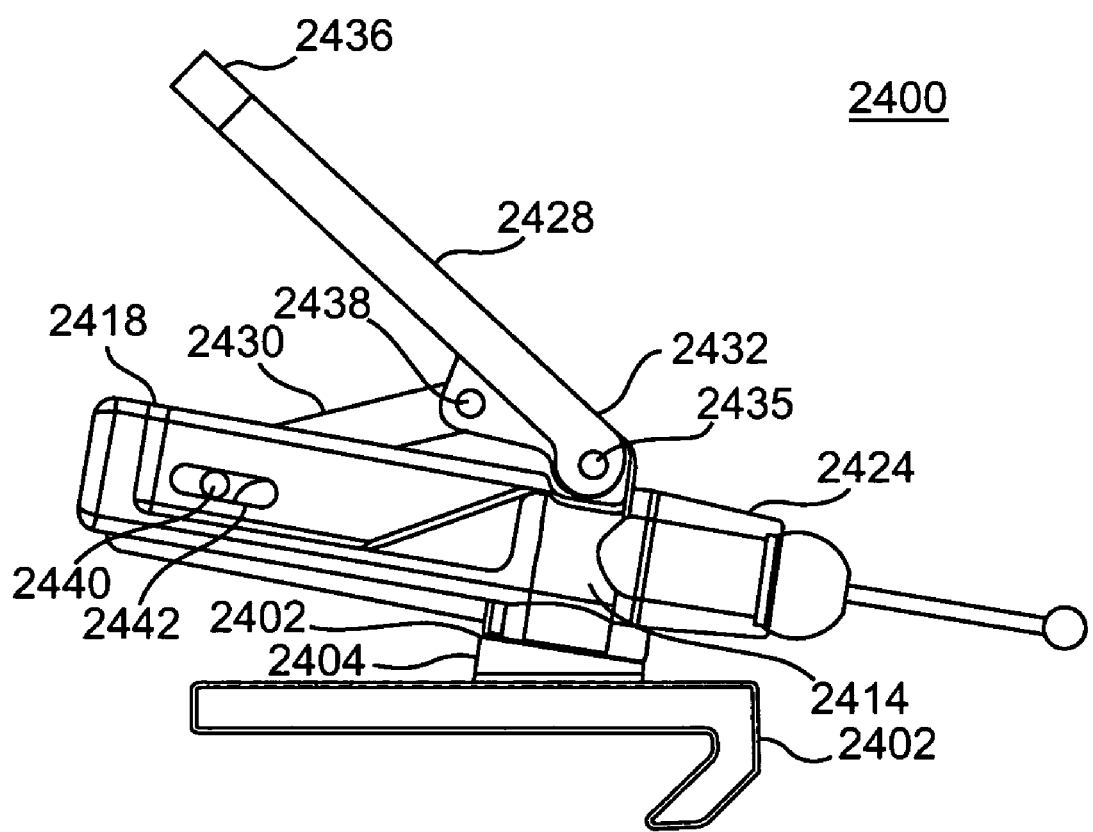
FIG. 43 is a side, partially transparent view of the turret assembly of FIG. 42 with the lever arm in the open position and the rear clamp removed.

A first end 2438 of the link 2430 can be pivotably coupled to the lever arm 2428 between the pivoting end 2432 and the free end 2436. A second end 2440 of the link 2430 can be slidable along a slot 2442 in the body 2418. In a similar manner as described with respect to the embodiment shown in FIGS. 35-39, when the free end 2436 of the lever arm 2428 is in an open position, the second end 2440 of the link 2430 can be positioned forward of the slot 2442 closer to the nose 2424 of the body 2418 (as shown in FIG. 42). When the free end 2436 of the lever arm 2428 is in a closed position, the second end 2440 of the link 2430 can be slid in the slot 2442 away from the nose 2424 (as shown in FIG. 43).

Figure 44:
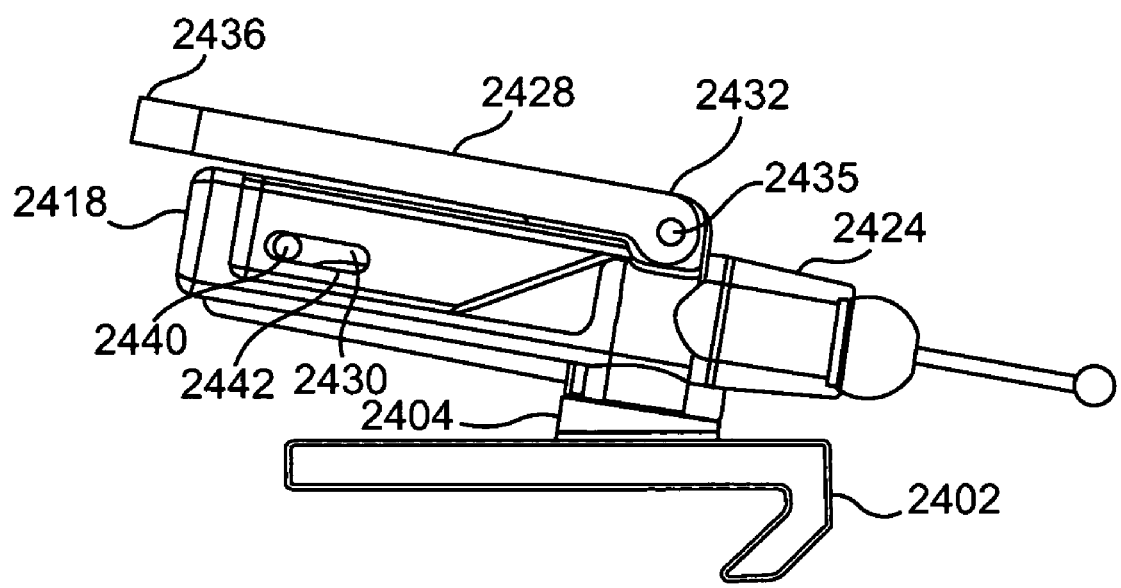
FIG. 44 is a side, partially transparent view of the turret assembly of FIG. 43 with the lever arm in the closed position.

A tension element (not shown) of an articulating arm can be coupled to the link 2430 so that a tensioning force can be exerted on the tension element when the lever arm 2428 in the closed position. Likewise, when the lever arm 2428 is moved to the open position, as shown in FIG. 43, the tensioning force can be released. As shown in FIG. 44, the second end 2440 of the link 2430 can be cammed to lock the locking mechanism 2420 into the closed position.

The locking mechanism 2420 can clamp the body 2418 onto the turret mount assembly 2404 in order to prevent rotation of the turret assembly 2400 relative to the clamp 2402. As the lever arm 2428 is moved toward the body 2418, the pivoting end 2432 of the lever arm 2428 can cam onto the body 2418, shifting the body 2418 down on the cylinder 2414. The body 2418 can be clamped between the cammed lever arm 2428 and the clamp 2402, preventing the turret assembly 2400 from rotating relative to the clamp 2402. When the lever arm 2428 is moved upwardly away from the body 2418, the cammed pivoting end 2432 can release the body 418, permitting the turret assembly 2400 to rotate relative to the clamp 2402.

The user can thus lock or immobilize the articulating arm as well as the turret assembly 2400 with a single action, i.e., by pivoting the lever arm 2428 downwardly. Likewise, the user can release the articulating arm for articulation and release the turret assembly 2400 for rotation by a single action, i.e., by pivoting the lever arm 2428 upwardly.

Figure 46:
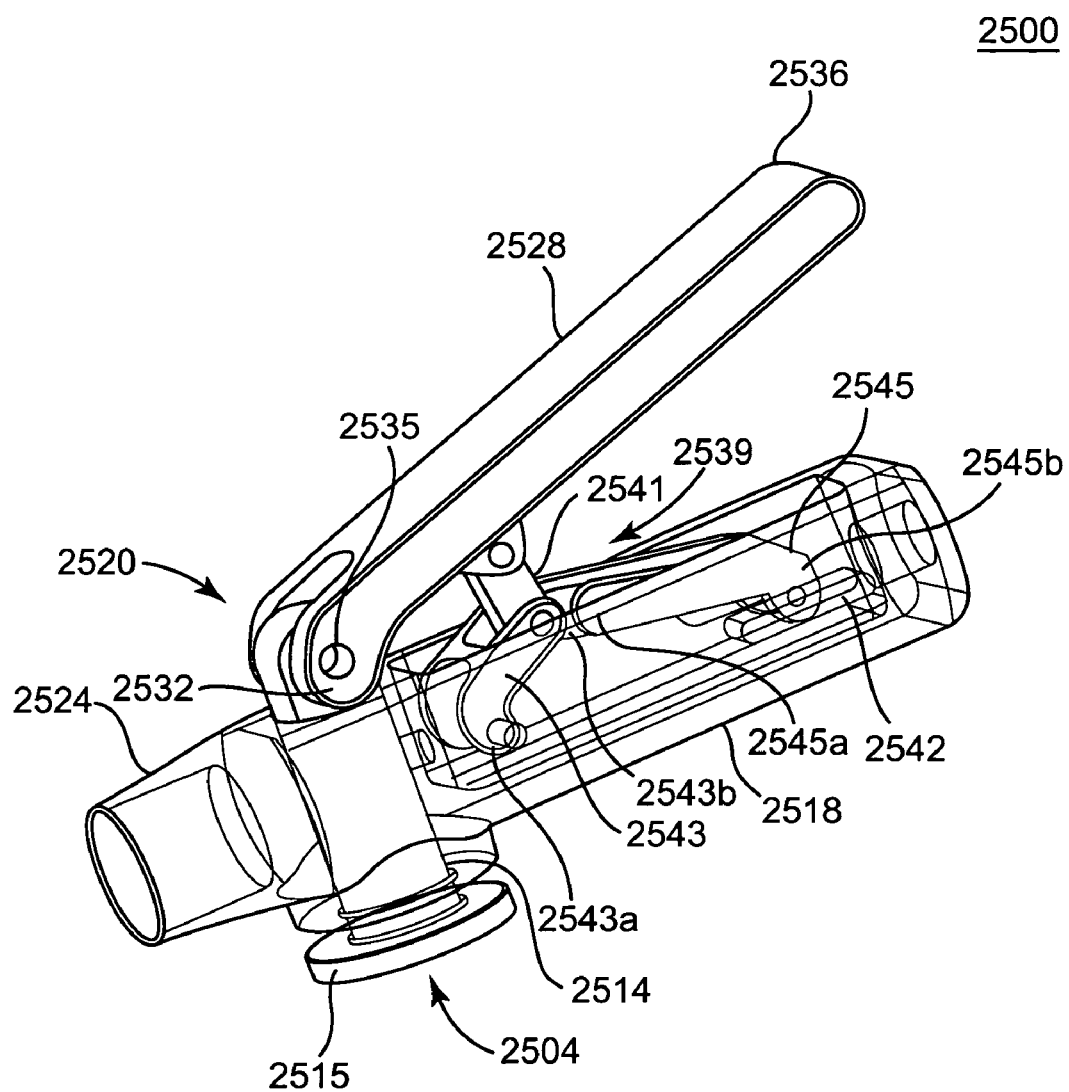
FIG. 46 is a perspective, partially transparent view of a turret assembly for a tissue stabilizer according to another embodiment of the invention.

FIG. 46 illustrates a turret assembly 2500 according to another embodiment of the invention. The turret assembly 2500 can be pivotably coupled to a clamp (not shown) with a turret mount assembly 2504. The turret mount assembly 2504 can include a plate 2515 that can be coupled to an angled turret mount (not shown) on the clamp and a cylinder 2514 supported by the plate 2515. The turret assembly 2500 can include a body 2518 and a locking mechanism 2520. The locking mechanism 2520 can include a lever arm 2528 having a cammed pivoting end 2532 pivotably coupled to the cylinder 2514 and a free end 2536. The locking mechanism 2520 can further include a linking mechanism 2539 coupled to the lever arm 2528 between the pivoting end 2532 and the free end 2536. The linking mechanism 2539 can include a connector 2541 coupled to the lever arm 2528. The connector 2541 can be coupled to a pivoting link 2543 and a sliding link 2545. The pivoting link 2543 can have a first end 2543a pivotably coupled to the body 2518 and a second end 2543b pivotably coupled to the connector 2541. The sliding link 2545 can have a first end 2545a pivotably coupled to the connector 2541 and a second end 2545b slidable within a slot 2542 in the body 2518.

Figure 47:
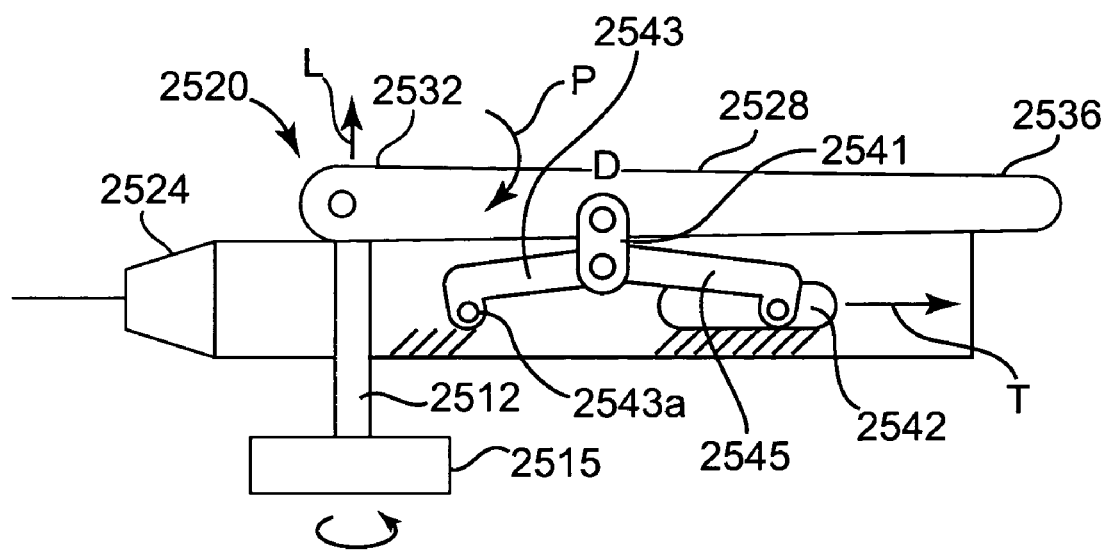
FIG. 47 is a free body diagram of the turret assembly of FIG. 46.

FIG. 47 is a free body diagram of the turret assembly 2500 of FIG. 46 and illustrates how the locking mechanism 2520 can exert a tensioning force on the tension element in order to lock the articulating arm. Pivoting the lever arm 2528 about the pins 2535, as indicated by arrow P, can push the connector 2541 toward the body 2518, causing the connector 2541 to act on the pivoting link 2543 and the sliding link 2545. The pivoting link 2543 pivots about the first end 2543a, while the sliding link 2545 slides in the slot 2542 away from the nose 2524 of the body 2518, exerting a tensioning force, as indicated by arrow T, on the tension element.

The tension element can be coupled to the sliding link 2545 so that a tensioning force can be exerted on the tension element when the sliding link 2545 is moved away from the nose 2524. For example, when the lever arm 2528 is moved into the closed position, the sliding link 2545 can be slid back in the slot 2542, exerting a tensioning force on the tension element. Likewise, when the lever arm 2528 is moved to the open position, the sliding link 2545 can slide forward in the slot 2542, releasing the tensioning force on the tension element.

The locking mechanism 2520 can clamp the body 2518 onto the turret mount assembly 2504 in order to prevent rotation of the turret assembly 2500 relative to the clamp. As the lever arm 2528 is moved toward the body 2518, the pivoting end 2532 of the lever arm 2528 can cam onto the body 2518, exerting a locking force, as indicated by arrow L in FIG. 47, that can shift the body 2518 down on the cylinder 2514. The body 2518 can be clamped between the cammed lever arm 2528 and the clamp, preventing the turret assembly 2500 from rotating relative to the clamp. When the lever arm 2528 is moved upwardly away from the body 2518, the cammed pivoting end 2532 can release the body 2518, permitting the turret assembly 2500 to rotate relative to the clamp.

The user can thus lock or immobilize the articulating arm as well as the turret assembly 2500 with a single action, i.e., by pivoting the lever arm 2528 downwardly into the closed position. Likewise, the user can release the articulating arm for articulation and release the turret assembly 2500 for rotation by a single action, i.e., by pivoting the lever arm 2528 upwardly into the open position.

Figure 48:
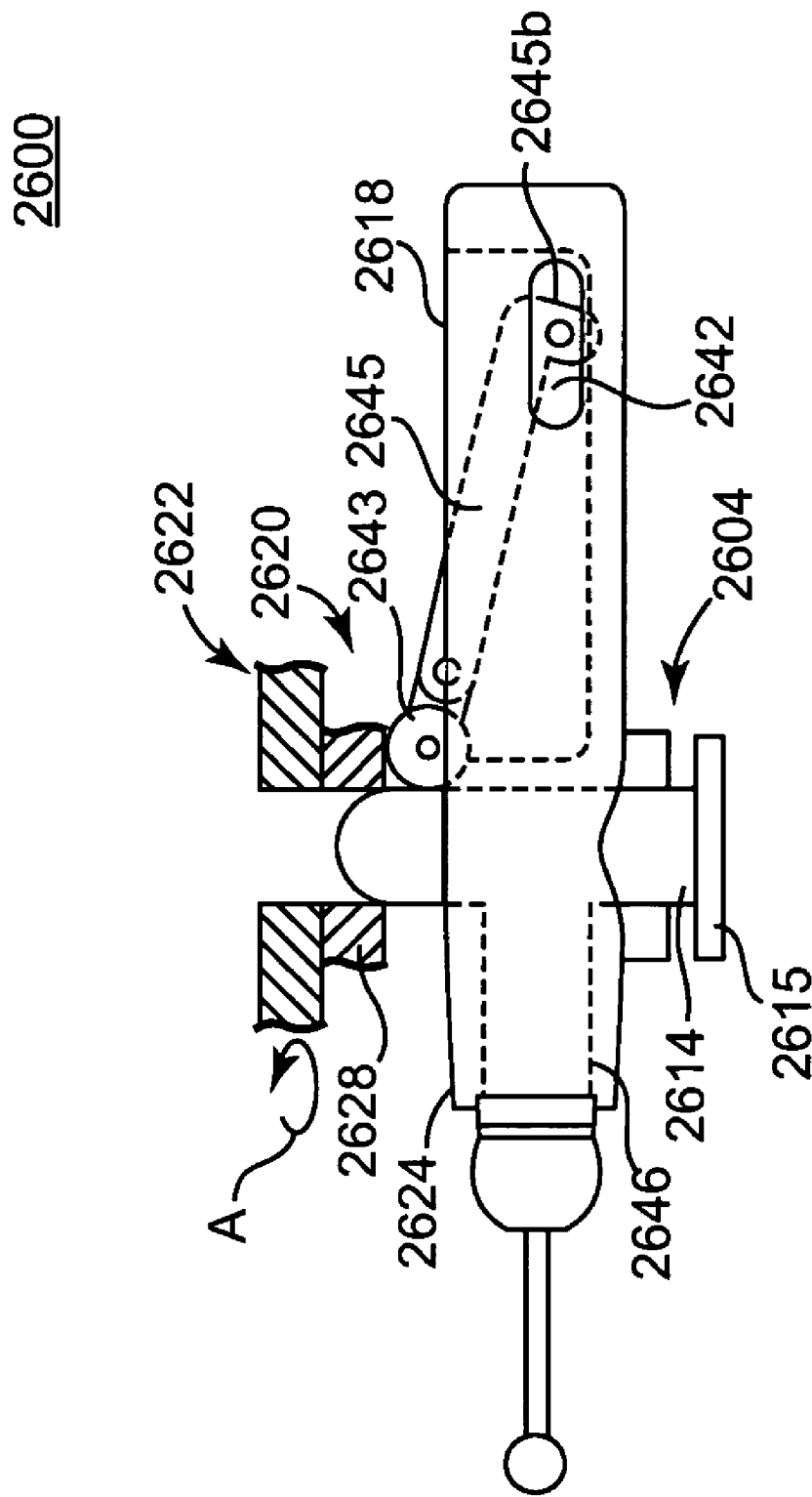
FIG. 48 is a side, partially transparent view of a turret assembly for a tissue stabilizer according to another embodiment of the invention.

FIG. 48 illustrates a turret assembly 2600 according to another embodiment of the invention. The turret assembly 2600 can be mounted to a clamp (not shown) with a turret mount assembly 2604. The turret mount assembly 2604 can include a plate 2615 for coupling to the clamp and a cylinder 2614 supported by the plate 2615. The turret assembly 2600 can include a body 2618 supporting a locking mechanism 2620 and an adjustment mechanism 2622.

The locking mechanism 2620 can include an actuator 2628 mounted to the cylinder 2614 and operably coupled to a roller 2643 and a link 2645. The actuator 2628 can be moved up and down on the cylinder 2614 and can cause the roller 2643 to roll up and down over the cylinder 2614. When the actuator 2628 is moved to a lowered or closed position, the roller 2643 can be rolled downwardly, which can cause the link 2645 to slide along the slot 2642 away from a nose 2624 of the body 2618. A second end 2645b of the link 2645 can be cammed to lock the link 2645 to the body 2618 when the actuator 2628 is in the closed position.

A tension element of an articulating arm can be coupled to the link 2645. When the actuator 2628 is in the closed position, so that the link 2645 is slid away from the nose 2624 of the body 2618, the locking mechanism 2620 can exert a tensioning force on the tension element. Likewise, when the actuator 2628 is moved to the open position, so that the link 2645 is slid toward the nose 2624 of the body 2618, the locking mechanism 2620 can release the tensioning force on the tension element.

The adjustment mechanism 2622 can include a threaded member 2646 rotatably coupled to the cylinder 2614. The threaded member 2646 can also be operably coupled to the roller 2641. As the threaded member 2646 is rotated in a first direction, for example, clockwise, as indicated by arrow A, the roller 2643 can be rolled downwardly, which can cause the link 2645 to slide along the slot 2642 away from a nose 2624 of the body 2618, which can preload the tension element. In one embodiment, the threaded member 2646 can include a ratchet mechanism for coupling to the cylinder 2614 (not shown). In this manner, the threaded member 2646 can be rotated about the ratchet mechanism to preload the tension element or slid down the cylinder 2614 to lock articulating arm. In some embodiments, the threaded member 2646 and the actuator 2628 can be the same member.

The user can thus lock the articulating arm as well as the turret assembly 2600 with a single action, i.e., by pushing the actuator 2628 downwardly. Likewise, the user can release the articulating arm for articulation and release the turret assembly 2600 for rotation by a single action, i.e., by pulling the actuator 2628 upward.

Figure 49:
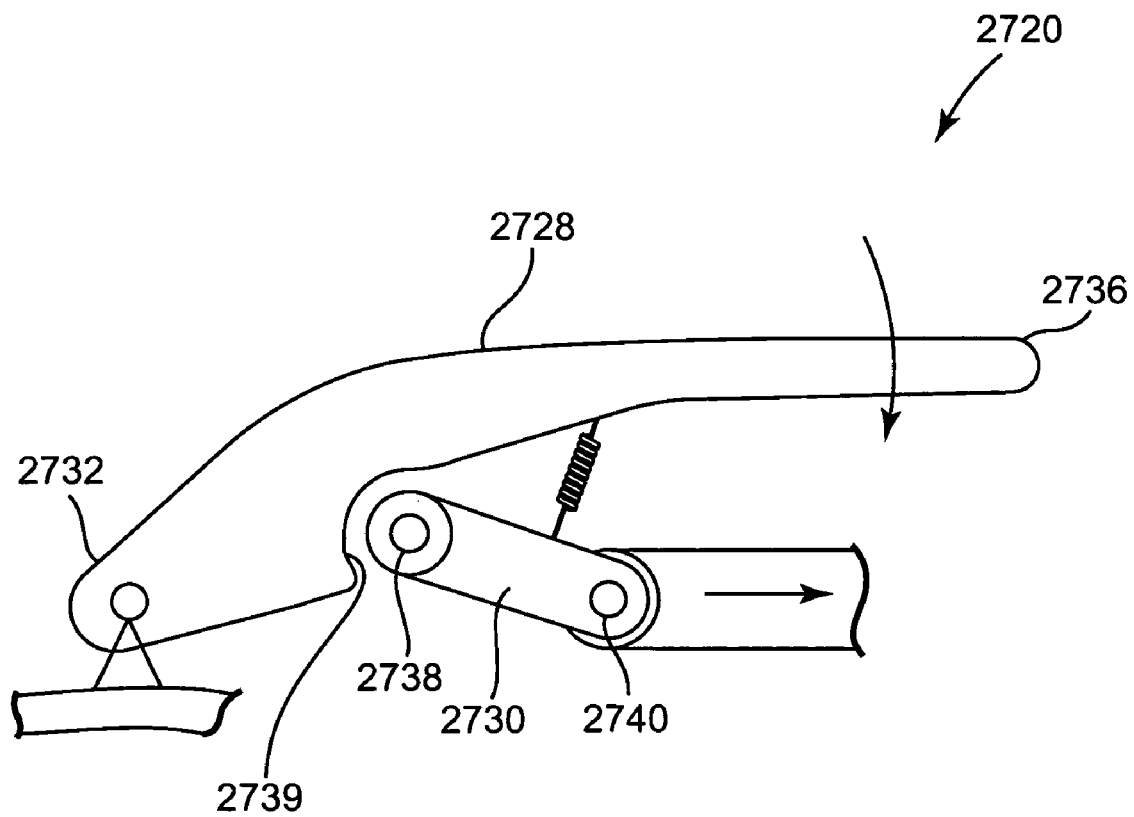
FIG. 49 is a side view of a locking mechanism for a turret assembly according to another embodiment of the invention.

FIG. 49 illustrates a locking mechanism 2720 for a turret assembly according to another embodiment of the invention. The locking mechanism 2720 can include a lever arm 2728 having a pivoting end 2732 for coupling to a turret assembly (not shown) and a free end 2736 for user manipulation. A roller 2730 can be coupled to the lever arm 2728. A first end 2738 of the roller 2730 can be positioned in a shoulder 2739 between the pivoting end 2732 and the free end 2736 and can be coupled to the lever arm 2728. A second end 2740 of the roller 2730 can be rollingly coupled to the turret assembly. In other words, the second end 2740 of the roller 2730 can be a bearing for sliding the second end 2740 of the roller 2730 relative to the turret assembly.

As the lever arm 2728 is pivoted about the pivoting end 2732 from an open position to a closed position, the first end 2738 of the roller 2730 rolls within the shoulder 2739. This can slide the second end 2740 of the roller 2730 over the bearing relative to the turret assembly. A tension element of an articulating arm can be coupled to the roller 2730 so that a tensioning force is exerted on the tension element as the lever arm 2728 is moved to the closed position. The lever arm 2728 can be biased away from the roller 2730, or toward the open position, by a biasing member. The biasing member can be, for example, a spring or other coiled member.

Figure 50:
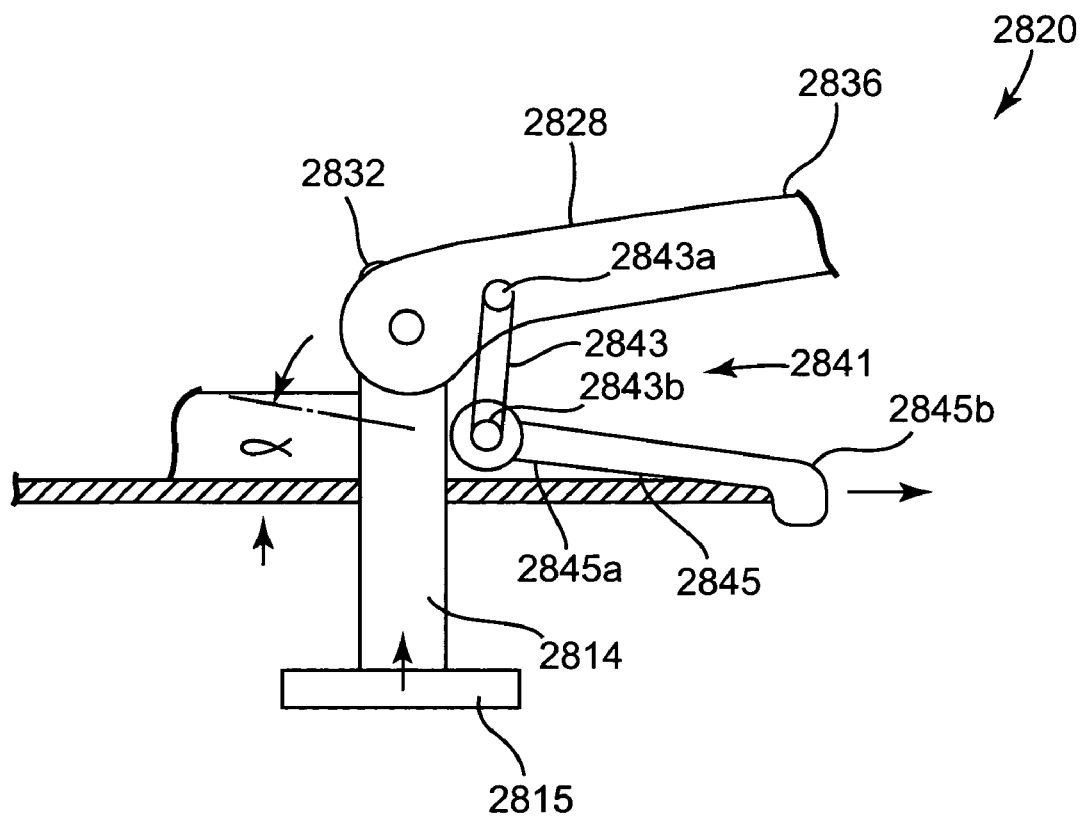
FIG. 50 is a side view of a locking mechanism for a turret assembly according to another embodiment of the invention.

FIG. 50 illustrates a locking mechanism 2820 for a turret assembly according to another embodiment of the invention. The locking mechanism 2820 can include a lever arm 2828 that has a first end 2832 pivotably coupled to a turret assembly and a second end 2836 that is free for manipulation. The locking mechanism 2820 can further include a link mechanism 2841 coupling the lever arm 2828 to a tension element. The link mechanism 2841 can include a vertical link 2843 and a horizontal link 2845. The vertical link 2843 can have a first end 2843a pivotably coupled to the lever arm 2828 between the pivoting end 2832 and the free end 2836. A second end 2843b of the vertical link 2843 can be a roller coupled to a cylinder 2814 that can be mounted to a plate 2815 for coupling the turret assembly to a clamp. The horizontal link 2845 can have a first end 2845a coupled to the vertical link second end 2843b and a second end 2845b rollingly coupled to the turret assembly. In other words, the second end 2845b of the horizontal link 2845 can be a bearing for sliding the second end 2845b of the horizontal link 2845 relative to the turret assembly.

As the lever arm 2828 is pivoted about the pivoting end 2832 from an open position to a closed position, the vertical link 2843 moves downwardly on the cylinder 2814. This can cause the second end 2845b of the horizontal link 2845 to roll away from a nose of the turret assembly. A tension element of an articulating arm can be coupled to the horizontal link 2845 so that a tensioning force is exerted on the tension element as the lever arm 2828 is moved to the closed position. The pivoting end 2832 of the lever arm 2828 can be cammed to lock the lever arm 2828 into the closed position.

Figure 51:
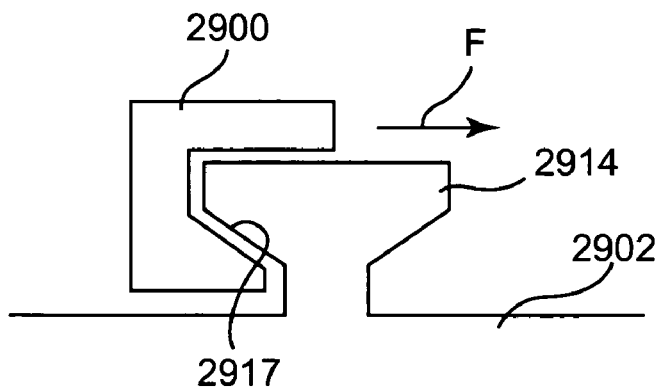
FIG. 51 is a schematic view of a portion of a turret assembly according to another embodiment of the present invention.

FIG. 51 illustrates a portion of a turret assembly 2900 mounted to a cylinder 2914. The turret assembly 2900 can be rotatable about the cylinder 2914. Alternately, the turret assembly 2900 and the cylinder 2914 can be rotatably mounted to a clamp member 2902. The cylinder 2914 has a bevel 2917 that helps to force the turret assembly 2900 downward toward the clamp member 2902 when the turret assembly 2900 is tightened onto the clamp member 2902. The turret assembly 2900 can be tightened by, for example, exerting a force as indicated by arrow F, on the turret assembly 2900. The bevel 2917 creates a locking force in both a downward and an inward direction. This can help to reduce rocking of the turret assembly 2900 relative to the clamp member 2902 when in a tightened or locked position. The turret assembly 2900 shown in FIG. 51 can be combined, for example, with the turret 10 shown in FIG. 1.

Figure 52:
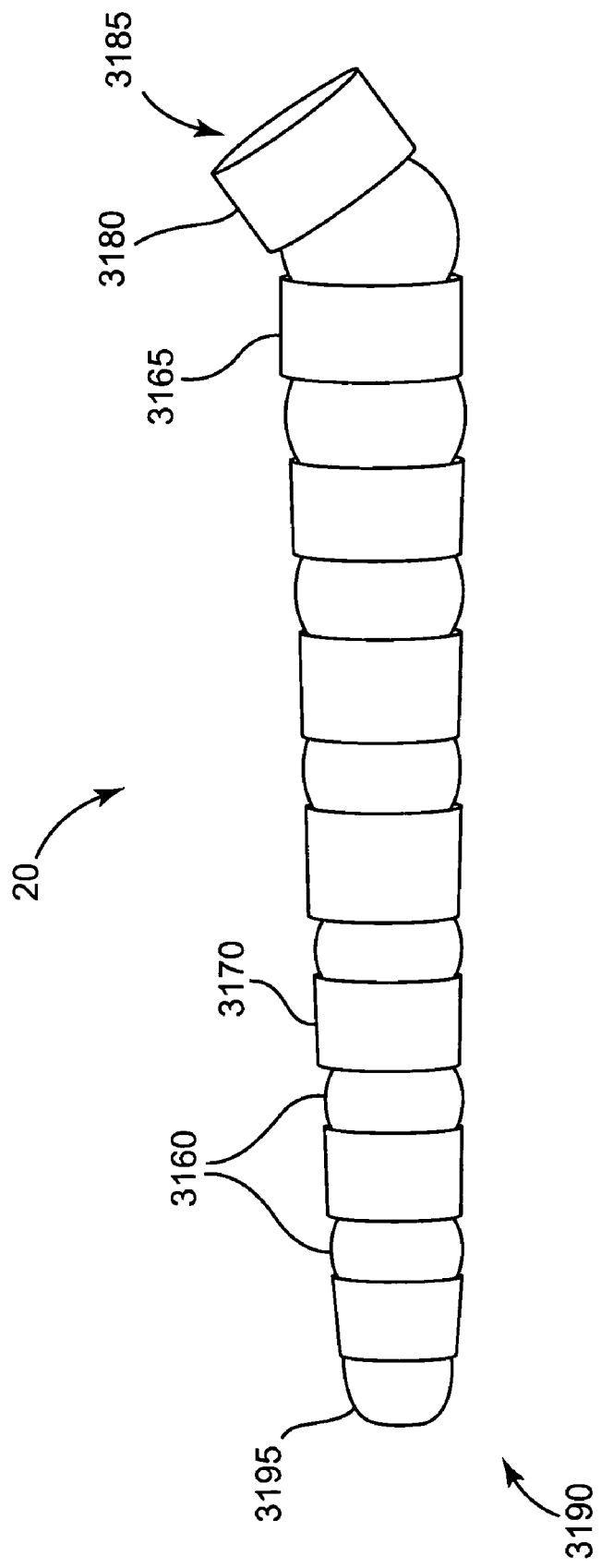
FIG. 52 is a perspective view of an articulating arm of the tissue stabilizer of FIG. 1.

FIG. 52 illustrates the articulating arm 20. In general, the articulating arm 20 can have an overall length greater than conventional tissue stabilizer arms so that the articulating arm 20 has a greater "effective reach" than conventional tissue stabilizer arms. The articulating arm 20 can include at least one ball element 3160, at least one base element 3165, and may include one or more reducing base elements 3170. A first base element 3180 can constitute a proximate end 3185 of the articulating arm 20 and can be mated to an end of the turret 10. The remainder of the articulating arm 20 can be formed by alternating ball elements 3160 and either base elements 3165 or reducing base elements 3170. In some embodiments, multiple sizes of ball elements 3160, base elements 3165, and reducing base elements 3170 can be used to create the articulating arm 20. A ball element 3195 can constitute a distal end 3190 of the articulating arm 20.

Figure 53:
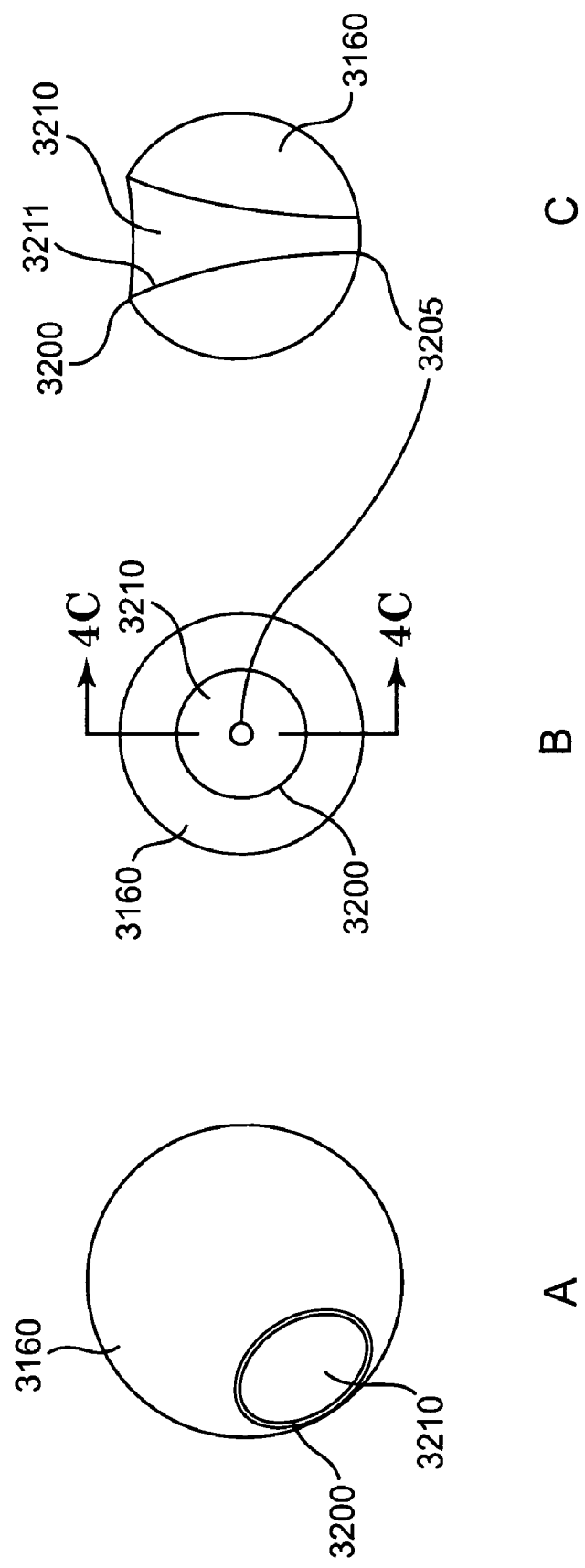
FIG. 53A is a perspective view of a ball element of the articulating arm of FIG. 52.
FIG. 53B is a top view of the ball element of the articulating arm of FIG. 52.
FIG. 53C is a cut-away view of the ball element of the articulating arm of FIG. 52.

FIGS. 53A-53C illustrate one embodiment of the ball element 3160. The ball element 3160 can be generally spherical in shape and can include a first aperture 3200 and a second aperture 3205. The first aperture 3200 can be substantially larger than the second aperture 3205. The first aperture 3200 and the second aperture 3205 can be positioned on opposite sides of the ball element 3160 and can be linked by a tapered or frusto-conical shaped bore 3210 having a sidewall 3211.

Figure 54:
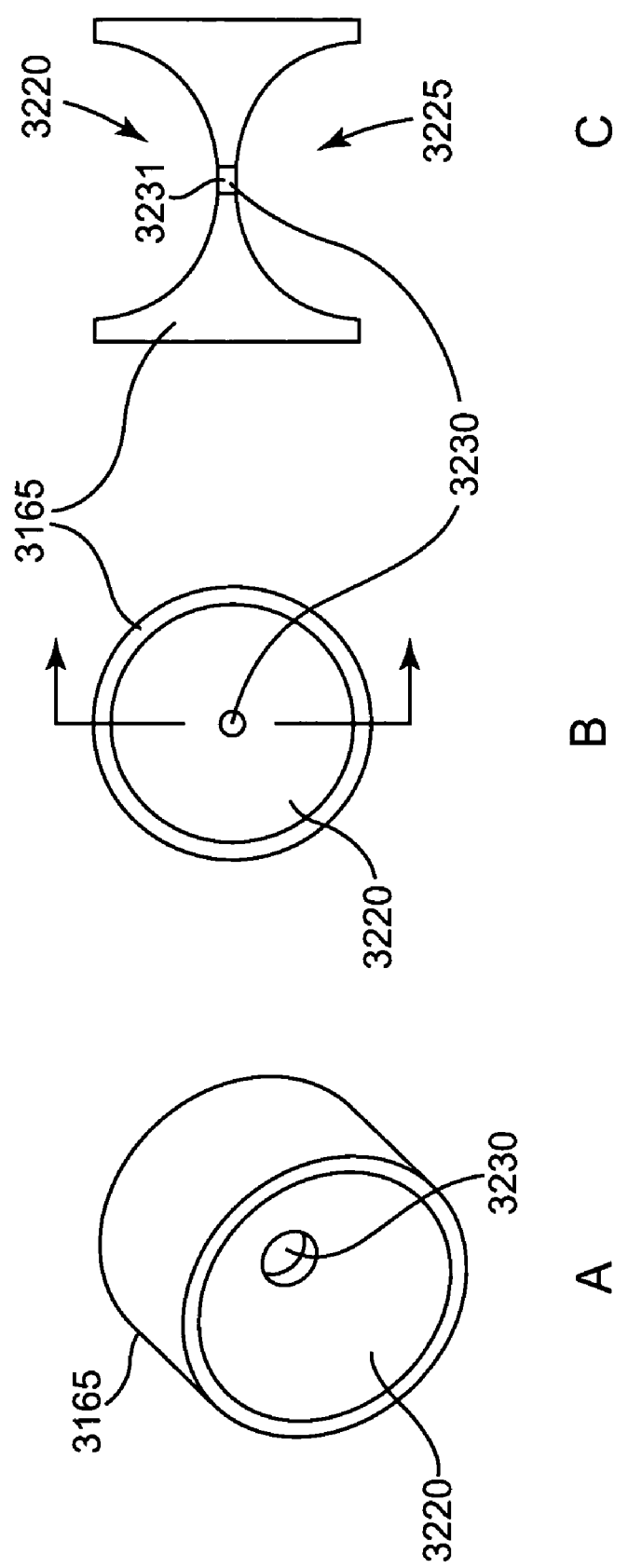
FIG. 54A is a perspective view of a base element of the articulating arm of FIG. 52.
FIG. 54B is a top view of the base element of the articulating arm of FIG. 52.
FIG. 54C is a cut-away view of the base element of the articulating arm of FIG. 52.

FIGS. 54A-54C illustrate an embodiment of the base element 3165. The base element 3165 can be cylindrical in shape and can include a first ball mating cavity 3220 and a second ball mating cavity 3225 on opposite sides of the base element 3165. The first ball mating cavity 3220 and the second ball mating cavity 3225 can be concave in shape and can be configured to receive portions of the ball element 3160. A centrally positioned aperture 3230 can be positioned between and link the first ball mating cavity 3220 and the second ball mating cavity 3225. The aperture 3230 can have an aperture sidewall 3231.

Figure 55:
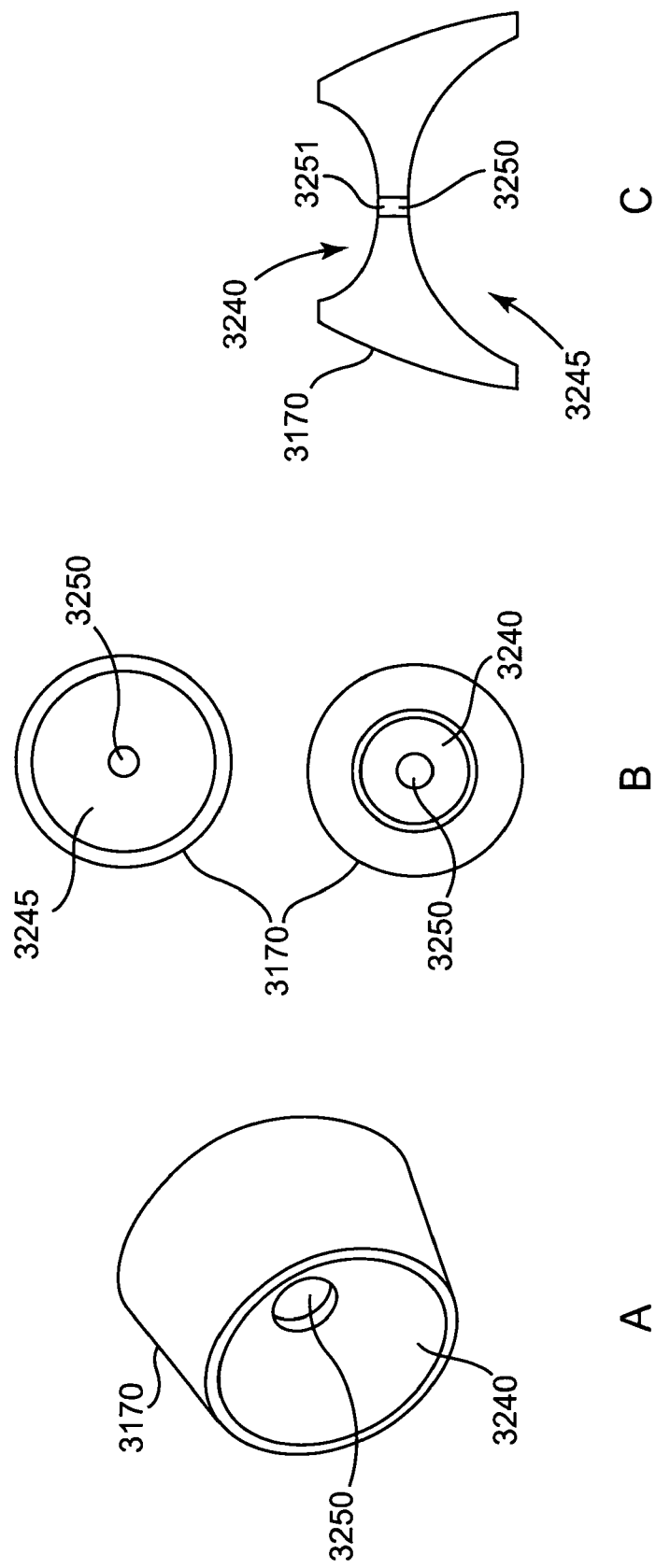
FIG. 55A is a perspective view of a reducing base element of the articulating arm of FIG. 3.
FIG. 55B is a top view of the reducing base element of the articulating arm of FIG. 52.
FIG. 55C is a cut-away view of the reducing base element of the articulating arm of FIG. 3.

FIGS. 55A-55C illustrate an embodiment of the reducing base element 3170. The reducing base element 3170 can have a tapered or frusto-conical shape. The reducing base element 3170 can also include a first ball mating cavity 3240 and a second ball mating cavity 3245. A diameter of the first ball mating cavity 3240 can be smaller than a diameter of the second ball mating cavity. The first ball mating cavity 3240 can be on an opposite side of the base element 3165 from the second ball mating cavity 3245. The first ball mating cavity 3240 and the second ball mating cavity 3245 can each be configured to receive a portion of the ball elements 3160. A centrally positioned aperture 3250 can be positioned between and link the first ball mating cavity 3240 and the second ball mating cavity 3245. The aperture 3250 can have an aperture sidewall 3251.

Figure 56:
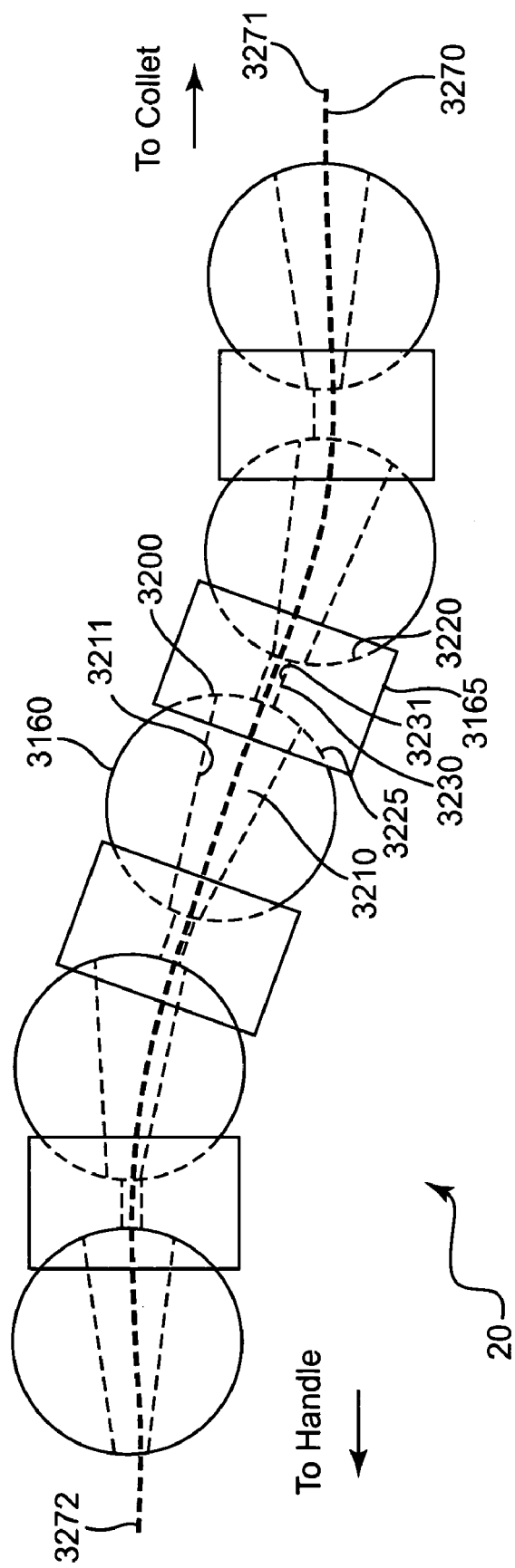
FIG. 56 is a schematic illustration of the interaction of the ball elements, base elements, and tension element of the articulating arm of FIG. 52.

FIG. 56 illustrates the engagement of a tension element 3270 with the sidewalls 3211 of the ball elements 3160 and the sidewalls 3231 of the base elements 3165 (reducing elements 3170 not shown) as the articulating arm 20 is bent. The tension element 3270 can extend through the bores 3210 and the apertures 3230 and can be coupled at a proximal end 3271 to the collet (not shown) and at a distal end 3272 to the handle (not shown). The spherical shapes of the ball elements 3160 are generally complementary to the ball cavities 3220, 3225 of the elements 3160, 3165 so that the elements 3160, 3165 rotate or slide smoothly against one another when tension element 3270 is loose. This action provides multiple degrees of freedom for the articulating arm 20 in order to position the head-link assembly 30.

Rotation of the handle 3115 in a tightening direction tightens the tension element 3270, causing the elements 3160, 3165 to be pressed more tightly against one another, thereby causing the elements 3160, 3165 to frictionally engage one another and reducing relative rotating and sliding therebetween. Stabilization or immobilization of the elements 3160, 3165 relative to each other during tightening of the tension element 3270 can be facilitated by the shape of the bores 3210. FIG. 56 illustrates the bore 3210 of the ball element 3160 being flared, having the larger opening 3200 facing the collet assembly 3125 or distal end 3190 of the articulating arm 20 and the smaller opening 3205 facing the handle 15 or proximate end 3185 of the articulating arm 20. The ball, base, and reducing elements 3160, 3165, 3170, as shown in FIG. 52, can vary in size along the length of the articulating arm 20, with the elements closer to the proximal end 3185 of the arm 20 being largest, and the elements closer to the distal end 3190 being the smallest, in one embodiment.

The ball, base, and reducing elements 3160, 3165, 3170 can be constructed out of a variety of materials, including, for example, highly rigid engineered thermoplastic or of a metal such as stainless steel. In some embodiments, the ball elements 3160 can be formed of a different material than the base elements 3165 and reducing elements 3170. In one embodiment, the ball elements 3160 can be manufactured of stainless steel and the base elements 3165 and 3170 can be manufactured of highly rigid engineered thermoplastic. The alternating of stainless steel and highly rigid engineered thermoplastic can provide relatively better stability and can allow smaller elements to be used in manufacturing the articulating arm 20, creating a reduced profile of the tissue stabilizer 100.

In one embodiment, the tension element 3270 can be a multi-stranded stainless steel cable, having approximately 7 to 19 strands. In some embodiments, the tension element 3270 can withstand forces up to about 715 foot pounds ("lbf") before breaking. The ball, base, and reducing elements 3160, 3165, 3170 and the tension element 3270 can also be manufactured from other materials, including other suitable metals or highly engineered polymers, including liquid crystal polymers, as well as many other types of cables, including bundle stranded, braided or cabled titanium, as well as Kevlar®. Some embodiments can include a textured surface molded, or otherwise formed, into the spherical features of the ball, base, and reducing elements 3160, 3165, 3170. When the ball, base, and reducing elements 3160, 3165, 3170 are pulled together during tightening, the textured surfaces can cause an increase in a coefficient of friction between the adjacent spherical surfaces. This can increase overall system stiffness.

Figure 57:
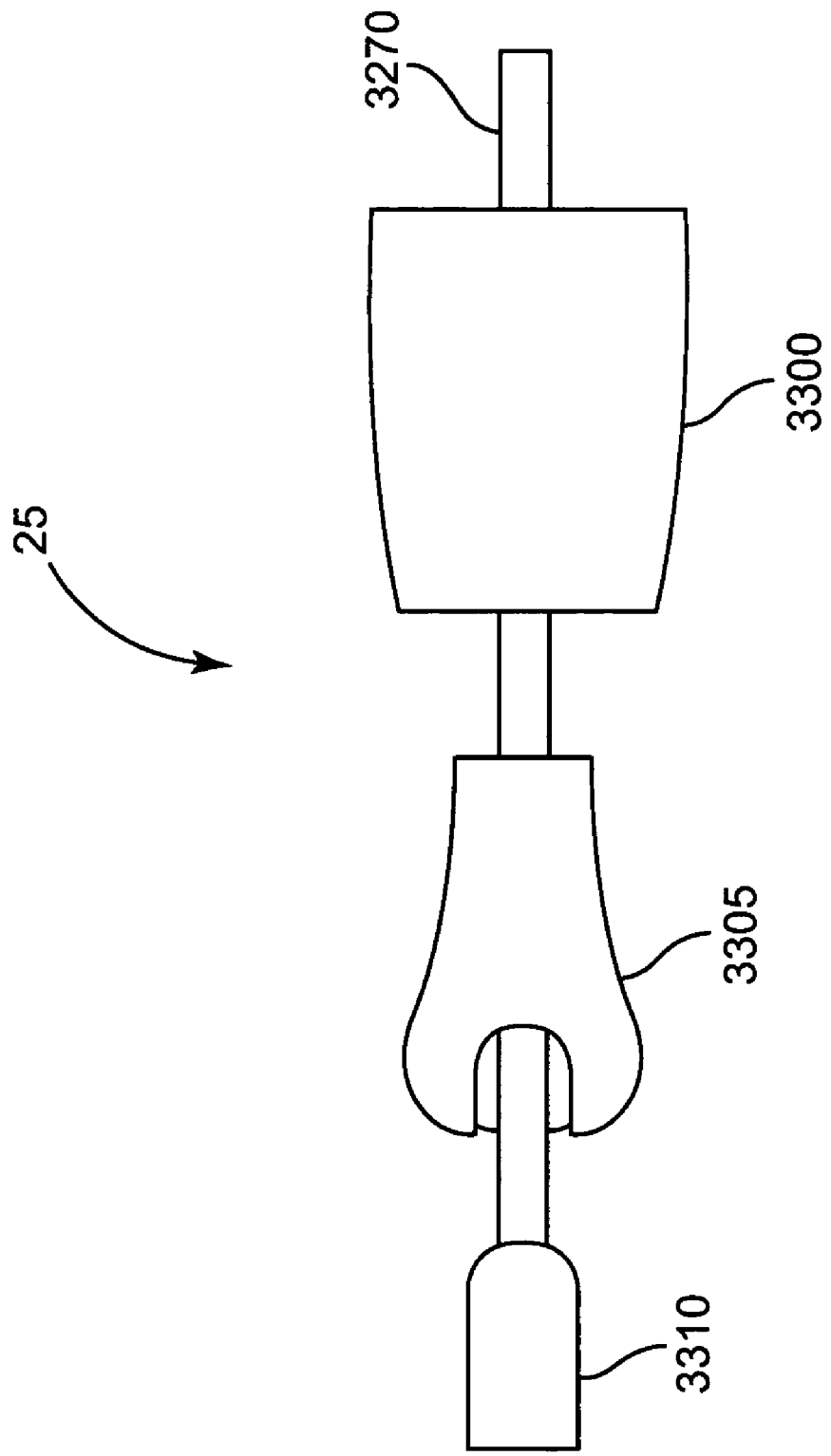
FIG. 57 is an exploded view of a collet assembly of the tissue stabilizer of FIG. 1.

FIG. 57 illustrates one embodiment of the collet assembly 25. The collet assembly 25 can be positioned on the distal end 3190 of the articulating arm 20 and can be configured to receive and support the head-link assembly 30 (as shown in FIG. 1). The collet assembly 25 can include a collet receiving element 3300 and a collet 3305. A tension element stop 3310 can be attached to an end of the tension element 3270. Tension can be applied to the tension element 3270 by rotating the handle 15 in a tightening direction. The tension can draw the tension element 3270 toward the proximate end 3185 of the articulating arm 20 and the handle 15. As the tension element 3270 is urged toward the proximate end 3185 of the articulating arm 20, the tension element stop 3310 can also be drawn toward the proximate end 3185 of the articulating arm 20. This motion can cause the tension element stop 3310 to seat in and engage the collet 3305, as shown in FIG. 12. Further tensioning of the tension element 3270 can draw the tension element stop 3310 toward the distal end 3190 of the articulating arm 20.

FIGS. 58A-58D illustrate the collet assembly 25. The collet receiving element 3300 can have a concave wall 3320 similar to the ball mating cavities 3220, 3225 of the base elements 3165. The concave wall 3320 can be configured to mate the collet receiving element 3300 to the ball element 3195 at the distal end 3190 of the articulating arm 20. The collet receiving element 3300 can also include a sleeve section 3325 configured to receive the collet 3305. A centrally-positioned hole 3330 can extend between the sleeve section 3325 and the concave wall 3320. In some embodiments, the collet receiving element 3300 can be constructed to withstand a tension element tension of about 268±14 lbf before breaking.

Figure 59:
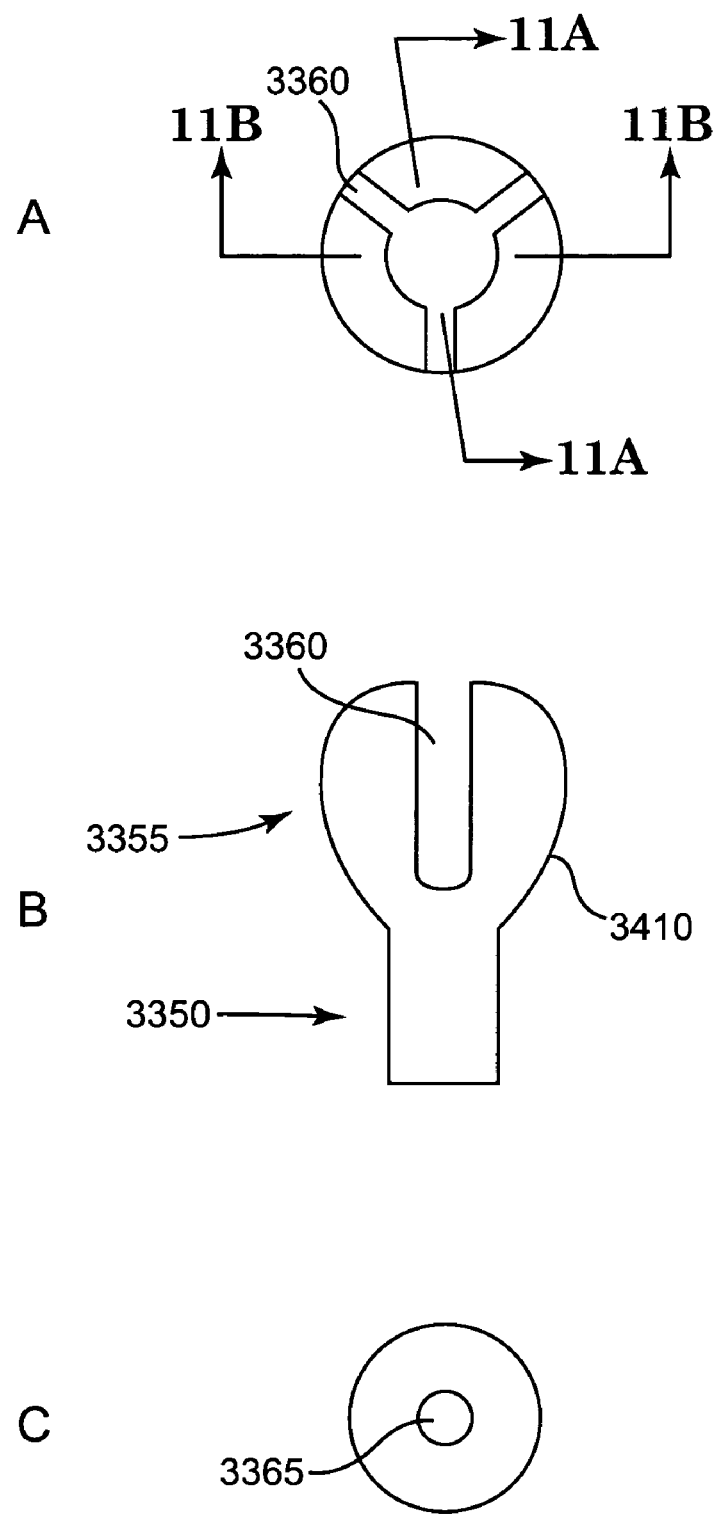
FIGS. 59A-59C are top, side, and bottom views, respectively, of a collet of the collet assembly of FIG. 57.
Figure 60A:
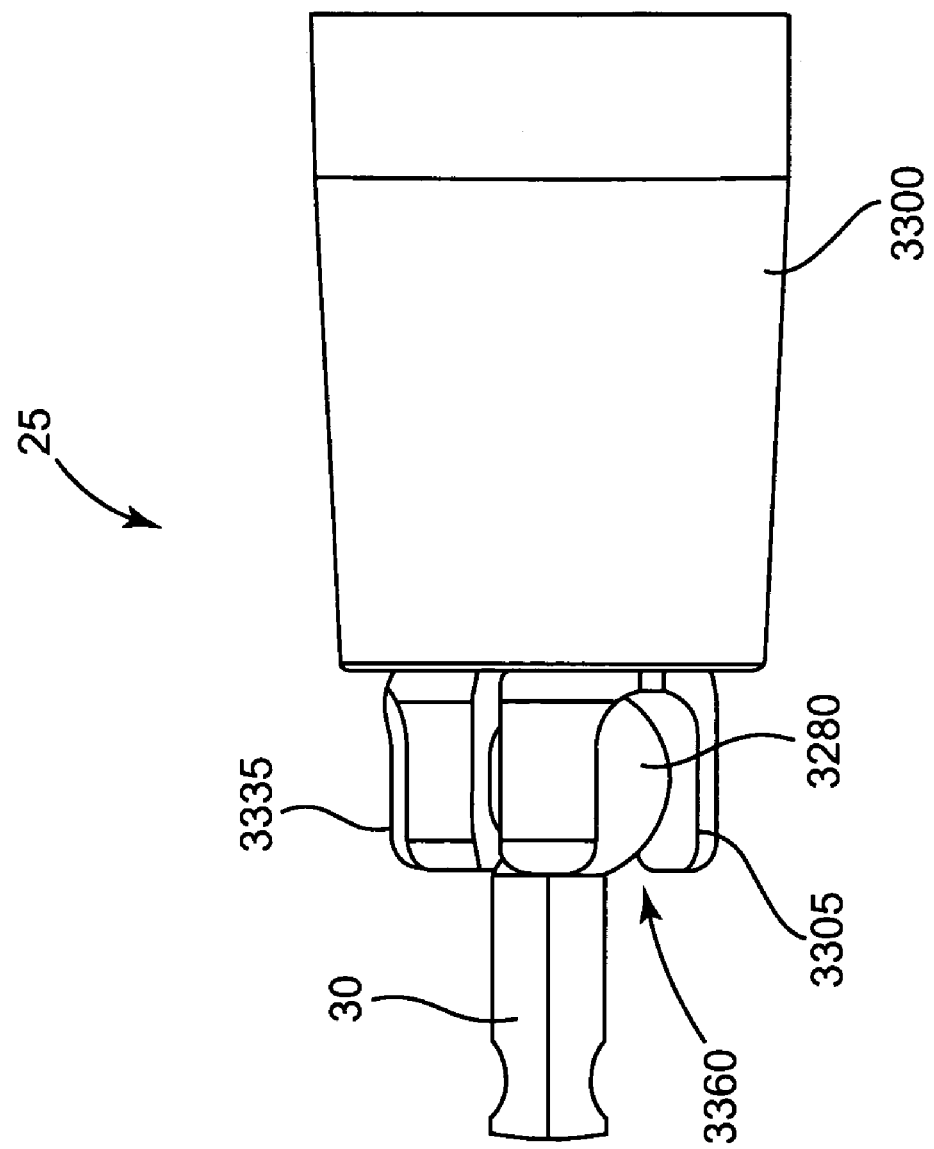
FIG. 60A is a side view of a collet assembly.
Figure 60B:
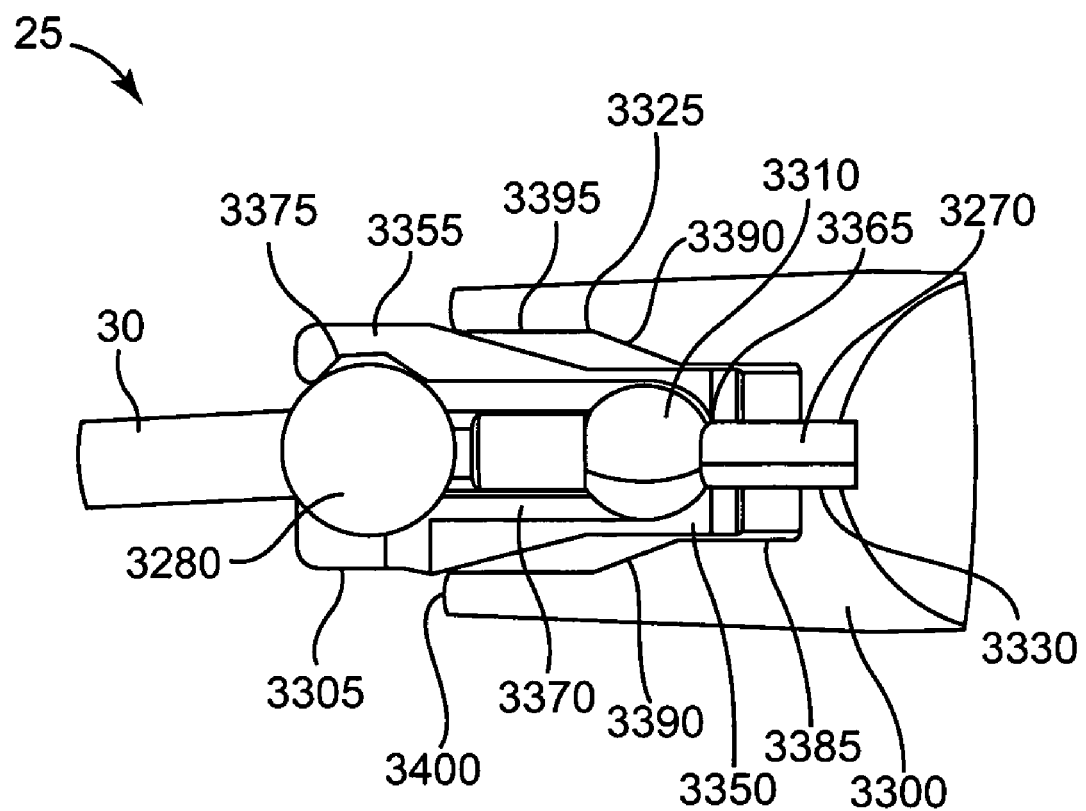
FIG. 60B is a cross-sectional view of a collet assembly.

FIGS. 59A-59C illustrate one embodiment of a collet 3305. FIGS. 60A-60B also illustrate one embodiment of collet 3305 of FIGS. 59A-59C. The collet 3305 can be generally hollow and can include a base 3350 and a head 3355. The head 3355 can have a generally spherical shape for receiving the head-link assembly 30. The head 3355 can also include slots 3360. The base 3350 can include a tension element opening 3365. The tension element opening 3365 can lead to a cylindrical cavity 3370 in the base 3350. The head 3355 can include a spherical cavity 3375 and can receive the base 3280 of the head-link assembly 30. In some embodiments, the collet 3305 can be constructed to withstand a tension element tension of about 431 lbf before breaking.

Figure 58:
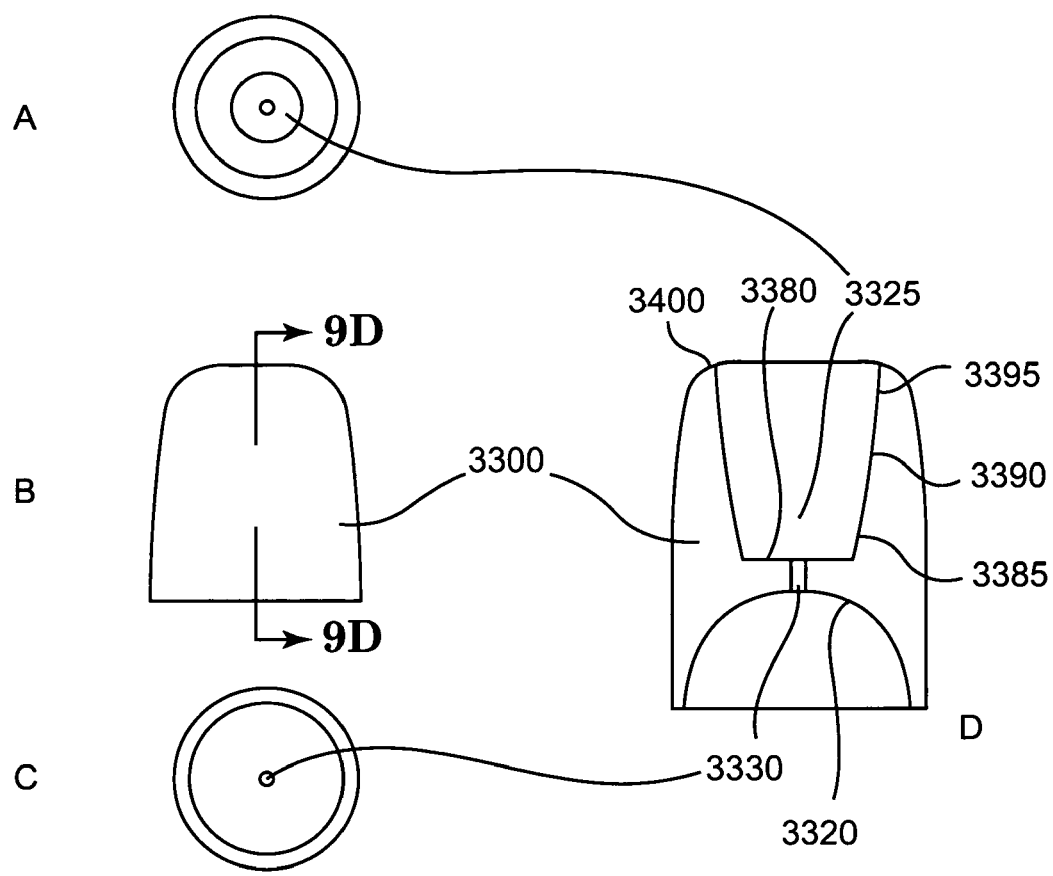
FIGS. 58A-58D are top, side, bottom, and cut-away views, respectively, of a collet receiving element of the collet assembly of FIG. 57.

As shown in FIGS. 58 and 60B, the sleeve section 3325 of the collet receiving element 3300 can include a base 3380, a first vertical wall 3385, an angled wall 3390, a second vertical wall 3395, and a lip 3400. The first vertical wall 3385 can form a cylinder which can have a diameter slightly larger than the diameter of the base 3350 of the collet 3305. The second vertical wall 3395 can form a cylinder which can have a diameter large than the cylinder formed by the first vertical wall 3385 but smaller than the diameter of the head 3355 of the collet 3305. The angled wall 3390 can connect the first vertical wall 3385 to the second vertical wall 3395. Other embodiments can incorporate different configurations of the walls forming the sleeve section 3325 of the collet receiving element 3300.

As shown in FIGS. 57 and 60B, the tension element stop 3310 can be attached to an end of the tension element 3270 and can be positioned in the cavity 3370 of the collet 3305. The tension element 3270 can pass through the hole 3330 of the collet receiving element 3300 and the tension element opening 3365 of the collet 3305. The tension element stop 3310 can be sized such that the tension element stop 3310 can be too large to pass through the tension element opening 3365 of the collet 3305.

FIGS. 60A and 60B illustrate one embodiment of the collet assembly 25 with the positioning of the collet receiving element 3300, the collet 3305, the tension element 3270, and the base 3280 of the head-link assembly 30. The hole 3330 of the collet receiving element 3300 and the tension element opening 3365 of the collet 3305 can be generally in alignment and can enable the tension element 3270 to pass through both the hole 3330 and the tension element opening 3365.

Figure 34A:
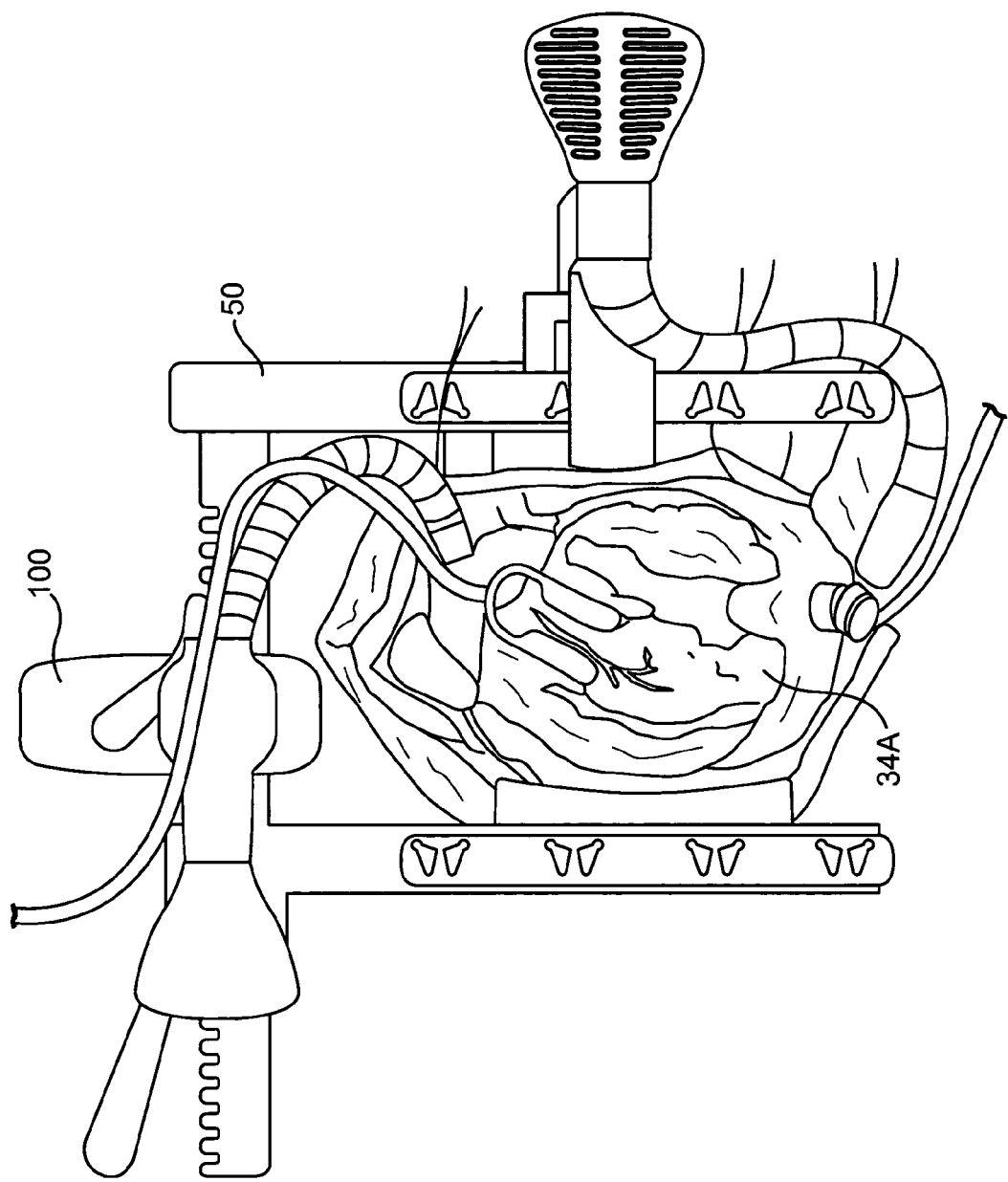
FIGS. 34A-34D are perspective views illustrating positioning of the tissue stabilizer of FIG. 1 in a surgical field.
Figure 34B:
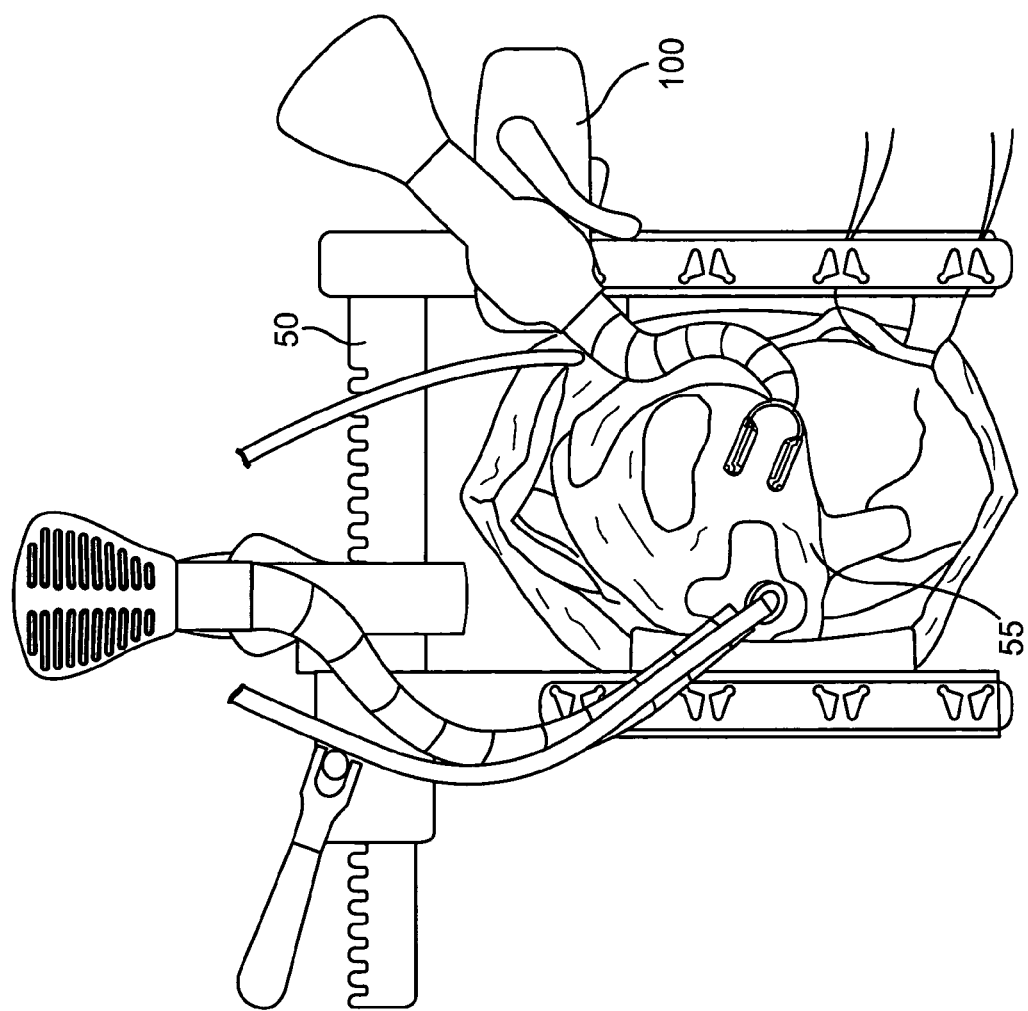
Figure 34C:
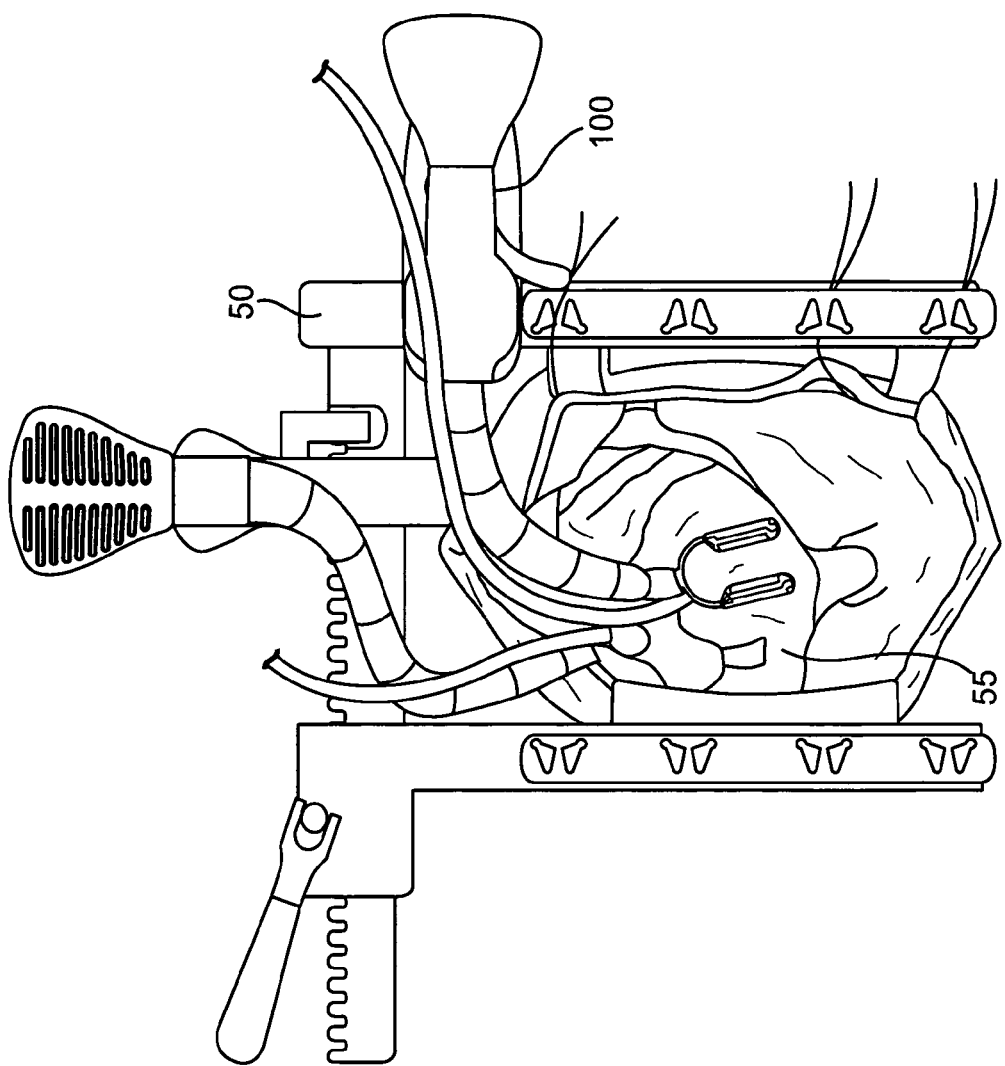
Figure 34D:
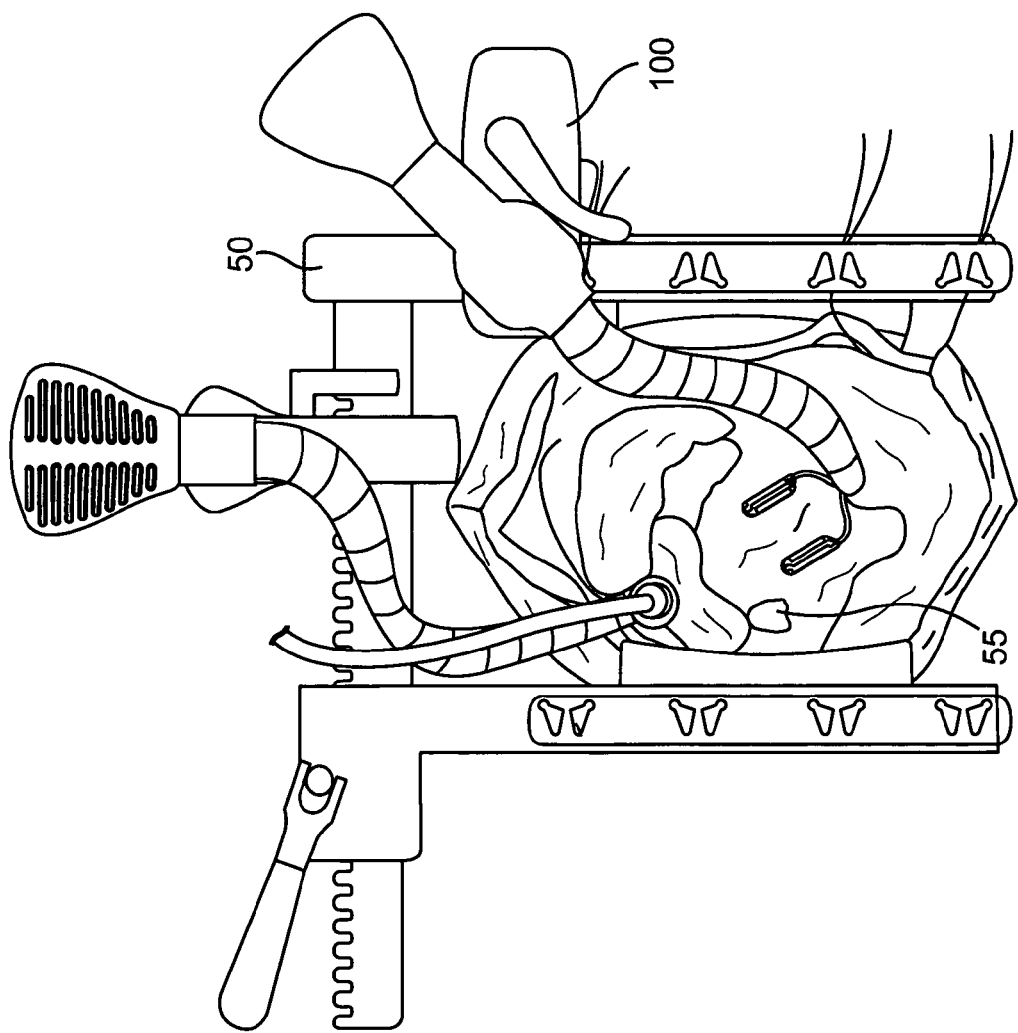
Figure 61:
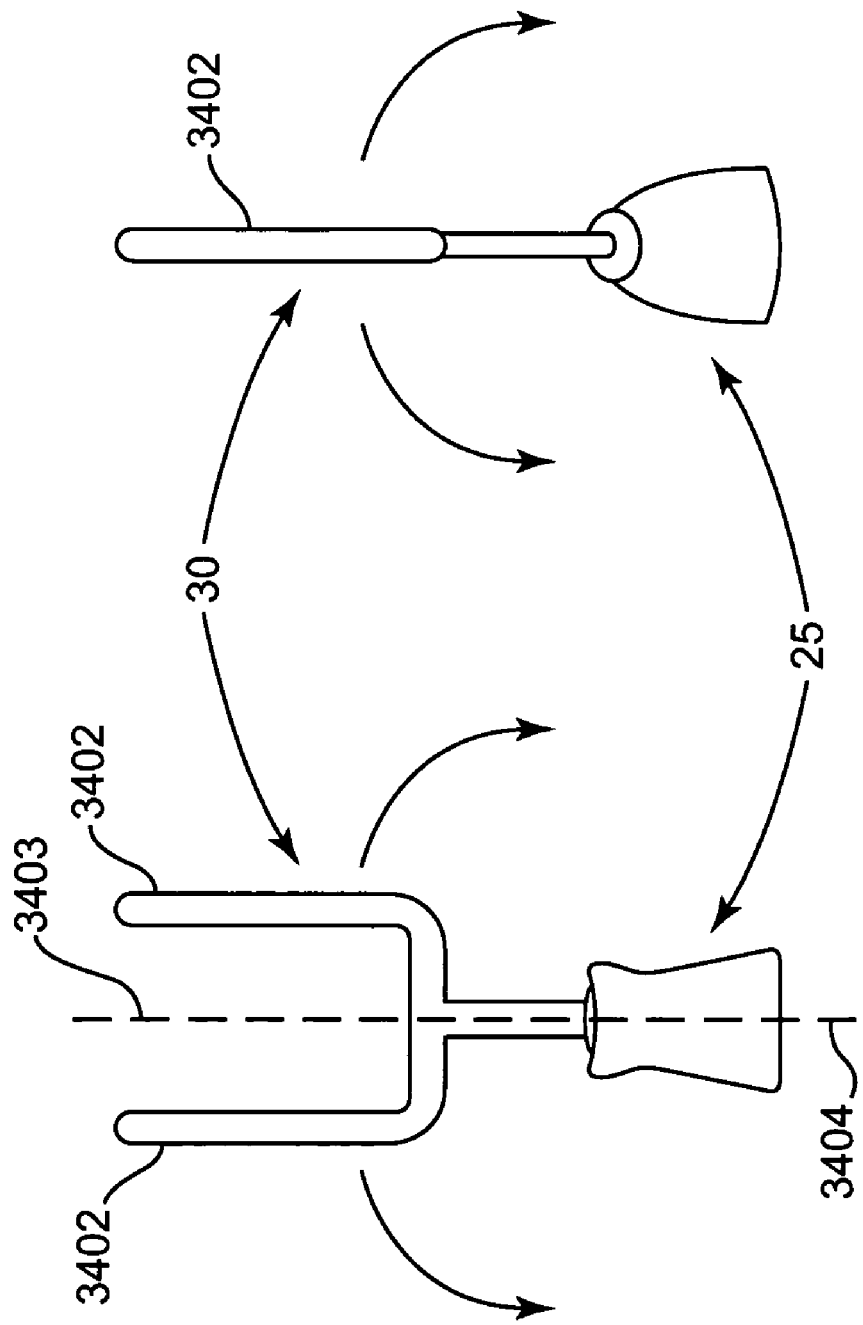
FIG. 61 is a schematic illustration of a range of motion of a head-link of the tissue stabilizer of FIG. 1.

FIG. 61 illustrates a range of motion of the head-link assembly 30 in one embodiment of the collet assembly 25 when the tension element 3270 is loosened. In some embodiments, the collet 3305 can hold the base 280 with about 6 lbf or more of force when the tension element 3270 is loose. In some embodiments, the collet assembly 25 can allow the head-link assembly 30 to be angled to any position in a semi-sphere residing above a plane perpendicular to the collet receiving element 3300. A pair of arms 3402 of the head-link assembly 30 can rotate about 360 degrees around a longitudinal axis 3403 of the head-link assembly 30. The head-link assembly 30 can also move from a position generally along a longitudinal axis 3404 parallel to the collet assembly 25 in any direction up to about 90 degrees. The range of motion can enable quicker and easier positioning of the head-link assembly 30 and can improve the positioning of the head-link assembly 30 for the surgery being performed including, for example, "pod up" and "pods down" positions, as shown in FIGS. 34C and 34D.

As the tension element 3270 is tensioned, the tension element stop 3310 can draw the collet 3305 into the sleeve 3325 of the collet receiving element 3300. As the collet 3305 is drawn into the collet receiving element 3300, the lip 3400 can force the collet 3305 to compress around the base 3280 of the head-link assembly 30, locking the head-link assembly 30 in position. The plurality slots 3360 can aid in compressing the head 3355 of the collet 3305. As the collet 3305 is drawn into the collet receiving element 3300, the size of the slots 3360 can decrease and the head 3355 can firmly hold the head-link assembly 30 in position. In addition, in some positions, an arm 3405 of the head-link assembly 30 can be positioned in one of the slots 3360 when the tension element 3270 is loosened. Positioning the arm 3405 of the head-link assembly 30 in one of the slots 3360 increases the range of motion of the head-link assembly 30. With the arm 3405 positioned in one of the slots 3360, the collet 3305 can be rotated about 3360 degrees in the sleeve section 3325 of the collet receiving element 3300.

As the collet 3305 is drawn into the sleeve 3325, an outer wall 3410 of the collet 3305 can be forced inward by the lip 3400 of the collet receiving element 3300 and can apply force to a head-link base 3280. As the force along the entire tissue stabilizer 100 increases, the coefficient of friction on the ball, base and reducing elements 3160, 3165, 3170 can cause them to be held in place and can hold the turret 10, the articulating arm 20, and the head-link assembly 30 in position. In some embodiments, the tissue stabilizer 100 can have holding torques equal to or greater than about 3.2 inch lbf ("inlbf"), about 5.5 inlbf, and about 7.5 inlbf when the tension element 3270 is tensioned to about 100 lbf, about 200 lbf, and about 300 lbf, respectively. The depth of the sleeve section 3325 of the collet receiving element 3300 can be sufficient to enable the collet 3305 to be drawn into the collet receiving element 3300 so that enough force can be applied to the collet 3305 by the lip 3400 to hold the base 3280 of the head-link assembly 30 in position before the base 3350 of the collet 3305 contacts the base 3380 of the collet receiving element 3300.

Rotating the handle 15 in the loosening direction can reduce the tension applied to the tension element 3270. Reducing tension on the tension element 3270 can reduce tension on the tension element stop 3310 and the outside wall 3410 of the collet 3305 can press against the lip 3400 of the collet receiving element 3300. The pressure of the outside wall 3410 on the lip 3400 can force the collet 3305 out of the collet receiving element 3300. When the collet 3305 moves out of the collet receiving element 3300 the head 3355 of the collet 3305 can become uncompressed and the base 3280 of the head-link assembly 30 can be free to move.

Figure 62:
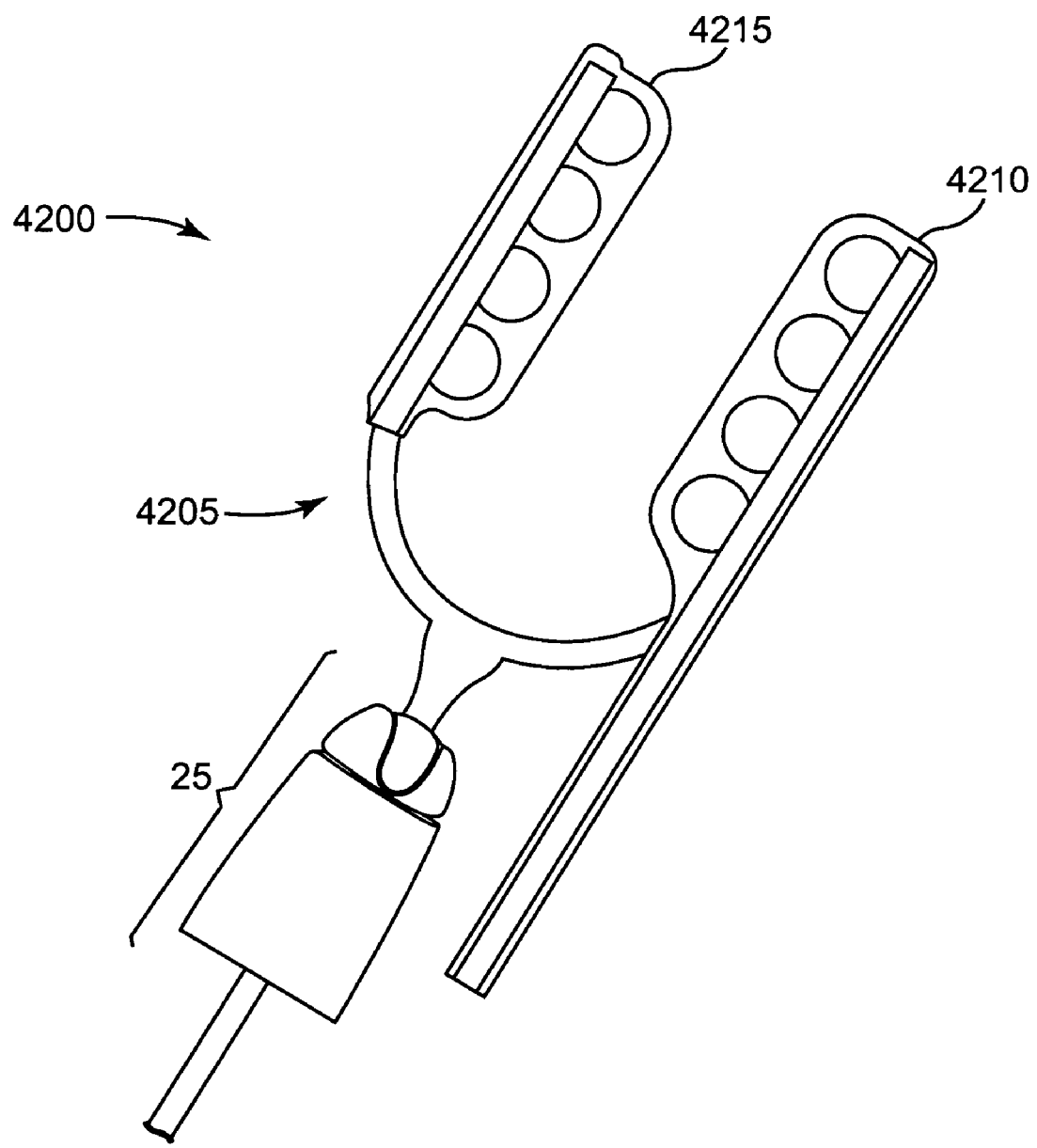
FIG. 62 is a perspective view of a head-link assembly according to one embodiment of the invention.

FIG. 62 illustrates a head-link assembly 4200 according to one embodiment of the invention. The head-link assembly 4200 can be mounted in the collet assembly 25 and can include a head-link 4205 supporting multiple pods, such as, for example, a first pod 4210 and a second pod 4215.

Figure 63:
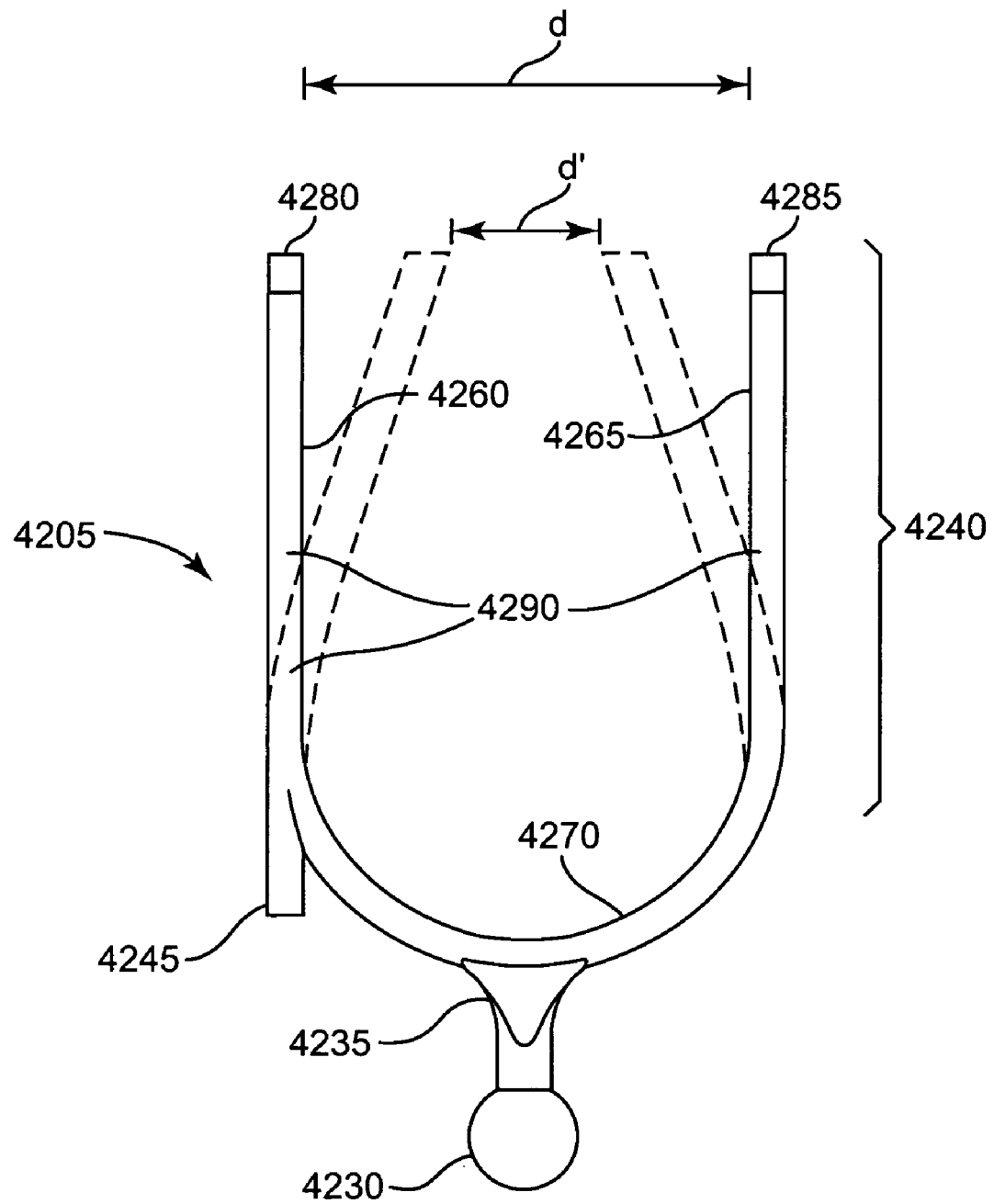
FIG. 63 is a detailed view of the head-link of the head-link assembly of FIG. 62.

FIG. 63 illustrates the head-link 4205 without the pods 4210, 4215. The head-link 4205 can include a base 4230, a neck 4235, a support 4240, and a vacuum port 4245. The base 4230 can be spherical in shape and can be sized to fit in the collet assembly 25. The neck 4235 can link the support 4240 to the base 4230. In some embodiments, the support 4240 is generally U-shaped and can include a first arm 4260, a second arm 4265, and a U-shaped header 4270. The first and second arms 4260, 4265 can support the first and second pods 4210, 4215, respectively.

In some embodiments, the support 4240 is a hollow member forming a conduit for pneumatically coupling the first and second pods 4210, 4215 to the vacuum port 4245. The first arm 4260 and the second arm 4265 can include a plurality of holes 4290 in positions corresponding to the first and second pods 4210, 4215. A negative or vacuum pressure supplied at the vacuum port 4245 can cause a vacuum or suction force at the pods 4210, 4215. This suction force can be used to temporarily and releasably couple tissue of the heart to the head-link assembly 4200 via the pods 4210, 4215 for tissue stabilization. In other embodiments, however, a separate conduit can be included on the support 4240 for pneumatically coupling the pods 4210, 4215 to the vacuum port 4245 (not shown).

The thickness of the support 4240, as well as an inside diameter and an outside diameter of the support 4240 (if hollow) may vary. In one embodiment, the support 4240 can have a thickness of from about 14 gauge ("GA") to about 15 GA. In other embodiments, other diameters of supports 4240 can be used. In one embodiment, the support 4240 can have a thickness of about 14 GA, an outside diameter of about 0.083 inches, and an inside diameter of about 0.063 inches. The size and position of the holes 4290 may also vary. In one embodiment, the holes 4290 can have a diameter of about 0.020 inches and can be slightly off-center (e.g., by about 0.012 inches).

In other embodiments, the support 4240 can have other shapes, including, for example, a V-shape or a squared-off U-shape. The first and second arms 4260, 4265 can be parallel to one another, as shown in FIG. 63, or in other embodiments, can point toward or away from one another. In some embodiments, the base 4230, the neck 4235, and the support 4240 can all be positioned in a single plane. In other embodiments, the neck 4235 can extend away from the support 4240 at an angle to a plane of the support 4240.

The head-link 4205 can be integrally formed by injection molding a thermoplastic or by other suitable methods using other suitable materials. In some embodiments, the base 4230 and the neck 4235 can be formed as one piece, and the support 4240 can be formed as a separate piece. The support 4240 can then be welded or adhered (e.g., laser welded) to the neck 4235. As shown in FIG. 63, ends 4280 and 4285 of the first and second arms 4260, 4265 can be crimped flat or plugged to create an airtight seal. Crimping the ends 4280 and 4285 flat can assist in over-molding the first and second-pods 4210 and 4215 onto the first and second arms 4260 and 4265.

In one embodiment, the arms 4260 and 4265 are sufficiently malleable so that the ends 4280 and 4285 can be flexed toward one another and can travel a distance of at least 2.5 mm each. In some embodiments, the first and second arms 4260 and 4265 of the head-link 4205 can be annealed to make them malleable. In some embodiments, the remainder of the head-link 4205, the U-shaped header 4270, the neck 4235, and the base 4230 can be hardened.

In operation, an external force can be applied to the ends 4280, 4285 of the arms 4260, 4265 to deflect them from a first or neutral position in which the ends 4280, 4285 are separated by a first distance (d) to a second position, shown in dotted lines in FIG. 63, in which the ends 4280, 4285 are separated by a second distance (d'). The external force can be applied by the surgeon's fingers after the head-link assembly 4200 has been positioned over the heart. A vacuum can then be applied to the vacuum pods 4210, 4215, causing the tissue of the heart to become secured to the pods 4210, 4215. The external force can then be released, allowing the arms 4260, 4265 to return to the first or neutral position. Typically, the arms 4260, 4265 can be moved closer to one another with a reduced second distance in the second position, so that upon release of the external force, the arms 4260, 4265 move apart, stretching the attached tissue between them. Return of the arms 4260, 4265 to the first position can be aided by a biasing force provided by the U-shaped header 4270.

Figure 64:
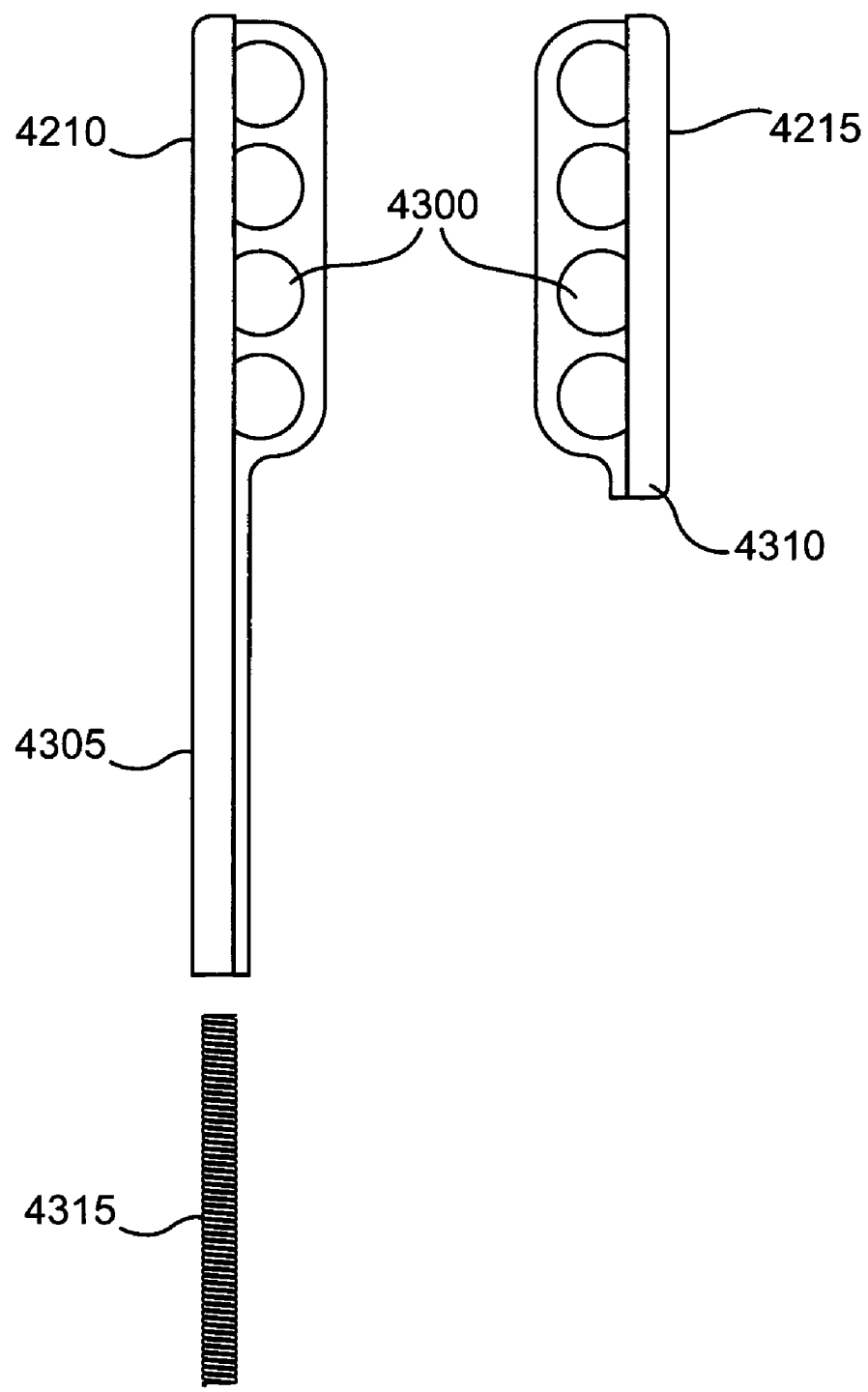
FIG. 64 is an exploded view of a first and second pod of the head-link assembly of FIG. 62.

FIG. 64 illustrates one embodiment of the first pod 4210 and the second pod 4215. The first and second pods 4210 and 4215 can include a plurality of pod cups 4300, a first channel 4305, a second channel 4310, and a spring 4315. The first and second pods 4210 and 4215 can be constructed of a suitable material, such as polyurethane or polyvinylchloride, and can be over-molded onto the head-link 4240 or can be manufactured separately. If manufactured separately, the first and second channels 4305 and 4310 can be sized to fit over the arms 4260 and 4265 of the support 4240. An inner diameter of the channels 4305 and 4310 can be slightly less than an outside diameter of the first and second arms 4260 and 4265, so that the first and second channels 4305 and 4310 can provide an air-tight seal when mounted to the first and second arms 4260 and 4265. In addition, the channels 4305 and 4310 can provide enough adhesion or friction to prevent the first and second pods 4210 and 4215 from twisting out of position.

The first and second pods 4210 and 4215 can include internal cavities that can pneumatically couple the plurality of holes 4290 with the plurality of pod cups 4300. A vacuum applied at the vacuum port 4245 can result in a suction force existing at each of the pod cups 4300.

The head-link assembly 4200 can be moved and rotated in many directions. As a result, there is a possibility that the vacuum tube 35 attached to the vacuum port 4245 can become kinked at or near the vacuum port 4245. To lessen the possibility of a kink occurring at or near the vacuum port 4245, a spring 4315 can be positioned within the first channel 4305.

Figure 65:
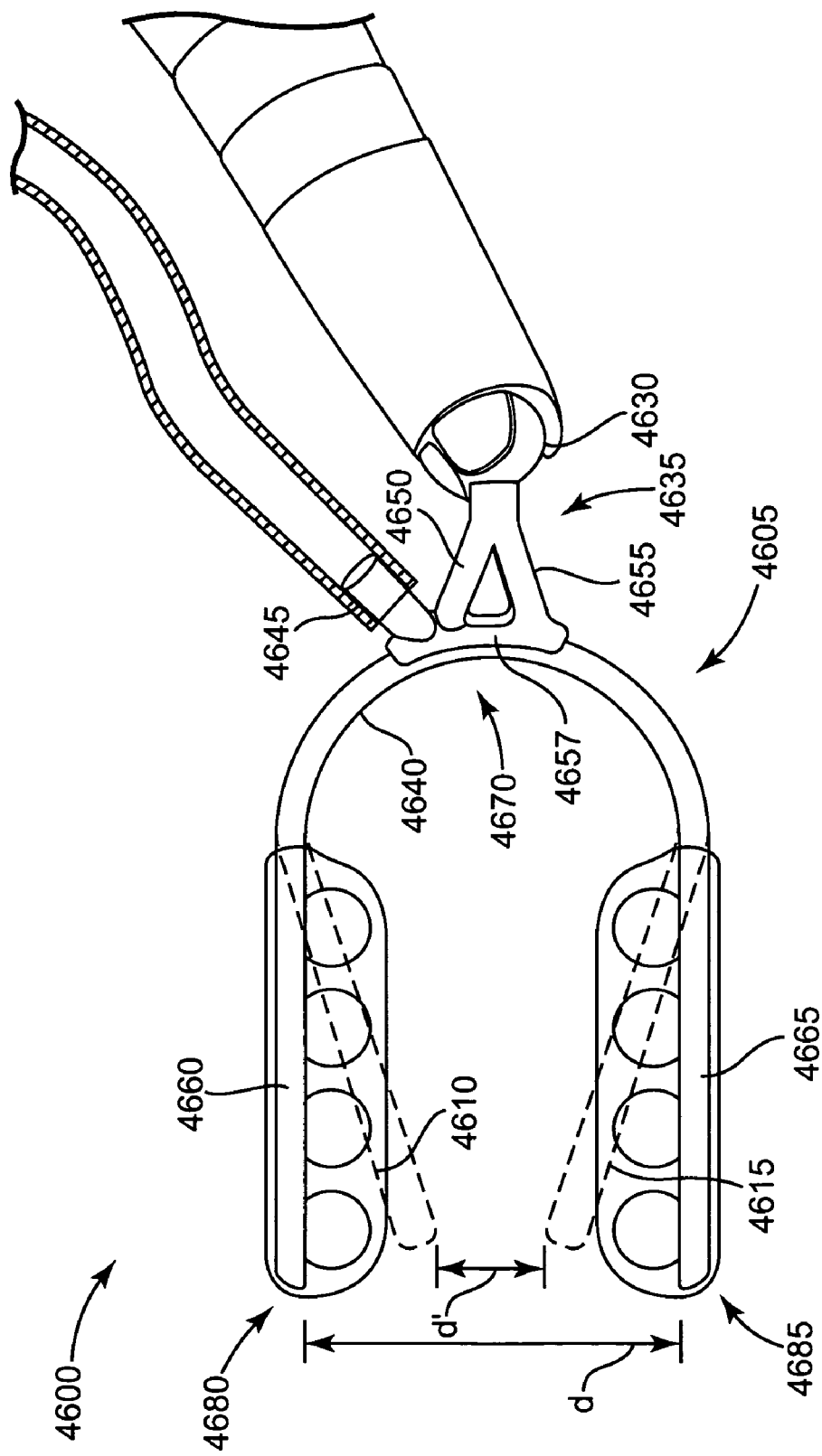
FIG. 65 is a perspective view of a head-link assembly according to another embodiment of the invention.

FIG. 65 illustrates a head-link assembly 4600 according to another embodiment of the invention. The head-link assembly 4600 can include a head-link 4605 supporting a first pod 4610 and a second pod 4615. The head-link 4605 can include a base 4630, a neck 4635, a support 4640, and a vacuum port 4645. In some embodiments, the neck 4635 is generally triangular in shape and the base 4630 can form one of the vertexes of the neck 4635. The neck 4635 can include two arms 4650 and 4655, extending from the base 4630, and a cross piece 4657. The cross piece 4657 can be shaped to match a curvature of the support 4640 and can surround a portion of the support 4640. In some embodiments, the vacuum port 4645 can be integrally formed in a side of the cross piece 4657.

In some embodiments, the arms 4660 and 4665 are sufficiently malleable so that they can be flexed in a direction toward one another and can travel a distance of at least 2.5 mm each. In some embodiments, the first and second arms 4660 and 4665 of the head-link 4605 can be annealed to make them malleable. In some embodiments, the remainder of the head-link 4605, including the support 4640, the neck 4635, the cross piece 4657 and the base 4630 can be hardened.

In operation, an external force can be applied to the arms 4660, 4665 to deflect them from a first or neutral position in which the arms 4660, 4665 are separated by a first distance (d) to a second position shown in dotted lines in which the arms 4660, 4665 are separated by a second distance (d'). Upon release of the external force, the arms 4660, 4665 can be biased to return to the first or neutral position. Return of the arms 4660, 4665 to the first position can be aided by a biasing force provided by the support 4640. While the first position is depicted in FIG. 65 as the arms 4660, 4665 being parallel, in other embodiments, the arms 4660, 4665 can point toward or away from one another in the first or neutral position.

FIGS. 66A and 66B illustrate a head-link assembly 4700 according to another embodiment of the invention. The head-link assembly 4700 can include a head-link 4705, a first pod 4710, and a second pod 4715. The head-link 4705 can include a base 4730, a neck 4735, a support 4740, a pair of arms 4760, 4765 and a vacuum port 4745. The neck 4735 can be generally triangular in shape and can extend from the base 4730. The neck 4735 can include two arms 4750 and 4755, extending from the base 4730, and a cross piece 4757. The cross piece 4757 can be shaped to fit the support 4740 and can surround a portion of the support 4740. In some embodiments, the vacuum port 4745 can be integrally formed into a center of the cross piece 4757. In some embodiments, the vacuum port 4745 can extend parallel to the support 4740 and the arms 4750 and 4755 can extend from the support 4740 at an angle to facilitate attachment of the vacuum tube 35 and ease positioning of the head-link assembly 4700.

In some embodiments, the arms 4760 and 4765 are sufficiently malleable so that they can be flexed in a direction towards one another and can travel a distance of at least 2.5 mm each. In some embodiments, the first and second arms 4760 and 4765 of the head-link 4705 can be annealed to make them malleable. In some embodiments, the remainder of the head-link 4705, the neck 4735, the base 4730, and the cross piece 4757 can be hardened.

In operation, an external force can be applied to the arms 4760, 4765 to deflect them from a first or neutral position in which the arms 4760, 4765 are separated by a first distance to a second position in which the arms 4760, 4765 are separated by a second distance (not shown). Upon release of the external force, the arms 4760, 4765 can be biased to return to the first or neutral position. Return of the arms 4760, 4765 to the first position can be aided by a biasing force provided by the support 4740. While the first position is depicted in FIGS. 66A and 66B as the arms 4760, 4765 being parallel, in other embodiments, the arms 4760, 4765 can point toward or away from one another in the first or neutral position.

Figure 67:
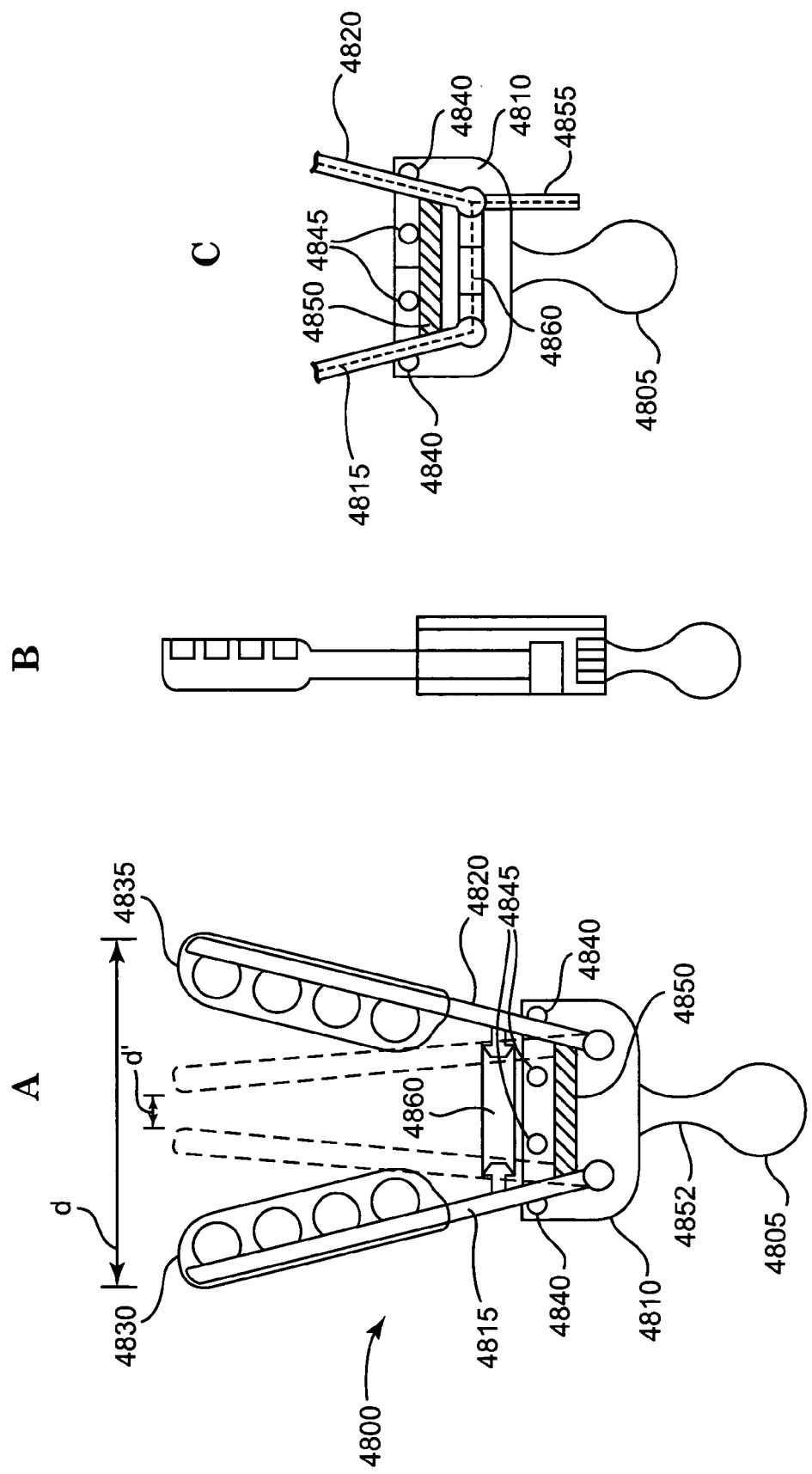
FIG. 67A is a front view of a head-link assembly according to another embodiment of the invention.
FIG. 67B is a side view of the head-link assembly of FIG. 67A.
FIG. 67C is a front view of the head-link assembly of FIG. 67A with a vacuum connector in a different position than shown in FIG. 67A.

FIGS. 67A and 67B illustrate a head-link assembly 4800 according to another embodiment of the invention. The head-link assembly 800 can include a base 4805, a support 4810, a first arm 4815, a second arm 4820, a first pod 4830, and a second pod 4835. The base 4805 can be spherical in shape and can be sized to fit in the collet assembly 25. The base 4805 can include a neck portion 4852 and can be molded into the support 4810. The first and second arms 4815 and 4820 can be pivotally coupled to the support 4810. The first and second arms 4815 and 4820 can be pivoted from a first position separated from one another by a first distance (d) in a direction toward one another to a second position, shown in dotted lines, separated by a second distance (d') and can travel a distance of at least 2.5 mm each. While the first position is depicted in FIGS. 67A and 67B as the arms 4810, 4815 pointing away from another, in other embodiments, the arms 4810, 4815 can be parallel or point toward one another in the first position.

The support 4810 can include a pair of outer arm stops 4840 and a pair of inner arm stops 4845. A spring 4850 can bias the first and second arms 4815 and 4820 away from each other so that the first and second arms 4815 and 4820 can contact the outer arm stops 4840 in the first position. The inner arm stops 4845 can limit the minimum second distance separating the arms 4815, 4820 in the second position.

In some embodiments, the arms 4815 and 4820 can be sufficiently malleable so that they can be flexed from a first position separated from one another by a first distance in a direction toward one another to a second position separated by a second distance and can travel a distance of at least 2.5 mm each. In other words, the arms 4815, 4820 may not need not to be pivotally coupled to the support 4810.

Each of the first and second arms 4815 and 4820 can include a plurality of holes. A vacuum port 4855 can be pneumatically coupled to the first arm 4815 and the holes of the first arm 4815. A flexible vacuum connector 4860 can pneumatically couple the first arm 815 to the second arm 4820 and the holes of the second arm 4820. The vacuum connector 4860 can be positioned above the support 4810, as shown in FIG. 67A, so that when the arms 4815 and 4820 are moved inward, the vacuum connector 4860 can flex. FIG. 67C illustrates another embodiment of a head-link assembly 4880 with the vacuum connector 4860 coupling the arms 4815 and 4820 at their pivot points.

Figure 68:
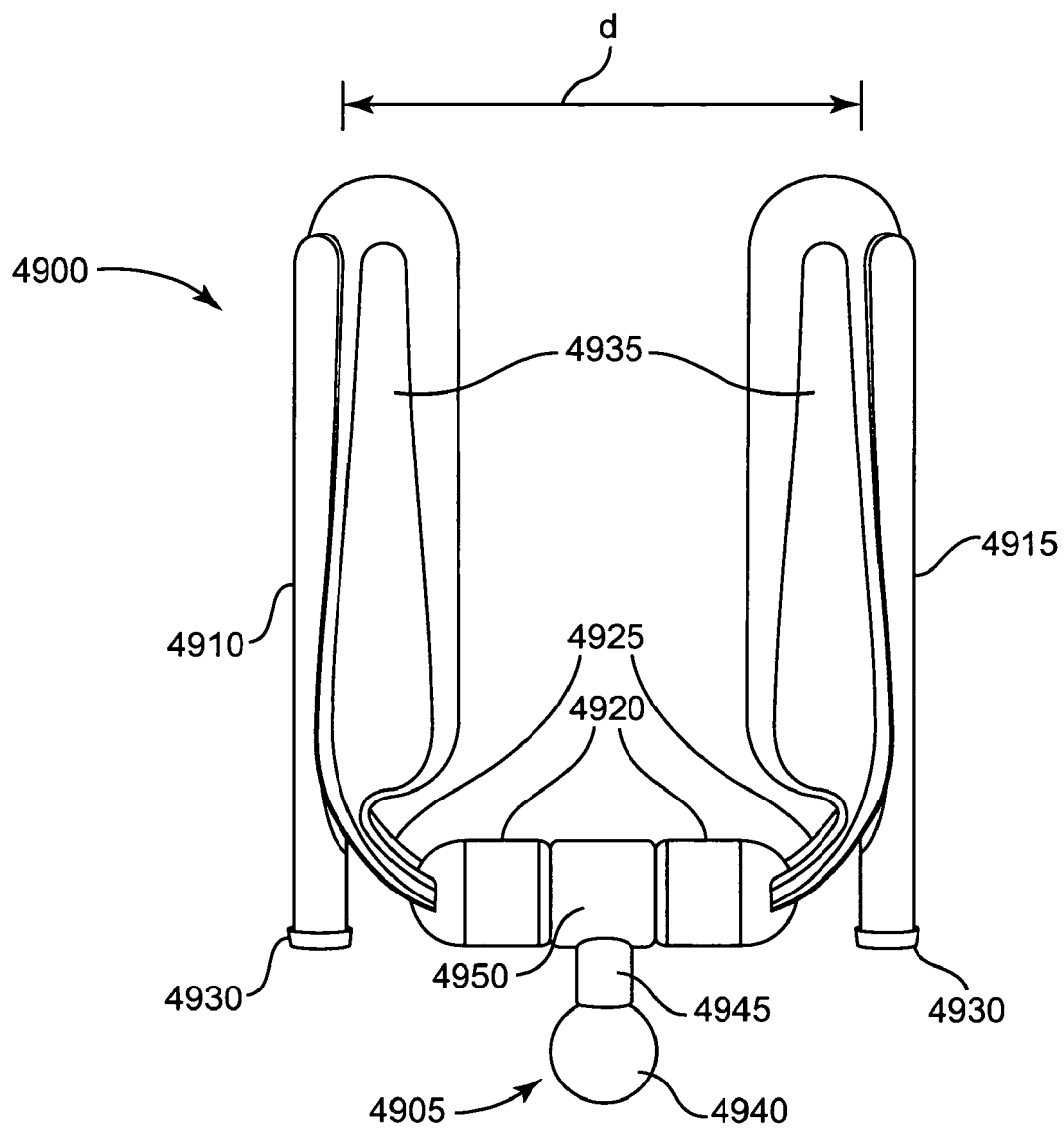
FIG. 68 is a perspective view of a head-link assembly according to another embodiment of the invention.

FIG. 68 illustrates a head-link assembly 4900 according to another embodiment of the invention. The head-link assembly 4900 can include a base 4905, a first arm 4910, and a second arm 4915. The first and second arms 4910 and 4915 can include a coupling 4920, a flexible link 4925, a vacuum port 4930, and a vacuum pod 4935. The base 4905 can include a ball 4940, a neck 4945, and a base coupling 4950.

The couplings 4920 of the arms 4910 and 4915 can be mounted to the base coupling 4950 so that the arms 4910 and 4915 and the base 4905 form a generally "Y" shape. The arms 4910 and 4915 can be pivoted independently of each other about the base coupling 4950. The links 4925 can bias the arms 4910 and 4915 to a first or neutral position, as shown in FIG. 68, in which the arms 4910, 4915 are separated from one another by a first distance (d). The arms 4910 and 4915 can be flexed inward or outward to a second position separated from one another by a second distance by applying a force to the arms 4910 and 4915 (not shown). Either or both of the arms 4910, 4915 and the links 4925 can be sufficiently flexible or malleable to permit movement of the arms 4910, 4915 from the first position to a second position. Upon release of the force, the arms 4910, 4915 can be biased to return to the first or neutral position. While the first position is depicted in FIG. 68 as the arms 4910, 4915 being parallel, in other embodiments, the arms 4910, 4915 can point toward or away from one another in the first or neutral position.

Figure 69:
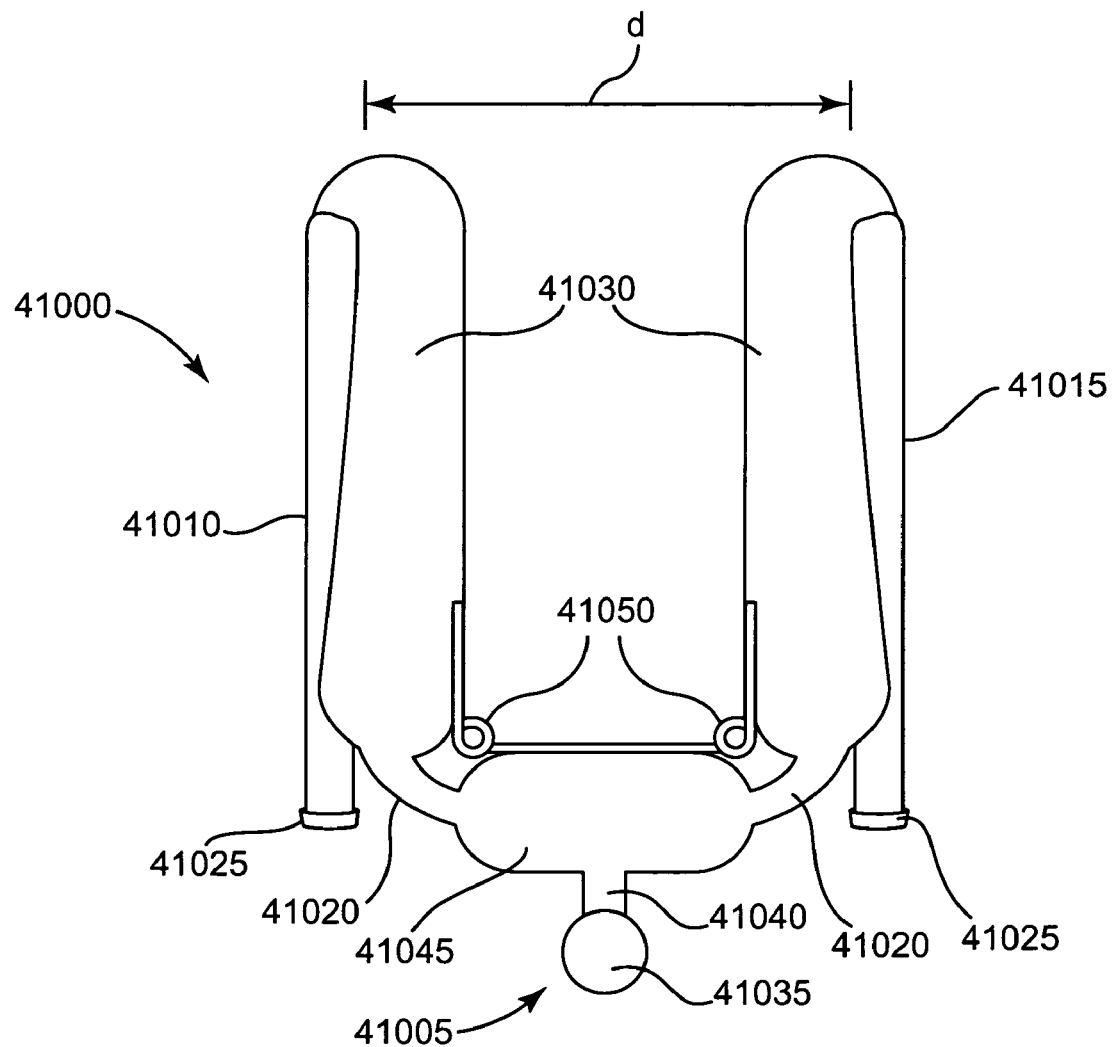
FIG. 69 is a perspective view of a head-link assembly according to another embodiment of the invention.

FIG. 69 illustrates a head-link assembly 41000 according to another embodiment of the invention. The head-link assembly 41000 can include a base 41005, a first arm 41010, and a second arm 41015. The first and second arms 41010 and 41015 can include a flexible link 41020, a vacuum port 41025, and a vacuum pod 41030. The base 41005 can include a ball 41035, a neck 41040, and a base coupling 41045. In some embodiments, the entire head-link assembly 41000 can be integrally formed via injection molding. In some embodiments, a biasing spring 41050 can be coupled to the arms 41010 and 41015 and the base coupling 41045. The links 41020 and the biasing spring 41050 can bias the arms 41010 and 41015 to a first or neutral position separated by a first distance (d) as shown in FIG. 69. The arms 41010 and 41015 can be flexed inward or outward to a second position separated by a second distance by applying a force to a distal end of the arms 41010 and 41015 (not shown). Upon release of the force, the arms 41010, 41015 can be biased to return to the first position. While the first position is depicted in FIG. 69 as the arms 41010, 41015 being parallel, in other embodiments, the arms 41010, 41015 can point toward or away from one another in the first or neutral position. The biasing spring 41050 can be over-molded into the head-link assembly 41000 or can be attached using a suitable adhesive or fasteners.

Figure 70:
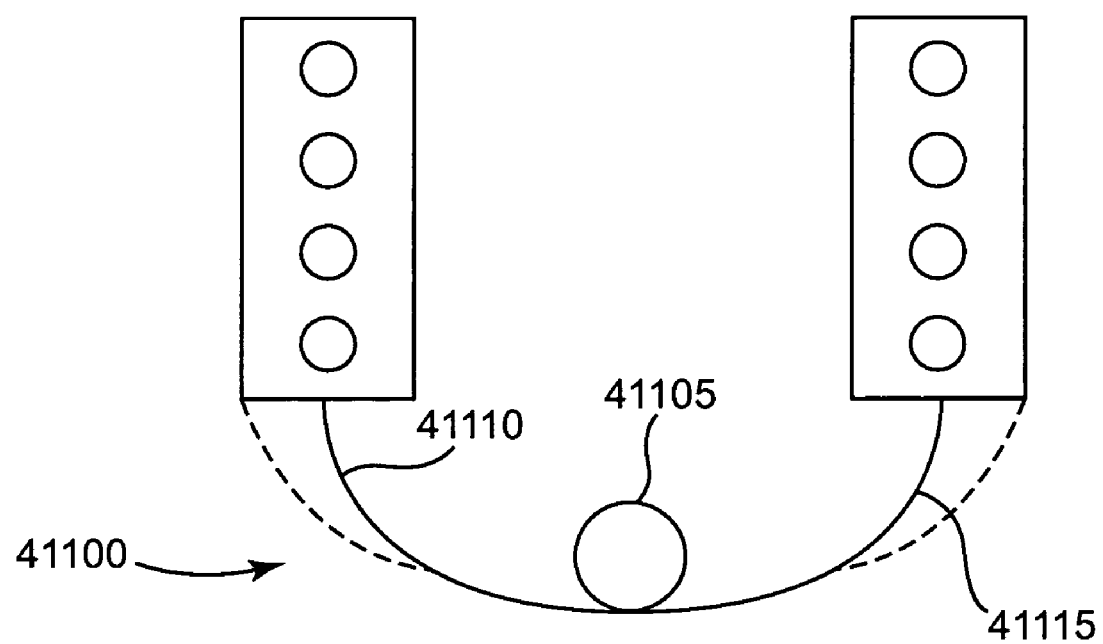
FIG. 70 is a front view of a biasing spring for use with a head-link assembly according to one embodiment of the invention.
Figure 71:
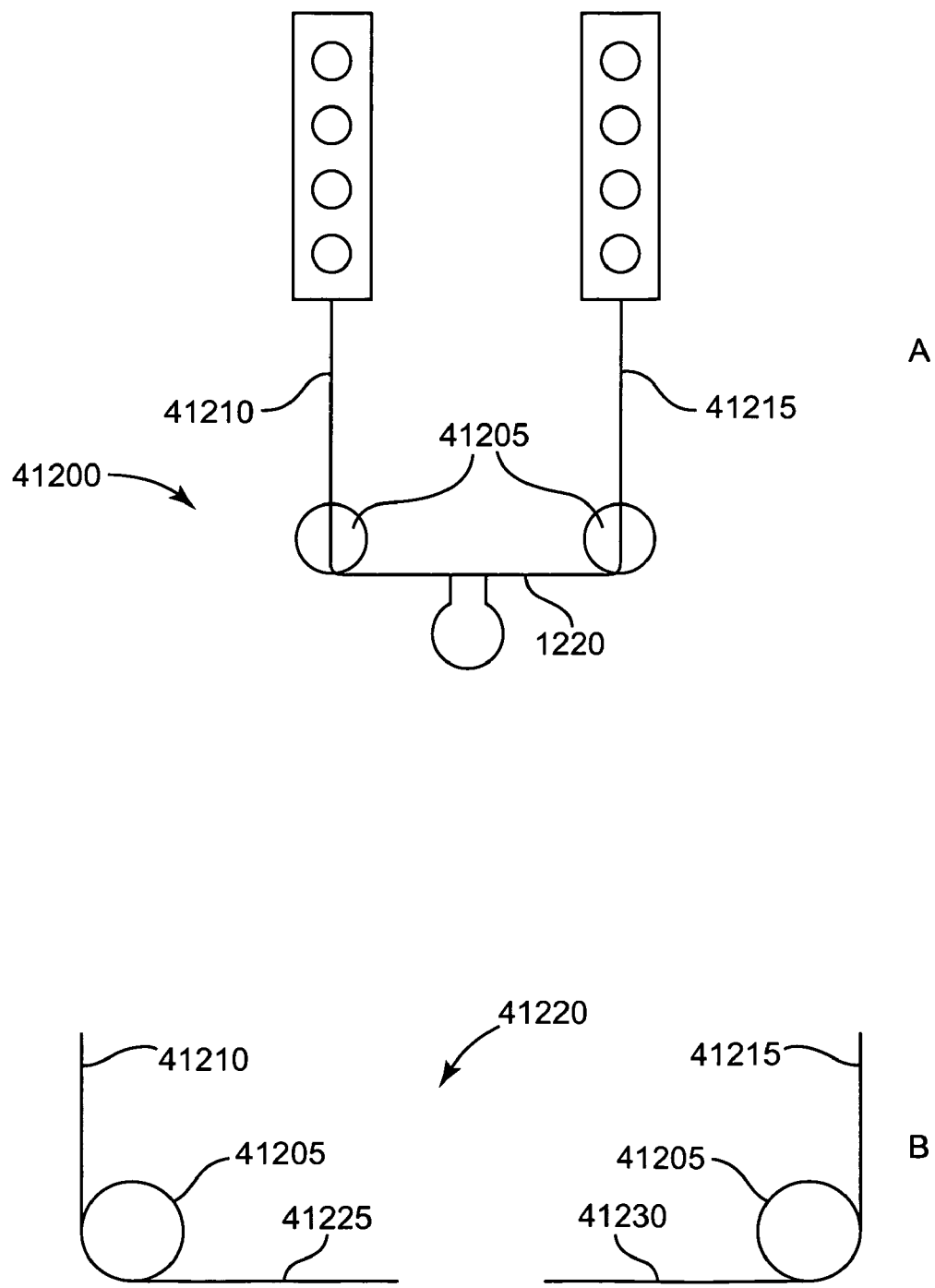
FIGS. 71A and 71B are front views of biasing springs for use with a head-link assembly according to another embodiment of the invention.

FIGS. 70, 71A, and 71B illustrate embodiments of biasing springs for use with the head-link assemblies as described with respect to FIGS. 62-69, for example. In one embodiment, as shown in FIG. 70, a biasing spring 41100 can include a single coil 41105 centrally located between a first biasing arm 41110 and a second biasing arm 41115. In another embodiment, as shown in FIGS. 71A and 71B, a biasing spring 41200 can include a pair of coils 41205 located at a base of a first biasing arm 41210 and a second biasing arm 41215. The coils 41205 can be linked by a center cable 41220 (as shown in FIG. 71A) or can include a third biasing arm 41225 and a fourth biasing arm 41230 (as shown in FIG. 71B). The biasing springs can be the sole source of bias for a head-link assembly or can assist other elements of a head-link in biasing arms of the head-link assembly.

In operation, the biasing element (e.g., the u-shaped support, the flexible link, or the biasing spring) can be connected to the arms of the head-link to bias the arms to a first or neutral position. A surgeon can squeeze the arms together and can place the cups on an epicardium of the heart. The surgeon can manually control how much spread (tension) is placed lateral to a coronary target and also the exact location where the spreading force is applied. Vacuum pressure can be applied to the cups via the vacuum port to engage the tissue and the arms can be released to return to the first position, providing tissue tension to the desired location. The surgeon can optimize the tissue retraction capabilities as needed in intramyocardial vessels and in deep fat areas. The surgeon can also optimize stabilization and reduce tissue movement between the arms by applying the correct amount of lateral traction at the correct location. The head-link can provide improved exposure by retracting fat/muscle and can present an artery.

Since cable tension need not be transferred from the articulating arm to the head-link, a shorter cable can be used for the tissue stabilizer and can result in a more rigid articulating arm. In addition, the articulating arm and the head-link can be locked in position before engaging the heart or the articulating arm and head-link can be free to move before and after engaging the heart.

In some embodiments, a head-link assembly can be deflected between about 17% and 32% of the head-link assembly's total possible deflection when a pair of arms are deflected about 5 mm. A force required to deflect the arms about 5 mm can be between about 2.84 foot pounds ("lbf") and 5.66 lbf. The number of deflection cycles that the head-link can withstand before failing can exceed ten.

Figure 72:
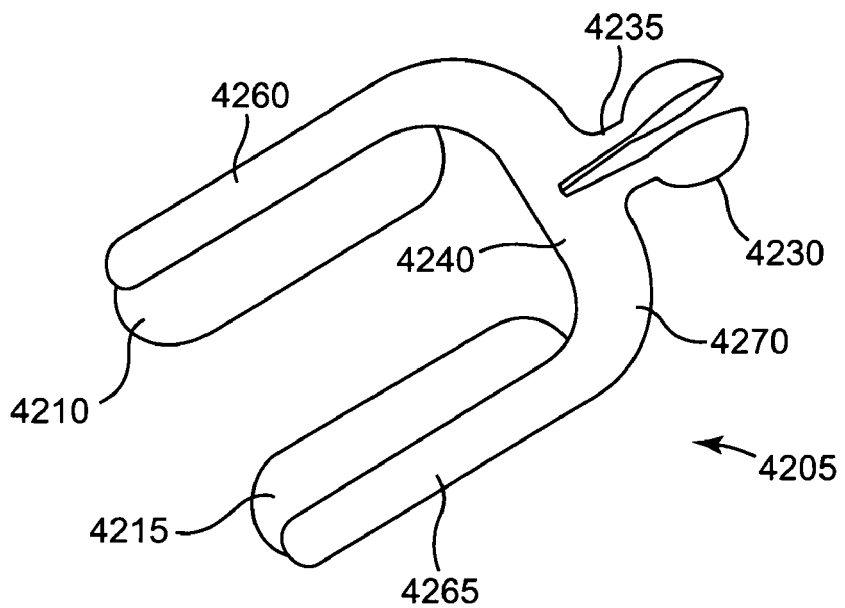
FIG. 72 is a perspective view of an embodiment of a head-link according to the invention.
Figure 73:
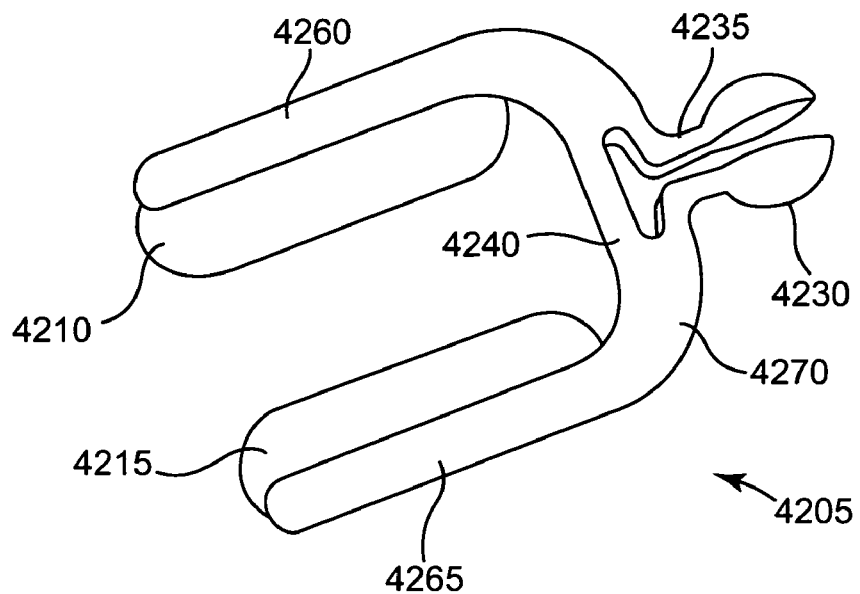
FIG. 73 is a perspective view of an embodiment of a head-link according to the invention.

In some embodiments, the invention provides a head-link assembly for automatically stretching the distance between two vacuum pods when a cable is tightened. FIGS. 72 and 73 illustrate two alternative embodiments of head-links according to the present invention. The alternative head-link assemblies 4205 may include first and second pods 4210 and 4215, first and second arms 4260 and 4265, a base (e.g., a split ball) 4230, a neck 4235, a support 4240, and a vacuum port (not shown). The base 4230 can be spherical in shape and can be sized to fit in the collet assembly 25. The neck 4235 can link the support 4240 to the base 4230. In some embodiments, the support 4240 is generally U-shaped and can include a first arm 4260, a second arm 4265, and a U-shaped header 4270. The first and second arms 4260, 4265 can support the first and second pods 4210, 4215, respectively. In some embodiments, the base 4230 may include a slot or may be separated into two halves and supported by a cross member. The slot or separation may be perpendicular to a plane formed by the arms and pods. The slot may exist at least on an end of the base or ball opposite where the arms are coupled to the base.

As the tension element 3270 is tensioned, the collet assembly 25 is forced to compress around the base 4230 of the head-link assembly 30. Compression of the base 4230 closes the slot or separation in the base, thereby forcing the pair of arms, and therefore the pods, connected to the base at the end opposite the slot or separation, to move in an outward direction. In operation, the pods can be attached to tissue to be stabilized and can stretch the tissue automatically as the tension element of the tissue stabilizer is tensioned.

Figure 74:
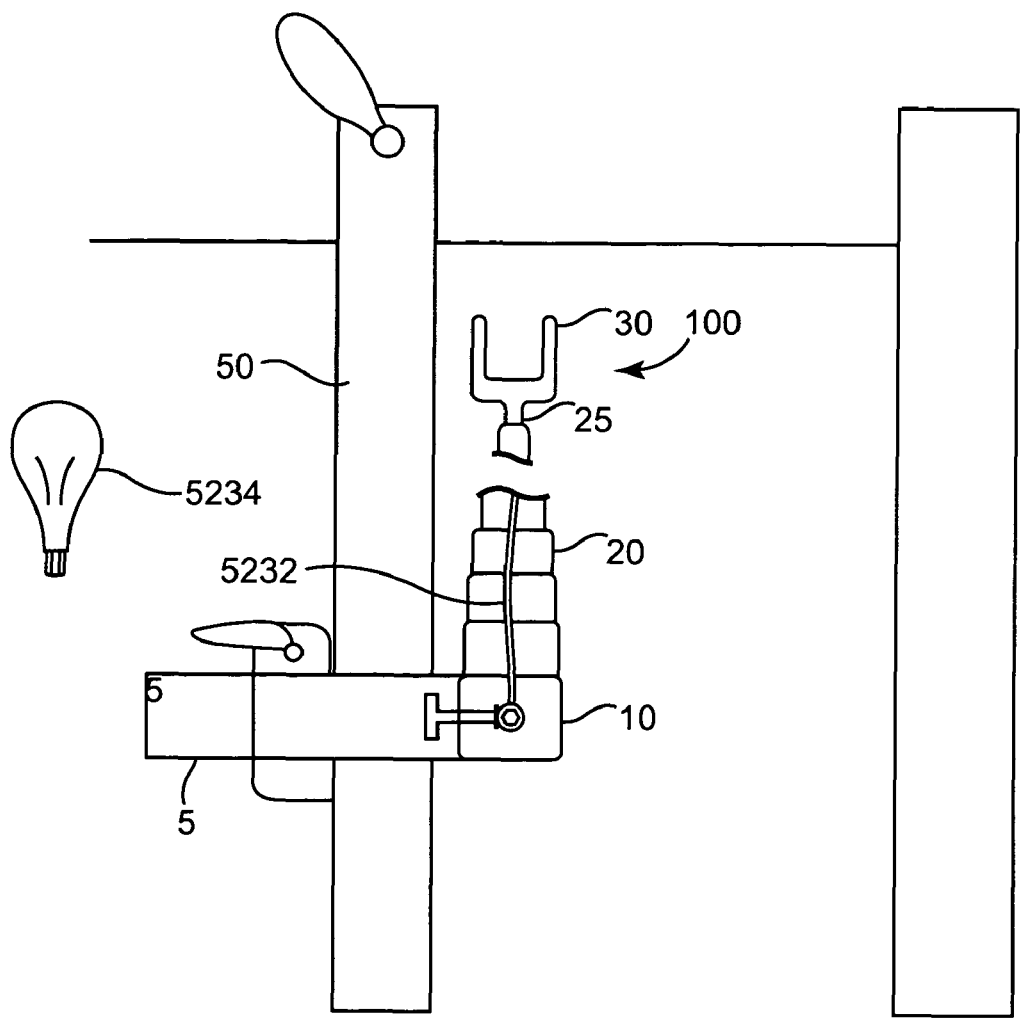
FIG. 74 is a top view of a tissue stabilizer according to one embodiment of the invention mounted to a sternal retractor.

FIG. 74 illustrates a tissue stabilizer 100 according to one embodiment of the invention. The tissue stabilizer 100 can include a clamp 5, a turret assembly 10, an articulating arm 20, a collet assembly 25 and a head-link assembly 30. A tension element 5232 can be coupled at one end to the collet assembly 25, can extend through the articulating arm 20, and can be coupled to the turret assembly 10 at the opposite end. In addition, the tissue stabilizer 100 can include a detachable key 5234 that can be used in conjunction with the turret assembly 10 to immobilize the articulating arm 20 and the turret assembly 10. The tissue stabilizer 100 can also include a vacuum system, including a vacuum tube, a vacuum tube clamp, and a vacuum tube valve.

Figure 75:
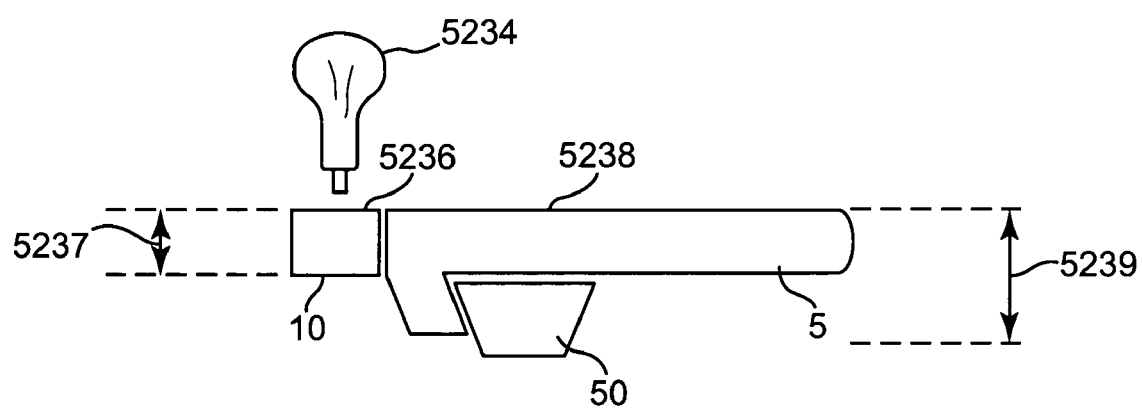
FIG. 75 is a side view of a turret according to one embodiment of the invention in relation to a clamp and sternal retractor.

FIG. 75 illustrates the tissue stabilizer 200 mounted to the sternal retractor 50. The tissue stabilizer 100 can have a relatively low-profile by the turret assembly 10 having an upper surface 236 that does not protrude upward of an upper surface 238 of the clamp 5. The tissue stabilizer 100 can also have a relatively low-profile by the turret assembly 10 being coupled to a front portion of the clamp 5, rather than to an upper portion of the clamp 5, as compared to the alternative tissue stabilizer embodiment 100 illustrated in FIG. 1. This can reduce the overall height clearance of the tissue stabilizer 100, which can be defined as the distance the tissue stabilizer 100 extends above the sternal retractor 50. In one embodiment, a height clearance 5237 of the turret assembly 10 can be less than or equal to a clearance 5239 of the clamp 5. The low-profile or reduced height clearance of the tissue stabilizer 100 can reduce the amount of obstruction, including, for example, visual obstruction and physical obstruction, of a surgical field caused by the tissue stabilizer 100.

FIG. 76 illustrates an alternative embodiment of turret assembly 10 in more detail. The turret assembly 10 includes a housing 5240, a spool 5242 inside of the housing 5240, and a locking mechanism 5246. The housing 5240 can be substantially hollow and can couple to the articulating arm 20 and to the clamp 5. As shown in FIG. 77, a first side 5240*a* of the housing 5240 can abut the clamp 5 and can have a first opening 5248. A second side 5240*b* of the housing 5240 and a third side 5240*c* opposite of the second side 5240*b* can have openings 5250, 5252 therethough that can be aligned with the spool 5242. A fourth side 5240*d* of the housing 5240 can have an opening 5254 therethrough that can be sized to accommodate the tension element 5232.

The spool 5242 can be positioned within the housing 5240 and can have a shaft 5256 connecting a first mating receptor 5258 and a second mating receptor 5260, and an attachment area 5262 on the shaft 5256 between the first and second mating receptors 5258, 5260. As shown in FIG. 78, the tension element 5232 can be coupled to the shaft 5256 at the attachment area 5262. For example, the attachment area 5262 can include an aperture for inserting a portion of the tension element 5232 inside of the shaft 5256, which can be hollow. The tension element 5232 can be knotted or provided with an anchor inside of the shaft 5256 to prevent the tension element 5232 from disengaging from the spool 5242. The spool 5242 can be crimped or otherwise clamped onto the tension element 5232. The tension element 5232 can be secured to the attachment area 5262 with an adhesive or a suitable fastener.

The first and second mating receptors 5258, 5260 can be rotatably mounted to the housing 5240 and can each include a hex-shaped (i.e., six-sided) inner wall defining an aperture or partial bore. The spool 5242 can be rotatable relative to the housing 5240 about an axis defined by the shaft 5256. The first mating receptor 5258 can be located on the second or nominally upper side 5240*b* of the housing 5240 while the second mating receptor 5260 can be located on the third or nominally lower side 5240*c* of the housing 5240. "Upper" and "lower" are relative terms, because the turret assembly 10 can be rotatable relative to the clamp 5 so that the spool 5242 can rotate end over end. Accordingly, while the first and second mating receptors 5258, 5260 are generally located opposite one another on the housing 5240, they can each be located 360 degrees about the clamp 5 as the turret assembly 10 is rotated relative to the clamp 5. In another embodiment, the spool 5242 can have a single mating receptor.

As shown in FIG. 79, the locking mechanism 5246 can include a pin 5244. The pin 5244 can have a first end 5264 rotatably coupled to the spool shaft 5256 and a second end 5266 coupled to the clamp 5. The second end 5266 of the pin 5244 can be coupled to an anchor 5268 or other structure within the clamp 5. As a result, the turret assembly 10 can rotate about the pin 5244 in a plane that can be approximately perpendicular to the plane of the clamp 5, as indicated by the arrow A, as shown in FIG. 74.

The locking mechanism 5246 can also include an approximately I-shaped spacer 5247. The spacer 5247 can have a bore 5270 that can receive the pin 5244 therein. The spacer 5247 can slide longitudinally over the pin 5244 and can also rotate about the pin 5244. The spacer 5247 can be retained inside of the housing 5240 due to the first aperture 5248 of the housing 5240 being sized larger than the pin 5244 but smaller than the spacer 5247.

Figure 80:
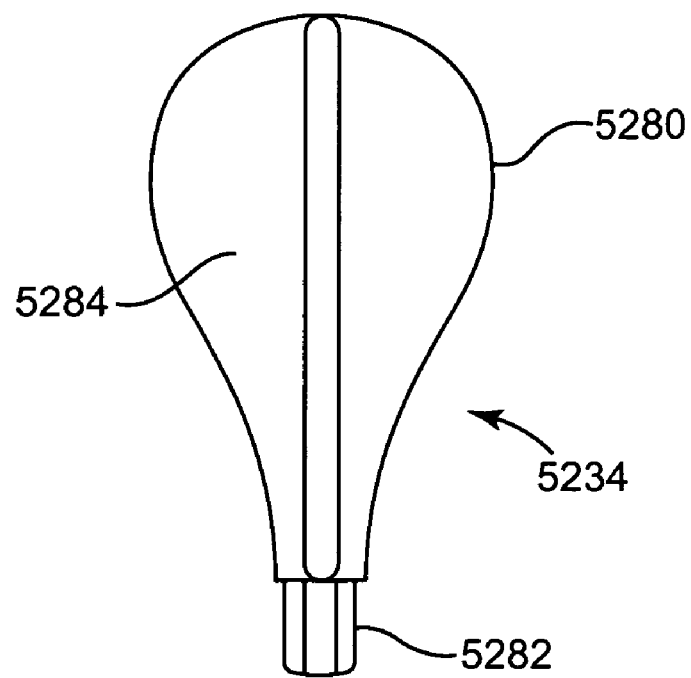
FIG. 80 is a side view of a detachable key according to one embodiment of the invention.
Figure 81:
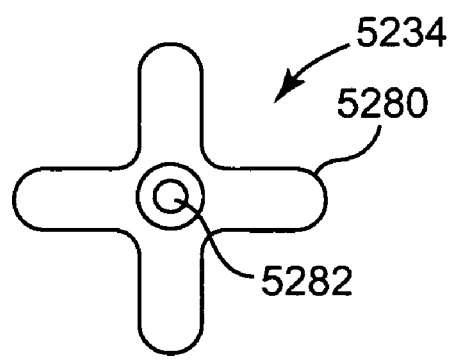
FIG. 81 is a bottom view of the key of FIG. 80.

As shown in FIGS. 80 and 81, the key 5234 can have a handle 5280 or other feature adapted for being gripped by a human hand and a mating protrusion 5282 coupled to the handle 5280. The handle 5280 can be shaped approximately as a "whale tail" or otherwise ergonomically shaped so as to be gripped comfortably and rotated easily. The handle 5280 can have a surface texture 5284 in order to provide a more firm gripping surface for the user.

In one embodiment, the mating protrusion 5282 can have six-sides and be sized and shaped to be matingly received in the mating receptors 5258, 5260. The mating protrusion 5282 and mating receptors 5258, 5260 are not limited to the hex or six-sided shape shown in FIG. 74, but can have a variety of shapes so that when the mating protrusion 5282 is inserted into the mating receptor 5258, 5260 the mating protrusion 5282 can engage the inner wall of the mating receptor 5258 to drive rotation of the spool 5242.

Figure 82:
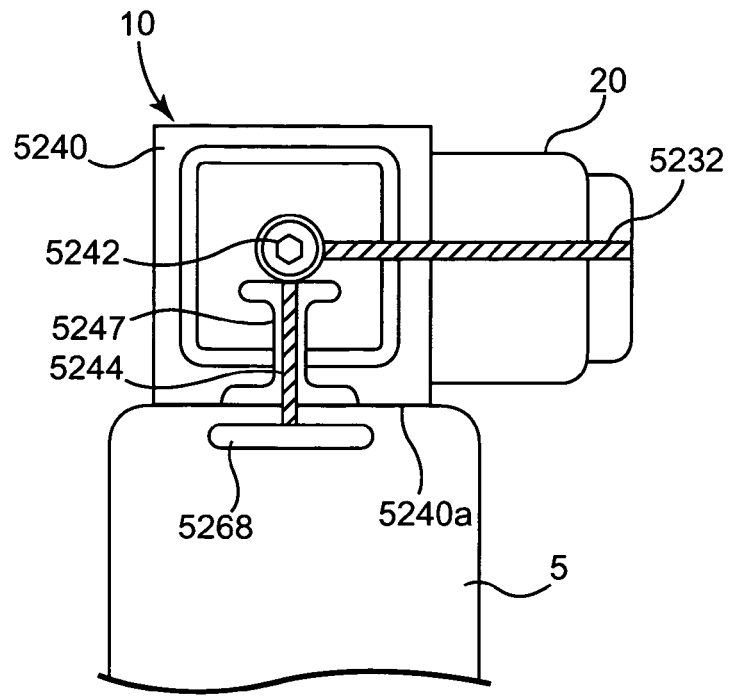
FIG. 82 is a top cut-away view of the turret in a neutral configuration in relation to the clamp and articulating arm.
Figure 83:
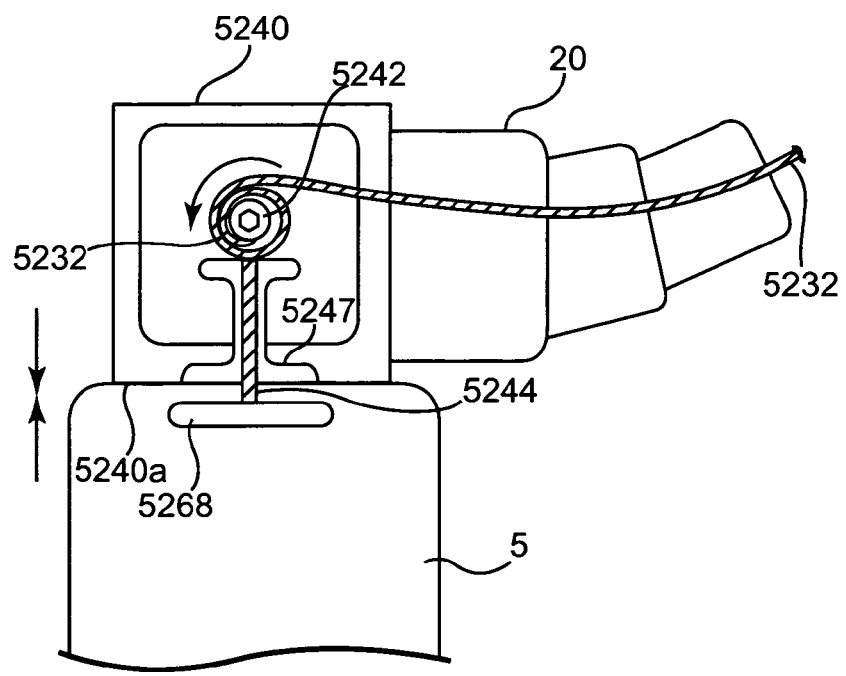
FIG. 83 is a top cut-away view of the turret of FIG. 82 after the tension element has been wound about the spool.

In some embodiments, the tissue stabilizer 100 may be mounted to the sternal retractor 50 with the clamp 5 and used to stabilize the articulating arm 20 as follows. The turret assembly 10 may be manually rotated relative to the clamp 5 in order to position the articulating arm 20 within the surgical field. The articulating arm 20 can be flexed or articulated to position the head-link assembly 30 within the surgical field. Once the articulating arm 20 is suitably positioned, the detachable key 5234 can be used to stiffen the articulating arm 20 in order to reduce or prevent articulation of the articulating arm 20, and also to prevent rotation of the turret assembly 10 with respect to the clamp 5. This can be accomplished by inserting the mating protrusion 5282 of the detachable key 5234 into one of the mating receptors 5258, 5260. In some embodiments, dual mating receptors are provided so that the likelihood of a mating receptor being conveniently accessible by the detachable key 5234 is increased regardless of the rotational position of the turret assembly 10 relative to the clamp 5. The mating protrusion 5282, after insertion into the mating receptor 5258, 5260, can be rotated in a first direction, for example, clockwise, with the handle 5280. FIG. 82 illustrates the turret assembly 10 in a neutral position before the detachable key 5234 is used to rotate the spool 5242. The mating protrusion 5282 engages the inner wall of the mating receptor 5258, 5260, causing the spool 5242 to rotate in a first direction, for example, clockwise. As the spool 5242 is rotated in the first direction, the tension element 5232 can be wound about the shaft 5256 of the spool 5242. The housing 5240, being hollow, can accommodate the coils of the tension element 5232 wound about the shaft 5256, as shown in FIG. 83.

As the tension element 5232 is wound about the shaft 5256, the length of the tension element 5232 relative to the articulating arm 20 can be reduced. This can exert a tensioning force on the tension element 5232, thereby stiffening the articulating arm 20. The detachable key 5234 can be rotated a sufficient number of turns to slightly stiffen the articulating arm 20 in order to provide the articulating arm 20 with shape-memory as the articulating arm 20 is maneuvered. The detachable key 5234 can be further rotated in order to exert a sufficient tensioning force to prevent articulation of the articulating arm 20, thereby stabilizing the articulating arm 20. The turret assembly 10 can include a ratchet mechanism (not shown) or other structure to help prevent the spool 5242 from inadvertently un-winding.

The detachable key 5234 can also be used to lock the turret assembly 10 to the clamp 5 in order to reduce or prevent rotation of the turret assembly 10 relative to the clamp 5. As the detachable key 5234 is rotated in the first direction to wind the tension element 5232 about the shaft 5256, the coils of the tension element 5232 about the shaft 5256 can build up between the shaft 5256 and the spacer 5247. This causes the spacer 5247 to slide longitudinally over the pin 5244 away from the spool 5242 and toward the clamp 5205. Additional rotation of the detachable key 5234 (i.e., windings of the tension element 5232 about the shaft 5256) exerts a tension force on the pin 5244 between the spool 5242 and the spacer 5247. Because the second end of the pin 5244 can be fixed to the clamp 5 at the anchor 5268, the tension force can be converted to a clamping force between the clamp 5 and the first surface 5240*a* of the housing 5240. The clamping force can provide enough friction between the housing 5240 and the clamp 5 to substantially prevent the housing 5240 from rotating relative to the clamp 5. As a result, the turret assembly 10 can be locked or made stationary in relation to the clamp 5.

In operation, the user can employ one hand to grasp and manipulate the articulating arm 20 to position the head-link assembly 30 within the surgical field. The user can employ the other hand to grasp the key 5234, insert the key 5234 into the turret assembly 10, and rotate the key 5234 to tighten the head-link assembly 30 in the collet assembly 25, to tighten the articulating arm 20 and to clamp the turret assembly 10 to the clamp 5, for example. The key 5234 can then removed from the turret assembly 10 by removing the mating protrusion 5282 from the mating receptor 5258 or 5260. With the key 5234 removed from the turret assembly 10, the tissue stabilizer 100 can have a lower profile or height clearance, reducing obstruction of the surgical field.

To un-clamp the turret assembly 10 from the clamp 5 and to loosen the articulating arm 20 and head-link 30, the key mating protrusion 5282 of the key 5234 can be inserted into either of the mating receptors 5258, 5260 and rotated in a second direction, for example, counterclockwise. This rotates the spool 5242 in the second direction, unwinding the tension element 5232 from the shaft 5256. As the tension element 5232 unwinds from the shaft 5256, the spacer 5247 can be allowed to slide away from the clamp 5, releasing the tension force of the pin 5244 and un-clamping the turret assembly 10 from the clamp 5. The turret assembly 10 can then be rotated relative to the clamp 5. In addition, as the tension element 5232 unwinds from the shaft 5256, the length of the tension element 5232 relative to the articulating arm 20 can be restored, loosening the articulating arm 20 for articulation and loosening the collet assembly 25 to allow movement of the head-link assembly 30.

The length of the tension element 5232 relative to the articulating arm 20 and the sizing of the locking mechanism 5246 can be adapted to determine the number of turns of the key 5234 needed to immobilize the articulating arm 20 and to clamp the turret assembly 10 to the clamp 5. In one embodiment, a lesser number of turns can be required to immobilize the articulating arm 20 than to clamp the turret assembly 10 to the clamp 5. In another embodiment, a greater number of turns can be required to immobilize the articulating arm 20 than to clamp the turret assembly 10 to the clamp 5. In another embodiment, an approximately equal number of turns can be required to immobilize the articulating arm 20 and to clamp the turret assembly 10 to the clamp 5.

In one embodiment, the key 5234 can be entirely detachable from the tissue stabilizer 100. In another embodiment, the key 5234 can be provided with a means of attachment to the tissue stabilizer 100 when not engaged with the turret assembly 10. For example, the key 5234 can be connected to the tissue stabilizer 100 by a length of cord or chain.

Figure 84:
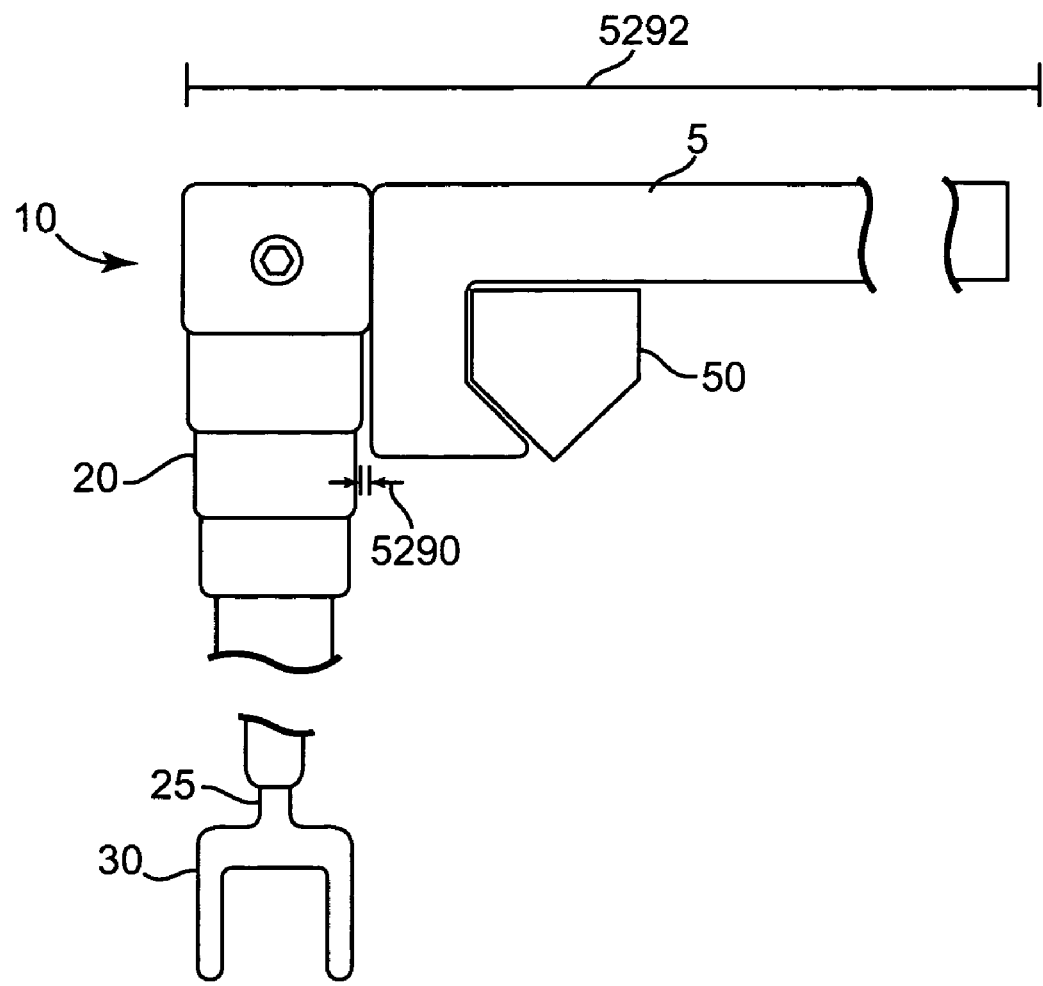
FIG. 84 is a side view of the tissue stabilizer mounted to the sternal retractor with the turret assembly rotated to orient the articulating arm perpendicular to the clamp.

FIG. 84 illustrates the tissue stabilizer 100 mounted to the sternal retractor 50 with the turret assembly 10 rotated so that the articulating arm 20 points downward relative to the clamp 5 or straight down into the surgical field. A "clamp clearance" can be defined as a distance between the distal face of the clamp 5 and the proximal end of the articulating arm 20, as indicated by the arrow at 5290 (with distal and proximal being defined with respect to the user of the tissue stabilizer 100). In one embodiment, the clamp clearance 5290 can approach zero. In another embodiment, the clamp clearance 5290 is less than about 2 mm. The clamp clearance 5290 can be reduced due to the turret assembly 10 being rotatable in order to orient the articulating arm 20 perpendicular relative to the clamp 5. A reduced clamp clearance 5290 allows the articulating arm 20 to reach further into the surgical field than if the clamp clearance 5290 were greater.

In the embodiment shown in FIG. 1 with the turret 10 positioned on top of the clamp 5, the "clamp clearance" can be defined as the distance between the proximal end of the articulating arm 20 and the distal face of the clamp 5, which in some embodiments, can approach zero or be up to about 2 mm. This reduced clamp clearance can allow the articulating arm 20 to reach further into the surgical field. Due to this reduced clamp clearance, from the assistant's side of the surgical field (i.e., the opposite side of the surgical field as the tissue stabilizer 100 is located), the tissue stabilizer 100 reach significantly farther with its "toes up" (i.e., the head-link assembly 30 in a U-shaped position).

Figure 85:
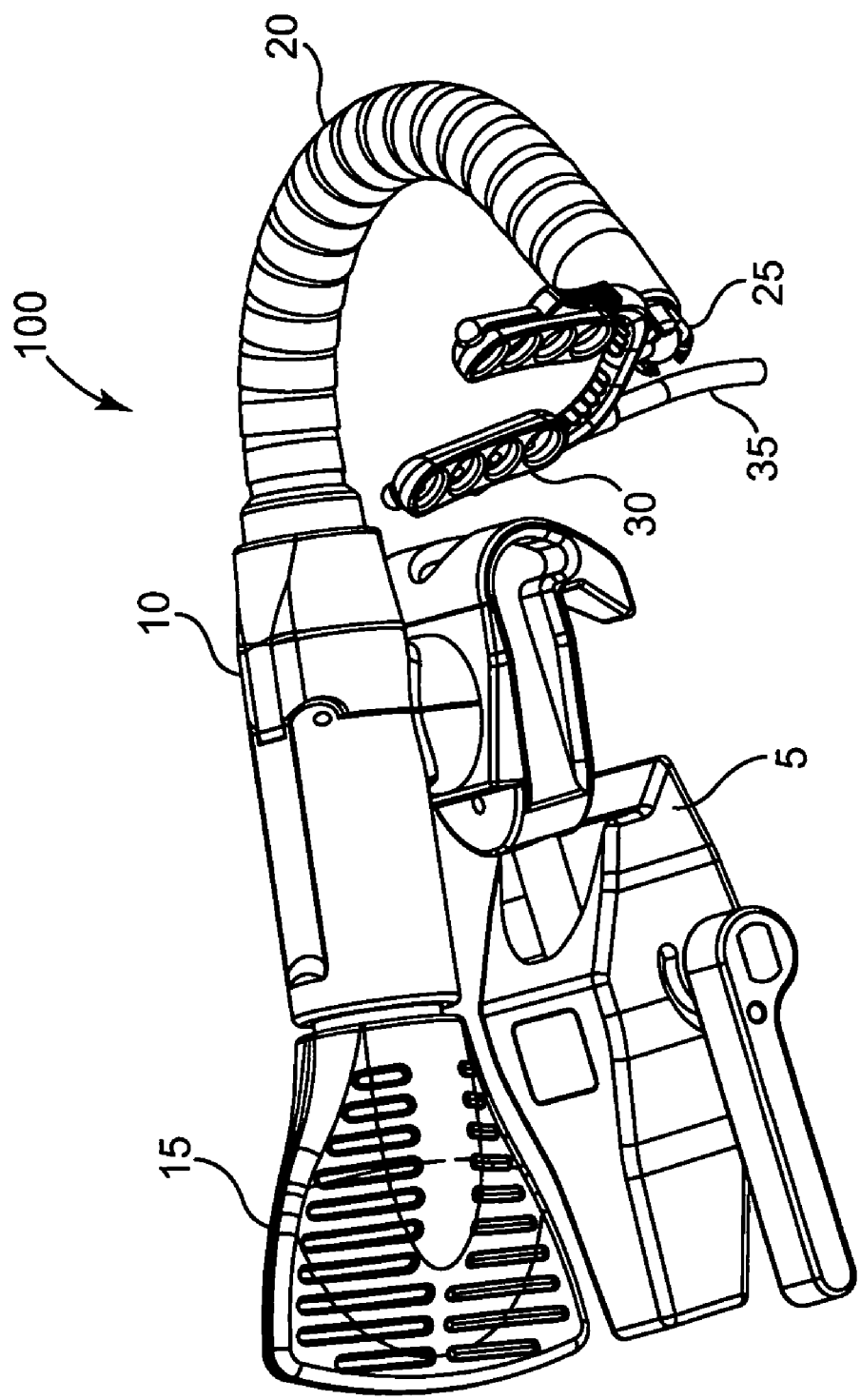
FIG. 85 is a perspective view of an embodiment of an entire tissue stabilizer assembly.

FIG. 85 illustrates a tissue stabilizer 100 according to one embodiment of the invention for use in supporting an organ, such as the heart, during a surgical procedure. The tissue stabilizer 100 can include a clamp 5, a turret 10, a handle 15, an articulating arm 20, a collet assembly 25, a head-link assembly 30, a vacuum tube 35, a vacuum tube clamp (not shown), and a vacuum tube valve (not shown).

Furthermore, other substitutions, modifications, changes, and omissions may be made in the design, operating conditions, and arrangements of the exemplary embodiments without departing from the scope of the invention as expressed in the appended claims. In addition, it will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A tissue stabilizer comprising:
   a clamp assembly comprising, a front clamp, a turret mount mounted to the front clamp, a rear clamp slidably coupled to the front clamp, a shaft mounted to one of the front clamp and the rear clamp, a clutch plate mounted to the shaft on a side of the rear clamp opposite the front and an actuator operably coupled to the clutch plate, the actuator being operable to rotate the clutch plate into the shaft to prevent the rear clamp from sliding, wherein the assembly is adapted to be clamped on a retractor;
   an articulating arm having a tension element extending therethrough;
   a turret assembly rotatably coupling a proximal end of the articulating arm to the clamp assembly, the turret assembly including a locking mechanism coupled to the tension element, the locking mechanism being capable of applying a tensioning force on the tension element;
   a head-link assembly;
   a collet assembly coupled to the tension element, the collet assembly rotatably coupling the head-link assembly to a distal end of the articulating arm, wherein tensioning of the tension element locks the head-link assembly to the collet assembly, locks the articulating arm in position, and locks the turret assembly to the clamp assembly, and wherein loosening of the tension element allows the head-link assembly to rotate relative to the collet assembly, the articulating arm to articulate, and the turret assembly to rotate relative to the clamp assembly.

2. The tissue stabilizer of claim 1, wherein the shaft is mounted to the front clamp and the rear clamp is slidably coupled to the shaft.

3. The tissue stabilizer of claim 1, wherein the shaft is mounted to the rear clamp.

4. The tissue stabilizer of claim 1 further comprising a spring biasing the rear clamp toward the front clamp.

5. The tissue stabilizer of claim 1 further comprising a handle coupled to the rear clamp.

6. The tissue stabilizer of claim 1 further comprising a spring biasing the clutch plate into engagement with the shaft.

7. The tissue stabilizer of claim 1 further comprising a cam operably coupling the actuator to the clutch plate.

8. The tissue stabilizer of claim 7 wherein the cam has a first stage that rotates the clutch plate and a second stage that urges the rear clamp towards the front clamp.

9. The tissue stabilizer of claim 1 wherein the turret assembly comprises a cylinder adapted to be coupled to the clamp assembly and a body supported by the cylinder, the body adapted to be coupled to the articulating arm.

10. The tissue stabilizer of claim 9, wherein the locking mechanism further comprises a lever arm pivotably coupled to the body and a link having a first end pivotably coupled to the lever arm and a second end slidable within a guide in the body, the second end of the link adapted to be coupled to the tension element.

11. The tissue stabilizer of claim 10 wherein the body is angled down toward a front portion of the clamp assembly.

12. The tissue stabilizer of claim 11 wherein the locking mechanism includes a connector coupled between the lever arm and the link and a pivoting link coupled to the link and to the body.

13. The tissue stabilizer of claim 10 wherein the lever arm cams against the body when pivoted into a closed position.

14. The tissue stabilizer of claim 9 wherein the turret assembly includes an adjustment mechanism adapted to be coupled to the tension element and capable of exerting a pre-load on the tension element.

15. The tissue stabilizer of claim 14 wherein the adjustment mechanism is rotatable to exert the pre-load on the tension element.

16. The tissue stabilizer of claim 9 wherein the cylinder includes a beveled region engaged by the body.

17. The tissue stabilizer of claim 1, wherein the collet assembly comprises a collet element, a base element, a head element, and a collet receiving element configured to receive the base element and to compress the head element when the collet element is drawn into the collet receiving element, wherein tensioning of the tension element draws the collet element into the collet receiving element, and loosening of the tension element allows the head element to move out of the collet receiving element, and wherein the head-link assembly is capable of being placed at any angle above a plane perpendicular to the collet receiving element when the tension element is loosened.

18. The tissue stabilizer of claim 17 wherein the collet assembly includes a tension element stop.

19. The tissue stabilizer of claim 17 wherein the head element of the collet assembly includes a plurality of slots.

20. The tissue stabilizer of claim 19 wherein at least a portion of the head-link assembly can be positioned in one of the plurality of slots.

21. The tissue stabilizer of claim 20 wherein the head-link assembly is held in place by the collet assembly when the tension element is tightened.

22. The tissue stabilizer of claim 17 wherein the collet assembly can withstand at least 430 foot pounds of force before breaking.

23. The tissue stabilizer of claim 17 wherein the collet receiving element can withstand at least 250 foot pounds of force before breaking.

24. The tissue stabilizer of claim 17 wherein the collet assembly is rotatable about 360 degrees.

25. The tissue stabilizer of claim 1 wherein the head-link assembly comprises a base configured to be received by the collet assembly, and a pair of arms coupled to the base, the arms deflecting from a first position in which the arms are separated from one another by a first distance to a second position in which the arms are separated from one another by a second distance and are biased to return to the first position in the absence of an external force.

26. The tissue stabilizer of claim 25 wherein the arms are biased to return to their original position by at least one of a spring, a link, and a support.

27. The tissue stabilizer of claim 25 wherein a first portion of the head-link assembly is hardened and a second portion of the head-link assembly is annealed.

28. The tissue stabilizer of claim 25 wherein the head-link assembly includes a support including the pair of arms, the support constructed of at least one of thermoplastic and stainless steel.

29. The tissue stabilizer assembly of claim 25 wherein a pod is over-molded onto each of the pair of arms.

30. The tissue stabilizer of claim 25 wherein a vacuum port is integrally formed with the pair of arms.

31. The tissue stabilizer of claim 25 wherein the base includes a neck and a support.

32. The tissue stabilizer of claim 31 wherein a vacuum port is integrated into the support.

33. The tissue stabilizer of claim 31 wherein the neck extends at an angle from a plane formed by the pair of arms.

34. The tissue stabilizer of claim 25 wherein the head-link assembly is positioned in a single plane.

35. The tissue stabilizer of claim 25 wherein the base is spherical.

36. The tissue stabilizer of claim 25 wherein the arms are each individually pivotally coupled to the base.

37. The tissue stabilizer of claim 25 wherein the head-link assembly includes an inner arm stop positioned to limit the first distance.

38. The tissue stabilizer of claim 25 wherein the head-link assembly includes an outer arm stop positioned to limit the second distance.

39. The tissue stabilizer of claim 1, wherein the turret assembly comprises a housing rotatably coupled to the clamp assembly and a spool within the housing, the spool being rotatable relative to the housing and coupled to the tension element, rotation of the spool in a first direction applies a tensioning force on the tension element and rotation of the spool in a second direction removes the tensioning force on the tension element.

40. The tissue stabilizer of claim 39 wherein the housing is coupled to a front portion of the clamp assembly.

41. The tissue stabilizer of claim 39 wherein the turret assembly includes a detachable key, wherein the detachable key can be received in a mating structure coupled to the spool so that rotation of the detachable key in the mating structure rotates the spool.

42. The tissue stabilizer of claim 41 wherein the spool has a mating receptor for receiving the mating structure, the mating receptor and the mating structure each being hex-shaped.

43. The tissue stabilizer of claim 41 wherein rotation of the spool in the first direction clamps the housing to the clamp assembly and rotation of the spool in the second direction un-clamps the housing from the clamp assembly.

44. The tissue stabilizer of claim 43 wherein the locking mechanism comprises a pin having a first end coupled to the spool and a second end coupled to the clamp assembly and a spacer positioned within the housing and slidable along the pin, wherein rotating the spool in the first direction winds the tension member around the spool between the spool and the spacer.

45. The tissue stabilizer of claim 44 wherein the spacer is approximately I-shaped.

46. The tissue stabilizer of claim 44 wherein the second end of the pin is fixed to an anchor in the clamp assembly.

47. The tissue stabilizer of claim 44 wherein the spacer is rotatable over the pin.

48. A method for stabilizing tissue comprising:
   clamping a tissue stabilizer to a retractor, the tissue stabilizer comprising:
      a clamp assembly comprising a front clamp, a turret mount mounted to the front clamp, a rear clamp slidably coupled to the front clamp, a shaft mounted to one of the front clamp and the rear clamp, a clutch plate mounted to the shaft on a side of the rear clamp opposite the front clam and an actuator operably coupled to the clutch plate the actuator being operable to rotate the clutch plate into the shaft to prevent the rear clamp from sliding, wherein the assembly is adapted to be clamped on a retractor;
      an articulating arm having a tension element extending therethrough;
      a turret assembly rotatably coupling a proximal end of the articulating arm to the clamp assembly, the turret assembly including a locking mechanism coupled to the tension element, the locking mechanism being capable of applying a tensioning force on the tension element;
      a head-link assembly;
      a collet assembly coupled to the tension element, the collet assembly rotatably coupling the head-link assembly to a distal end of the articulating arm, wherein tensioning of the tension element locks the head-link assembly to the collet, locks the articulating arm in position, and locks the turret assembly to the clamp assembly, and wherein loosening of the tension element allows the head-link assembly to rotate relative to the collet, the articulating arm to articulate, and the turret assembly to rotate relative to the clamp assembly;
   applying a deflecting force on a pair of arms of the head-link to deflect the arms from a first position to a second position in which the pair of arms are closer to one another;
   positioning at least a portion of the deflected arms against the tissue;
   applying a vacuum to the head-link assembly to create a suction force at a plurality of cups on each one of the pair of arms, the vacuum securing the arms to the tissue;
   removing the deflecting force to allow the pair of arms to return to the first position in order to stretch a portion of the tissue; and
   applying a tensioning force to the tension element to simultaneously lock the head-link assembly to the collet assembly, lock the articulating arm in position, and lock the turret assembly to the clamp assembly.

* * * * *